US012559769B2

(12) United States Patent　(10) Patent No.: US 12,559,769 B2
Pauza et al.　(45) Date of Patent:　Feb. 24, 2026

(54) METHODS AND COMPOSITIONS FOR THE ACTIVATION OF TUMOR CYTOTOXICITY VIA HUMAN GAMMA-DELTA T-CELLS

(71) Applicant: American Gene Technologies International Inc., Rockville, MD (US)

(72) Inventors: Charles David Pauza, Rockville, MD (US); Tyler Lahusen, Rockville, MD (US); Haishan Li, Rockville, MD (US); Mei-Ling Liou, Rockville, MD (US); Lingzhi Xiao, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 455 days.

(21) Appl. No.: 16/614,682

(22) PCT Filed: Jun. 15, 2018

(86) PCT No.: PCT/US2018/037924
§ 371 (c)(1),
(2) Date: Nov. 18, 2019

(87) PCT Pub. No.: WO2018/232359
PCT Pub. Date: Dec. 20, 2018

(65) Prior Publication Data
US 2020/0181645 A1　Jun. 11, 2020

Related U.S. Application Data

(60) Provisional application No. 62/633,461, filed on Feb. 21, 2018, provisional application No. 62/521,274, filed on Jun. 16, 2017.

(51) Int. Cl.
*C12N 15/86*　(2006.01)
*A61K 35/76*　(2015.01)
*A61K 48/00*　(2006.01)
*A61P 35/00*　(2006.01)
*C12N 7/00*　(2006.01)

(52) U.S. Cl.
CPC .............. *C12N 15/86* (2013.01); *A61K 35/76* (2013.01); *A61K 48/005* (2013.01); *A61P 35/00* (2018.01); *C12N 7/00* (2013.01); *C12N 2740/15023* (2013.01); *C12N 2740/15043* (2013.01)

(58) Field of Classification Search
CPC .............................. A61K 48/005; C12N 15/86
See application file for complete search history.

(56) References Cited

U.S. PATENT DOCUMENTS

| | | | |
|---|---|---|---|
| 5,668,255 A | 9/1997 | Murphy | |
| 5,674,703 A | 10/1997 | Woo et al. | |
| 6,156,514 A | 12/2000 | Acevedo et al. | |
| 6,399,383 B1 | 6/2002 | Apt et al. | |
| 6,635,472 B1 | 10/2003 | Lauermann | |
| 7,371,542 B2 | 5/2008 | Ivanova et al. | |
| 8,124,752 B2 | 2/2012 | Bumcrot et al. | |
| 8,287,857 B2 | 10/2012 | Dudley et al. | |
| 8,993,532 B2 | 3/2015 | Hannon et al. | |
| 9,522,176 B2 | 12/2016 | DeRosa et al. | |
| 9,527,904 B2 | 12/2016 | Balazs | |
| 9,834,790 B1 * | 12/2017 | Pauza et al. ........... | C12N 15/86 |
| 9,834,791 B2 | 12/2017 | Zhang | |
| 9,914,938 B2 * | 3/2018 | Pauza et al. ........... | C12N 15/86 |
| 10,023,880 B2 * | 7/2018 | Pauza et al. ........... | C12N 15/86 |
| 10,036,038 B2 | 7/2018 | Pauza et al. | |
| 10,036,040 B2 * | 7/2018 | Pauza et al. ........... | C12N 15/86 |
| 10,137,144 B2 * | 11/2018 | Pauza et al. ....... | A61K 31/7105 |
| 10,208,295 B2 | 2/2019 | DeRosa et al. | |
| 10,233,464 B2 | 3/2019 | Pauza et al. | |
| 10,420,789 B2 * | 9/2019 | Pauza et al. ....... | A61K 31/7105 |
| 10,428,350 B2 * | 10/2019 | Pauza et al. ........... | C12N 15/86 |
| 10,472,649 B2 * | 11/2019 | Pauza et al. ........... | C12N 15/86 |
| 10,767,183 B2 * | 9/2020 | Lahusen et al. ... | C12N 15/1135 |
| 10,772,905 B2 * | 9/2020 | Pauza et al. ....... | A61K 31/7105 |
| 11,242,527 B1 | 2/2022 | Lahusen et al. | |
| 11,519,006 B2 | 12/2022 | Pauza et al. | |
| 11,534,450 B2 | 12/2022 | Pauza et al. | |
| 2002/0168345 A1 | 11/2002 | Dong et al. | |
| 2003/0013196 A1 | 1/2003 | Engelman et al. | |
| 2003/0096787 A1 | 5/2003 | Perridcaudet et al. | |
| 2003/0119770 A1 | 6/2003 | Lai | |
| 2003/0138444 A1 | 7/2003 | Zavitz et al. | |
| 2004/0142416 A1 | 7/2004 | Laipis et al. | |
| 2004/0161412 A1 | 8/2004 | Penn et al. | |
| 2004/0180847 A1 | 9/2004 | Dobie et al. | |
| 2004/0192629 A1 | 9/2004 | Xu et al. | |

(Continued)

FOREIGN PATENT DOCUMENTS

| | | |
|---|---|---|
| BR | 2515 | 3/2019 |
| CN | 101516365 | 8/2009 |

(Continued)

OTHER PUBLICATIONS

Jiang et al. (2012) "A novel EST-derived RNAi screen reveals a critical role for farnesyl diphosphate synthase in β2-adrenergic receptor internalization and down-regulation" The FASEB Journal, 26(5), 1995-2007. (Year: 2012).*

Li et al. (2009) "Reduced Expression of the Mevalonate Pathway Enzyme Farnesyl Pyrophosphate Synthase Unveils Recognition of Tumor Cells by Vγ9Vδ2 T Cells" J Immunol 182 (12) 8118-8124. (Year: 2009).*

Riaño et al. (2014) "Vγ9Vδ2 TCR-activation by phosphorylated antigens requires butyrophilin 3 A1 (BTN3A1) and additional genes on human chromosome 6" Eur J Immunol 44: 2571-2576. (Year: 2014).*

Chen et al. (2013) "An unconventional TRAIL to cancer therapy" Eur J Immunol 43: 3159-3162. (Year: 2013).*

Brake et al. (2008) "Lentiviral vector design for multiple shRNA expression and durable HIV-1 inhibition" Molecular Therapy, 16(3), 557-564, describes a single lentiviral construct design encoding up to four short hairpin RNAs (shRNAs). (Year: 2008).*

(Continued)

*Primary Examiner* — James Joseph Graber
(74) *Attorney, Agent, or Firm* — COOLEY LLP

(57) ABSTRACT

The present disclosure relates generally to methods and compositions for activating gamma-delta (GD) T cells. Such methods and compositions can be used to treat cancer.

8 Claims, 30 Drawing Sheets

Specification includes a Sequence Listing.

(56)     References Cited

U.S. PATENT DOCUMENTS

| 2004/0214158 A1 | 10/2004 | Sethi et al. |
| 2004/0248296 A1 | 12/2004 | Beresford et al. |
| 2004/0265306 A1 | 12/2004 | Arthos et al. |
| 2005/0019927 A1 | 1/2005 | Markus et al. |
| 2005/0138677 A1 | 6/2005 | Pfister et al. |
| 2006/0057553 A1 | 3/2006 | Aguilar-Cordova |
| 2006/0073576 A1 | 4/2006 | Barnett et al. |
| 2006/0183230 A1 | 8/2006 | Silla et al. |
| 2006/0246520 A1 | 11/2006 | Champagne et al. |
| 2007/0026521 A1 | 2/2007 | Colosi |
| 2007/0141679 A1 | 6/2007 | Sodroski |
| 2007/0203333 A1 | 8/2007 | McSwiggen et al. |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu |
| 2008/0153737 A1 | 6/2008 | Lieberman et al. |
| 2008/0199961 A1 | 8/2008 | Rasko et al. |
| 2008/0227736 A1 | 9/2008 | Chen et al. |
| 2008/0293142 A1 | 11/2008 | Liu et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Pey Rodriguez et al. |
| 2010/0316676 A1 | 12/2010 | Sanders |
| 2011/0008803 A1 | 1/2011 | Stockwell et al. |
| 2011/0177155 A1 | 7/2011 | Peer et al. |
| 2011/0207226 A1 | 8/2011 | Ni et al. |
| 2012/0027725 A1 | 2/2012 | Galvin et al. |
| 2012/0034197 A1 | 2/2012 | Young et al. |
| 2012/0053223 A1 | 3/2012 | Benkirane et al. |
| 2012/0114607 A1 | 5/2012 | Lai et al. |
| 2012/0201794 A1 | 8/2012 | Chen et al. |
| 2013/0078276 A1 | 3/2013 | Robinson et al. |
| 2013/0090371 A1 | 4/2013 | Lu et al. |
| 2013/0122380 A1 | 5/2013 | Visco et al. |
| 2013/0142766 A1 | 6/2013 | Dodo et al. |
| 2013/0211380 A1 | 8/2013 | Cabrera Aquino et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kashara et al. |
| 2014/0248277 A1 | 9/2014 | Hoffman et al. |
| 2014/0336245 A1 | 11/2014 | Mingozzi et al. |
| 2014/0348794 A1 | 11/2014 | Chiorini et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1 | 6/2015 | Krause et al. |
| 2016/0060707 A1 | 3/2016 | Goldenberg et al. |
| 2016/0243169 A1 | 8/2016 | Chen et al. |
| 2016/0287635 A1 | 10/2016 | Hariri et al. |
| 2016/0289681 A1 | 10/2016 | Rossi |
| 2017/0015976 A1 | 1/2017 | Nelson |
| 2017/0028036 A1 | 2/2017 | Mingozzi et al. |
| 2017/0037369 A1 | 2/2017 | Ramsborg et al. |
| 2017/0335344 A1 | 11/2017 | Pauza et al. |
| 2018/0010147 A1 | 1/2018 | Pauza |
| 2018/0142257 A1 | 5/2018 | Pauza |
| 2018/0142258 A1 | 5/2018 | Pauza |
| 2018/0161455 A1 | 6/2018 | Pauza |
| 2018/0177866 A1 | 6/2018 | Pauza |
| 2018/0195046 A1 | 7/2018 | Deng |
| 2018/0195050 A1 | 7/2018 | Szalay |
| 2018/0256624 A1 | 9/2018 | Pauza |
| 2018/0305716 A1 | 10/2018 | Pauza et al. |
| 2018/0355032 A1 | 12/2018 | Roberts |
| 2019/0046633 A1 | 2/2019 | Pauza et al. |
| 2019/0062786 A1 | 2/2019 | Pauza et al. |
| 2019/0078096 A1 | 3/2019 | Lahusen et al. |
| 2019/0083523 A1 | 3/2019 | Pauza |
| 2019/0218573 A1 | 7/2019 | Pauza et al. |
| 2019/0388456 A1 | 12/2019 | Pauza et al. |
| 2020/0017570 A1 | 1/2020 | Walcheck et al. |
| 2020/0063161 A1 | 2/2020 | Pauza |
| 2020/0087682 A1 | 3/2020 | Lahusen et al. |
| 2020/0109417 A1 | 4/2020 | Pauza et al. |
| 2020/0155590 A1 | 5/2020 | Zhennan |
| 2020/0318081 A1 | 10/2020 | Lahusen et al. |
| 2020/0354679 A1 | 11/2020 | Niazi |
| 2021/0047644 A1 | 2/2021 | Lahusen |

FOREIGN PATENT DOCUMENTS

| CN | 101679466 | 3/2010 |
| CN | 101805750 | 8/2010 |
| CN | 103184224 | 7/2013 |
| CN | 105112370 | 12/2015 |
| CN | 108883100 | 11/2018 |
| EP | 1647595 | 4/2006 |
| EP | 3402483 | 11/2018 |
| EP | 3413926 | 12/2018 |
| EP | 3426777 | 1/2019 |
| EP | 3468617 | 4/2019 |
| EP | 3468618 | 4/2019 |
| EP | 3481418 | 5/2019 |
| EP | 3481435 | 5/2019 |
| IN | 201947000153 | 2/2019 |
| JP | 2002506652 | 3/2002 |
| JP | 2007-527240 | 9/2007 |
| JP | 2008518591 | 6/2008 |
| JP | 2008-538174 | 10/2008 |
| JP | 2012508591 | 4/2012 |
| JP | 2013-5300152 | 7/2013 |
| JP | 2015-518838 | 7/2015 |
| JP | 2016-502404 | 1/2016 |
| JP | 2019-509029 | 4/2019 |
| WO | 199947691 | 9/1999 |
| WO | 2002020554 | 3/2002 |
| WO | 2003093436 | 11/2003 |
| WO | 2004053137 | 6/2004 |
| WO | 2005028634 | 3/2005 |
| WO | 2005033282 | 4/2005 |
| WO | 2006039721 | 4/2006 |
| WO | 2006048215 | 5/2006 |
| WO | 2007000668 | 1/2007 |
| WO | 2007015122 | 2/2007 |
| WO | 2007132292 | 11/2007 |
| WO | 2007133674 | 11/2007 |
| WO | 2008025025 | 2/2008 |
| WO | 2008090185 | 7/2008 |
| WO | WO 2009001224 A2 | 12/2008 |
| WO | 2009100928 | 8/2009 |
| WO | 2009147445 | 12/2009 |
| WO | 2010051521 | 5/2010 |
| WO | WO2010111522 | 9/2010 |
| WO | 2010117974 | 10/2010 |
| WO | WO2010119039 | 10/2010 |
| WO | 2010127166 | 11/2010 |
| WO | 2011008348 | 1/2011 |
| WO | WO2012071559 | 5/2011 |
| WO | 2011071476 | 6/2011 |
| WO | 2011119942 | 9/2011 |
| WO | 2012048303 | 4/2012 |
| WO | 2012061075 | 5/2012 |
| WO | 2012145624 | 10/2012 |
| WO | WO2013056148 | 4/2013 |
| WO | 2013096455 | 6/2013 |
| WO | 2014016817 | 1/2014 |
| WO | 2014117050 | 7/2014 |
| WO | 2014187881 | 11/2014 |
| WO | WO2014195159 | 12/2014 |
| WO | 2015017755 | 2/2015 |
| WO | 2015042308 | 3/2015 |
| WO | 2015061491 | 4/2015 |
| WO | 2015078999 | 6/2015 |
| WO | PCT/CN2015/086854 | 8/2015 |
| WO | WO2015164759 | 10/2015 |
| WO | 2016046234 | 3/2016 |
| WO | 2016061232 | 4/2016 |

(56) References Cited

FOREIGN PATENT DOCUMENTS

| WO | 2016069716 | 5/2016 |
| WO | 2016200997 | 7/2016 |
| WO | 2016189159 | 12/2016 |
| WO | 2017007994 | 1/2017 |
| WO | 20170068077 | 4/2017 |
| WO | 2017100551 | 6/2017 |
| WO | 2017123918 | 7/2017 |
| WO | 2017139065 | 8/2017 |
| WO | 2017156311 | 9/2017 |
| WO | WO2017165641 | 9/2017 |
| WO | 20170173453 | 10/2017 |
| WO | 2017213697 | 12/2017 |
| WO | 2017214327 | 12/2017 |
| WO | 2018009246 | 1/2018 |
| WO | 2018009847 | 1/2018 |
| WO | 2018017882 | 1/2018 |
| WO | 2018126112 | 7/2018 |
| WO | 2018129540 | 7/2018 |
| WO | 20180148443 | 8/2018 |
| WO | 2018187231 | 10/2018 |
| WO | 2018232359 | 12/2018 |
| WO | 2019070674 | 4/2019 |
| WO | 2020011247 | 1/2020 |
| WO | 2020097049 | 5/2020 |
| WO | 2020243717 | 12/2020 |
| WO | 2021178571 | 9/2021 |

OTHER PUBLICATIONS

Pallikkuth et al., "Human Immunodeficiency Virus (HIV) gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, vol. 14(9) pp. 1196-1202, (2007).

USPTO; Non-Final Office Action dated Feb. 21, 2020 in the U.S. Appl. No. 16/076,655.

EPO; Extended European Supplementary Search Report dated Feb. 6, 2020 in the Application No. 17825011.4.

EPO; Extended European Supplementary Search Report dated Feb. 6, 2020 in the Application No. 17824652.6.

Wang et al., "HIV Vaccine Research: The Challenge and the Way Forward," Journal of Immunology Research, vol. 2015, Article ID 503978, 5 pages.

Bourguigon et al., "Processing of blood samples influences PBMC viability and outcome of cell-mediated immune responses in antiretroviral therapy-naïve HIV-1-infected patients," Journal of Immunological Methods, vol. 414, p. 1-10 (2014).

Briz et al., "Validation of Generation 4 Phosphorus-Containing Polycationic Dendrimer for Gene Delivery Against HIV-1," Current Medical Chemistry, vol. 19, p. 5044-5051, (2012).

Anderson et al., "Preintegration HIV-1 Inhibition by a Combination Lentiviral Vector Containing a Chimeric TRIM5a Protein, a CCR5 shRNA, and TAR Decoy," Molecular Therapy, vol. 17, No. 12, p. 2103-2114, Dec. 2009.

JP; Japanese Office Action in the Application No. 2017-567175 dated Jun. 15, 2020.

EPO; Extended European Search Report in the Application No. 18736295.9 dated Aug. 20, 2020.

USPTO; Notice of Allowance dated Jan. 26, 2021 in the U.S. Appl. No. 16/593,882.

Nada et al, "Enhancing adoptive cancer immunotherapy with Vγ2Vδ2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 *the whole document*.

Benyamine et al., "BTN3A molecules considerably improve Vγ9Vδ2T cells-based immunotherapy in acute myeloid leukemia," Oncolmmunology, vol. 5, No. 10, 10 pages, (Oct. 2, 2016), E1146843 *the whole document*.

Harly et al., "Key implication of CD277/butyrophilin-3 (BTN3A) in cellular stress sensing by a major human γδ T-cell subset," American Society of Hematology , vol. 120, No. 11, (Sep. 13, 2012), pp. 2269-2279, XP055081172, ISSN: 0006-4971, DOI: 10.1182/blood-2012-05-430470 *the whole document*.

Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.

USPTO; Notice of Allowance dated Feb. 10, 2021 in the U.S. Appl. No. 16/943,800.

USPTO; Non-Final Office Action dated Feb. 19, 2021 in the U.S. Appl. No. 15/580,661.

USPTO; Final Office Action dated Feb. 26, 2021 in the U.S. Appl. No. 16/312,056.

USPTO; Corrected Notice of Allowance dated Mar. 3, 2021 in the U.S. Appl. No. 16/687,525.

USPTO; Non-Final Office Action dated Mar. 12, 2021 in the U.S. Appl. No. 16/563,738.

CN; 1st Office Action in the CN Application No. 202010396594.8 dated Jan. 15, 2021.

EP; Supplementary Search Report in the EP Application No. 18817253 dated Feb. 10, 2021.

JP; Office Action in the JP Application No. 2018-547354 dated Feb. 16, 2021.

JP; Office Action in the JP Application No. 2018-541270 mailed Jan. 8, 2021.

USPTO; Non-Final Office Action dated Oct. 29, 2020 in the U.S. Appl. No. 15/736,284.

JP; Japanese Office Action in the JP Application No. 2018-563892 dated Oct. 14, 2020.

Quan Jun-Jie et al., "Parp3 interacts with FoxM1 to confer glioblastoma cell radio resistance", Tumor Biology, Karger, Basel, CH, vol. 36, No. 11, Jun. 4, 2015 (Jun. 4, 2015), pp. 8617-8624, XP036217799, ISSN: 1010-4283, DOI: 10.1007/S13277-015-3554-4 on [retrieved on Jun. 4, 2015] *whole document*.

Jakobsson J. and Lundberg C.: "Lentiviral 1, 2, 4-10 vectors for use in the central nervous system", Molecular Therapy: The Journal of the American Society of Gene Therapy, Cell Press, US, vol. 13, No. 3, Mar. 1, 2006 (Mar. 1, 2006), pp. 484-493, XP005326761, ISSN: 1525-0016, DOI: 10.1016/J.Ymthe.2005.11.012 *the whole document*.

Yun Jong Lee et al., "Poly (ADP-ribose) in 1-15 the pathogenesis of Parkinson's disease", BMB Reports, vol. 47, No. 8, Aug. 31, 2014 (Aug. 31, 2014), pp. 424-432, XP55671927, KR, ISSN: 1976-6696, DOI: 10.5483/BMBRep.2014.47.8.119 *the whole document*.

Lang Yoo et al., "Parp-1 regulates the expression of caspase-11", Biochemical and Biophysical Research Communications, vol. 408, No. 3, Apr. 22, 2011 (Apr. 22, 2011), pp. 489-493, XP028209824, ISSN: 0006-291X, DOI: 10.1016/ J. BBRC.2011.04.070 [retrieved on Apr. 22, 2011] *whole document*.

Tae-In Kam et al., "Poly (ADP-ribose) derived pathologic [alpha]-synuclein neurodegeneration in Parkinson's disease", Science, vol. 362, No. 6414, Nov. 1, 2018 (Nov. 1, 2018), p. eaat8407, XP55672116, US, ISSN: 00368075, DOI: 10.1126/science. aat8407 *whole document*.

Olsen A.L. and Feany M.B., "PARP Inhibitors and Parkinson's Disease", Jan. 1, 2019 (Jan. 1, 2019), XP55672111, retrieved from the Internet: URL: https://mfprac.com/web2019/07literature/literature/Neurology/ParkinsonPARPI_Olsen.pdf [retrieved on Feb. 27, 2020] *the whole document*.

Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, Jan. 2004, p. 658-668. DOI: 10.1128/JVI.78.2658-668.2004.

FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.

Kathleen Van Craenenbroeck et al., "Episomal vectors for gene expression in mammalian cells", Eur J. Biochem, vol. 267, p. 5665-5678, Jul. 14, 2000.

USPTO; Non-Final Office Action dated Mar. 16, 2020 in the U.S. Appl. No. 16/083,384.

(56) References Cited

OTHER PUBLICATIONS

EPO; Extended European Supplemental Search Report dated Mar. 11, 2020 in the Application No. 17831904.2.

JP; Japanese Office Action in the Application No. 2017-564550 dated Mar. 18, 2020.

Bergvall et al. "The E1 proteins", Virology 445; p. 35-56, (Year:2013).

McBride, A., "The Papillomavirus E2 proteins", Virology 445: p. 57-79, (Year: 2013).

Chiang C-m et al., "Viral E1 and E2 proteins support replication of homologous and heterologous papillomaviral origins." PNAS 89: p. 5799-5803, (Year: 1992).

Krajinovic et al., "Sequencing data on the long control region of human papillomavirus type 16." Journal of General Viology 72:2573-2576, (Year: 1991).

Seedorg et al., "Human Papillomavirus type 16 DNA sequence." Virology 145: p. 181-185, (Year: 1985).

Jaalouk, et al. "A Self-inactivating retrovector incorporating the IL-2 promoter for activation-induced transgene expression engineered t-cells," Virology Journal: p. 1-12, (Year: 2006).

USPTO; Non-Final Office Action dated Sep. 22, 2020 in the U.S. Appl. No. 16/308,373.

USPTO; Notice of Allowance dated Jul. 10, 2020 in the U.S. Appl. No. 16/530,908.

USPTO; Final Office Action dated Jul. 27, 2020 in the U.S. Appl. No. 16/076,655.

JP; Japanese Office Action in the Application No. 2018-536892 dated Jun. 26, 2020.

Davis-Gardner et al., "eCD4-Ig promotes ADCC activity of sera from HIV-1-infected patients", Department of Immunology and Microbiology, The Scripps Research Institute, PLOS Pathogen, Dec. 18, 2017, https://doi.org/10.1371/journal.ppat.1006786.

PCT; International Search Report and Written Opinion in the PCT Application No. PCT/US2021/020721 dated Jul. 21, 2021.

USPTO; Non-Final Office Action dated Jul. 20, 2021 in the U.S. Appl. No. 17/198,017.

Brites, C., M. Abrahao, P. Bozza, E. M. Netto, A. Lyra and F. Bahia (2018). "Infection by HTLV-1 Is Associated with High Levels of Proinflammatory Cytokines in HIV-HCV-Coinfected Patients." J Acquir Immune Defic Syndr 77(2): 230-234.

Douek, D. C., J. M. Brenchley, M. R. Betts, D. R. Ambrozak, B. J. Hill, et al. (2002). "HIV preferentially infects HIV-specific CD4+ T cells." Nature 417(6884): 95-98.

Eguchi, K., N. Matsuoka, H. Ida, M. Nakashima, M. Sakai, et al. (1992). "Primary Sjogren's syndrome with antibodies to HTLV-I: clinical and laboratory features." Ann Rheum Dis 51(6): 769-776.

Futsch, N., R. Mahieux and H. Dutartre (2017). "HTLV-1, the Other Pathogenic Yet Neglected Human Retrovirus: From Transmission to Therapeutic Treatment." Viruses, 10, 1; doi:10.3390/v10010001.

Gessain, A., F. Barin, J. C. Vernant, O. Gout, L. Maurs, A. Calender and G. de The (1985). "Antibodies to human T-lymphotropic virus type-I in patients with tropical spastic paraparesis." Lancet 2(8452): 407-410.

Gessain, A. and O. Cassar (2012). "Epidemiological Aspects and World Distribution of HTLV-1 Infection." Front Microbiol 3: 388.

Goncalves, D. U., F. A. Proietti, J. G. Ribas, M. G. Araujo, S. R. Pinheiro, A. C. Guedes and A. B. Carneiro-Proietti (2010). "Epidemiology, treatment, and prevention of human T-cell leukemia virus type 1-associated diseases." Clin Microbiol Rev 23(3): 577-589.

Kagdi, H., M. A. Demontis, J. C. Ramos and G. P. Taylor (2018). "Switching and loss of cellular cytokine producing capacity characterize in vivo viral infection and malignant transformation in human T-lymphotropic virus type 1 infection." PLoS Pathog 14(2): e1006861.

Kagdi, H. H., M. A. Demontis, P. A. Fields, J. C. Ramos, C. R. Bangham and G. P. Taylor (2017). "Risk stratification of adult T-cell leukemia/lymphoma using immunophenotyping." Cancer Med 6(1): 298-309.

Macnamara, A., A. Rowan, S. Hilburn, U. Kadolsky, H. Fujiwara, et al. (2010). "HLA class I binding of HBZ determines outcome in HTLV-1 infection." PLoS Pathog 6(9): e1001117.

Manel, N., F. J. Kim, S. Kinet, N. Taylor, M. Sitbon and J. L. Battini (2003). "The ubiquitous glucose transporter GLUT-1 is a receptor for HTLV." Cell 115(4): 449-459.

Martinez, M. P., J. Al-Saleem and P. L. Green (2019). "Comparative virology of HTLV-1 and HTLV-2." Retrovirology 16(1): 21.

Mochizuki, M., T. Watanabe, K. Yamaguchi, K. Takatsuki, K. Yoshimura, et al. (1992). "HTLV-I uveitis: a distinct clinical entity caused by HTLV-I." Jpn J Cancer Res 83(3): 236-239.

Mosley, A. J., B. Asquith and C. R. Bangham (2005). "Cell-mediated immune response to human T-lymphotropic virus type I." Viral Immunol 18(2): 293-305.

Nagai, M. and M. Osame (2003). "Human T-cell lymphotropic virus type I and neurological diseases." J Neurovirol 9(2): 228-235.

Yamano, Y. and T. Sato (2012). "Clinical pathophysiology of human T-lymphotropic virus-type 1-associated myelopathy/tropical spastic paraparesis." Front Microbiol 3: 389.

Nishioka, K., I. Maruyama, K. Sato, I. Kitajima, Y. Nakajima and M. Osame (1989). "Chronic inflammatory arthropathy associated with HTLV-I." Lancet 1(8635): 441.

Osame, M., K. Usuku, S. Izumo, N. Ijichi, H. Amitani, et al. (1986). "HTLV-I associated myelopathy, a new clinical entity." Lancet 1(8488): 1031-1032.

Poiesz, B. J., F. W. Ruscetti, A. F. Gazdar, P. A. Bunn, J. D. Minna and R. C. Gallo (1980). "Detection and isolation of type C retrovirus particles from fresh and cultured lymphocytes of a patient with cutaneous T-cell lymphoma." Proc Natl Acad Sci U S A 77(12): 7415-7419.

Poiesz, B. J., F. W. Ruscetti, J. W. Mier, A. M. Woods and R. C. Gallo (1980). "T-cell lines established from human T-lymphocytic neoplasias by direct response to T-cell growth factor." Proc Natl Acad Sci U S A 77(11): 6815-6819.

Roc, L., C. de Mendoza, M. Fernandez-Alonso, G. Reina, V. Soriano and H. N. Spanish (2019). "Rapid subacute myelopathy following kidney transplantation from HTLV-1 donors: role of immunosuppresors and failure of antiretrovirals." Ther Adv Infect Dis 6: 2049936119868028.

Soker, S., S. Takashima, H. Q. Miao, G. Neufeld and M. Klagsbrun (1998). "Neuropilin-1 is expressed by endothelial and tumor cells as an isoform-specific receptor for vascular endothelial growth factor." Cell 92(6): 735-745.

Uchiyama, T., J. Yodoi, K. Sagawa, K. Takatsuki and H. Uchino (1977). "Adult T-cell leukemia: clinical and hematologic features of 16 cases." Blood 50(3): 481-492.

Dickler, H. B., et al. (1973). "Lymphocyte binding of aggregated IgG and surface Ig staining in chronic lymphocytic leukaemia." Clin Exp Immunol 14(1): 97-106.

USPTO; Notice of Allowance dated May 18, 2020 in the U.S. Appl. No. 16/083,384.

USPTO; Final Office Action dated Jun. 2, 2020 in the U.S. Appl. No. 15/580,661.

USPTO; Non-Final Office Action dated Jun. 1, 2020 in the U.S. Appl. No. 16/530,908.

CN; 1st Office Action in the CN Application No. 20170017712.6 dated May 8, 2020.

EPO; Office Action in the EPO Application No. 16808223.8 dated May 11, 2020.

Yang et al., "Construction of PARP-1 gene silencing cell lines by lentiviral-mediated RNA interference," School of Public Health, Guangdong Medical College, Abstract (2009).

Zhaobing Ding et al., "Liver-Directed, AAV-and Lentivirus-Mediated Gene Therapy in the Phenylketonuria Mouse Model Pah-enu2", Molecular Therapy, vol. 11, Supp. 1. (May 2005) XP055751452.

Ledley et al., "Retroviral-mediated gene transfer of human phenylalanine hydroxylase into NIH 3T3 and hepatoma cells", Proceedings of the National Academy of Sciences, vol. 83, No. 2. (Jan. 1, 1986), pp. 409-413, XP002583115.

Ledley et al., "Molecular biology of phenylalanine hydroxylase and phenylketonurina", Trends in Genetics, Elsevier Science Publishers B.V. Amsterdam, NL, vol. 1. (Jan. 1, 1985), pp. 309-313, XP025943064.

(56)　　　　References Cited

OTHER PUBLICATIONS

USPTO; Notice of Allowance dated Jan. 13, 2021 in the U.S. Appl. No. 16/687,525.

EP; Supplementary Search Report in the EP Application No. 18781288.8 dated Dec. 8, 2020.

JP; Final Office Action in the JP Application No. 2018-536892 dated Nov. 16, 2020.

PCT; International Search Report and Written Opinion in the PCT Application No. PCT/US2019/059828 dated Feb. 14, 2020.

USPTO; Restriction Requirement dated Jan. 29, 2020 in the U.S. Appl. No. 16/312,056.

EPO; Supplementary European Search Report dated Dec. 19, 2019 in the Application No. 16904834.5.

EPO; Supplementary European Search Report dated Dec. 19, 2019 in the Application No. 17810976.5.

Vargas, J. Jr. et al., "Conditionally replicating lentiviral-hybrid episomal vectors for suicide gene therapy," Antiviral Res. Dec. 2008 vol. 80 No. 3, pp. 288-294.

Thompson et al., "Alkylamines cause Vγ9Vδ2 T-cell activation and proliferation by inhibiting the mevalonate pathway," Blood, Jan. 15, 2006, vol. 107, pp. 651-654.

Gober et al., "Human T Cell Receptor γδ Cells Recognize Endogenous Mevalonate Metabolites in Tumor Cells," J. of Experimental Med., Jan. 20, 2003, vol. 197, pp. 163-168.

Goepfert, et al., "Specificity and 6-Month Durability of Immune Responses Induced by DNA and Recombinant Modified Vaccinia Ankara Vaccines Expressing HIV-2 Virus-Like Particles," J. Infectious Diseases, Jul. 1, 2014, vol. 210, pp. 99-110.

Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank=22&RID=H3E1THFU014; pp. 1-4.

{Long control region} [human papillomavirus, type 16, Genomic, 860 nt]; Accession S60559. Publication [online]. May 7, 1993, https://www.ncbi.nlm.nih.gov/nucleotide/237343?report=genbank&log$=nucltop&blast_rank=1&RID=H3FCKA00014; pp. 1.

Tebas, P. et al., "Antiviral effects of autologous CD4 T cells genetically modified with a conditionally replicating lentiviral vector expressing long antisense to HIV," Blood, 2013, vol. 121, No. 9, pp. 1524-1533.

Tebas, p. et al., "Gene Editing of CCR5 in Autologous CD4 T Cells of Persons Infected with HIV," The New England Journal of Medicine, vol. 370 (10), pp. 901-910, Mar. 6, 2014.

Li et al., "Reduced Expression of the Mevalonate Pathway Enzyme Farnesyl Pyrophosphate Synthase Unveils Recognition of Tumor Cells by Vy2Vδ2 T Cells," J. of Immunology, 2009, vol. 182, pp. 8118-8124.

Wang et al., "Indirect Stimulation of Human Vy2Vδ2 T Cells through Alterations in Isoprenoid Metabolism," J. of Immunology, vol. 187 pp. 5099-5113, (Nov. 15, 2011).

Stunkel et al., "The Chromatin Structure of the Long Control Region of Human Papillomavirus Type 16 Repress Viral Oncoprotein Expression," Journal Of Virology, vol. 73, No. 3, pp. 1918-1930 (Mar. 1999).

Lu et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).

Dieli et al., "Targeting Human yδ T Cells with Zoledronate and Interleukin-2 for Immunotherapy of Hormone-Refractory Prostate Cancer," Europe PMC Funders Group, Cancer Research, vol. 67(15), pp. 7450-1451, (Aug. 1, 2007).

GenBank Accession No. S60559 "(long control region) [human papillomavirus, type 16, Genomic, 860 nt]" May 7, 1993 [located online Nov. 21, 2017 at https://ncbi.nlm.nih.gov/nuccore/S60559] entire DNA sequence.

GenBank Accession No. JG619773, MNESCING-T3-001_L15_6FEB2009_054 Mnescing cell culture from Mahonia nervosa Berberis nervosa cDNA, mRNA sequence, Feb. 13, 2014 (online). [Retrieved on Dec. 5, 2017]. Retrieved from the internet:<URL: https://www.ncbi.nlm.nih.gov/nucest/JG619773 > entire document.

Moser et al., "yδ T cells: novel initiators of adaptive immunity," Immunological Reviews, vol. 215, pp. 89-102 (Feb. 2, 2007).

Capietto, A. H. et al., "Stimulated yδ T Cells Increase the in Vivo Efficacy of Trastuzumab in HER-2+ Breast Cancer," J Immunology, vol. 187(2), pp. 1031-1038, (2011).

Chen, Z. and M. S. Freedman, "CD16+ yδ T Cells Mediate Antibody Dependent Cellular Cytotoxicity: Potential Mechanism in the Pathogenesis of Multiple Sclerosis," Clin Immunology, vol. 128(2), pp. 219-227, (2008).

Couzi, L. et al., "Antibody-Dependent Anti-Cytomegalovirus Activity of Human yδ T Cells Expressing CD16 (FcyRIIIa)," Blood, vol. 119(6), pp. 1418-1427, (2012).

Fisher, J. P. et al., "Effective Combination Treatment of GD2-Expressing Neuroblastoma and Ewing's Sarcoma Using Anti-GD2 ch14.18/CHO Antibody with Vy9Vδ2+ yδT Cells," OncoImmunology, vol. 5(1), pp. e1025194, (2016).

Gertner-Dardenne, J. et al., "Bromohydrin pyrophosphate enhances antibody-dependent cell-mediated cytotoxicity induced by therapeutic antibodies," Blood 113(20): 4875-4884, (2009).

Poonia, B. and C. D. Pauza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).

Schiller, C. B. et al., "CD19-Specific Triplebody SPM-1 Engages NK and yδ T Cells for Rapid and Efficient Lysis of Malignant B-Lymphoid Cells," Oncotarget, vol. 7(50), pp. 83392-83408, (2016).

Tokuyama, H. et al., "Vy9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).

Zufferey et al., "Self-Inactivating Lentivirus Vector for Safe and Efficient In Vivo Gene Delivery," Journal of Virology, vol. 72(12), pp. 9873-9880, (1998).

Ostertag et al., "Brain Tumor Eradication and Prolonged Survival from Intratumoral Conversion of 5-Fluorocytosine to 5-fluorouracil Using a Nonlytic Retroviral Replicating Vector," Neoro-Oncology 14(2), pp. 145-159, Feb. 2012.

Twitty et al., "Retroviral Replicating Vectors Deliver Cytosine Deaminase Leading to Targeted 5-Fluorouracil-Mediated Cytotoxicity in Multiple Human Cancer Types, Human Gene Therapy Methods", 27(1), pp. 17-31, Feb. 1, 2016.

Charron et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11, pp. S163-S164, (2005).

Fusetti, et al., "Structure of Tetrameric Human Phenylalanine Hydroxylase and Its Implications for Phenylketonuria," J. Bio. Chem., vol. 273, No. 27, pp. 16962-16967 (1998).

Hafid et al., "Phenylketonuria: A Review of Current and Future Treatments," Translational Pediatrics, vol. 4(4), pp. 304-317, (2015).

Blau et al., "Phenylketonuria," The Lancet, vol. 376(9750), pp. 1417-1427, (2010).

Chandler et al., "Vector Design Influences Hepatic Genotoxicity After Adeno-Associated Virus Gene Therapy," Journal of Clinical Investigation, vol. 125(2), pp. 870-880, (2015).

Christophersen et al., "A Technique of Transumbilical Portal Vein Catheterization in Adults," The Archives of Surgery, vol. 95(6), pp. 960-963, (1967). (Abstract Only).

Bartholome, "Genetics and Biochemistry of the Phenylketonuria-Present State," Human Genetics, vol. 51(3), pp. 241-245, (1979).

Donsante et al., "AAV Vector Integration Sites in Mouse Hepatocellular Carcinoma," Science, vol. 317(5837, p. 477, (2007).

Eisensmith et al., "Multiple Origins for Phenylketonuria in Europe," American Journal of Human Genetics, vol. 51(6), pp. 1355-1365, (1992).

Fisher et al., "The Inhibition of Phenylalanine and Tyrosine Hydroxylases by High Oxygen Levels," Journal of Neurochemistry, vol. 19(5), pp. 1359-1365, (1972). (Abstract Only).

(56) References Cited

OTHER PUBLICATIONS

Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).

Guldberg et al., "Aberrant Phenylalanine Metabolism in Phenylketonuria Heterozygotes," Journal of Inherited Metabolic Disease, vol. 21(4), pp. 365-372, (1998).

Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).

Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).

Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial," The Lancet, vol. 384(9937), pp. 37-44, (2014).

Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).

Nault et al., "Adeno-Associated Virus Type 2 as an Oncogenic Virus in Human Hepatocellular Carcinoma," Molecular & Cellular Oncology, vol. 3(2), p. e1095271, (2016).

Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-S132, (2005).

Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).

Oh et al. "Lentiviral Vector Design Using Alternative RNA Export Elements," Retrovirology, vol. 4:38, pp. 1-10, (2007).

Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).

Shedlovsky et al., "Mouse Models of Human Phenylketonuria," Genetics, vol. 134(4), pp. 1205-1210, (1993).

Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).

Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, vol. 11(8), p. e0160892, (2016).

Mason et al., "Inactivated Simian Immunodeficiency Virus-Pulsed Autologous Fresh Blood Cells as an Immunotherapy Strategy," Journal of Virology, vol. 83(3), pp. 1501-1510, (2009).

Blick et al., "Cyclophosphamide Enhances SB-728-T Engraftment to Levels Associated with HIV-RNA Control," CROI Conference on Retroviruses and Opportunistic Infections, Boston, Massachusetts, p. 141, (2014), (Abstract Only).

De Rose et al., "Safety, Immunogenicity and Efficacy of Peptide-Pulsed Cellular Immunotherapy in Macaques," Journal of Medical Primatology, vol. 27(2), pp. 69-78, (2008).

Smith et al., "Developments in HIV-1 Immunotherapy and therapeutic Vaccination," F1000Prime Reports, vol. 6, p. 42, (2014).

Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).

Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).

Nowacki et al., "The PAH Mutation Analysis Consortium Database: Update 1996," Nucleic Acid Research, vol. 25(1), pp. 139-142, (Jan. 1, 1997).

Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).

Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).

Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).

Miettinen et al., "Mevalonate Pathway Regulates Cell Size Homeostasis and Proteostasis Through Autophagy," Cell Reports, vol. 13(11), pp. 2610-2620, (Dec. 2015).

Tolmachov, "Designing Lentiviral Gene Vectors," Viral Gene Therapy, Chapter 13, pp. 263-284, (2011).

Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).

Gorziglia et al., "Elimination of Both El and E2A from Adenovirus Vectors Further Improves Prospects for In Vivo Human gene Therapy," Journal of Virology, vol. 70(6), pp. 4173-4178, (1996).

Vargas et al., "Novel Integrase-Defective Lentiviral Episomal Vectors for Gene Transfer," Human Gene Therapy, vol. 15(4), pp. 361-372, (Apr. 2004).

Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).

Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).

Lam et al., "T-Cell Therapies for HIV," Immunotherapy, Future Medicine, vol. 5(4), pp. 407-414, (Apr. 2013).

Munoz et al., "Ex Vivo Expansion and Lentiviral Transduction of Macaca Nemestrina CD4+ T Cells," Journal of Medical Primatology, vol. 38(6), pp. 438-443, (Dec. 2009).

Porichis et al., "HIV-Specific CD4 T Cells and Immune Control of Viral Replication," Current Opinion in HIV and Aids, vol. 6(3), pp. 174-180, (May 2011).

Kavanagh et al., "Expansion of HIV-Specific CD4+ and CD8+ T Cells by Dendritic Cells Transfected with mRNA Encoding Cytoplasm- or Lysosome-Targeted Nef," Blood, American Society of Hematology, vol. 107(5), pp. 1963-1969, (Mar. 2006).

Akinsheye et al., "Fetal Hemoglobin in Sickle Cell Anemia," Blood, vol. 118(1), pp. 19-27, (2011).

Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).

GenBank Sequence M65141.1 Retrieved from the Internet <URL: https://www.ncbi.ntm.nih.gov/nuccore/M65141.1. Especially Sequence, nt 301-420, (Retrieved Mar. 31, 2019).

Hee Yeon Kim., "Farnesyl diphosphate synthase is important for the maintenance of glioblastoma stemness," Experimental & Molecular Medicine, (2018).

Hong Wang., "Indirect Stimulation of Human V2V2 Cells Through Aleterations in Isoprenoid Metabolism," The Journal of Immunology, (2011).

(56) References Cited

OTHER PUBLICATIONS

Z. Li, "Inhibition of farnesyl pyrophosphate synthase prevents angiotensin II-induced cardiac fibrosis in vitro," Clinical & Experimental Immunology, (2014).

Xiaofeng Jiang, "A novel EST-derived RNAi screen reveals a critical role for farnesyl diphophate in B2-adrenerigic receptor internalization and down-regulation," The FASEB Journal, vol. 26, pp. 1-13(1995).

Jian Yang, "Lentiviral-Mediated Silencing of Farnelsyl Pyrophosphate Synthase through RNA Interference in Mice," Biomed Research International, vol. 2015, Article ID 914026, 6 pages, (2015).

Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).

Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).

Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).

Hassan et al., "Isolation of umbilical cord mesenchymal stem cells using human blood derivative accompanied with explant method," Stem Cell Investigation, pp. 1-8, (2019).

Huang et al., "An Efficient protocol to generate placental chorionic plate-derived mesenchymal stem cells with superior proliferative and immunomodulatory properties," Stem Cell Research & Therapy, pp. 1-15, (2019).

PCT: International Search Report dated Nov. 7, 2016 in Application No. PCT/US2016/036519.

PCT: Written Opinion dated Nov. 7, 2016 in Application No. PCT/US2016/036519.

PCT: International Search Report dated Oct. 19, 2016 in Application No. PCT/US2016/041456.

PCT: Written Opinion dated Oct. 19, 2016 in Application No. PCT/US2016/041456.

PCT: International Search Report dated Jul. 20, 2017 in Application No. PCT/US2017/043157.

PCT: Written Opinion dated Jul. 20, 2017 in application No. PCT/US2017/043157.

PCT: International Search Report dated Jun. 9, 2017 in Application No. PCT/US2016/066185.

PCT: Written Opinion dated Jun. 9, 2017 in Application No. PCT/US2016/066185.

PCT: International Search Report dated Jul. 17, 2017 in Application No. PCT/US2017/013019.

PCT: Written Opinion dated Jul. 17, 2017 in Application No. PCT/US2017/013019.

PCT: International Search Report dated May 26, 2017 in Application No. PCT/US2017/013399.

PCT: Written Opinion dated May 26, 2017 in Application No. PCT/US2017/013399.

PCT: International Search report dated Aug. 25, 2017 in Application No. PCT/US2017/021639.

PCT: Written Opinion dated Aug. 25, 2017 Application No. PCT/US2017/021639.

PCT: International Search Report dated Nov. 8, 2017 Application No. PCT/US2017/041168.

PCT: Written Opinion dated Nov. 8, 2017 in Application No. PCT/US2017/041168.

PCT: International Search Report dated Dec. 15, 2017 in Application No. PCT/US2017/36433.

PCT: Written Opinion dated Dec. 15, 2017 in Application No. PCT/US2017/36433.

PCT: International Search Report date Jul. 14, 2017 in Application No. PCT/US2017/013024.

PCT: Written Opinion dated Jul. 14, 2017 in application No. PCT/US2017/013024.

PCT: International Search Report dated May 29, 2018 in Application No. PCT/US2018/012998.

PCT: Written Opinion dated May 29, 2018 in Application No. PCT/US2018/012998.

PCT; International Search Report dated Sep. 24, 2018 in Application No. PCT/US2018/025733.

PCT; Written Opinion dated Sep. 24, 2018 in Application No. PCT/US2018/025733.

PCT; International Preliminary Report on Patentability dated Oct. 8, 2019 in the Application No. PCT/ US2018/025733.

PCT; International Search Report dated Nov. 9, 2018 in Application No. PCT/US2018/037924.

PCT; Written Opinion dated Nov. 9, 2018 in Application No. PCT/US2018/037924.

PCT; Invitation to Pay Additional Fees in Application No. PCT/ US2018/053919 dated Feb. 22, 2019.

PCT; Written Opinion dated Apr. 12, 2019 in Application No. PCT/US2018/053919.

PCT; International Search Report dated Apr. 12, 2019 in Application No. PCT/ US2018/053919.

PCT; International Search Report dated Jul. 22, 2019 in the Application No. PCT/US2019/24410.

PCT; Written Opinion of the International Search Report dated Jul. 22, 2019 in the Application No. PCT/US2019/24410.

PCT; International Preliminary Report on Patentability dated Jul. 9, 2019 in the Application No. PCT/US2018/012998.

PCT; International Search Report and Written Opinion of the International Search Report dated Jul. 22, 2019 in the Application No. PCT/US2019/024410.

USPTO; Notice of Allowance dated Oct. 13, 2017 in U.S. Appl. No. 14/706,481.

USPTO; Requirement for Restriction dated Oct. 23, 2017 in U.S. Appl. No. 15/668,223.

USPTO; Notice of Allowance dated Nov. 2, 2017 in U.S. Appl. No. 15/652,080.

USPTO; Non-Final Office Action dated Feb. 22, 2018 in U.S. Appl. No. 15/850,937.

USPTO; Non-Final Office Action dated Feb. 22, 2018 in U.S. Appl. No. 15/849,062.

USPTO; Non-Final Office Action dated Feb. 22, 2018 in U.S. Appl. No. 13/333,882.

USPTO; Notice of Allowance dated Mar. 26, 2018 in U.S. Appl. No. 15/668,223.

USPTO; Notice of Allowance dated Apr. 23, 2018 in U.S. Appl. No. 15/850,937.

USPTO; Notice Allowance dated Apr. 26, 2018 in U.S. Appl. No. 15/849,062.

USPTO; Non-Final Office Action dated Jun. 15, 2018 in U.S. Appl. No. 15/904,131.

USPTO; Requirement for Restriction dated Jul. 12, 2018 in U.S. Appl. No. 15/736,284.

USPTO; Invitation to Pay Additional Fees And, Where Applicable, Protest Fee dated Jul. 17, 2018 in Application No. PCT/US2018/ 25733.

USPTO; Requirement for Restriction dated Aug. 3, 2018 in U.S. Appl. No. 16/011,550.

USPTO; Notice of Allowance dated Aug. 10, 2018 in U.S. Appl. No. 15/904,131.

USPTO; Final Office Action dated Aug. 27, 2018 in U.S. Appl. No. 13/333,882.

USPTO; Non-Final Office Action dated Sep. 17, 2018 in U.S. Appl. No. 16/011,550.

USPTO; Invitation to Pay Additional Fees And, Where Applicable, Protest Fee dated Sep. 11, 2018 in Application No. PCT/US2018/ 37924.

USPTO; Non-Final Office Action dated Oct. 19, 2018 in U.S. Appl. No. 15/736,284.

USPTO; Notice of Allowance dated Oct. 31, 2018 in U.S. Appl. No. 16/011,550.

USPTO; Advisory Action dated Nov. 16, 2018 in U.S. Appl. No. 13/333,882.

USPTO; Non-Final Office Action dated Dec. 31, 2018 in U.S. Appl. No. 16/182,443.

(56)        References Cited

OTHER PUBLICATIONS

USPTO; Non-Final Office Action dated Apr. 18, 2019 in U.S. Appl. No. 13/333,882.
USPTO; Final Office Action dated May 2, 2019 in U.S. Appl. No. 15/736,284.
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 16, 2019 in U.S. Appl. No. 16/132,247.
USPTO; Non-Final Office Action dated May 24, 2019 in U.S. Appl. No. 16/218,010.
USPTO; Notice of Allowance dated Jun. 18, 2019 in the U.S. Appl. No. 16/182,443.
USPTO; Notice of Allowance dated Jul. 3, 2019 in U.S. Appl. No. 16/182,443.
USPTO; Advisory Action dated Jul. 23, 2019 in the U.S. Appl. No. 15/736,284.
USPTO; Notice of Allowance dated Aug. 14, 2019 in the U.S. Appl. No. 16/008,991.
USPTO; Notice of Allowance dated Sep. 25, 2019 in the U.S. Appl. No. 16/218,010.
USPTO; Final Office Action dated Jul. 1, 2019 in the U.S. Appl. No. 16/132,247.
USPTO; Notice of Allowance dated Jul. 19, 2019 in the U.S. Appl. No. 16/132,247.
USPTO; Restriction Requirement dated Oct. 22, 2019 in the U.S. Appl. No. 15/580,661.
USPTO; Restriction Requirement dated Nov. 4, 2019 in the U.S. Appl. No. 16/076,655.
USPTO; Notice of Allowance mailed Oct. 29, 2019 in the U.S. Appl. No. 13/333,882.
USPTO; Restriction Requirement dated Nov. 7, 2019 in the U.S. Appl. No. 16/083,384.
USPTO; Notice of Allowance dated Nov. 27, 2019 in the U.S. Appl. No. 13/333,882.
USPTO; Non-Final Office Action dated Jan. 13, 2020 in the U.S. Appl. No. 15/580,661.
EPO; Extended Search Report dated Dec. 12, 2018 in EP Application No. 16808223.8.
EPO; Extended Search Report dated Dec. 11, 2018 in EP Application No. 16822021.8.
EPO; Extended Search Report dated Jun. 6, 2019 in EP Application No. 17739028.3.
EPO; European Search Report dated Aug. 12, 2019 in the EP Application No. 17764128.9.
EPO; Supplementary European Search Report dated Sep. 6, 2019 in the Application No. 17750547.6.
CN Office Action in Chinese Application No. 201780017712.6, dated Feb. 3, 2021, 10 pages (with English translation).
CN Office Action in Chinese Application No. 201780017712.6, dated May 14, 2021, 8 pages (with English translation).
JP Notice of Allowance in Japanese Application No. 2018-547354, dated Dec. 17, 2021, 6 pages (with English translation).
US Notice of Allowance in United States U.S. Appl. No. 17/198,017, dated Nov. 3, 2021, 6 pages.
US Notice of Allowance in United States U.S. Appl. No. 17/289,653, dated Jan. 5, 2022, 9 pages.
Lee et al., "Lentiviral delivery of short hairpin RNAs protects CD4 cells from multiple clades and primary isolates of HIV." Blood, 2005, vol. 106(3):818-826. (Year: 2005).
Choi et al., "Multiplexing Seven miRNA-Based shRNAs to Suppress HIV Replication." Molecular Therapy, 2015, vol. 23(2):310-320. Supplementary materials.
Spartevello et al., Development of Lentiviral Vectors Simultaneously Expressing Multiple siRNAs Against CCR5, vif and tat/rev Genes for an HIV-1 Gene Therapy Approach, Molecular Therapy Nucleic Acids, 2016, vol. 5:1-12.

USPTO; Restriction Requirement dated Jun. 15, 2020 in the U.S. Appl. No. 16/308,373.
USPTO; Restriction Requirement dated Jun. 26, 2020 in the U.S. Appl. No. 16/318,345.
USPTO; Office Action dated Jul. 6, 2020 in the U.S. Appl. No. 16/312,056.
JP; Japanese Office Action in the Application No. 2019-500475 dated Jun. 12, 2020.
Cronin et al., "Altering the Tropism of Lentiviral Vectors through Pseudotyping", Curr Gene Ther, Aug. 2005, vol. 5(4), pp. 687-398.
Cannon et al., "Pseudotype-Dependent Lentiviral Transduction of Astrocytes or Neurons in the Rat Substantia Nigra", Experimental Neurology, vol. 228, (Year: 2011), pp. 41-52, doi:10.1016/J.expneurol. 2010.10.016.
USPTO; Non-Final Office Action dated Nov. 18, 2020 in the U.S. Appl. No. 16/318,34.
USPTO; Restriction Requirement dated Nov. 19, 2020 in the U.S. Appl. No. 16/593,882.
USPTO; Non-Final Office Action dated Nov. 25, 2020 in the U.S. Appl. No. 16/943,800.
USPTO; Notice of Allowance dated Dec. 2, 2020 in the U.S. Appl. No. 16/076,655.
USPTO; Restriction Requirement dated Dec. 8, 2020 in the U.S. Appl. No. 16/563,738.
CN Office Action in Chinese Application No. 201780017712.6, dated Nov. 3, 2021, 18 pages (with English translation).
Cheng et al., "Establishment, Characterization, and Successful Adaptive Therapy Against Human Tumors of NKG Cell, a New Human NK Cell Line", Cell Transplantation, Jun. 2011, 20:1731-1746.
Herrera et al., "Adult peripheral blood and umbilical cord blood NK cells are good sources for effective CAR therapy against CD19 positive leukemic cells", Scientific Reports, Dec. 2019, 9(18729), 2 pages.
Mensali et al., "NK cells specifically TCR-dressed to kill cancer cells", EBioMedicine, Jan. 2019, 40:106-117.
PCT International Search Report and Written Opinion in International Application No. PCT/US2022/013422, dated May 13, 2022, 20 pages.
Shalova et al., "CD16 Regulates TRIF-Dependent TLR4 Response in Human Monocytes and Their Subsets", The Journal of Immunology, 2012, 188:3584-3593.
Altschul et al., "Basic local alignment search tool", J. Mol. Biol., May 1990, 215:403-410.
Altschul et al., "Gapped BLAST and PSI-BLAST: a new generation of protein database search programs", Nucleic Acids Res., Jul. 1997, 25(17):3389-3402.
Berge et al. "Pharmaceutical salts", J Pharm Sci, Jan. 1977, 66(1):1-19.
Coligan et al., "Current Protocols in Protein Science", Short Protocols in Protein Science, 1996, 24:409, 1 page.
Deveraux et al., "A comprehensive set of sequence analysis programs for the VAX", Nucleic Acids Research, 1984, 12(1):387-395.
Gagniuc et al., "Eukaryotic genomes may exhibit up to 10 generic classes of gene promoters", BMC Genomics, 2012, 13:512, 17 pages.
JP Office Action in Japanese Application No. 2021-045605, dated Apr. 1, 2022, 5 pages (with English translation).
Myers et al., "Optimal alignments in linear space", CABIOS, 1989, 4:11-17.
Needleman et al., "A general method applicable to the search for similarities in the amino acid sequence of two proteins", Mol. Biol., 1970, 48:444-453.
Pauza et al., "Evolution and function of the TCR Vgamma9 chain repertoire: It's good to be public", Cell Immunol., Jul. 2015, 296(1):22-30.
Pauza et al., "γδ T cells in HIV disease: past, present, and future", Frontiers in Immunol., Jan. 2015, 5:687, 12 pages.
Pearson et al., "Improved tools for biological sequence comparison", Proc. Nat'l. Acad. Sci., Apr. 1988, 85:2444-2448.
Sambrook et al., Molecular Cloning: A Laboratory Manual, 3rd ed., Cold Spring Harbor Laboratory Press, 2000, 2272 pages.

(56)         References Cited

OTHER PUBLICATIONS

Smith et al., "Comparison of Biosequences", Adv. Appl. Math., 1981, 2:482-489.
EP Office Action in European Application No. 17739028.3, dated Mar. 18, 2022, 5 pages.
AU; Examination Report issued in Application No. 2021203836 on Jan. 30, 2024.
EP; Search Report issued in Application No. 23199847.7 on Mar. 5, 2024.
Fujiwara et al., "A Nucleolar Stress-Specific p53-miR-101 Molecular Circuit Functions as an Intrinsic Tumor-Suppressor Network," EBioMedicine 33, pp. 33-48, 2018.
Tian et al., "MicroRNA-30a Promotes Chondrogenic Differentiation of Mesenchymal Stem Cells Through Inhibiting Delta-Like 4 Expression," Life Sciences, 148, pp. 220-228, 2016.
Wang et al., "Kinesin Family Member 11 is a Potential Therapeutic Target and is Suppressed by MicroRNA-30a in Breast Cancer," Molecular Carcinogenesis, 59, pp. 908-922, 2020.
Ueda et al., "CD47-dependent molecular mechanisms of blood outgrowth endothelial call attachment on cholesterol-modified polyurethane," Biomaterials, vol. 31, No. 25, pp. 6394-6399, Sep. 1, 2010.
Sandstrom et al., The Intracellular B30.2 Domain of Butrophilin 3Al Binds Phosphoantigens to Mediate Activation of Human Vγ9Vδ2 T Cells, Immunity, vol. 40, No. 4, pp. 490-500, 2014.
Wilkin et al. "Isolation and Sequence of the Human Farnesyl Pyrophosphate Synthetase eDNA," The Journal of Biological Chemestry, vol. 265, No. 8, pp. 4607-4614, Mar. 15, 1990.
JP Office Action issued Jul. 11, 2022 in App. No. 2018-536892.
JP Office Action issued Jul. 12, 2022 in App. No. 2021-523916.
EPO; Extended Search Report dated Jul. 4, 2022 in EP Application No. 22154806.8.
EPO; Extended Search Report dated Jul. 21, 2022 in EP Application No. 19883230.5.
CN Notice of Allowance in Chinese Application No. 201780017712.6, dated Aug. 25, 2022, 4 pages (with English translation).
US Notice of Allowance in U.S. Appl. No. 16/563,738, dated Aug. 31, 2022, 5 pages.
US Notice of Allowance in U.S. Appl. No. 16/988,427, dated Aug. 26, 2022, 9 pages.
Office Action for European Patent Application No. 17739028.3, mailed May 22, 2023, 125 pages.
JP Office Action in Japanese Application No. 2022-006999, dated Jan. 5, 2023, 20 pages (with English translation).
JP; Office Action issued in Application No. 2022-006999 on Sep. 20, 2023.
Brake et al., "Lentiviral Vector Design for Multiple shRNA Expression and Durable HIV-1 Inhibition," Molecular Therapy, 16(3), 557-564, 2008.

KR; Office Action issued Oct. 20, 2023 in Application No. 10-2020-7000631.
UAE; Office Action issued Oct. 20, 2023 in Application No. P6001801/2019.
JP; Office Action issued Oct. 19, 2023 in Application No. 2021-523916.
CA Office Action in Canadian Application No. 3,011,529, dated Feb. 21, 2023, 7 pages.
JP Office Action in Japanese Application No. 2018-536892, dated Jan. 30, 2023, 4 pages (with English translation).
IL Office Action issued in Application No. 271274 on Aug. 6, 2023, 11 pages.
JP Office Action in Japanese Application No. 2021-523916, dated Apr. 18, 2023.
JP Office Action in Japanese Application No. 2021-045605, dated Apr. 19, 2023.
CN Office Action in Chinese Application No. 201880039828.4, dated Mar. 1, 2023, 19 pages (with English translation).
JP Notice of Allowance in Japanese Application No. 2018-536892, dated Mar. 29, 2023, 4 pages (with English translation).
JP Office Action in Japanese Application No. 2019-569226, dated Mar. 20, 2023, 5 pages (with English translation).
US; Restriction Requirement issued in U.S. Appl. No. 17/570,313 on Nov. 15, 2023.
CN; Office Action issued in Application No. 201880039828.4 on Nov. 30, 2023.
IL; Notice of Allowance issued in Application No. 297238 on Dec. 11, 2023.
JP Office Action in Japanese Application No. 2021-045605, dated Nov. 2, 2022, 8 pages (with English translation).
Decision of Refusal for Japanese Application No. 2023-118187 mailed Nov. 20, 2024, with English translation, 2 pages.
Decision on Rejection for Chinese Application No. 201880039828.4, dated May 14, 2024, with English translation, 14 pages.
Harding C.O., et al. "Complete Correction of Hyperphenylalaninemia Following Liver-directed, Recombinant AAV2/8 Vector-mediated Gene Therapy In Murine Phenylketonuria," Gene Therapy, Mar. 2006; 13(5):457-462.
International Preliminary Report on Patentability for International Application No. PCT/US2018/037924 mailed Dec. 26, 2019, 13 pages.
Notice of Final Rejection for Korean Application No. 10-2020-7000631 mailed Jul. 12, 2024, with English translation, 7 pages.
Notice of Reasons for Refusal for Japanese Application No. 2019-569226 mailed Jun. 2, 2022, with English translation, 13 pages.
Notice of Reasons for Refusal for Japanese Application No. 2019-569226 mailed May 23, 2025, with English translation, 13 pages.
Notice of Reasons for Refusal for Japanese Application No. 2023-118187 mailed May 31, 2024, with English translation, 4 pages.

* cited by examiner

γδ T treated Lv-FDPSsh (N=6)

Untreated Lv-FDPSsh (N=2)

SEQUENCE LISTING

<160> NUMBER OF SEQ ID NOS: 83

<210> SEQ ID NO 1
<211> LENGTH: 53
<212> TYPE: DNA
<213> ORGANISM: Artificial Sequence
<220> FEATURE:

-continued

<223> OTHER INFORMATION: FDPS shRNA sequence #1

<400> SEQUENCE: 1
gtcctggagt acaatgccat tctcgagaat ggcattgtac tccaggactt ttt                53

<210> SEQ ID NO 2
<211> LENGTH: 53
<212> TYPE: DNA
<213> ORGANISM: Artificial Sequence
<220> FEATURE:
<223> OTHER INFORMATION: FDPS shRNA sequence #2

<400> SEQUENCE: 2
gcaggatttc gttcagcact tctcgagaag tgctgaacga aatcctgctt ttt                53

<210> SEQ ID NO 3
<211> LENGTH: 53
<212> TYPE: DNA
<213> ORGANISM: Artificial Sequence
<220> FEATURE:
<223> OTHER INFORMATION: FDPS shRNA sequence #3

<400> SEQUENCE: 3
gccatgtaca tggcaggaat tctcgagaat tcctgccatg tacatggctt ttt                53

<210> SEQ ID NO 4
<211> LENGTH: 53
<212> TYPE: DNA
<213> ORGANISM: Artificial Sequence
<220> FEATURE:
<223> OTHER INFORMATION: FDPS shRNA sequence #4

<400> SEQUENCE: 4
gcagaaggag gctgagaaag tctcgagact ttctcagcct ccttctgctt ttt                53

<210> SEQ ID NO 5
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 5
gtagtcttat gcaatactct tgtagtcttg caacatggta acgatgagtt agcaacatgc        60
cttacaagga gagaaaaagc accgtgcatg ccgattggtg gaagtaaggt ggtacgatcg       120
tgccttatta ggaaggcaac agacgggtct gacatggatt ggacgaacca ctgaattgcc       180
gcattgcaga gatattgtat ttaagtgcct agctcgatac aataaacg                   228

<210> SEQ ID NO 6
<211> LENGTH: 180
<212> TYPE: DNA
<213> ORGANISM: Artificial Sequence
<220> FEATURE:
<223> OTHER INFORMATION: 5 Long terminal repeat (LTR)

<400> SEQUENCE: 6
ggtctctctg gttagaccag atctgagcct gggagctctc tggctaacta gggaacccac        60
tgcttaagcc tcaataaagc ttgccttgag tgcttcaagt agtgtgtgcc cgtctgttgt       120
gtgactctgg taactagaga tccctcagac ccttttagtc agtgtggaaa atctctagca       180

<210> SEQ ID NO 7
<211> LENGTH: 41

<212> TYPE: DNA
<213> ORGANISM: Artificial Sequence
<220> FEATURE:
<223> OTHER INFORMATION: Psi Packaging signal

<400> SEQUENCE: 7
tacgccaaaa attttgacta gcggaggcta gaaggagaga g                          41

<210> SEQ ID NO 8
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 8
aggagctttg ttccttgggt tcttgggagc agcaggaagc actatgggcg cagcctcaat      60
gacgctgacg gtacaggcca gacaattatt gtctggtata gtgcagcagc agaacaattt     120
gctgagggct attgaggcgc aacagcatct gttgcaactc acagtctggg gcatcaagca     180
gctccaggca agaatcctgg ctgtggaaag atacctaaag gatcaacagc tcc            233

<210> SEQ ID NO 9
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 9
ttttaaaaga aaaggggggga ttggggggta cagtgcaggg gaaagaatag tagacataat     60
agcaacagac atacaaacta agaattaca aaaacaaatt acaaaattca aaattttta      118

<210> SEQ ID NO 10
<211> LENGTH: 217
<212> TYPE: DNA
<213> ORGANISM: Artificial Sequence
<220> FEATURE:
<223> OTHER INFORMATION: Polymerase III shRNA promoters-H1 promoter

<400> SEQUENCE: 10
gaacgctgac gtcatcaacc cgctccaagg aatcgcgggc ccagtgtcac taggcgggaa      60
cacccagcgc gcgtgcgccc tggcaggaag atggctgtga gggacagggg agtggcgccc     120
tgcaatattt gcatgtcgct atgtgttctg ggaaatcacc ataaacgtga aatgtctttg     180
gatttgggaa tcttataagt tctgtatgag accactt                             217

<210> SEQ ID NO 11
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 11
aatcaacctc tgattacaaa atttgtgaaa gattgactgg tattcttaac tatgttgctc      60
cttttacgct atgtggatac gctgctttaa tgcctttgta tcatgctatt gcttcccgta     120
tggctttcat tttctcctcc ttgtataaat cctggttgct gtctctttat gaggagttgt     180
ggcccgttgt caggcaacgt ggcgtggtgt gcactgtgtt tgctgacgca accccccactg     240 gttgggggcat tgccaccacc tgtcagctcc tttccgggac tttcgctttc ccctccccta     300

-continued

```
ttgccacggc ggaactcatc gccgcctgcc ttgcccgctg ctggacaggg gctcggctgt      360
tgggcactga caattccgtg gtgttgtcgg ggaaatcatc gtcctttcct tggctgctcg      420
cctgtgttgc cacctggatt ctgcgcggga cgtccttctg ctacgtccct tcggccctca      480
atccagcgga ccttccttcc cgcggcctgc tgccggctct gcggcctctt ccgcgtcttc      540
gccttcgccc tcagacgagt cggatctccc tttgggccgc ctccccgcct               590
```

```
<210> SEQ ID NO 12
<211> LENGTH: 250
<212> TYPE: DNA
<213> ORGANISM: Artificial Sequence
<220> FEATURE:
<223> OTHER INFORMATION: 3 delta LTR

<400> SEQUENCE: 12
tggaagggct aattcactcc caacgaagat aagatctgct ttttgcttgt actgggtctc       60
tctggttaga ccagatctga gcctgggagc tctctggcta actagggaac ccactgctta      120
agcctcaata aagcttgcct tgagtgcttc aagtagtgtg tgcccgtctg ttgtgtgact      180
ctggtaacta gagatccctc agaccctttt agtcagtgtg gaaaatctct agcagtagta      240
gttcatgtca                                                           250
```

```
<210> SEQ ID NO 13
<211> LENGTH: 290
<212> TYPE: DNA
<213> ORGANISM: Artificial Sequence
<220> FEATURE:
<223> OTHER INFORMATION: Helper/Rev-Chicken beta actin (CAG) promoter-
      Transcription

<400> SEQUENCE: 13
gctattacca tgggtcgagg tgagccccac gttctgcttc actctcccca tctcccccc       60 ctccccaccc ccaattttgt atttatttat tttttaatta ttttgtgcag cgatgggggc      120 ggggggggg ggggcgcgcg ccaggcgggg cggggcgggg cgaggggcgg ggcggggcga      180
ggcggagagg tgcggcggca gccaatcaga gcggcgcgct ccgaaagttt cctttttatgg      240 cgaggcggcg gcggcggcgg ccctataaaa agcgaagcgc gcggcgggcg               290
```

```
<210> SEQ ID NO 14
<211> LENGTH: 1503
<212> TYPE: DNA
<213> ORGANISM: Artificial Sequence
<220> FEATURE:
<223> OTHER INFORMATION: Helper/Rev-HIV Gag-Viral capsid

<400> SEQUENCE: 14
atgggtgcga gagcgtcagt attaagcggg ggagaattag atcgatggga aaaaattcgg       60
ttaaggccag ggggaaagaa aaaatataaa ttaaaacata tagtatgggc aagcagggag      120
ctagaacgat tcgcagttaa tcctggcctg ttagaaacat cagaaggctg tagacaaata      180
ctgggacagc tacaaccatc ccttcagaca ggatcagaag aacttagatc attatataat      240
acagtagcaa ccctctattg tgtgcatcaa aggatagaga taaaagacac caaggaagct      300
ttagacaaga tagaggaaga gcaaaacaaa agtaagaaaa aagcacagca agcagcagct      360
gacacaggac acagcaatca ggtcagccaa aattacccta tagtgcagaa catccagggg      420
caaatggtac atcaggccat atcacctaga actttaaatg catgggtaaa agtagtagaa      480
gagaaggctt tcagcccaga agtgataccc atgttttcag cattatcaga aggagccacc      540
```

```
ccacaagatt taaacaccat gctaaacaca gtggggggac atcaagcagc catgcaaatg      600
ttaaaagaga ccatcaatga ggaagctgca gaatgggata gagtgcatcc agtgcatgca      660
gggcctattg caccaggcca gatgagagaa ccaaggggaa gtgacatagc aggaactact      720
agtacccttc aggaacaaat aggatggatg acacataatc cacctatccc agtaggagaa      780
atctataaaa gatggataat cctgggatta aataaaatag taagaatgta tagccctacc      840
agcattctgg acataagaca aggaccaaag gaacccttta gagactatgt agaccgattc      900
tataaaactc taagagccga gcaagcttca caagaggtaa aaaattggat gacagaaacc      960
ttgttggtcc aaaatgcgaa cccagattgt aagactattt taaaagcatt gggaccagga     1020
gcgacactag aagaaatgat gacagcatgt cagggagtgg ggggacccgg ccataaagca     1080
agagttttgg ctgaagcaat gagccaagta acaaatccag ctaccataat gatacagaaa     1140
ggcaattttt ggaaccaaag aaagactgtt aagtgtttca attgtggcaa agaagggcac     1200
atagccaaaa attgcagggc ccctaggaaa aagggctgtt ggaaatgtgg aaaggaagga     1260
caccaaatga aagattgtac tgagagacag gctaattttt tagggaagat ctggccttcc     1320
cacaagggaa ggccagggaa ttttcttcag agcagaccag agccaacagc cccaccagaa     1380
gagagcttca ggtttgggga agagacaaca actccctctc agaagcagga gccgatagac     1440
aaggaactgt atcctttagc ttccctcaga tcactctttg gcagcgaccc ctcgtcacaa     1500
taa                                                                    1503

<210> SEQ ID NO 15
<211> LENGTH: 1872
<212> TYPE: DNA
<213> ORGANISM: Artificial Sequence
<220> FEATURE:
<223> OTHER INFORMATION: Helper/Rev-HIV Pol-Protease and reverse
      transcriptase

<400> SEQUENCE: 15
atgaatttgc caggaagatg gaaaccaaaa atgatagggg gaattggagg ttttatcaaa       60
gtaggacagt atgatcagat actcatagaa atctgcggac ataaagctat aggtacagta      120
ttagtaggac ctacacctgt caacataatt ggaagaaatc tgttgactca gattggctgc      180
actttaaatt ttcccattag tcctattgag actgtaccag taaaattaaa gccaggaatg      240
gatggcccaa aagttaaaca atggccattg acagaagaaa aaataaaagc attagtagaa      300
atttgtacag aaatggaaaa ggaaggaaaa atttcaaaaa ttgggcctga aaatccatac      360
aatactccag tatttgccat aaagaaaaaa gacagtacta atggagaaaa attagtagat      420
ttcagagaac ttaataagag aactcaagat ttctgggaag ttcaattagg aataccacat      480
cctgcagggt taaaacagaa aaaatcagta acagtactgg atgtgggcga tgcatatttt      540
tcagttccct tagataaaga cttcaggaag tatactgcat ttaccatacc tagtataaac      600
aatgagacac cagggattag atatcagtac aatgtgcttc cacagggatg gaaaggatca      660
ccagcaatat tccagtgtag catgacaaaa atcttagagc ctttagaaaa acaaaatcca      720
gacatagtca tctatcaata catggatgat ttgtatgtag gatctgactt agaaataggg      780
cagcatagaa caaaaataga ggaactgaga caacatctgt tgaggtgggg atttaccaca      840
ccagacaaaa aacatcagaa agaacctcca ttcctttgga tgggttatga actccatcct      900
gataaatgga cagtacagcc tatagtgctg ccagaaaagg acagctggac tgtcaatgac      960
atacagaaat tagtgggaaa attgaattgg gcaagtcaga tttatgcagg gattaaagta     1020
```

```
aggcaattat gtaaacttct taggggaacc aaagcactaa cagaagtagt accactaaca    1080
gaagaagcag agctagaact ggcagaaaac agggagattc taaaagaacc ggtacatgga    1140
gtgtattatg acccatcaaa agacttaata gcagaaatac agaagcaggg gcaaggccaa    1200
tggacatatc aaatttatca agagccattt aaaaatctga aaacaggaaa atatgcaaga    1260
atgaagggtg cccacactaa tgatgtgaaa caattaacag aggcagtaca aaaaatagcc    1320
acagaaagca tagtaatatg gggaaagact cctaaattta aattacccat acaaaaggaa    1380
acatgggaag catggtggac agagtattgg caagccacct ggattcctga gtgggagttt    1440
gtcaataccc ctcccttagt gaagttatgg taccagttag agaaagaacc cataatagga    1500
gcagaaactt tctatgtaga tggggcagcc aatagggaaa ctaaattagg aaaagcagga    1560
tatgtaactg acagaggaag acaaaaagtt gtccccctaa cggacacaac aaatcagaag    1620
actgagttac aagcaattca tctagctttg caggattcgg gattagaagt aaacatagtg    1680
acagactcac aatatgcatt gggaatcatt caagcacaac cagataagag tgaatcagag    1740
ttagtcagtc aaataataga gcagttaata aaaaaggaaa aagtctacct ggcatgggta    1800
ccagcacaca aaggaattgg aggaaatgaa caagtagatg ggttggtcag tgctggaatc    1860
aggaaagtac ta                                                        1872
```

```
<210> SEQ ID NO 16
<211> LENGTH: 867
<212> TYPE: DNA
<213> ORGANISM: Artificial Sequence
<220> FEATURE:
<223> OTHER INFORMATION: Helper Rev-HIV Integrase-Integration of viral
      RNA

<400> SEQUENCE: 16
```

```
tttttagatg gaatagataa ggcccaagaa gaacatgaga aatatcacag taattggaga     60
gcaatggcta gtgattttaa cctaccacct gtagtagcaa aagaaatagt agccagctgt    120
gataaatgtc agctaaaagg ggaagccatg catggacaag tagactgtag cccaggaata    180
tggcagctag attgtacaca tttagaagga aaagttatct tggtagcagt tcatgtagcc    240
agtggatata tagaagcaga agtaattcca gcagagacag ggcaagaaac agcatacttc    300
ctcttaaaat tagcaggaag atggccagta aaaacagtac atacagacaa tggcagcaat    360
ttcaccagta ctacagttaa ggccgcctgt tggtgggcgg ggatcaagca ggaatttggc    420
attccctaca atccccaaag tcaaggagta atagaatcta tgaataaaga attaaagaaa    480
attataggac aggtaagaga tcaggctgaa catcttaaga cagcagtaca atggcagta    540 ttcatccaca attttaaaag aaaagggggg attggggggt acagtgcagg ggaaagaata    600
gtagacataa tagcaacaga catacaaact aaagaattac aaaaacaaat tacaaaaatt    660
caaaattttc gggtttatta cagggacagc agagatccag tttggaaagg accagcaaag    720
ctcctctgga aaggtgaagg ggcagtagta atacaagata atagtgacat aaaagtagtg    780
ccaagaagaa aagcaaagat catcagggat tatggaaaac agatggcagg tgatgattgt    840
gtggcaagta gacaggatga ggattaa                                        867
```

```
<210> SEQ ID NO 17
<211> LENGTH: 1755
<212> TYPE: DNA
<213> ORGANISM: Artificial Sequence
<220> FEATURE:
<223> OTHER INFORMATION: Lenti-BTN3A3(BTN3A3)
```

<400> SEQUENCE: 17
atgaaaatgg caagttccct ggctttcctt ctgctcaact ttcatgtctc cctcttcttg    60
gtccagctgc tcactccttg ctcagctcag tttttctgtgc ttggaccctc tgggcccatc   120
ctggccatgg tgggtgaaga cgctgatctg ccctgtcacc tgttcccgac catgagtgca   180
gagaccatgg agctgaggtg ggtgagttcc agcctaaggc aggtggtgaa cgtgtatgca   240
gatggaaagg aagtggaaga caggcagagt gcaccgtatc gagggagaac ttcgattctg   300
cgggatggca tcactgcagg gaaggctgct ctccgaatac acaacgtcac agcctctgac   360 agtgaaagt acttgtgtta tttccaagat ggtgacttct acgaaaaagc cctggtggag   420
ctgaaggttg cagcattggg ttctgatctt cacattgaag tgaagggtta tgaggatgga   480
gggatccatc tggagtgcag gtccactggc tggtaccccc aaccccaaat aaagtggagc   540
gacgccaagg gagagaacat cccggctgtg gaagcacctg tggttgcaga tggagtgggc   600
ctgtatgcag tagcagcatc tgtgatcatg agaggcagct ctggtggggg tgtatcctgc   660
atcatcagaa attccctcct cggcctggaa aagacagcca gcatatccat cgcagacccc   720
ttcttcagga gcgcccagcc ctggatcgcg ccctggcag ggaccctgcc tatctcgttg   780
ctgcttctcg caggagccag ttacttcttg tggagacaac agaaggaaaa aattgctctg   840
tccagggaga cagaaagaga gcgagagatg aaagaaatgg gatacgctgc aacagagcaa   900
gaaataagcc taagagagaa gctccaggag gaactcaagt ggaggaaaat ccagtacatg   960
gctcgtggag agaagtcttt ggcctatcat gaatggaaaa tggccctctt caaacctgcg  1020
gatgtgattc tggatccaga cacggcaaac gccatcctcc ttgtttctga ggaccagagg  1080
agtgtgcagc gtgctgaaga gccgcgggat ctgccagaca accctgagag atttgaatgg  1140
cgttactgtg tccttggctg tgaaaacttc acatcaggga gacattactg ggaggtggaa  1200
gtgggggaca gaaaagagtg gcatattggg gtatgtagta agaacgtgga gaggaaaaaa  1260
ggttgggtca aaatgacacc ggagaacgga tactggacta tgggcctgac tgatgggaat  1320
aagtatcggg ctctcactga gcccagaacc aacctgaaac ttcctgagcc tcctaggaaa  1380
gtggggatct tcctggacta tgagactgga gagatctcgt tctataatgc cacagatgga  1440
tctcatatct acacctttcc gcacgcctct ttctctgagc ctctatatcc tgttttcaga  1500
attttgacct tggagcccac tgccctgacc atttgcccaa taccaaaaga agtagagagt  1560
tcccccgatc ctgacctagt gcctgatcat tccctggaga caccactgac cccgggctta  1620
gctaatgaaa gtggggagcc tcaggctgaa gtaacatctc tgcttctccc tgcccaccct  1680
ggagctgagg tctcccttc tgcaacaacc aatcagaacc ataagctaca ggcacgcact  1740
gaagcacttt actga                                                   1755

<210> SEQ ID NO 18
<211> LENGTH: 351
<212> TYPE: DNA
<213> ORGANISM: Artificial Sequence
<220> FEATURE:
<223> OTHER INFORMATION: Helper/Rev-HIV Rev-Nuclear export and stabilize
     viral mRNA

<400> SEQUENCE: 18
atggcaggaa gaagcggaga cagcgacgaa gaactcctca aggcagtcag actcatcaag    60
tttctctatc aaagcaaccc acctcccaat cccgagggga cccgacaggc ccgaaggaat   120
agaagaagaa ggtggagaga gagacagaga cagatccatt cgattagtga acggatcctt   180

```
agcacttatc tgggacgatc tgcggagcct gtgcctcttc agctaccacc gcttgagaga    240
cttactcttg attgtaacga ggattgtgga acttctggga cgcagggggt gggaagccct    300
caaatattgg tggaatctcc tacaatattg gagtcaggag ctaaagaata g    351

<210> SEQ ID NO 19
<211> LENGTH: 577
<212> TYPE: DNA
<213> ORGANISM: Artificial Sequence
<220> FEATURE:
<223> OTHER INFORMATION: Envelope-CMV promoter-Transcription

<400> SEQUENCE: 19
acattgatta ttgactagtt attaatagta atcaattacg gggtcattag ttcatagccc    60
atatatggag ttccgcgtta cataacttac ggtaaatggc ccgcctggct gaccgcccaa    120
cgacccccgc ccattgacgt caataatgac gtatgttccc atagtaacgc caatagggac    180
tttccattga cgtcaatggg tggagtattt acggtaaact gcccacttgg cagtacatca    240
agtgtatcat atgccaagta cgcccctat tgacgtcaat gacggtaaat ggcccgcctg    300
gcattatgcc cagtacatga ccttatggga ctttcctact tggcagtaca tctacgtatt    360
agtcatcgct attaccatgg tgatgcggtt ttggcagtac atcaatgggc gtggatagcg    420
gtttgactca cggggatttc caagtctcca ccccattgac gtcaatggga gtttgttttg    480
gcaccaaaat caacgggact ttccaaaatg tcgtaacaac tccgccccat tgacgcaaat    540
gggcggtagg cgtgtacggt gggaggtcta tataagc    577

<210> SEQ ID NO 20
<211> LENGTH: 1519
<212> TYPE: DNA
<213> ORGANISM: Artificial Sequence
<220> FEATURE:
<223> OTHER INFORMATION: Envelope-VSV-G-Glycoprotein envelope-cell entry

<400> SEQUENCE: 20
atgaagtgcc ttttgtactt agcctttttta ttcattgggg tgaattgcaa gttcaccata    60
gtttttccac acaaccaaaa aggaaactgg aaaaatgttc cttctaatta ccattattgc    120
ccgtcaagct cagatttaaa ttggcataat gacttaatag gcacagcctt acaagtcaaa    180
atgcccaaga gtcacaaggc tattcaagca gacggttgga tgtgtcatgc ttccaaatgg    240
gtcactactt gtgatttccg ctggtatgga ccgaagtata taacacattc catccgatcc    300
ttcactccat ctgtagaaca atgcaaggaa agcattgaac aaacgaaaca aggaacttgg    360
ctgaatccag gcttccctcc tcaaagttgt ggatatgcaa ctgtgacgga tgccgaagca    420
gtgattgtcc aggtgactcc tcaccatgtg ctggttgatg aatacacagg agaatgggtt    480
gattcacagt tcatcaacgg aaaatgcagc aattacatat gccccactgt ccataactct    540
acaacctggc attctgacta taaggtcaaa gggctatgtg attctaacct catttccatg    600
gacatcacct tcttctcaga ggacggagag ctatcatccc tgggaaagga gggcacaggg    660
ttcagaagta actactttgc ttatgaaact ggaggcaagg cctgcaaaat gcaatactgc    720
aagcattggg gagtcagact cccatcaggt gtctggttcg agatggctga taaggatctc    780
tttgctgcag ccagattccc tgaatgccca gaagggtcaa gtatctctgc tccatctcag    840
acctcagtgg atgtaagtct aattcaggac gttgagagga tcttggatta ttccctctgc    900
caagaaacct ggagcaaaat cagagcgggt cttccaatct ctccagtgga tctcagctat    960
cttgctccta aaaacccagg aaccggtcct gctttcacca taatcaatgg taccctaaaa    1020
```

```
tactttgaga ccagatacat cagagtcgat attgctgctc caatcctctc aagaatggtc      1080
ggaatgatca gtggaactac cacagaaagg gaactgtggg atgactgggc accatatgaa      1140
gacgtggaaa ttggacccaa tggagttctg aggaccagtt caggatataa gtttccttta      1200
tacatgattg gacatggtat gttggactcc gatcttcatc ttagctcaaa ggctcaggtg      1260
ttcgaacatc ctcacattca agacgctgct tcgcaacttc ctgatgatga gagtttattt      1320
tttggtgata ctgggctatc caaaaatcca atcgagcttg tagaaggttg gttcagtagt      1380
tggaaaagct ctattgcctc tttttttcttt atcataggt taatcattgg actattcttg       1440
gttctccgag ttggtatcca tctttgcatt aaattaaagc acaccaagaa aagacagatt      1500
tatacagaca tagagatga                                                   1519
```

<210> SEQ ID NO 21
<211> LENGTH: 352
<212> TYPE: DNA
<213> ORGANISM: Artificial Sequence
<220> FEATURE:
<223> OTHER INFORMATION: Helper/Rev-CMV early (CAG) enhancer-
      EnhanceTranscription

<400> SEQUENCE: 21

```
tagttattaa tagtaatcaa ttacggggtc attagttcat agcccatata tggagttccg        60
cgttacataa cttacggtaa atggcccgcc tggctgaccg cccaacgacc cccgcccatt       120
gacgtcaata atgacgtatg ttcccatagt aacgccaata gggactttcc attgacgtca       180
atgggtggac tatttacggt aaactgccca cttggcagta catcaagtgt atcatatgcc       240
aagtacgccc cctattgacg tcaatgacgg taaatggccc gcctggcatt atgcccagta       300
catgacctta tgggactttc ctacttggca gtacatctac gtattagtca tc              352
```

<210> SEQ ID NO 22
<211> LENGTH: 960
<212> TYPE: DNA
<213> ORGANISM: Artificial Sequence
<220> FEATURE:
<223> OTHER INFORMATION: Helper/Rev-Chicken beta actin intron-Enhance
      gene expression

<400> SEQUENCE: 22

```
ggagtcgctg cgttgccttc gccccgtgcc ccgctccgcg ccgcctcgcg ccgcccgccc        60
cggctctgac tgaccgcgtt actcccacag gtgagcgggc gggacggccc ttctcctccg       120
ggctgtaatt agcgcttggt ttaatgacgg ctcgtttctt ttctgtggct gcgtgaaagc       180
cttaaagggc tccgggaggg ccctttgtgc ggggggagc ggctcggggg gtgcgtgcgt       240
gtgtgtgtgc gtggggagcg ccgcgtgcgg cccgcgctgc ccggcggctg tgagcgctgc       300
gggcgcggcg cggggctttg tgcgctccgc gtgtgcgcga ggggagcgcg gccgggggcg       360
gtgccccgcg gtgcgggggg gctgcgaggg gaacaaaggc tgcgtgcggg gtgtgtgcgt       420 ggggggtga gcagggggtg tgggcgcggc ggtcgggctg taacccccc ctgcacccc         480 ctccccgagt tgctgagcac ggcccggctt cgggtgcggg gctccgtgcg gggcgtggcg       540
cggggctcgc cgtgccgggc ggggggtggc ggcaggtggg ggtgccgggc ggggcggggc       600
cgcctcgggc cggggagggc tcggggagg ggcgcggcgg ccccggagcg ccggcggctg        660
tcgaggcgcg gcgagccgca gccattgcct tttatggtaa tcgtgcgaga gggcgcaggg      720
acttcctttg tcccaaatct ggcggagccg aaatctggga ggcgccgccg cacccctct        780
```

```
agcgggcgcg ggcgaagcgg tgcggcgccg gcaggaagga aatgggcggg gagggccttc      840
gtgcgtcgcc gcgccgccgt cccctctcc atctccagcc tcggggctgc cgcaggggga      900
cggctgcctt cgggggggac ggggcagggc ggggttcggc ttctggcgtg tgaccggcgg      960
```

```
<210> SEQ ID NO 23
<211> LENGTH: 448
<212> TYPE: DNA
<213> ORGANISM: Artificial Sequence
<220> FEATURE:
<223> OTHER INFORMATION: Helper/Rev-Rabbit beta globin poly A-RNA
      stability

<400> SEQUENCE: 23
agatcttttt ccctctgcca aaaattatgg ggacatcatg aagccccttg agcatctgac       60
ttctggctaa taaaggaaat ttattttcat tgcaatagtg tgttggaatt ttttgtgtct      120
ctcactcgga aggacatatg ggagggcaaa tcatttaaaa catcagaatg agtatttggt      180
ttagagtttg gcaacatatg ccatatgctg gctgccatga acaaaggtgg ctataaagag      240
gtcatcagta tatgaaacag ccccctgctg tccattcctt attccataga aaagccttga      300
cttgaggtta gatttttttt atattttgtt ttgtgttatt tttttcttta acatccctaa      360
aattttcctt acatgtttta ctagccagat ttttcctcct ctcctgacta ctcccagtca      420
tagctgtccc tcttctctta tgaagatc                                       448
```

```
<210> SEQ ID NO 24
<211> LENGTH: 573
<212> TYPE: DNA
<213> ORGANISM: Artificial Sequence
<220> FEATURE:
<223> OTHER INFORMATION: Envelope-Beta globin intron-Enhance gene
      expression

<400> SEQUENCE: 24
gtgagtttgg ggacccttga ttgttctttc ttttttcgcta ttgtaaaatt catgttatat       60
ggagggggca aagttttcag ggtgttgttt agaatgggaa gatgtccctt gtatcaccat      120
ggaccctcat gataattttg tttctttcac tttctactct gttgacaacc attgtctcct      180 cttatttttct tttcatttttc tgtaacttttt tcgttaaact ttagcttgca tttgtaacga      240 attttttaaat tcacttttgt ttatttgtca gattgtaagt actttctcta atcacttttt      300
tttcaaggca atcagggtat attatattgt acttcagcac agttttagag aacaattgtt      360
ataattaaat gataaggtag aatatttctg catataaatt ctggctggcg tggaaatatt      420
cttattggta gaaacaacta caccctggtc atcatcctgc ctttctcttt atggttacaa      480
tgatatacac tgtttgagat gaggataaaa tactctgagt ccaaaccggg cccctctgct      540
aaccatgttc atgccttctt ctctttccta cag                                573
```

```
<210> SEQ ID NO 25
<211> LENGTH: 450
<212> TYPE: DNA
<213> ORGANISM: Artificial Sequence
<220> FEATURE:
<223> OTHER INFORMATION: Envelope-Rabbit beta globin poly A-RNA
      stability

<400> SEQUENCE: 25
agatcttttt ccctctgcca aaaattatgg ggacatcatg aagccccttg agcatctgac       60
ttctggctaa taaaggaaat ttattttcat tgcaatagtg tgttggaatt ttttgtgtct      120
```

-continued

```
ctcactcgga aggacatatg ggagggcaaa tcatttaaaa catcagaatg agtatttggt      180
ttagagtttg gcaacatatg cccatatgct ggctgccatg aacaaaggtt ggctataaag      240
aggtcatcag tatatgaaac agcccctgc tgtccattcc ttattccata gaaaagcctt       300
gacttgaggt tagatttttt ttatattttg ttttgtgtta tttttttctt taacatccct      360
aaaattttcc ttacatgttt tactagccag atttttcctc ctctcctgac tactcccagt      420
catagctgtc cctcttctct tatggagatc                                       450

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
taagcagaat tcatgaattt gccaggaaga t                                      31

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
ccatacaatg aatggacact aggcggccgc acgaat                                 36

<210> SEQ ID NO 28
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 28
gaattcatga atttgccagg aagatggaaa ccaaaaatga taggggaat tggaggtttt        60 atcaaagtaa gacagtatga tcagatactc atagaaatct gcggacataa agctataggt       120
acagtattag taggacctac acctgtcaac ataattggaa gaaatctgtt gactcagatt       180
ggctgcactt taaatttttcc cattagtcct attgagactg taccagtaaa attaaagcca      240
ggaatggatg gcccaaaagt taaacaatgg ccattgacag aagaaaaaat aaaagcatta       300
gtagaaattt gtacagaaat ggaaaaggaa ggaaaaattt caaaaattgg gcctgaaaat       360
ccatacaata ctccagtatt tgccataaag aaaaaagaca gtactaaatg gagaaaatta       420
gtagatttca gagaacttaa taagagaact caagatttct gggaagttca attaggaata      480
ccacatcctg cagggttaaa acagaaaaaa tcagtaacag tactggatgt gggcgatgca       540 tattttttcag ttcccttaga taaagacttc aggaagtata ctgcatttac catacctagt      600
ataaacaatg agacaccagg gattagatat cagtacaatg tgcttccaca gggatggaaa       660
ggatcaccag caatattcca gtgtagcatg acaaaaatct tagagccttt tagaaaacaa       720
aatccagaca tagtcatcta tcaatacatg gatgatttgt atgtaggatc tgacttagaa       780 ataggggcagc atagaacaaa atagaggaa ctgagacaac atctgttgag gtggggattt       840
accacaccag acaaaaaaca tcagaaagaa cctccattcc tttggatggg ttatgaactc       900
catcctgata atggacagt acagcctata gtgctgccag aaaaggacag ctggactgtc        960
aatgacatac agaaattagt gggaaaattg aattgggcaa gtcagattta tgcagggatt      1020
```

```
aaagtaaggc aattatgtaa acttcttagg ggaaccaaag cactaacaga agtagtacca   1080
ctaacagaag aagcagagct agaactggca gaaaacaggg agattctaaa agaaccggta   1140
catggagtgt attatgaccc atcaaaagac ttaatagcag aaatacagaa gcaggggcaa   1200
ggccaatgga catatcaaat ttatcaagag ccatttaaaa atctgaaaac aggaaagtat   1260
gcaagaatga agggtgccca cactaatgat gtgaaacaat taacagaggc agtacaaaaa   1320
atagccacag aaagcatagt aatatgggga aagactccta aatttaaatt acccatacaa   1380
aaggaaacat gggaagcatg gtggacagag tattggcaag ccacctggat tcctgagtgg   1440
gagtttgtca atacccctcc cttagtgaag ttatggtacc agttagagaa agaacccata   1500
ataggagcag aaactttcta tgtagatggg gcagccaata gggaaactaa attaggaaaa   1560
gcaggatatg taactgacag aggaagacaa aaagttgtcc ccctaacgga cacaacaaat   1620
cagaagactg agttacaagc aattcatcta gctttgcagg attcgggatt agaagtaaac   1680
atagtgacag actcacaata tgcattggga atcattcaag cacaaccaga taagagtgaa   1740
tcagagttag tcagtcaaat aatagagcag ttaataaaaa aggaaaaagt ctacctggca   1800
tgggtaccag cacacaaagg aattggagga aatgaacaag tagataaatt ggtcagtgct   1860
ggaatcagga aagtactatt tttagatgga atagataagg cccaagaaga acatgagaaa   1920
tatcacagta attggagagc aatggctagt gattttaacc taccacctgt agtagcaaaa   1980
gaaatagtag ccagctgtga taaatgtcag ctaaaagggg aagccatgca tggacaagta   2040
gactgtagcc caggaatatg gcagctagat tgtacacatt tagaaggaaa agttatcttg   2100
gtagcagttc atgtagccag tggatatata gaagcagaag taattccagc agagacaggg   2160
caagaaacag catacttcct cttaaaatta gcaggaagat ggccagtaaa aacagtacat   2220
acagacaatg gcagcaattt caccagtact acagttaagg ccgcctgttg gtgggcgggg   2280
atcaagcagg aatttggcat tccctacaat ccccaaagtc aaggagtaat agaatctatg   2340
aataaagaat taaagaaaat tataggacag gtaagagatc aggctgaaca tcttaagaca   2400
gcagtacaaa tggcagtatt catccacaat tttaaaagaa aagggggggat tggggg5tac   2460 agtgcagggg aaagaatagt agacataata gcaacagaca tacaaactaa agaattacaa   2520
aaacaaatta caaaaattca aaattttcgg gtttattaca gggacagcag agatccagtt   2580
tggaaaggac cagcaaagct cctctggaaa ggtgaagggg cagtagtaat acaagataat   2640
agtgacataa aagtagtgcc aagaagaaaa gcaaagatca tcagggatta tggaaaacag   2700
atggcaggtg atgattgtgt ggcaagtaga caggatgagg attaa              2745
```

```
<210> SEQ ID NO 29
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 29
tctagaatgg caggaagaag cggagacagc gacgaagagc tcatcagaac agtcagactc    60
atcaagcttc tctatcaaag caacccacct cccaatcccg aggggacccg acaggcccga   120
aggaatagaa gaagaaggtg gagagagaga cagagacaga tccattcgat tagtgaacgg   180
atccttggca cttatctggg acgatctgcg gagcctgtgc ctcttcagct accaccgctt   240
gagagactta ctcttgattg taacgaggat tgtggaactt ctgggacgca gggggtggga   300
```

```
agccctcaaa tattggtgga atctcctaca atattggagt caggagctaa agaatagagg      360
agctttgttc cttgggttct tgggagcagc aggaagcact atgggcgcag cgtcaatgac      420
gctgacggta caggccagac aattattgtc tggtatagtg cagcagcaga acaatttgct      480
gagggctatt gaggcgcaac agcatctgtt gcaactcaca gtctgggca tcaagcagct       540 ccagcaaga atcctggctg tggaaagata cctaaaggat caacagctcc tagatctttt       600
tccctctgcc aaaaattatg gggacatcat gaagcccctt gagcatctga cttctggcta      660
ataaaggaaa tttattttca ttgcaatagt gtgttggaat tttttgtgtc tctcactcgg      720
aaggacatat gggagggcaa atcatttaaa acatcagaat gagtatttgg tttagagttt      780
ggcaacatat gccatatgct ggctgccatg aacaaaggtg ctataaaga ggtcatcagt       840 atatgaaaca gccccctgct gtccattcct tattccatag aaaagccttg acttgaggtt      900 agatttttt tatattttgt tttgtgttat tttttttctt aacatcccta aaattttcct       960
tacatgtttt actagccaga tttttcctcc tctcctgact actcccagtc atagctgtcc      1020
ctcttctctt atgaagatcc ctcgacctgc agcccaagct tggcgtaatc atggtcatag      1080
ctgtttcctg tgtgaaattg ttatccgctc acaattccac acaacatacg agccggaagc      1140
ataaagtgta aagcctgggg tgcctaatga gtgagctaac tcacattaat tgcgttgcgc      1200
tcactgcccg ctttccagtc gggaaacctg tcgtgccagc ggatccgcat ctcaattagt      1260
cagcaaccat agtcccgccc ctaactccgc ccatcccgcc cctaactccg cccagttccg      1320
cccattctcc gccccatggc tgactaattt tttttattta tgcagaggcc gaggccgcct      1380
cggcctctga gctattccag aagtagtgag gaggcttttt tggaggccta ggcttttgca      1440
aaaagctaac ttgtttattg cagcttataa tggttacaaa taaagcaata gcatcacaaa      1500
tttcacaaat aaagcatttt tttcactgca ttctagttgt ggtttgtcca aactcatcaa      1560
tgtatcttat cagcggccgc cccggg                                          1586
```

<210> SEQ ID NO 30
<211> LENGTH: 1614
<212> TYPE: DNA
<213> ORGANISM: Artificial Sequence
<220> FEATURE:
<223> OTHER INFORMATION: DNA fragment containing the CAG enhancer/
      promoter/intron sequence

<400> SEQUENCE: 30

```
acgcgttagt tattaatagt aatcaattac ggggtcatta gttcatagcc catatatgga       60
gttccgcgtt acataactta cggtaaatgg cccgcctggc tgaccgccca acgacccccg      120
cccattgacg tcaataatga cgtatgttcc catagtaacg ccaatagga ctttccattg       180 acgtcaatgg gtggactatt tacggtaaac tgcccacttg gcagtacatc aagtgtatca      240
tatgccaagt acgccccta ttgacgtcaa tgacggtaaa tggcccgcct ggcattatgc       300
ccagtacatg accttatggg actttcctac ttggcagtac atctacgtat tagtcatcgc      360
tattaccatg gtcgaggtg agccccacgt tctgcttcac tctccccatc tccccccct       420 ccccaccccc aattttgtat ttatttattt tttaattatt ttgtgcagcg atggggcgg       480 gggggggggg ggcgcgcgcc aggcggggcg gggcggggcg agggcggggg cggggcgagg      540
cggagaggtg cggcggcagc caatcagagc ggcgcgctcc gaaagtttcc ttttatggcg      600
aggcggcggc ggcggcggcc ctataaaaag cgaagcgcgc ggcgggcggg agtcgctgcg      660
ttgccttcgc cccgtgcccc gctccgcgcc gcctcgcgcc gcccgccccg gctctgactg      720
```

```
accgcgttac tcccacaggt gagcgggcgg gacggccctt ctcctccggg ctgtaattag      780
cgcttggttt aatgacggct cgtttctttt ctgtggctgc gtgaaagcct taaagggctc      840
cgggagggcc ctttgtgcgg gggggagcgg ctcgggggt gcgtgcgtgt gtgtgtgcgt      900
ggggagcgcc gcgtgcggcc cgcgctgccc ggcggctgtg agcgctgcgg gcgcggcgcg      960
gggctttgtg cgctccgcgt gtgcgcgagg ggagcgcggc cggggcggt gccccgcggt     1020 gcggggggc tgcgagggga acaaaggctg cgtgcggggt gtgtgcgtgg gggggtgagc     1080 aggggtgtg ggcgcggcgg tcgggctgta accccccct gcacccccct ccccgagttg     1140
ctgagcacgg cccggcttcg ggtgcgggc tccgtgcggg gcgtggcgcg gggctcgccg     1200
tgccgggcgg ggggtggcgg caggtggggg tgccgggcgg ggcggggccg cctcgggccg     1260
gggagggctc ggggggaggg cgcggcggcc ccggagcgcc ggcggctgtc gaggcgcggc     1320
gagccgcagc cattgccttt tatggtaatc gtgcgagagg gcgcagggac ttcctttgtc     1380
ccaaatctgg cggagccgaa atctgggagg cgccgccgca ccccctctag cgggcgcggg     1440
cgaagcggtg cggcgccggc aggaaggaaa tgggcggggga gggccttcgt gcgtcgccgc     1500
gccgccgtcc ccttctccat ctccagcctc ggggctgccg caggggggacg gctgccttcg     1560 gggggacgg ggcagggcgg ggttcggctt ctggcgtgtg accggcggga attc           1614
```

<210> SEQ ID NO 31
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 31

```
gaattcatga agtgcctttt gtacttagcc ttttattca ttggggtgaa ttgcaagttc        60
accatagttt ttccacacaa ccaaaaagga aactggaaaa atgttccttc taattaccat       120
tattgcccgt caagctcaga tttaaattgg cataatgact taataggcac agccttacaa       180
gtcaaaatgc ccaagagtca caggctatt caagcagacg gttggatgtg tcatgcttcc       240
aaatgggtca ctacttgtga tttccgctgg tatggaccga agtatataac acattccatc       300
cgatccttca ctccatctgt agaacaatgc aaggaaagca ttgaacaaac gaaacaagga       360
acttggctga atccaggctt ccctcctcaa agttgtggat atgcaactgt gacggatgcc       420
gaagcagtga ttgtccaggt gactcctcac catgtgctgg ttgatgaata cacaggagaa       480
tgggttgatt cacagttcat caacggaaaa tgcagcaatt acatatgccc cactgtccat       540
aactctacaa cctggcattc tgactataag gtcaaagggc tatgtgattc taacctcatt       600
tccatggaca tcaccttctt ctcagaggac ggagagctat catccctggg aaaggagggc       660
acagggttca gaagtaacta ctttgcttat gaaactggag gcaaggcctg caaaatgcaa       720
tactgcaagc attggggagt cagactccca tcaggtgtct ggttcgagat ggctgataag       780
gatctctttg ctgcagccag attccctgaa tgcccagaag ggtcaagtat ctctgctcca       840
tctcagacct cagtggatgt aagtctaatt caggacgttg agaggatctt ggattattcc       900
ctctgccaag aaacctggag caaaatcaga gcgggtcttc caatctctcc agtggatctc       960
agctatcttg ctcctaaaaa cccaggaacc ggtcctgctt tcaccataat caatggtacc      1020
ctaaaatact ttgagaccag atacatcaga gtcgatattg ctgctccaat cctctcaaga      1080
atggtcggaa tgatcagtgg aactaccaca gaaagggaac tgtgggatga ctgggcacca      1140
```
tatgaagacg tggaaattgg acccaatgga gttctgagga ccagttcagg atataagttt      1200
cctttataca tgattggaca tggtatgttg gactccgatc ttcatcttag ctcaaaggct      1260
caggtgttcg aacatcctca cattcaagac gctgcttcgc aacttcctga tgatgagagt      1320 ttatttttg gtgatactgg gctatccaaa aatccaatcg agcttgtaga aggttggttc       1380
agtagttgga aaagctctat tgcctctttt ttctttatca tagggttaat cattggacta      1440
ttcttggttc ccgagttgg tatccatctt tgcattaaat taaagcacac caagaaaaga       1500
cagatttata cagacataga gatgagaatt c                                    1531

<210> SEQ ID NO 32
<211> LENGTH: 1227
<212> TYPE: DNA
<213> ORGANISM: Artificial Sequence
<220> FEATURE:
<223> OTHER INFORMATION: DNA fragment of Helper plasmid without Rev
      containing RRE and rabbit beta globin poly A

<400> SEQUENCE: 32
tctagaagga gctttgttcc ttgggttctt gggagcagca ggaagcacta tgggcgcagc      60
gtcaatgacg ctgacggtac aggccagaca attattgtct ggtatagtgc agcagcagaa      120
caatttgctg agggctattg aggcgcaaca gcatctgttg caactcacag tctggggcat      180
caagcagctc caggcaagaa tcctggctgt ggaaagatac ctaaaggatc aacagctcct      240 agatctttt ccctctgcca aaaattatgg ggacatcatg aagccccttg agcatctgac       300
ttctggctaa taaaggaaat ttattttcat tgcaatagtg tgttggaatt ttttgtgtct      360
ctcactcgga aggacatatg ggagggcaaa tcatttaaaa catcagaatg agtatttggt      420
ttagagtttg gcaacatatg ccatatgctg gctgccatga acaaaggtgg ctataaagag      480
gtcatcagta tatgaaacag ccccctgctg tccattcctt attccataga aaagccttga      540
cttgaggtta gatttttttt atattttgtt ttgtgttatt tttttcttta acatccctaa      600
aattttcctt acatgtttta ctagccagat ttttcctcct ctcctgacta ctcccagtca     660
tagctgtccc tcttctctta tgaagatccc tcgacctgca gcccaagctt ggcgtaatca      720
tggtcatagc tgtttcctgt gtgaaattgt tatccgctca caattccaca caacatacga      780
gccggaagca taaagtgtaa agcctggggt gcctaatgag tgagctaact cacattaatt      840
gcgttgcgct cactgcccgc tttccagtcg ggaaacctgt cgtgccagcg gatccgcatc      900
tcaattagtc agcaaccata gtcccgcccc taactccgcc catcccgccc ctaactccgc      960
ccagttccgc ccattctccg ccccatggct gactaattt ttttatttat gcagaggccg       1020
aggccgcctc ggcctctgag ctattccaga gtagtgagg aggctttttt ggaggcctag       1080
gcttttgcaa aaagctaact tgtttattgc agcttataat ggttacaaat aaagcaatag      1140
catcacaaat ttcacaaata aagcattttt ttcactgcat tctagttgtg gtttgtccaa      1200
actcatcaat gtatcttatc acccggg                                         1227

<210> SEQ ID NO 33
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 33
caattgcgat gtacgggcca gatatacgcg tatctgaggg gactagggtg tgtttaggcg      60

```
aaaagcgggg cttcggttgt acgcggttag gagtcccctc aggatatagt agtttcgctt      120
ttgcataggg aggggaaat gtagtcttat gcaatacact tgtagtcttg caacatggta      180
acgatgagtt agcaacatgc cttacaagga gagaaaaagc accgtgcatg ccgattggtg      240
gaagtaaggt ggtacgatcg tgccttatta ggaaggcaac agacaggtct gacatggatt      300
ggacgaacca ctgaattccg cattgcagag ataattgtat ttaagtgcct agctcgatac      360
aataaacgcc atttgaccat tcaccacatt ggtgtgcacc tccaagctcg agctcgttta      420
gtgaaccgtc agatcgcctg gagacgccat ccacgctgtt ttgacctcca tagaagacac      480
cgggaccgat ccagcctccc ctcgaagcta gcgattaggc atctcctatg gcaggaagaa      540
gcggagacag cgacgaagaa ctcctcaagg cagtcagact catcaagttt ctctatcaaa      600
gcaacccacc tcccaatccc gaggggaccc gacaggcccg aaggaataga agaagaaggt      660
ggagagagag acagagacag atccattcga ttagtgaacg gatccttagc acttatctgg      720
gacgatctgc ggagcctgtg cctcttcagc taccaccgct tgagagactt actcttgatt      780
gtaacgagga ttgtggaact tctgggacgc aggggtggg aagccctcaa atattggtgg      840
aatctcctac aatattggag tcaggagcta agaatagtc taga                      884
```

```
<210> SEQ ID NO 34
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 34
```

```
ccggtgccta gagaaggtgg cgcggggtaa actgggaaag tgatgtcgtg tactggctcc       60
gcctttttcc cgagggtggg ggagaaccgt atataagtgc agtagtcgcc gtgaacgttc      120
tttttcgcaa cgggtttgcc gccagaacac aggtaagtgc cgtgtgtggt tcccgcgggc      180
ctggcctctt tacgggttat ggcccttgcg tgccttgaat tacttccacg cccctggctg      240
cagtacgtga ttcttgatcc cgagcttcgg gttggaagtg ggtgggagag ttcgaggcct      300
tgcgcttaag gagcccttc gcctcgtgct tgagttgagg cctggcctgg gcgctggggc      360
cgccgcgtgc gaatctggtg gcaccttcgc gcctgtctcg ctgctttcga taagtctcta      420
gccatttaaa attttgatg acctgctgcg acgctttttt tctggcaaga tagtcttgta      480
aatgcgggcc aagatctgca cactggtatt tcggtttttg gggccgcggg cggcgacggg      540
gcccgtgcgt cccagcgcac atgttcggcg aggcgggcc tgcgagcgcg gccaccgaga      600
atcggacggg ggtagtctca agctggccgg cctgctctgg tgcctggcct cgcgccgccg      660
tgtatcgccc cgccctgggc ggcaaggctg gcccggtcgg caccagttgc gtgagcggaa      720
agatggccgc ttcccggccc tgctgcaggg agctcaaaat ggaggacgcg gcgctcggga      780
gagcgggcgg gtgagtcacc cacacaaagg aaaaggcct ttccgtcctc agccgtcgct      840
tcatgtgact ccacggagta ccgggcgccg tccaggcacc tcgattagtt ctcgagcttt      900
tggagtacgt cgtctttagg ttgggggag gggtttatg cgatggagtt tccccacact      960
gagtgggtgg agactgaagt taggccagct tggcacttga tgtaattctc cttggaattt     1020
gccctttttg agtttggatc ttggttcatt ctcaagcctc agacagtggt tcaaagtttt     1080
tttcttccat ttcaggtgtc gtga                                          1104
```

```
<210> SEQ ID NO 35
<211> LENGTH: 511
```

<212> TYPE: DNA
<213> ORGANISM: Artificial Sequence
<220> FEATURE:
<223> OTHER INFORMATION: Promoter-PGK

<400> SEQUENCE: 35
ggggttgggg ttgcgccttt tccaaggcag ccctgggttt gcgcagggac gcggctgctc       60
tgggcgtggt tccgggaaac gcagcggcgc cgaccctggg tctcgcacat tcttcacgtc      120
cgttcgcagc gtcacccgga tcttcgccgc taccctgtg ggcccccgg cgacgcttcc       180 tgctccgccc ctaagtcggg aaggttcctt gcggttcgcg gcgtgccgga cgtgacaaac      240
ggaagccgca cgtctcacta gtaccctcgc agacggacag cgccagggag caatggcagc      300
gcgccgaccg cgatgggctg tggccaatag cggctgctca gcagggcgcg ccgagagcag      360
cggccgggaa ggggcggtgc gggaggcggg gtgtggggcg gtagtgtggg ccctgttcct      420
gcccgcgcgg tgttccgcat tctgcaagcc tccggagcgc acgtcggcag tcggctccct      480
cgttgaccga atcaccgacc tctctcccca g                                    511

<210> SEQ ID NO 36
<211> LENGTH: 1162
<212> TYPE: DNA
<213> ORGANISM: Artificial Sequence
<220> FEATURE:
<223> OTHER INFORMATION: Promoter-UbC

<400> SEQUENCE: 36
gcgccgggtt ttggcgcctc ccgcgggcgc cccctcctc acggcgagcg ctgccacgtc       60
agacgaaggg cgcaggagcg ttcctgatcc ttccgcccgg acgctcagga cagcggcccg      120
ctgctcataa gactcggcct tagaacccca gtatcagcag aaggacattt taggacggga      180
cttgggtgac tctagggcac tggttttctt tccagagagc ggaacaggcg aggaaaagta      240
gtcccttctc ggcgattctg cggagggatc tccgtggggc ggtgaacgcc gatgattata      300
taaggacgcg ccgggtgtgg cacagctagt tccgtcgcag ccgggatttg ggtcgcggtt      360
cttgtttgtg gatcgctgtg atcgtcactt ggtgagttgc gggctgctgg gctggccggg      420
gctttcgtgg ccgccgggcc gctcggtggg acggaagcgt gtggagagac cgccaagggc      480
tgtagtctgg gtccgcgagc aaggttgccc tgaactgggg gttggggga gcgcacaaaa      540 tggcggctgt tcccgagtct tgaatggaag acgcttgtaa ggcgggctgt gaggtcgttg      600
aaacaaggtg gggggcatgg tgggcggcaa gaacccaagg tcttgaggcc ttcgctaatg      660
cgggaaagct cttattcggg tgagatgggc tggggcacca tctggggacc ctgacgtgaa      720
gtttgtcact gactggagaa ctcgggtttg tcgtctggtt gcgggggcgg cagttatgcg      780
gtgccgttgg gcagtgcacc cgtacctttg ggagcgcgcg cctcgtcgtg tcgtgacgtc      840
acccgttctg ttggcttata atgcagggtg gggccacctg ccggtaggtg tgcggtaggc      900
ttttctccgt cgcaggacgc agggttcggg cctagggtag gctctcctga atcgacaggc      960
gccggacctc tggtgagggg aggataagt gaggcgtcag tttctttggt cggttttatg     1020
tacctatctt cttaagtagc tgaagctccg gttttgaact atgcgctcgg ggttggcgag     1080 tgtgtttttgt gaagttttt aggcacctt tgaaatgtaa tcatttgggt caatatgtaa     1140
ttttcagtgt tagactagta aa                                            1162

<210> SEQ ID NO 37
<211> LENGTH: 120
<212> TYPE: DNA

-continued

```
<213> ORGANISM: Artificial Sequence
<220> FEATURE:
<223> OTHER INFORMATION: Poly A-SV40

<400> SEQUENCE: 37
gtttattgca gcttataatg gttacaaata aagcaatagc atcacaaatt tcacaaataa      60
agcatttttt tcactgcatt ctagttgtgg tttgtccaaa ctcatcaatg tatcttatca     120

<210> SEQ ID NO 38
<211> LENGTH: 227
<212> TYPE: DNA
<213> ORGANISM: Artificial Sequence
<220> FEATURE:
<223> OTHER INFORMATION: Poly A-bGH

<400> SEQUENCE: 38
gactgtgcct tctagttgcc agccatctgt tgtttgcccc tcccccgtgc cttccttgac      60
cctggaaggt gccactccca ctgtcctttc ctaataaaat gaggaaattg catcgcattg     120
tctgagtagg tgtcattcta ttctgggggg tggggtgggg caggacagca aggggggagga    180 ttgggaagac aatagcaggc atgctgggga tgcggtgggc tctatgg                   227

<210> SEQ ID NO 39
<211> LENGTH: 1695
<212> TYPE: DNA
<213> ORGANISM: Artificial Sequence
<220> FEATURE:
<223> OTHER INFORMATION: Envelope-RD114

<400> SEQUENCE: 39
atgaaactcc caacaggaat ggtcatttta tgtagcctaa taatagttcg ggcagggttt      60
gacgaccccc gcaaggctat cgcattagta caaaaacaac atggtaaacc atgcgaatgc     120
agcggagggc aggtatccga ggccccaccg aactccatcc aacaggtaac ttgcccaggc     180
aagacggcct acttaatgac caaccaaaaa tggaaatgca gagtcactcc aaaaaatctc     240 accccctagcg ggggagaact ccagaactgc ccctgtaaca ctttccagga ctcgatgcac    300
agttcttgtt atactgaata ccggcaatgc agggcgaata ataagacata ctacacggcc     360
accttgctta aaatacggtc tgggagcctc aacgaggtac agatattaca aaaccccaat     420
cagctcctac agtccccttg tagggggctct ataaatcagc ccgtttgctg gagtgccaca    480
gcccccatcc atatctccga tggtggagga ccectcgata ctaagagagt gtggacagtc     540
caaaaaaggc tagaacaaat tcataaggct atgcatcctg aacttcaata ccaccccctta    600 gccctgccca aagtcagaga tgaccttagc cttgatgcac ggacttttga tatcctgaat     660
accactttta ggttactcca gatgtccaat tttagccttg cccaagattg ttggctctgt     720
ttaaaactag gtaccectac ccctcttgcg atacccactc cctctttaac ctactcccta     780
gcagactccc tagcgaatgc ctcctgtcag attatacctc ccctcttggt tcaaccgatg     840
cagttctcca actcgtcctg tttatcttcc cctttcatta cgatacggga acaaatagac     900
ttaggtgcag tcacctttac taactgcacc tctgtagcca atgtcagtag tccttatgt      960 gccctaaacg ggtcagtctt cctctgtgga ataacatgg catacaccta tttaccccaa     1020
aactggacag gactttgcgt ccaagcctcc ctcctccccg acattgacat catcccgggg    1080
gatgagccag tccccattcc tgccattgat cattatatac atagacctaa acgagctgta    1140
cagttcatcc ctttactagc tggactggga atcaccgcag cattcaccac cggagctaca    1200
ggcctaggtg tctccgtcac ccagtataca aaattatccc atcagttaat atctgatgtc    1260
```

-continued

```
caagtcttat ccggtaccat acaagattta caagaccagg tagactcgtt agctgaagta      1320
gttctccaaa ataggagggg actggaccta ctaacggcag aacaaggagg aatttgttta      1380
gccttacaag aaaaatgctg tttttatgct aacaagtcag gaattgtgag aaacaaaata      1440
agaaccctac aagaagaatt acaaaaacgc agggaaagcc tggcatccaa ccctctctgg      1500
accgggctgc agggctttct tccgtacctc ctacctctcc tgggacccct actcaccctc      1560
ctactcatac taaccattgg gccatgcgtt ttcaatcgat tggtccaatt tgttaaagac      1620
aggatctcag tggtccaggc tctggttttg actcagcaat atcaccagct aaaacccata      1680
gagtacgagc catga                                                      1695
```

```
<210> SEQ ID NO 40
<211> LENGTH: 2013
<212> TYPE: DNA
<213> ORGANISM: Artificial Sequence
<220> FEATURE:
<223> OTHER INFORMATION: Envelope-GALV

<400> SEQUENCE: 40
```

```
atgcttctca cctcaagccc gcaccacctt cggcaccaga tgagtcctgg gagctggaaa        60
agactgatca tcctcttaag ctgcgtattc ggagacggca aaacgagtct gcagaataag       120
aacccccacc agcctgtgac cctcacctgg caggtactgt cccaaactgg ggacgttgtc       180
tgggacaaaa aggcagtcca gcccctttgg acttggtggc cctctcttac acctgatgta       240
tgtgccctgg cggccggtct tgagtcctgg gatatcccgg gatccgatgt atcgtcctct       300
aaaagagtta gacctcctga ttcagactat actgccgctt ataagcaaat cacctgggga       360
gccatagggt gcagctaccc tcgggctagg accaggatgg caaattcccc cttctacgtg       420
tgtccccgag ctggccgaac ccattcagaa gctaggaggt gtgggggct agaatcccta       480 tactgtaaag aatggagttg tgagaccacg ggtaccgttt attggcaacc caagtcctca       540
tgggacctca taactgtaaa atgggaccaa aatgtgaaat gggagcaaaa atttcaaaag       600
tgtgaacaaa ccggctggtg taaccccctc aagatagact tcacagaaaa aggaaaactc       660
tccagagatt ggataacgga aaaaacctgg gaattaaggt tctatgtata tggacaccca       720
ggcatacagt tgactatccg cttagaggtc actaacatgc cggttgtggc agtgggccca       780
gaccctgtcc ttgcggaaca gggacctcct agcaagcccc tcactctccc tctctcccca       840
cggaaagcgc cgcccacccc tctacccccg gcggctagtg agcaaacccc tgcggtgcat       900
ggagaaactg ttaccctaaa ctctccgcct cccaccagtg cgaccgact ctttggcctt       960 gtgcagggg ccttcctaac cttgaatgct accaacccag gggccactaa gtcttgctgg      1020
ctctgtttgg gcatgagccc cccttattat gaagggatag cctcttcagg agaggtcgct      1080
tatacctcca accatacccg atgccactgg ggggcccaag aaagcttac cctcactgag      1140 gtctccggac tcgggtcatg cataggggaag gtgcctctta cccatcaaca tctttgcaac      1200
cagaccttac ccatcaattc ctctaaaaac catcagtatc tgctcccctc aaaccatagc      1260
tggtgggcct gcagcactgg cctcacccc tgcctctcca cctcagtttt taatcagtct      1320
aaagacttct gtgtccaggt ccagctgatc ccccgcatct attaccattc tgaagaaacc      1380
ttgttacaag cctatgacaa atcacccccc aggtttaaaa gagagcctgc ctcacttacc      1440
ctagctgtct tcctggggtt agggattgcg gcaggtatag gtactggctc aaccgcccta      1500
attaaagggc ccatagacct ccagcaaggc ctaaccagcc tccaaatcgc cattgacgct      1560
```

-continued

```
gacctccggg cccttcagga ctcaatcagc aagctagagg actcactgac ttccctatct    1620
gaggtagtac tccaaaatag gagaggcctt gacttactat tccttaaaga aggaggcctc    1680
tgcgcggccc taaaagaaga gtgctgtttt tatgtagacc actcaggtgc agtacgagac    1740
tccatgaaaa aacttaaaga aagactagat aaaagacagt tagagcgcca gaaaaaccaa    1800
aactggtatg aagggtggtt caataactcc ccttggttta ctaccctact atcaaccatc    1860
gctgggcccc tattgctcct cctttttgtta ctcactcttg ggccctgcat catcaataaa    1920
ttaatccaat tcatcaatga taggataagt gcagtcaaaa ttttagtcct tagacagaaa    1980
tatcagaccc tagataacga ggaaaacctt taa                                 2013
```

<210> SEQ ID NO 41
<211> LENGTH: 1530
<212> TYPE: DNA
<213> ORGANISM: Artificial Sequence
<220> FEATURE:
<223> OTHER INFORMATION: Envelope-FUG

<400> SEQUENCE: 41

```
atggttccgc aggttctttt gtttgtactc cttctgggtt tttcgttgtg tttcgggaag      60
ttccccattt acacgatacc agacgaactt ggtccctgga gccctattga catacaccat     120
ctcagctgtc caaataacct ggttgtggag gatgaaggat gtaccaacct gtccgagttc     180
tcctacatgg aactcaaagt gggatacatc tcagccatca aagtgaacgg gttcacttgc     240
acaggtgttg tgacagaggc agagacctac accaactttg ttggttatgt cacaaccaca     300
ttcaagagaa agcatttccg ccccacccca gacgcatgta gagccgcgta taactggaag     360
atggccggtg accccagata tgaagagtcc ctacacaatc catccccga ctaccactgg     420 cttcgaactg taagaaccac caaagagtcc ctcattatca tatccccaag tgtgacagat     480
ttggacccat atgacaaatc ccttcactca agggtcttcc ctggcggaaa gtgctcagga     540
ataacggtgt cctctaccta ctgctcaact aaccatgatt acaccatttg gatgcccgag     600
aatccgagac caaggacacc ttgtgacatt tttaccaata gcagagggaa gagagcatcc     660
aacgggaaca agacttgcgg ctttgtggat gaaagaggcc tgtataagtc tctaaaagga     720
gcatgcaggc tcaagttatg tggagttctt ggacttagac ttatggatgg aacatgggtc     780
gcgatgcaaa catcagatga gaccaaatgg tgccctccag atcagttggt gaatttgcac     840
gactttcgct cagacgagat cgagcatctc gttgtggagg agttagttaa gaaaagagag     900
gaatgtctgg atgcattaga gtccatcatg accaccaagt cagtaagttt cagacgtctc     960
agtcacctga aaaacttgt cccagggttt ggaaaagcat ataccatatt caacaaaacc    1020
ttgatggagg ctgatgctca ctacaagtca gtccggacct ggaatgagat catcccctca    1080
aaagggtgtt tgaaagttgg aggaaggtgc catcctcatg tgaacggggt gtttttcaat    1140
ggtataatat tagggcctga cgaccatgtc ctaatcccag agatgcaatc atccctcctc    1200
cagcaacata tggagttgtt ggaatcttca gttatccccc tgatgcaccc cctggcagac    1260
ccttctacag ttttcaaaga aggtgatgag gctgaggatt ttgttgaagt tcacctcccc    1320
gatgtgtaca acagatctc aggggttgac ctgggtctcc cgaactgggg aaagtatgta    1380
ttgatgactg caggggccat gattggcctg gtgttgatat tttccctaat gacatggtgc    1440
agagttggta tccatctttg cattaaatta aagcacacca agaaaagaca gatttataca    1500
gacatagaga tgaaccgact tggaaagtaa                                     1530
```

-continued

```
<210> SEQ ID NO 42
<211> LENGTH: 1497
<212> TYPE: DNA
<213> ORGANISM: Artificial Sequence
<220> FEATURE:
<223> OTHER INFORMATION: Envelope-LCMV

<400> SEQUENCE: 42
atgggtcaga ttgtgacaat gtttgaggct ctgcctcaca tcatcgatga ggtgatcaac        60
attgtcatta ttgtgcttat cgtgatcacg ggtatcaagg ctgtctacaa ttttgccacc       120
tgtgggatat tcgcattgat cagtttccta cttctggctg gcaggtcctg tggcatgtac       180
ggtcttaagg gacccgacat ttacaaagga gtttaccaat ttaagtcagt ggagtttgat       240
atgtcacatc tgaacctgac catgcccaac gcatgttcag ccaacaactc ccaccattac       300
atcagtatgg ggacttctgg actagaattg accttcacca atgattccat catcagtcac       360
aacttttgca atctgacctc tgccttcaac aaaaagacct ttgaccacac actcatgagt       420
atagtttcga gcctacacct cagtatcaga gggaactcca actataaggc agtatcctgc       480
gacttcaaca atggcataac catccaatac aacttgacat tctcagatcg acaaagtgct       540
cagagccagt gtagaacctt cagaggtaga gtcctagata tgtttagaac tgccttcggg       600
gggaaataca tgaggagtgg ctggggctgg acaggctcag atggcaagac cacctggtgt       660
agccagacga gttaccaata cctgattata caaaatagaa cctgggaaaa ccactgcaca       720
tatgcaggtc ctttttgggat gtccaggatt ctcctttccc aagagaagac taagttcttc       780
actaggagac tagcgggcac attcacctgg actttgtcag actcttcagg ggtggagaat       840
ccaggtggtt attgcctgac caaatggatg attcttgctg cagagcttaa gtgtttcggg       900
aacacagcag ttgcgaaatg caatgtaaat catgatgccg aattctgtga catgctgcga       960
ctaattgact acaacaaggc tgctttgagt aagttcaaag aggacgtaga atctgccttg      1020
cacttattca aaacaacagt gaattctttg atttcagatc aactactgat gaggaaccac      1080
ttgagagatc tgatggggggt gccatattgc aattactcaa agttttggta cctagaacat      1140
gcaaagaccg gcgaaactag tgtccccaag tgctggcttg tcaccaatgg ttcttactta      1200
aatgagaccc acttcagtga tcaaatcgaa caggaagccg ataacatgat tacagagatg      1260
ttgaggaagg attacataaa gaggcagggg agtacccccc tagcattgat ggaccttctg      1320
atgtttccca catctgcata tctagtcagc atcttcctgc accttgtcaa aataccaaca      1380
cacaggcaca taaaaggtgg ctcatgtcca aagccacacc gattaaccaa caaaggaatt      1440
tgtagttgtg gtgcatttaa ggtgcctggt gtaaaaaccg tctggaaaag acgctga       1497

<210> SEQ ID NO 43
<211> LENGTH: 1692
<212> TYPE: DNA
<213> ORGANISM: Artificial Sequence
<220> FEATURE:
<223> OTHER INFORMATION: Envelope-FPV

<400> SEQUENCE: 43
atgaacactc aaatcctggt tttcgcccct gtggcagtca tccccacaaa tgcagacaaa        60
atttgtcttg acatcatgc tgtatcaaat ggcaccaaag taaacacact cactgagaga       120
ggagtagaag ttgtcaatgc aacggaaaca gtggagcgga caaacatccc caaaatttgc       180
tcaaaaggga aagaaccac tgatcttggc caatgcggac tgttagggac cattaccgga       240
ccacctcaat gcgaccaatt tctagaattt tcagctgatc ta taatcga gagacgagaa       300
```

-continued

```
ggaaatgatg tttgttaccc ggggaagttt gttaatgaag aggcattgcg acaaatcctc      360
agaggatcag gtgggattga caaagaaaca atgggattca catatagtgg aataaggacc      420
aacggaacaa ctagtgcatg tagaagatca gggtcttcat tctatgcaga aatggagtgg      480
ctcctgtcaa atacagacaa tgctgctttc ccacaaatga caaaatcata caaaaacaca      540
aggagagaat cagctctgat agtctgggga atccaccatt caggatcaac caccgaacag      600
accaaactat atgggagtgg aaataaactg ataacagtcg ggagttccaa atatcatcaa      660
tcttttgtgc cgagtccagg aacacgaccg cagataaatg gccagtccgg acggattgat      720
tttcattggt tgatcttgga tcccaatgat acagttactt ttagtttcaa tggggctttc      780
atagctccaa atcgtgccag cttcttgagg ggaaagtcca tggggatcca gagcgatgtg      840
caggttgatg ccaattgcga aggggaatgc taccacagtg gagggactat aacaagcaga      900
ttgccttttc aaaacatcaa tagcagagca gttggcaaat gcccaagata tgtaaaacag      960
gaaagtttat tattggcaac tgggatgaag aacgttcccg aaccttccaa aaaaaggaaa     1020
aaaagaggcc tgtttggcgc tatagcaggg tttattgaaa atggttggga aggtctggtc     1080
gacgggtggt acggtttcag gcatcagaat gcacaaggag aaggaactgc agcagactac     1140
aaaagcaccc aatcggcaat tgatcagata accggaaagt aaatagact cattgagaaa     1200 accaaccagc aatttgagct aatagataat gaattcactg aggtggaaaa gcagattggc     1260
aatttaatta actggaccaa agactccatc acagaagtat ggtcttacaa tgctgaactt     1320
cttgtggcaa tggaaaacca gcacactatt gatttggctg attcagagat gaacaagctg     1380
tatgagcgag tgaggaaaca attaagggaa aatgctgaag aggatggcac tggttgcttt     1440 gaaattttc ataaatgtga cgatgattgt atggctagta taaggaacaa tacttatgat     1500
cacagcaaat acagagaaga agcgatgcaa aatagaatac aaattgaccc agtcaaattg     1560
agtagtggct acaaagatgt gatactttgg tttagcttcg gggcatcatg ctttttgctt     1620
cttgccattg caatgggcct tgttttcata tgtgtgaaga acggaaacat gcggtgcact     1680
atttgtatat aa                                                        1692
```

<210> SEQ ID NO 44
<211> LENGTH: 1266
<212> TYPE: DNA
<213> ORGANISM: Artificial Sequence
<220> FEATURE:
<223> OTHER INFORMATION: Envelope-RRV

<400> SEQUENCE: 44

```
agtgtaacag agcactttaa tgtgtataag gctactagac catacctagc acattgcgcc       60
gattgcgggg acgggtactt ctgctatagc ccagttgcta tcgaggagat ccgagatgag      120
gcgtctgatg gcatgcttaa gatccaagtc tccgcccaaa taggtctgga caaggcaggc      180
acccacgccc acacgaagct ccgatatatg gctggtcatg atgttcagga atctaagaga      240
gattccttga gggtgtacac gtccgcagcg tgctccatac atgggacgat gggacacttc      300
atcgtcgcac actgtccacc aggcgactac ctcaaggttt cgttcgagga cgcagattcg      360
cacgtgaagg catgtaaggt ccaatacaag cacaatccat tgccggtggg tagagagaag      420
ttcgtggtta gaccacactt tggcgtagag ctgccatgca cctcatacca gctgacaacg      480
gctcccaccg acgaggagat tgacatgcat acaccgccag atataccgga tcgcaccctg      540
ctatcacaga cggcgggcaa cgtcaaaata acagcaggcg gcaggactat caggtacaac      600
tgtacctgcg gccgtgacaa cgtaggcact accagtactg acaagaccat caacacatgc      660
```

-continued

```
aagattgacc aatgccatgc tgccgtcacc agccatgaca aatggcaatt tacctctcca      720
tttgttccca gggctgatca gacagctagg aaaggcaagg tacacgttcc gttccctctg      780
actaacgtca cctgccgagt gccgttggct cgagcgccgg atgccaccta tggtaagaag      840
gaggtgaccc tgagattaca cccagatcat ccgacgctct tctcctatag gagtttagga      900
gccgaaccgc accgtacga ggaatgggtt gacaagttct ctgagcgcat catcccagtg       960
acggaagaag ggattgagta ccagtggggc aacaacccgc cggtctgcct gtgggcgcaa     1020
ctgacgaccg agggcaaacc ccatggctgg ccacatgaaa tcattcagta ctattatgga     1080
ctataccccg ccgccactat tgccgcagta tccggggcga gtctgatggc cctcctaact     1140
ctggcggcca catgctgcat gctggccacc gcgaggagaa agtgcctaac accgtacgcc     1200
ctgacgccag gagcggtggt accgttgaca ctggggctgc tttgctgcgc accgagggcg     1260
aatgca                                                                1266
```

```
<210> SEQ ID NO 45
<211> LENGTH: 1938
<212> TYPE: DNA
<213> ORGANISM: Artificial Sequence
<220> FEATURE:
<223> OTHER INFORMATION: Envelope-MLV 10A1

<400> SEQUENCE: 45
```

```
atggaaggtc cagcgttctc aaaacccctt aaagataaga ttaacccgtg gaagtcctta       60
atggtcatgg gggtctattt aagagtaggg atggcagaga gcccccatca ggtctttaat      120
gtaacctgga gagtcaccaa cctgatgact gggcgtaccg ccaatgccac ctcccttta      180 ggaactgtac aagatgcctt cccaagatta tattttgatc tatgtgatct ggtcggagaa      240
gagtgggacc cttcagacca ggaaccatat gtcgggtatg ctgcaaata ccccggaggg      300 agaaagcgga cccggacttt tgactttttac gtgtgccctg ggcataccgt aaaatcgggg      360
tgtggggggc aagagagggg ctactgtggt gaatggggtt gtgaaaccac cggacaggct      420
tactggaagc ccacatcatc atgggaccta atctcccta agcgcggtaa cacccccctgg      480 gacacgggat gctccaaaat ggcttgtggc ccctgctacg acctctccaa agtatccaat      540
tccttccaag gggctactcg aggggggcaga tgcaaccctc tagtcctaga attcactgat      600
gcaggaaaaa aggctaattg ggacgggccc aaatcgtggg gactgagact gtaccggaca      660
ggaacagatc ctattaccat gttctccctg acccgccagg tcctcaatat agggccccgc      720
atccccattg gcctaatccc cgtgatcact ggtcaactac cccctcccg acccgtgcag      780 atcaggctcc ccaggcctcc tcagcctcct cctacaggcg cagcctctat agtccctgag      840
actgccccac cttctcaaca acctgggacg ggagacaggc tgctaaacct ggtagaagga      900
gcctatcagg cgcttaacct caccaatccc gacaagaccc aagaatgttg gctgtgctta      960
gtgtcgggac ctcctatta cgaaggagta gcggtcgtgg gcacttatac caatcattct     1020
accgccccgg ccagctgtac ggccacttcc aacataagc ttaccctatc tgaagtgaca      1080
ggacagggcc tatgcatggg agcactacct aaaactcacc aggccttatg taacaccacc     1140
caaagtgccg gctcaggatc ctactacctt gcagcacccg ctggaacaat gtgggcttgt     1200
agcactggat tgactccctg cttgtccacc acgatgctca atctaaccac agactattgt     1260
gtattagttg agctctggcc cagaataatt taccactccc ccgattatat gtatggtcag     1320
cttgaacagc gtaccaaata taagagggag ccagtatcgt tgaccctggc ccttctgcta     1380
```

-continued

```
ggaggattaa ccatgggagg gattgcagct ggaatagggga cggggaccac tgccctaatc        1440
aaaacccagc agtttgagca gcttcacgcc gctatccaga cagacctcaa cgaagtcgaa        1500
aaatcaatta ccaacctaga aaagtcactg acctcgttgt ctgaagtagt cctacagaac        1560
cgaagaggcc tagatttgct cttcctaaaa gaggggaggtc tctgcgcagc cctaaaagaa       1620
gaatgttgtt tttatgcaga ccacacggga ctagtgagag acagcatggc caaactaagg        1680
gaaaggctta atcagagaca aaaactattt gagtcaggcc aaggttggtt cgaagggcag        1740
tttaatagat cccctggtt taccacctta atctccacca tcatgggacc tctaatagta         1800
ctcttactga tcttactctt tggaccctgc attctcaatc gattggtcca atttgttaaa        1860
gacaggatct cagtggtcca ggctctggtt ttgactcaac aatatcacca gctaaaacct        1920
atagagtacg agccatga                                                      1938
```

```
<210> SEQ ID NO 46
<211> LENGTH: 2030
<212> TYPE: DNA
<213> ORGANISM: Artificial Sequence
<220> FEATURE:
<223> OTHER INFORMATION: Envelope-Ebola

<400> SEQUENCE: 46
```

```
atgggtgtta caggaatatt gcagttacct cgtgatcgat tcaagaggac atcattcttt          60
ctttgggtaa ttatcctttt ccaaagaaca ttttccatcc cacttggagt catccacaat         120
agcacattac aggttagtga tgtcgacaaa ctggtttgcc gtgacaaact gtcatccaca        180
aatcaattga gatcagttgg actgaatctc gaagggaatg gagtggcaac tgacgtgcca         240
tctgcaacta aaagatgggg cttcaggtcc ggtgtcccac caaaggtggt caattatgaa        300
gctggtgaat gggctgaaaa ctgctacaat cttgaaatca aaaaacctga cgggagtgag         360
tgtctaccag cagcgccaga cgggattcgg ggcttccccc ggtgccggta tgtgcacaaa        420
gtatcaggaa cgggaccgtg tgccggagac tttgccttcc acaaagaggg tgctttcttc        480
ctgtatgacc gacttgcttc cacagttatc taccgaggaa cgactttcgc tgaaggtgtc        540
gttgcatttc tgatactgcc ccaagctaag aaggacttct tcagctcaca ccccttgaga        600
gagccggtca atgcaacgga ggaccgtct agtggctact attctaccac aattagatat          660
caagctaccg gttttggaac caatgagaca gagtatttgt tcgaggttga caatttgacc         720
tacgtccaac ttgaatcaag attcacacca cagtttctgc tccagctgaa tgagacaata         780
tatacaagtg ggaaaaggag caataccacg ggaaaactaa tttggaaggt caaccccgaa         840
attgatacaa caatcgggga gtgggccttc tgggaaacta aaaaaacctc actagaaaaa        900
ttcgcagtga gagttgtct ttcacagctg tatcaaacag agccaaaaac atcagtggtc          960
agagtccggc gcgaacttct tccgacccag ggaccaacac aacaactgaa gaccacaaaa       1020
tcatggcttc agaaaattcc tctgcaatgg ttcaagtgca cagtcaagga agggaagctg       1080
cagtgtcgca tctgacaacc cttgccacaa tctccacgag tcctcaaccc cccacaacca       1140
aaccaggtcc ggacaacagc acccacaata caccgtgta taaacttgac atctctgagg         1200
caactcaagt tgaacaacat caccgcagaa cagacaacga cagcacagcc tccgacactc       1260
cccccgccac gaccgcagcc ggacccctaa aagcagagaa caccaacacg agcaagggta       1320
ccgacctcct ggaccccgcc accacaacaa gtccccaaaa ccacagcgag accgctggca       1380
acaacaacac tcatcaccaa gataccggag aagagagtgc cagcagcggg aagctaggct       1440
taattaccaa tactattgct ggagtcgcag gactgatcac aggcgggagg agagctcgaa       1500
```

-continued

```
gagaagcaat tgtcaatgct caacccaaat gcaaccctaa tttacattac tggactactc    1560
aggatgaagg tgctgcaatc ggactggcct ggataccata tttcgggcca gcagccgagg    1620
gaatttacat agaggggctg atgcacaatc aagatggttt aatctgtggg ttgagacagc    1680
tggccaacga gacgactcaa gctcttcaac tgttcctgag agccacaacc gagctacgca    1740
ccttttcaat cctcaaccgt aaggcaattg atttcttgct gcagcgatgg ggcggcacat    1800
gccacatttt gggaccggac tgctgtatcg aaccacatga ttggaccaag aacataacag    1860
acaaaattga tcagattatt catgattttg ttgataaaac ccttccggac cagggggaca    1920
atgacaattg gtggacagga tggagacaat ggataccggc aggtattgga gttacaggcg    1980
ttataattgc agttatcgct ttattctgta tatgcaaatt tgtctttttag               2030
```

```
<210> SEQ ID NO 47
<211> LENGTH: 237
<212> TYPE: DNA
<213> ORGANISM: Artificial Sequence
<220> FEATURE:
<223> OTHER INFORMATION: Polymerase III shRNA promoters-U6 promoter

<400> SEQUENCE: 47
tttcccatga ttccttcata tttgcatata cgatacaagg ctgttagaga gataattgga      60
attaatttga ctgtaaacac aaagatatta gtacaaaata cgtgacgtag aaagtaataa     120
tttcttgggt agtttgcagt tttaaaatta tgttttaaaa tggactatca tatgcttacc     180
gtaacttgaa agtatttcga tttcttggct ttatatatct tgtggaaagg acgaaac        237
```

```
<210> SEQ ID NO 48
<211> LENGTH: 243
<212> TYPE: DNA
<213> ORGANISM: Artificial Sequence
<220> FEATURE:
<223> OTHER INFORMATION: Polymerase III shRNA promoters-7SK promoter

<400> SEQUENCE: 48
ctgcagtatt tagcatgccc cacccatctg caaggcattc tggatagtgt caaaacagcc      60
ggaaatcaag tccgtttatc tcaaacttta gcattttggg aataaatgat atttgctatg     120
ctggttaaat tagattttag ttaaatttcc tgctgaagct ctagtacgat aagcaacttg     180
acctaagtgt aaagttgaga tttccttcag gtttatatag cttgtgcgcc gcctggctac     240
ctc                                                                   243
```

```
<210> SEQ ID NO 49
<211> LENGTH: 21
<212> TYPE: DNA
<213> ORGANISM: Artificial Sequence
<220> FEATURE:
<223> OTHER INFORMATION: FDPS target sequence #1

<400> SEQUENCE: 49
gtcctggagt acaatgccat t                                                21
```

```
<210> SEQ ID NO 50
<211> LENGTH: 21
<212> TYPE: DNA
<213> ORGANISM: Artificial Sequence
<220> FEATURE:
<223> OTHER INFORMATION: FDPS target sequence #2

<400> SEQUENCE: 50
```

-continued gcaggatttc gttcagcact t                                         21

<210> SEQ ID NO 51
<211> LENGTH: 21
<212> TYPE: DNA
<213> ORGANISM: Artificial Sequence
<220> FEATURE:
<223> OTHER INFORMATION: FDPS target sequence #3

<400> SEQUENCE: 51
gccatgtaca tggcaggaat t                                         21

<210> SEQ ID NO 52
<211> LENGTH: 21
<212> TYPE: DNA
<213> ORGANISM: Artificial Sequence
<220> FEATURE:
<223> OTHER INFORMATION: FDPS target sequence #4

<400> SEQUENCE: 52
gcagaaggag gctgagaaag t                                         21

<210> SEQ ID NO 53
<211> LENGTH: 1542
<212> TYPE: DNA
<213> ORGANISM: Artificial Sequence
<220> FEATURE:
<223> OTHER INFORMATION: Lenti-BTN3A1(LV-BTN3A1, lentivirus expressing
      BTN3A1)

<400> SEQUENCE: 53
atgaaaatgg caagtttcct ggccttcctt ctgctcaact ttcgtgtctg cctccttttg      60
cttcagctgc tcatgcctca ctcagctcag ttttctgtgc ttggaccctc tgggcccatc     120
ctggccatgg tgggtgaaga cgctgatctg ccctgtcacc tgttcccgac catgagtgca     180
gagaccatgg agctgaagtg ggtgagttcc agcctaaggc aggtggtgaa cgtgtatgca     240
gatggaaagg aagtggaaga caggcagagt gcaccgtatc gagggagaac ttcgattctg     300
cgggatggca tcactgcagg gaaggctgct ctccgaatac acaacgtcac agcctctgac     360
agtggaaagt acttgtgtta tttccaagat ggtgacttct atgaaaaagc cctggtggag     420
ctgaaggttg cagcactggg ttctgatctt cacgttgatg tgaagggtta caaggatgga     480
gggatccatc tggagtgcag gtccactggc tggtacccc aaccccaaat acagtggagc     540
aacaacaagg agagaacat cccgactgtg gaagcacctg tggttgcaga cggagtgggc     600
ctgtatgcag tagcagcatc tgtgatcatg agaggcagct ctggggaggg tgtatcctgt     660
accatcagaa gttccctcct cggcctggaa aagacagcca gcatttccat cgcagacccc     720
ttcttcagga gcgcccagag gtggatcgcc gccctggcag ggaccctgcc tgtcttgctg     780
ctgcttcttg ggggagccgg ttacttcctg tggcaacagc aggaggaaaa aaagactcag     840
ttcagaaaga aaagagaga gcaagagttg agagaaatgg catggagcac aatgaagcaa     900
gaacaaagca caagagtgaa gctcctggag gaactcagat ggagaagtat ccagtatgca     960
tctcggggag agagacattc agcctataat gaatggaaaa aggccctctt caagcctgcg    1020
gatgtgattc tggatccaaa aacagcaaac cccatcctcc ttgtttctga ggaccagagg    1080
agtgtgcagc gtgccaagga gccccaggat ctgccagaca accctgagag atttaattgg    1140
cattattgtg ttctcggctg tgagagcttc atatcaggga cacattactg ggaggtggag    1200 gtagggggaca ggaaagagtg gcatatagggg gtgtgcagta agaatgtgca gagaaaaggc    1260

```
tgggtcaaaa tgacacctga gaatggattc tggactatgg ggctgactga tgggaataag   1320
tatcggactc taactgagcc cagaaccaac ctgaaacttc ctaagccccc taagaaagtg   1380
ggggtcttcc tggactatga gactggagat atctcattct acaatgctgt ggatggatcg   1440
catattcata ctttcctgga cgtctccttc tctgaggctc tatatcctgt tttcagaatt   1500
ttgaccttgg agcccacggc cctgactatt tgtccagcgt ga                      1542
```

```
<210> SEQ ID NO 54
<211> LENGTH: 1755
<212> TYPE: DNA
<213> ORGANISM: Artificial Sequence
<220> FEATURE:
<223> OTHER INFORMATION: Lenti-BTN3A3  (R381H)

<400> SEQUENCE: 54
```

```
atgaaaatgg caagttccct ggctttcctt ctgctcaact ttcatgtctc cctcttcttg     60
gtccagctgc tcactccttg ctcagctcag ttttctgtgc ttggaccctc tgggcccatc    120
ctggccatgg tgggtgaaga cgctgatctg ccctgtcacc tgttcccgac catgagtgca    180
gagaccatgg agctgaggtg ggtgagttcc agcctaaggc aggtggtgaa cgtgtatgca    240
gatggaaagg aagtggaaga caggcagagt gcaccgtatc gagggagaac ttcgattctg    300
cgggatggca tcactgcagg gaaggctgct ctccgaatac acaacgtcac agcctctgac    360
agtggaaagt acttgtgtta tttccaagat ggtgacttct acgaaaaagc cctggtggag    420
ctgaaggttg cagcattggg ttctgatctt cacattgaag tgaagggtta tgaggatgga    480
gggatccatc tggagtgcag gtccactggc tggtacccccc aaccccaaat aaagtggagc    540
gacaccaagg agagaacat cccggctgtg gaagcacctg tggttgcaga tggagtgggc     600
ctgtatgcag tagcagcatc tgtgatcatg agaggcagct ctggtggggg tgtatcctgc    660
atcatcagaa attccctcct cggcctggaa aagacagcca gcatatccat cgcagacccc    720
ttcttcagga gcgcccagcc ctggatcgcg ccctggcag ggaccctgcc tatctcgttg     780
ctgcttctcg caggagccag ttacttcttg tggagacaac agaaggaaaa aattgctctg    840
tccagggaga cagaaagaga gcgagagatg aaagaaatgg gatacgctgc aacagagcaa    900
gaaataagcc taagagagaa gctccaggag gaactcaagt ggaggaaaat ccagtacatg    960
gctcgtggag agaagtcttt ggcctatcat gaatggaaaa tggcccctct caaacctgcg   1020
gatgtgattc tggatccaga cacggcaaac gccatcctcc ttgtttctga ggaccagagg   1080
agtgtgcagc gtgctgaaga gccgcgggat ctgccagaca accctgagag atttgaatgg   1140
cactactgtg tccttggctg tgaaaacttc acatcaggga gacattactg ggaggtggaa   1200
gtgggggaca gaaagagtg gcatattggg gtatgtagta agaacgtgga gaggaaaaaa   1260
ggttgggtca aaatgacacc ggagaacgga tactggacta tgggcctgac tgatgggaat   1320
aagtatcggg ctctcactga gcccagaacc aacctgaaac ttcctgagcc tcctaggaaa   1380
gtggggatct tcctggacta tgagactgga gagatctcgt ctataatgc cacagatgga    1440 tctcatatct acacctttcc gcacgcctct ttctctgagc ctctatatcc tgttttcaga   1500
attttgacct tggagcccac tgccctgacc atttgcccaa taccaaaaga gtagagagt    1560 tcccccgatc ctgacctagt gcctgatcat tccctggaga caccactgac cccgggctta   1620
gctaatgaaa gtgggagcc tcaggctgaa gtaacatctc tgcttctccc tgcccaccct    1680
ggagctgagg tctcccttc tgcaacaacc aatcagaacc ataagctaca ggcacgcact    1740
gaagcacttt actga                                                    1755
```

-continued

```
<210> SEQ ID NO 55
<211> LENGTH: 2292
<212> TYPE: DNA
<213> ORGANISM: Artificial Sequence
<220> FEATURE:
<223> OTHER INFORMATION: BTN3A3-FDPSsh-IL-2 (BTN3A3 (R381H) T2A IL-2)

<400> SEQUENCE: 55
atgaaaatgg caagttccct ggctttcctt ctgctcaact ttcatgtctc cctcttcttg      60
gtccagctgc tcactccttg ctcagctcag tttctgtgc ttggaccctc tgggcccatc      120
ctggccatgt ggggtgaaga cgctgatctg ccctgtcacc tgttcccgac catgagtgca      180
gagaccatgg agctgaggtg ggtgagttcc agcctaaggc aggtggtgaa cgtgtatgca      240
gatggaaagg aagtggaaga caggcagagt gcaccgtatc gagggagaac ttcgattctg      300
cgggatggca tcactgcagg gaaggctgct ctccgaatac acaacgtcac agcctctgac      360 agtgaaagt acttgtgtta tttccaagat ggtgacttct acgaaaaagc cctggtggag      420
ctgaaggttg cagcattggg ttctgatctt cacattgaag tgaagggtta tgaggatgga      480
gggatccatc tggagtgcag gtccactggc tggtacccc aacccaaat aaagtggagc      540 gacaccaagg agagaacat cccggctgtg gaagcacctg tggttgcaga tggagtgggc      600
ctgtatgcag tagcagcatc tgtgatcatg agaggcagct ctggtggggg tgtatcctgc      660
atcatcagaa attccctcct cggcctggaa aagacagcca gcatatccat cgcagacccc      720
ttcttcagga gcgcccagcc ctggatcgcg gccctggcag ggaccctgcc tatctcgttg      780
ctgcttctcg caggagccag ttacttcttg tggagacaac agaaggaaaa aattgctctg      840
tccagggaga cagaaagaga gcgagagatg aaagaaatgg gatacgctgc aacagagcaa      900
gaaataagcc taagagagaa gctccaggag gaactcaagt ggaggaaat ccagtacatg      960 gctcgtggag agaagtcttt ggcctatcat gaatggaaaa tggccctctt caaacctgcg     1020
gatgtgattc tggatccaga cacggcaaac gccatcctcc ttgtttctga ggaccagagg     1080
agtgtgcagc gtgctgaaga gccgcgggat ctgccagaca accctgagag atttgaatgg     1140
cactactgtg tccttggctg tgaaaacttc acatcaggga gacattactg ggaggtggaa     1200
gtgggggaca gaaagagtg gcatattggg gtatgtagta agaacgtgga gaggaaaaaa     1260
ggttgggtca aaatgacacc ggagaacgga tactggacta tgggcctgac tgatgggaat     1320
aagtatcggg ctctcactga gcccagaacc aacctgaaac ttcctgagcc tcctaggaaa     1380
gtggggatct tcctggacta tgagactgga gagatctcgt tctataatgc cacagatgga     1440
tctcatatct acaccttcc gcacgcctct ttctctgagc tctatatcc tgttttcaga     1500 attttgacct tggagcccac tgccctgacc atttgcccaa taccaaaaga gtagagagt     1560 tcccccgatc ctgacctagt gcctgatcat tccctggaga caccactgac cccgggctta     1620
gctaatgaaa gtggggagcc tcaggctgaa gtaacatctc tgcttctccc tgcccaccct     1680
ggagctgagg tctccccttc tgcaacaacc aatcagaacc ataagctaca ggcacgcact     1740
gaagcacttt accgtagacg aaagcgcgga agcggagagg cagaggaag tctgctaaca     1800 tgcggtgacg tcgaggagaa tcctggacct atgtacagga tgcaactcct gtcttgcatt     1860
gcactaagtc ttgcacttgt cacaaacagt gcacctactt caagttctac aaagaaaaca     1920
cagctacaac tggagcattt actgctggat ttacagatga ttttgaatgg aattaataat     1980
tacaagaatc ccaaactcac caggatgctc acatttaagt tttacatgcc caagaaggcc     2040
```

```
acagaactga aacatcttca gtgtctagaa gaagaactca aacctctgga ggaagtgcta    2100
aatttagctc aaagcaaaaa ctttcactta agacccaggg acttaatcag caatatcaac    2160
gtaatagttc tggaactaaa gggatctgaa acaacattca tgtgtgaata tgctgatgag    2220
acagcaacca ttgtagaatt tctgaacaga tggattacct tttgtcaaag catcatctca    2280
acactgactt ga                                                        2292

<210> SEQ ID NO 56
<211> LENGTH: 462
<212> TYPE: DNA
<213> ORGANISM: Artificial Sequence
<220> FEATURE:
<223> OTHER INFORMATION: Cytokine IL-2 (IL-2, or IL2)

<400> SEQUENCE: 56
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga tttttgaatgg aattaataat tacaagaatc ccaaactcac caggatgctc     180
acatttaagt tttacatgcc caagaaggcc acagaactga aacatcttca gtgtctagaa     240
gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                       462

<210> SEQ ID NO 57
<211> LENGTH: 489
<212> TYPE: DNA
<213> ORGANISM: Artificial Sequence
<220> FEATURE:
<223> OTHER INFORMATION: Cytokine IL-15(IL15, or IL-15)

<400> SEQUENCE: 57
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca aagtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca aagaatgtga ggaactggag     420
gaaaaaaata ttaaagaatt tttgcagagt tttgtacata ttgtccaaat gttcatcaac     480
acttcttga                                                            489

<210> SEQ ID NO 58
<211> LENGTH: 757
<212> TYPE: DNA
<213> ORGANISM: Artificial Sequence
<220> FEATURE:
<223> OTHER INFORMATION: Cytokine IL-18(IL-18, or IL18)

<400> SEQUENCE: 58
ctggacagtc agcaaggaat tgtctcccag tgcattttgc cctcctggct gccaactctg      60
gctgctaaag cggctgccac ctgctgcagt ctacacagct cgggaagag gaaaggaacc     120 tcagaccttc cagatcgctt cctctcgcaa caaactattt gtcgcaggaa taaagatggc     180
```

```
tgctgaacca gtagaagaca attgcatcaa ctttgtggca atgaaattta ttgacaatac      240
gctttacttt atagctgaag atgatgaaaa cctggaatca gattactttg gcaagcttga      300
atctaaatta tcagtcataa gaaatttgaa tgaccaagtt ctcttcattg accaaggaaa      360
tcggcctcta tttgaagata tgactgattc tgactgtaga gataatgcac cccggaccat      420
atttattata agtatgtata aagatagcca gcctagaggt atggctgtaa ctatctctgt      480
gaagtgtgag aaaatttcaa ctctctcctg tgagaacaaa attatttcct ttaaggaaat      540
gaatcctcct gataacatca aggatacaaa aagtgacatc atattctttc agagaagtgt      600
cccaggacat gataataaga tgcaatttga atcttcatca tacgaaggat actttctagc      660
ttgtgaaaaa gagagagacc tttttaaact cattttgaaa aaagaggatg aattggggga      720
tagatctata atgttcactg ttcaaaacga agactag                               757
```

<210> SEQ ID NO 59
<211> LENGTH: 279
<212> TYPE: DNA
<213> ORGANISM: Artificial Sequence
<220> FEATURE:
<223> OTHER INFORMATION: Lenti-AFP tumor-specific promoter (BTN3A3)
      [LTSP-AFP BTN3A3]

<400> SEQUENCE: 59

```
cgatagtttg aggagaatat ttgttatatt tgcaaaataa aataagtttg caagtttttt       60
ttttctgccc caaagagctc tgtgtccttg aacataaaat acaaataacc gctatgctgt      120
taattattgg caaatgtccc attttcaacc taaggaaata ccataaagta acagatatac      180
caacaaaagg ttactagtta acaggcattg cctgaaaaga gtataaaaga atttcagcat      240
gattttccat attgtgcttc caccactgcc aataacacg                             279
```

<210> SEQ ID NO 60
<211> LENGTH: 618
<212> TYPE: DNA
<213> ORGANISM: Artificial Sequence
<220> FEATURE:
<223> OTHER INFORMATION: Cytokine IL-23(IL-23, or IL23) alpha subunit
      p19

<400> SEQUENCE: 60

```
agagccagcc agatttgaga agaaggcaaa aagatgctgg ggagcagagc tgtaatgctg       60
ctgttgctac tgccctggac agctcagggc agagctgtgc ctgggggcag cagccctgcc      120
tggactcagt gccagcagct ttcacagaag ctctgcacac tggcctggag tgcacatcca      180
ctagtgggac acatggatct aagagaagag ggagatgaag agactacaaa tgatgttccc      240
catatccagt gtggagatgg ctgtgacccc caaggactca gggacaacag tcagttctgc      300
ttgcaaagga tccaccaggg tctgattttt tatgagaagc tgctaggatc ggatattttc      360
acaggggagc cttctctgct ccctgatagc cctgtgggcc agcttcatgc ctccctactg      420
ggcctcagcc aactcctgca gcctgagggt caccactggg agactcagca gattccaagc      480
ctcagtccca gccagccatg gcagcgtctc cttctccgct tcaagatcct tcgcagcctc      540
caggcctttg tggccgtagc cgcccgggtc tttgcccatg agcagcaac cctgagtccc      600 taaaggcagc agctcaag                                                    618
```

<210> SEQ ID NO 61
<211> LENGTH: 888
<212> TYPE: DNA

<213> ORGANISM: Artificial Sequence
<220> FEATURE:
<223> OTHER INFORMATION: Cytokine IL-36A(IL-36A, or IL36A) alpha

<400> SEQUENCE: 61

```
aaaacccaag tgcagtagaa gccattgttc ataatggtag ggatacaggg tccttcgtaa      60
cagattatca gtgtggccta tgctggaaag tctggtgacc tctgattttt tttgcttcca     120
ggtctttggc cttggcactc tttgtcatat tagagttcct gggtctaggc ctgggcagga     180
ttcataggtg cagctgcttc tgctggaggt agactgcatc caacaaagta agggtgctgg     240
gtgagttctg ggagtataga ttctgactgg ggtcactgct gggctggccg ccagtctttc     300
atctgaccca gggttaaact gtggcttggg actgactcag gtcctctctt ggggtcggtc     360
tgcacataaa aggactccta tccttggcag ttctgaaaca acaccaccac aatggaaaaa     420
gcattgaaaa ttgacacacc tcagcagggg agcattcagg atatcaatca tcgggtgtgg     480
gttcttcagg accagacgct catagcagtc ccgaggaagg accgtatgtc tccagtcact     540
attgccttaa tctcatgccg acatgtggag acccttgaga aagacagagg gaaccccatc     600
tacctgggcc tgaatggact caatctctgc ctgatgtgtg ctaaagtcgg ggaccagccc     660
acactgcagc tgaaggaaaa ggatataatg gatttgtaca accaacccga gcctgtgaag     720
tcctttctct tctaccacag ccagagtggc aggaactcca ccttcgagtc tgtggctttc     780
cctggctggt tcatcgctgt cagctctgaa ggaggctgtc ctctcatcct tacccaagaa     840
ctggggaaag ccaacactac tgactttggg ttaactatgc tgttttaa             888
```

<210> SEQ ID NO 62
<211> LENGTH: 1186
<212> TYPE: DNA
<213> ORGANISM: Artificial Sequence
<220> FEATURE:
<223> OTHER INFORMATION: Cytokine IL-36B(IL-36B, or IL36B) beta

<400> SEQUENCE: 62

```
cacgggttcc tccccactct gtctttctca cctctccttc acttttccta gcctcctcac      60
caccatctga tctatcttgt tctcttcaca aaaggctctg aagacatcat gaacccacaa     120
cgggaggcag cacccaaatc ctatgctatt cgtgattctc gacagatggt gtgggtcctg     180
agtggaaatt ctttaatagc agctcctctt agccgcagca ttaagcctgt cactcttcat     240
ttaatagcct gtagagacac agaattcagt gacaaggaaa agggtaatat ggtttacctg     300
ggaatcaagg gaaaagatct ctgtctcttc tgtgcagaaa ttcagggcaa gcctactttg     360
cagcttaagc ttcagggctc ccaagataac atagggaagg acacttgctg gaaactagtt     420
ggaattcaca catgcataaa cctggatgtg agagagagct gcttcatggg aacccttgac     480
caatggggaa taggagtggg tagaaagaag tggaagagtt cctttcaaca tcaccatctc     540
aggaagaagg acaaagattt ctcatccatg cggaccaaca taggaatgcc aggaaggatg     600
tagaaataag gggaggaaga ttcccatctc tacaatcttt gagtgggttt gctatcaatg     660
aaatgctaca aatggaataa gttgcagaaa ttttttctctt ttcttgggtt ctggagagtt     720
tgtaaaacaa ggacactatg tatttttaaa gagttggtaa atcttacctg taaagctaga     780
gaaggtcgga gtctttttag gagtagattt ggactacata acctgtaaat gtgttttgtc     840
cagtccttag agtgtttttt aaaaaattgt aaagtcaagg ttttcatgaa aaatgggaag     900
atcagacaac attgctcctg aattcccaca gagcagcaag ctactagagc tcaatctgtt     960
atttcttttc ctgatgtaca ggggttaagt cctatggaag aaacagcaga attattcaaa    1020
```

```
attatttaca taatgtgcaa ttattcacta gagcatgagg agtgaaacgc tctgtttagt      1080
atgtataact taaaaggaac acatacaatt aaaagtaatt gaaagacatt tcttcttaaa      1140
aattctataa tcttacactg gtaaaataaa ctagtttttc ccatgt                     1186
```

```
<210> SEQ ID NO 63
<211> LENGTH: 1107
<212> TYPE: DNA
<213> ORGANISM: Artificial Sequence
<220> FEATURE:
<223> OTHER INFORMATION: Cytokine IL-36G (IL-36G, or IL-36G) gamma

<400> SEQUENCE: 63
gaagctgctg gagccacgat tcagtcccct ggactgtaga taaagaccct ttcttgccag       60
gtgctgagac aaccacacta tgagaggcac tccaggagac gctgatggtg gaggaagggc      120
cgtctatcaa tcaatcactg ttgctgttat cacatgcaag tatccagagg ctcttgagca      180
aggcagaggg gatcccattt atttgggaat ccagaatcca gaaatgtgtt tgtattgtga      240
gaaggttgga gaacagccca cattgcagct aaaagagcag aagatcatgg atctgtatgg      300
ccaacccgag cccgtgaaac ccttcctttt ctaccgtgcc aagactggta ggacctccac      360
ccttgagtct gtggccttcc cggactggtt cattgcctcc tccaagagag accagcccat      420
cattctgact tcagaacttg ggaagtcata caacactgcc tttgaattaa atataaatga      480
ctgaactcag cctagaggtg gcagcttggt ctttgtctta aagtttctgg ttcccaatgt      540
gttttcgtct acattttctt agtgtcattt tcacgctggt gctgagacag gggcaaggct      600
gctgttatca tctcatttta taatgaagaa gaagcaatta cttcatagca actgaagaac      660
aggatgtggc ctcagaagca ggagagctgg gtggtataag gctgtcctct caagctggtg      720
ctgtgtaggc cacaaggcat ctgcatgagt gactttaaga ctcaaagacc aaacactgag      780
ctttcttcta ggggtgggta tgaagatgct tcagagctca tgcgcgttac ccacgatggc      840
atgactagca cagagctgat ctctgtttct gttttgcttt attccctctt gggatgatat      900
catccagtct ttatatgttg ccaatatacc tcattgtgtg taatagaacc ttcttagcat      960
taagaccttg taaacaaaaa taattcttgt gttaagttaa atcatttttg tcctaattgt     1020
aatgtgtaat cttaaagtta aataaacttt gtgtatttat ataataataa agctaaaact     1080
gatataaaat aaagaaagag taaactg                                         1107
```

```
<210> SEQ ID NO 64
<211> LENGTH: 53
<212> TYPE: DNA
<213> ORGANISM: Artificial Sequence
<220> FEATURE:
<223> OTHER INFORMATION: FDPS shRNA sequence #4A

<400> SEQUENCE: 64
actttctcag cctccttctg cctcgaggca gaaggaggct gagaaagttt ttt             53
```

```
<210> SEQ ID NO 65
<211> LENGTH: 47
<212> TYPE: DNA
<213> ORGANISM: Artificial Sequence
<220> FEATURE:
<223> OTHER INFORMATION: FDPS shRNA sequence #4R

<400> SEQUENCE: 65
gcagaaggag gctgagaaag tgagctcact ttctcagcct ccttctg                    47
```

-continued

<210> SEQ ID NO 66
<211> LENGTH: 49
<212> TYPE: DNA
<213> ORGANISM: Artificial Sequence
<220> FEATURE:
<223> OTHER INFORMATION: FDPS shRNA sequence #4TT

<400> SEQUENCE: 66
gcagaaggag gctgagaaag tttactttct cagcctcctt ctgcttttt                 49

<210> SEQ ID NO 67
<211> LENGTH: 47
<212> TYPE: DNA
<213> ORGANISM: Artificial Sequence
<220> FEATURE:
<223> OTHER INFORMATION: FDPS sequence #4L

<400> SEQUENCE: 67
gcagaaggag gctgagaaag tactttctca gcctccttct gctttt                    47

<210> SEQ ID NO 68
<211> LENGTH: 116
<212> TYPE: DNA
<213> ORGANISM: Artificial Sequence
<220> FEATURE:
<223> OTHER INFORMATION: FDPS miR30 sequence #1

<400> SEQUENCE: 68
aaggtatatt gctgttgaca gtgagcgaca ctttctcagc ctccttctgc gtgaagccac     60
agatggcaga aggaggctga gaaagtgctg cctactgcct cggacttcaa ggggct        116

<210> SEQ ID NO 69
<211> LENGTH: 114
<212> TYPE: DNA
<213> ORGANISM: Artificial Sequence
<220> FEATURE:
<223> OTHER INFORMATION: FDPS miR30 sequence #3

<400> SEQUENCE: 69
aaggtatatt gctgttgaca gtgagcgaca ctttctcagc ctccttctgc gtgaagccac     60
agatggcaga agggctgaga aagtgctgcc tactgcctcg gacttcaagg ggct          114

<210> SEQ ID NO 70
<211> LENGTH: 53
<212> TYPE: DNA
<213> ORGANISM: Artificial Sequence
<220> FEATURE:
<223> OTHER INFORMATION: GGPS1 shRNA sequence #1

<400> SEQUENCE: 70
gcttgaagct aaagcctata actcgagtta taggctttag cttcaagctt ttt           53

<210> SEQ ID NO 71
<211> LENGTH: 53
<212> TYPE: DNA
<213> ORGANISM: Artificial Sequence
<220> FEATURE:
<223> OTHER INFORMATION: GGPS1 shRNA sequence #2

<400> SEQUENCE: 71
gtacattatc ttgaggatgt actcgagtac atcctcaaga taatgtactt ttt           53

<210> SEQ ID NO 72
<211> LENGTH: 53

```
<212> TYPE: DNA
<213> ORGANISM: Artificial Sequence
<220> FEATURE:
<223> OTHER INFORMATION: GGPS1 shRNA sequence 3

<400> SEQUENCE: 72
cctgagctag tagccttagt actcgagtac taaggctact agctcaggtt ttt            53

<210> SEQ ID NO 73
<211> LENGTH: 21
<212> TYPE: DNA
<213> ORGANISM: Artificial Sequence
<220> FEATURE:
<223> OTHER INFORMATION: GGPS1 target sequence #1

<400> SEQUENCE: 73
gcttgaagct aaagcctata a                                               21

<210> SEQ ID NO 74
<211> LENGTH: 21
<212> TYPE: DNA
<213> ORGANISM: Artificial Sequence
<220> FEATURE:
<223> OTHER INFORMATION: GGPS1 target sequence #2

<400> SEQUENCE: 74
gtacattatc ttgaggatgt a                                               21

<210> SEQ ID NO 75
<211> LENGTH: 21
<212> TYPE: DNA
<213> ORGANISM: Artificial Sequence
<220> FEATURE:
<223> OTHER INFORMATION: GGPS1 target sequence #3

<400> SEQUENCE: 75
cctgagctag tagccttagt a                                               21

<210> SEQ ID NO 76
<211> LENGTH: 53
<212> TYPE: DNA
<213> ORGANISM: Artificial Sequence
<220> FEATURE:
<223> OTHER INFORMATION: IDI1 shRNA sequence

<400> SEQUENCE: 76
gccagtggtg aaattaagat actcgagtat cttaatttca ccactggctt ttt            53

<210> SEQ ID NO 77
<211> LENGTH: 21
<212> TYPE: DNA
<213> ORGANISM: Artificial Sequence
<220> FEATURE:
<223> OTHER INFORMATION: IDI1 target sequence

<400> SEQUENCE: 77
gccagtggtg aaattaagat a                                               21

<210> SEQ ID NO 78
<211> LENGTH: 25
<212> TYPE: DNA
<213> ORGANISM: Artificial Sequence
<220> FEATURE:
<223> OTHER INFORMATION: Fam-labeled TaqMan probe

<400> SEQUENCE: 78
```

-continued

```
tagcatctcc tatctctggg tgccc                                              25

<210> SEQ ID NO 79
<211> LENGTH: 21
<212> TYPE: DNA
<213> ORGANISM: Artificial Sequence
<220> FEATURE:
<223> OTHER INFORMATION: FDPS forward primer

<400> SEQUENCE: 79
gtgctgactg aggatgagat g                                                  21

<210> SEQ ID NO 80
<211> LENGTH: 21
<212> TYPE: DNA
<213> ORGANISM: Artificial Sequence
<220> FEATURE:
<223> OTHER INFORMATION: FDPS reverse primer

<400> SEQUENCE: 80
ccggttatac ttgcctccaa t                                                  21

<210> SEQ ID NO 81
<211> LENGTH: 20
<212> TYPE: DNA
<213> ORGANISM: Artificial Sequence
<220> FEATURE:
<223> OTHER INFORMATION: Fam-labeled TaqMan probe

<400> SEQUENCE: 81
agcgggaaat cgtgcgtgac                                                    20

<210> SEQ ID NO 82
<211> LENGTH: 21
<212> TYPE: DNA
<213> ORGANISM: Artificial Sequence
<220> FEATURE:
<223> OTHER INFORMATION: Actin forward primer

<400> SEQUENCE: 82
ggacctgact gactacctca t                                                  21

<210> SEQ ID NO 83
<211> LENGTH: 22
<212> TYPE: DNA
<213> ORGANISM: Artificial Sequence
<220> FEATURE:
<223> OTHER INFORMATION: Actin reverse primer

<400> SEQUENCE: 83
cgtagcacag cttctcctta at                                                 22
```

METHODS AND COMPOSITIONS FOR THE ACTIVATION OF TUMOR CYTOTOXICITY VIA HUMAN GAMMA-DELTA T-CELLS

CROSS-REFERENCE TO RELATED APPLICATIONS

This application claims priority to: U.S. Provisional Patent Application No. 62/521,274, filed on Jun. 16, 2017, and entitled "Methods and Compositions for the Activation of Tumor Cytotoxicity Via Human Gamma-Delta T-Cells", and U.S. Provisional Patent Application No. 62/633,461, filed on Feb. 21, 2018, and entitled "Methods and Compositions for the Activation of Tumor Cytotoxicity Via Human Gamma-Delta T-Cells", which are each incorporated herein by reference.

FIELD

The present disclosure relates generally to the fields of gene therapy and immunotherapy, specifically in relation to increased activation and effector cell function of gamma delta ("GD") T cells.

BACKGROUND

Human T cells are distinguished on the basis of T cell receptor structure. The major populations, including CD4+ and CD8+ subsets, express a receptor composed of alpha and beta chains. A smaller subset expresses T cell receptor made from gamma and delta chains. Gamma delta ("GD") T cells make up 3-10% of circulating lymphocytes, and a Vδ2+ subset makes up 75% of GD T cells in blood. Vδ2+ cells recognize non-peptide epitopes and do not require antigen presentation by a major histocompatibility complex ("MHC") or human leukocyte antigen ("HLA"). The majority of Vδ2+ T cells also express a Vγ9 chain and are stimulated by exposure to 5-carbon pyrophosphate compounds that are intermediates in mevalonate and non-mevalonate sterol/isoprenoid synthesis pathways. The response to isopentenyl pyrophosphate (5-carbon) is nearly universal among healthy human beings.

Another subset of GD T cells, Vδ1+, make up a much smaller percentage of the T cells circulating in the blood, but Vδ+1 cells are most commonly found in the epithelial mucosa and the skin. Minor cell populations express other Vδ chains and may be associated with specific responses during allergy, transplantation or viral and bacterial diseases.

In general, GD T cells have several functions, including killing tumor cells and pathogen-infected cells. Stimulation through their unique T cell receptor ("TCR") composed of two glycoprotein chains, γ and δ that interact with CD3 complex proteins to create a functional TCR, improves the capacity for cellular cytotoxicity, cytokine secretion and other effector functions. The TCRs of GD T cells have unique specificities and the cells themselves occur in high clonal frequencies, thus allowing rapid innate-like responses to tumors and pathogens.

Bisphosphonate drugs and other inhibitors of farnesyl diphosphate synthase ("FDPS"), which are downstream from isopentenyl pyrophosphate ("IPP") in the mevalonate pathway (see, e.g., FIG. 1), have been used to treat various diseases, including cancers, specifically those involving bone metastasis. Bisphosphonate drugs include, for example, trade names such as Zometa® (Novartis), Actonel® (Procter & Gamble), Aredia® (Novartis) and Fosamax® (Merck).

Certain bisphosphonates have also been investigated for stimulation of GD T cells. This may be because inhibition of FDPS in myeloid or tumor cells, blocks the conversion of IPP to farnesyl diphosphate causing IPP to accumulate while simultaneously reducing levels of geranylgeranyl pyrophosphate ("GGPP"), a downstream product of FDPS that normally suppresses activation of the NLRP3 inflammasome pathway. The reduction in GGPP removes an inhibitor of the caspase-dependent inflammasome pathway and allows secretion of cytokines including interleukin-1 beta and interleukin-18, the latter being especially important for gamma delta T cell activation.

Thus, when FDPS is blocked, the increased IPP and decreased GGPP modify the myeloid or tumor cells and the modified cells gain an increased capacity for activating GD T cells and specifically the Vδ2+ subset. Activated Vδ2+ cells proliferate rapidly, express multiple cytokines and chemokines, and can function to cytotoxically destroy tumor cells or pathogen-infected cells. GD T cell effector activities include secretion of IFN-gamma, which activates macrophages and antigen-presenting cells, secretion of TNF-alpha among other cytokines and chemokines that activate other innate and acquired immune mechanisms, activation of granzyme B that attacks and destroys target cells and cell surface expression of FasL that triggers cellular apoptosis in Fas+ target cells.

A significant problem with traditional cancer treatment is that patients become insensitive to chemotherapy treatments. Chemo-resistant tumor cells in particular become very difficult to treat. As an alternative therapy to treat chemo-resistant patients, or as a primary therapy in place of chemotherapy and/or radiation therapy the present application proposes the use of a recombinant lentivirus to express genes at the tumor site, where manipulation of proteins that impact GD T cell activity may slow down tumor growth and activate the patient's own innate immune response to recognize and kill cancers.

SUMMARY OF THE INVENTION

In an aspect of the disclosure, a viral vector comprising first and second encoded genetic elements is disclosed. The first encoded genetic element comprises at least one small RNA capable of inhibiting production of at least one enzyme involved in the mevalonate pathway, and the second encoded genetic element comprises one of a butyrophilin family member, a cytokine, or a chemokine. In embodiments, the viral vector also includes a third encoded genetic element, wherein the third encoded genetic element comprises one of a butyrophilin family member, a cytokine, or a chemokine. In embodiments, the viral vector also includes a fourth encoded genetic element, wherein the fourth encoded genetic element comprises one of a butyrophilin family member, a cytokine, or a chemokine. In embodiments, the at least one enzyme is farnesyl diphosphate synthase (FDPS), geranylgeranyl-diphosphate synthase 1 (GGPS1), isopentyl-disphosphate delta isomerase 1 (IDI1), or farnesyl transferase (F-Tase). In embodiments, the first encoded genetic element comprises a microRNA or a shRNA.

In embodiments, the microRNA comprises a sequence having at least 80%, or at least 85%, or at least 90%, or at least 95% percent identity with:

(SEQ ID NO: 68)
AAGGTATATTGCTGTTGACAGTGAGCGACACTTTCTCAGCCTCCTTCTGC
GTGAAGCCACAGATGGCAGAAGGAGGCTGAGAAAGTGCTGCCTACTGCCT
CGGACTTCAAGGGGCT,
or (SEQ ID NO: 69)
AAGGTATATTGCTGTTGACAGTGAGCGACACTTTCTCAGCCTCCTTCTGC
GTGAAGCCACAGATGGCAGAAGGGCTGAGAAAGTGCTGCCTACTGCCTCG
GACTTCAAGGGGCT.

In embodiments, the microRNA comprises (SEQ ID NO: 68)
AAGGTATATTGCTGTTGACAGTGAGCGACACTTTCTCAGCCTCCTTCTGC
GTGAAGCCACAGATGGCAGAAGGAGGCTGAGAAAGTGCTGCCTACTGCCT
CGGACTTCAAGGGGCT,
or (SEQ ID NO: 69)
AAGGTATATTGCTGTTGACAGTGAGCGACACTTTCTCAGCCTCCTTCTGC
GTGAAGCCACAGATGGCAGAAGGGCTGAGAAAGTGCTGCCTACTGCCTCG
GACTTCAAGGGGCT.

In embodiments, the shRNA comprises a sequence having at least 80%, at least 81%, at least 82%, at least 83%, at least 84%, at least 85%, at least 86%, at least 87%, at least 88%, at least 89%, at least 90%, at least 95% or more than 95% percent identity with (SEQ ID NO: 1)
GTCCTGGAGTACAATGCCATTCTCGAGAATGGCATTGTACTCCAGGACTT
TTT;

(SEQ ID NO: 2)
GCAGGATTTCGTTCAGCACTTCTCGAGAAGTGCTGAACGAAATCCTGCTT
TTT;

(SEQ ID NO: 3)
GCCATGTACATGGCAGGAATTCTCGAGAATTCCTGCCATGTACATGGCTT
TTT;

(SEQ ID NO: 4)
GCAGAAGGAGGCTGAGAAAGTCTCGAGACTTTCTCAGCCTCCTTCTGCTT
TTT.

In embodiments, the shRNA comprises a sequence having at least 80%, at least 81%, at least 82%, at least 83%, at least 84%, at least 85%, at least 86%, at least 87%, at least 88%, at least 89%, at least 90%, at least 95% or more than 95% percent identity with SEQ ID NO: 64, SEQ ID NO: 65, SEQ ID NO: 66, SEQ ID NO: 67, SEQ ID NO: 70, SEQ ID NO: 71, SEQ ID NO: 72, or SEQ ID NO: 76.

In embodiments, the shRNA comprises:

(SEQ ID NO: 1)
GTCCTGGAGTACAATGCCATTCTCGAGAATGGCATTGTACTCCAGGACTT
TTT;

(SEQ ID NO: 2)
GCAGGATTTCGTTCAGCACTTCTCGAGAAGTGCTGAACGAAATCCTGCTT
TTT;

(SEQ ID NO: 3)
GCCATGTACATGGCAGGAATTCTCGAGAATTCCTGCCATGTACATGGCTT
TTT;
or (SEQ ID NO: 4)
GCAGAAGGAGGCTGAGAAAGTCTCGAGACTTTCTCAGCCTCCTTCTGCTT
TTT.

In embodiments, the shRNA comprises SEQ ID NO: 64, SEQ ID NO: 65, SEQ ID NO: 66, SEQ ID NO: 67, SEQ ID NO: 70, SEQ ID NO: 71, SEQ ID NO: 72, or SEQ ID NO: 76.

In embodiments, the butyrophilin family member comprises BTN3A3, BTN3A2, or BTN3A1 or variants thereof. In embodiments, the butyrophilin family member comprises BTN3A3 (R381H). In embodiments, the cytokine comprises IL-1, IL-1B, IL-2, IL-4, IL-7, IL-12, IL-15, IL-17, IL-18, IL-23, IL-33, IL-36, TNF-α, or interferon-y. In embodiments, the chemokine comprises a CC chemokine, a CXC chemokine, a CX3C chemokine, a C chemokine, or a XC chemokine. In further embodiments, the CC chemokine comprises RANTES. In embodiments, the viral vector is a lentiviral vector.

In another aspect, a lentiviral vector system for expressing a lentiviral particle is disclosed. The system includes a lentiviral vector as detailed herein: at least one envelope plasmid for expressing an envelope protein optimized for infecting a target cell; and at least one helper plasmid for expressing gag, pol, and rev genes, wherein when the lentiviral vector, the at least one envelope plasmid, and the at least one helper plasmid are transfected into a packaging cell, the lentiviral particle is produced by the packaging cell, wherein the lentiviral particle is capable of infecting the target cell and inhibiting the at least one enzyme involved in the mevalonate pathway within the target cell.

In another aspect, a lentiviral particle capable of infecting a target cell is disclosed. The lentiviral particle comprises an envelope protein optimized for infecting the target cell, and a lentiviral vector as detailed herein. In embodiments, the target cell is a cancer cell.

In another aspect, a method of activating a gamma delta (GD) T cell is disclosed. The method includes infecting, or having infected, in the presence of the GD T cell, a target cell with a lentiviral particle, wherein the lentiviral particle comprises a viral vector comprising first and second encoded genetic elements wherein the first encoded genetic element comprises at least one small RNA capable of inhibiting production of at least one enzyme involved in the mevalonate pathway, and the second encoded genetic element comprises one of a butyrophilin family member, a cytokine, or a chemokine, wherein when the at least one enzyme is inhibited in the target cell, the target cell activates the GD T cell. In embodiments, the target cell is a cancer cell. In embodiments, the method further comprises contacting, or having contacted, the target cell and the GD T cell with an amount of an aminobisphosphonate drug. In embodiments. the aminobisphosphonate drug is zoledronic acid. In embodiments, the at least one enzyme is farnesyl diphosphate synthase (FDPS), geranylgeranyl-diphosphate synthase 1 (GGPS1). isopentenyl-diphosphate delta isomerase 1 (IDI1), or farnesyl transferase (F-Tase).

In another aspect, a method of treating cancer in a subject is disclosed. The method includes administering, or having administered, to the subject a therapeutically effective amount of a lentiviral particle wherein the lentiviral particle comprises a viral vector comprising first and second encoded genetic elements wherein the first encoded genetic element comprises at least one small RNA capable of inhibiting production of at least one enzyme involved in the mevalonate pathway, and the second encoded genetic element comprises one of a butyrophilin family member, a cytokine, or a chemokine, wherein when the at least one enzyme is inhibited in a cancer cell in the presence of a GD T cell, the target cell activates the GD T cell, to thereby treat the cancer. In embodiments, the method further comprises contacting, or having contacted, the target cell and the GD T cell with an amount of an aminobisphosphonate drug. In embodiments, the aminobisphosphonate drug is zoledronic acid. In embodiments, the butyrophilin family member includes BTN3A3 (SEQ ID NO: 17) or 30) BTN3A3 (R381H) (SEQ ID NO: 54). In further embodiments, the cytokine includes IL-1. IL-2. IL-12. IL-15. IL-17. IL-18. IL-23, or IL-36.

In another aspect, a viral vector is disclosed. The viral vector comprises a first small RNA that targets a first target of the mevalonate pathway and is capable of increasing a first product of the mevalonate pathway, and a second small RNA that targets a second target of the mevalonate pathway and is capable of decreasing a second product of the mevalonate pathway. In embodiments, the first target is a first enzyme of the mevalonate pathway and the second target is a second enzyme of the mevalonate pathway. In embodiments, at least one of the first enzyme and the second enzyme comprises farnesyl diphosphate synthase (FDPS), geranylgeranyl-diphosphate synthase 1 (GGPS1), isopentenyl-diphosphate delta isomerase 1 (IDI1), or farnesyl transferase (F-Tase). In embodiments, the first product of the mevalonate pathway comprises isopentenyl pyrophosphate (IPP). In embodiments, the second product of the mevalonate pathway comprises geranylgeranyl pyrophosphate (GGPP).

In another aspect, a method of treating cancer in a subject is disclosed. The method comprises administering, or having administered, to the subject a therapeutically effective amount of a lentiviral particle wherein the lentiviral particle comprises a viral vector as described herein. In embodiments, the method further comprises administering, or having administered, to the subject a therapeutically effective amount of an aminobisphosphonate drug.

DETAILED DESCRIPTION

Overview of Disclosure

Figure 1:
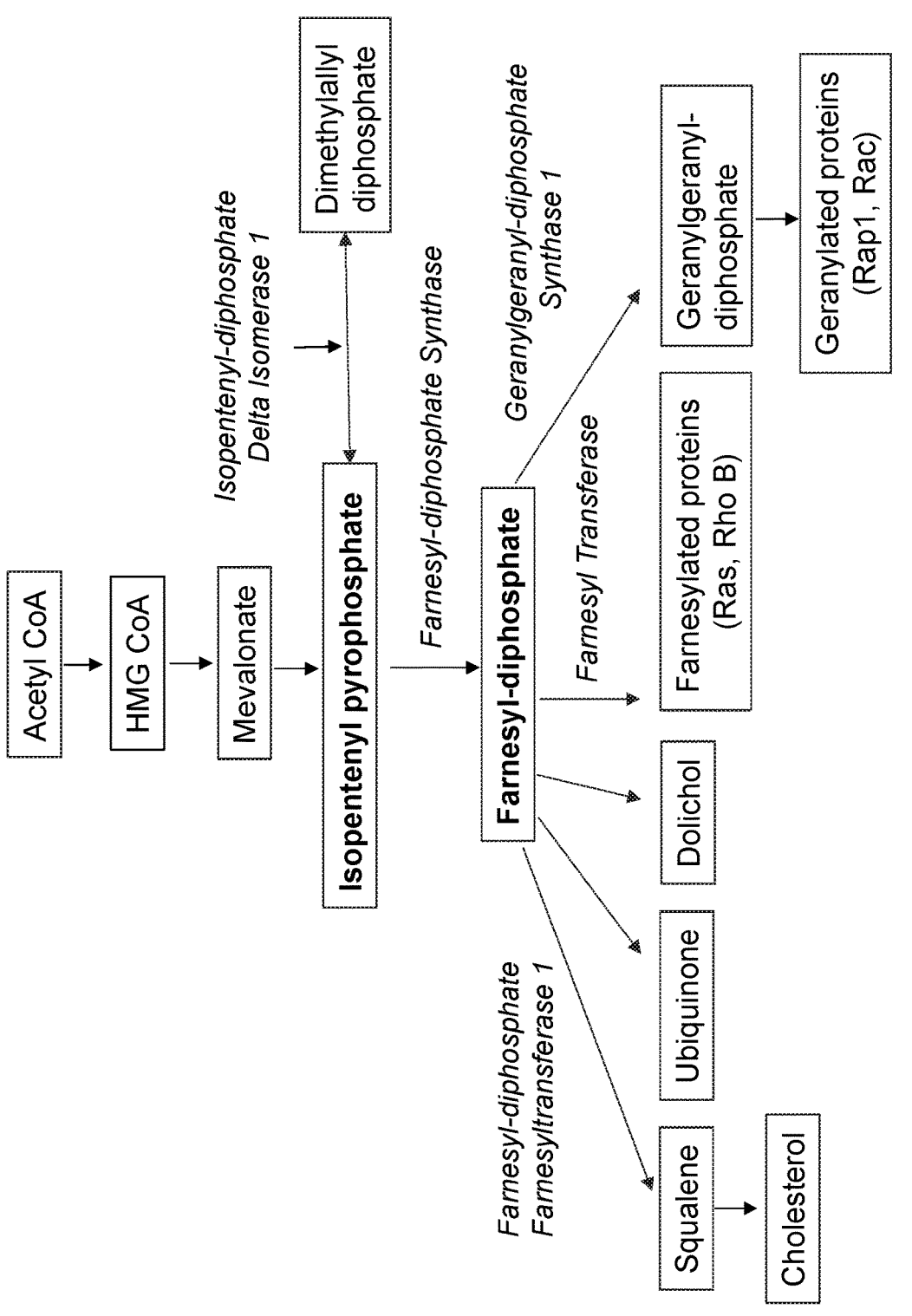
FIG. 1 depicts an overview of the major steps in the mevalonate pathway for biosynthesis of steroids and isoprenoids.

The present disclosure relates to gene therapy constructs and delivery of the same to cells, resulting in suppression of Farnesyl diphosphate synthase ("FDPS") or other enzymes of the mevalonate pathway, which are necessary to convert isopentenyl phosphate (IPP) to farnesyl diphosphate (FDP) and other downstream products of the mevalonate pathway, as shown, for example, in FIG. 1. In embodiments, one or more viral vectors are provided with microRNAs or short hairpin RNAs (shRNA) that target one or more of FDPS, GGPS1, IDI1, F-Tase, or squalene synthase, thereby reducing expression levels of these enzymes. The viral vectors include lentiviral vectors and AAV vectors. A consequence of modulating expression of FDPS and other enzymes of the mevalonate pathway is to increase the accumulation of IPP, which is a stimulator of GD T cell proliferation and differentiation. A consequence of modulating expression of GGPSI and other enzymes of the mevalonate pathway is to decrease GGPP levels, which allows secretion of cytokines including interleukin-1 beta and interleukin-18. Accordingly, the constructs provided herein are used to activate GD T cells, and are used to treat cancers and infectious diseases.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000): Ausubel et al., Short Protocols in Molecular Biology: A Compendium of Methods from Current Protocols in Molecular Biology, Wiley, John & Sons, Inc. (2002): Harlow and Lane Using Antibodies: A Laboratory Manual: Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the terms "administration of" or "administering" refer to providing an active agent to a subject in need of treatment in a form that can be introduced into that individual's body in a therapeutically useful form and therapeutically effective amount.

As used herein, the term "butyrophilin 3A" may be referred to herein as "BTN3A". Further, "butyrophilin 3Al" may be referred to herein as "BTN3Al", and may include the BTN3A1 portion of SEQ ID NO: 53. Butyrophilin 3A3 may be referred to herein as "BTN3 A3" (SEQ ID NO: 17). Variants of BTN3A3, include, but are not limited to, BTN3A3 (R381H), and may include the BTN3A3 portion of SEQ ID NO: 54 or SEQ ID NO: 55 or SEQ ID NO: 20) 59. Reference to "R381H" is reference to an arginine (R) amino acid being substituted by a histidine (H) amino acid at amino acid position 381. This convention for defining amino acid substitutions may be used for other positions and other amino acids herein.

As used herein, the term "CA19-9" refers to carbohydrate antigen 19-9. As used herein, the term "CC chemokine" refers to a class of chemokine proteins characterized by having two adjacent cysteines near their amino terminus. The term "CXC chemokine" refers to a class of chemokine proteins characterized by having two cysteines separated by one amino acid near their amino terminus. The term "CX3C chemokine" refers to a class of chemokine proteins characterized by having two cysteines separated by three amino acids near their amino terminus. The term "XC chemokine" refers to a class of chemokine proteins characterized by having one cysteine adjacent an amino acid near their amino terminus.

As used herein, the term "CD" refers to a cluster of differentiation protein. Examples of such proteins include, but are not limited to CD4 and CD8. Reference, for example, to CD4+ indicates that the CD4 protein is positively expressed.

As used herein, the term "CEA" refers to carcinoembryonic antigen.

As used herein, the terms "bisphosphonates" and "bisphosphonate drugs" refer to therapeutic agents of various embodiments, and encompass any of aminobisphosphonates, diphosphonates, biphosphonic acids, and diphosphonic acids, as well as pharmaceutically acceptable salts and derivatives thereof. The use of a specific nomenclature in referring to bisphosphonates is not meant to limit the scope of the present invention, unless specifically indicated.

As used herein, the terms "co-administration" or "combined administration" or "combined use" or "combination therapy" or the like as utilized herein refer to administration of a therapeutic vector or a lentiviral particle and a bisphosphonate drug or any combination of these to a single subject in need thereof (e.g., a patient), and are intended to include treatment regimens in which the agents are not necessarily administered by the same route of administration and/or at the same time.

As used herein, the term "fixed combination" refers to two or more active ingredients or components, including any of their respective compositions, formulations or drug forms, e.g., a therapeutic vector or a lentiviral particle and a bisphosphonate drug or any combination of these, that are administered essentially in combination to a patient, for example essentially simultaneously, in the form of a single entity or dosage or combined entities or dosages, e.g., in one tablet or in one capsule or in combined tablets or capsules or combined liquid forms.

As used herein, the term "non-fixed combination" refers to two or more active ingredients or components, including any of their respective compositions, formulations or drug forms, e.g., a therapeutic vector or a lentiviral particle and a bisphosphonate drug or any combination of these, that are administered in combination to a patient as separate entities either simultaneously, concurrently or sequentially with no specific time limits, wherein such administration provides therapeutically effective levels of the active components in the patient. The non-fixed combination can be dosed independently of each other or by use of different fixed combinations e.g., simultaneously or at different time points. The active components may be administered as separate pharmaceutical dosage forms or pharmaceutical formulations that may be, for example, sold independently of each other, with or without label instructions concerning the possibility of a combined use. Such instructions may be provided in the package equipment, e.g., leaflet or the like, or in other information, e.g., provided to physicians and medical staff. A non-fixed combination, its respective active ingredients or components, including any of their respective compositions, formulations or drug forms, or the parts thereof, can be administered simultaneously or chronologically staggered, e.g., at different time points and with equal or different time intervals for any part of the administration. Such time intervals may be chosen such that the effect on the treated disease, when treated in combination, is more effective than would be obtained by use of only any one of the active components.

As used herein, the terms "combination," "in combination" and "combination therapies," may refer generally to any or both of the "fixed combination" and "non-fixed combination" definitions and embodiments described above.

As used herein, the transitional term "comprising." when used to define compositions and methods, means that the compositions and methods include the recited elements, but does not exclude others. As used herein, "consisting essentially of," when used to define compositions and methods, means that the composition and methods include additional elements, but only if those additional elements do not materially affect the basic and novel characteristics of the composition or methods. As used herein, "consisting of," when used to define compositions and methods, means that the compositions and methods exclude more than trace elements of other ingredients for compositions and substantial method steps. Embodiments defined by each of these transitional terms are within the scope of this disclosure.

For example, it is intended that the methods and compositions can include additional steps and components (comprising) or alternatively including steps and compositions of no significance (consisting essentially of) or alternatively, intending only the stated method steps or compositions (consisting of).

As used herein, the terms "expression," "expressed," or "encodes" refer to a process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

As used herein, the term "farnesyl diphosphate synthase" may also be referred to herein as FDPS, and may also be referred to herein as farnesyl pyrophosphate synthase or FPPS.

As used herein, the term "gamma delta T cell" may also be referred to herein as a γδ T cell, a Vγ9Vδ2 T cell, a Vgamma9Vdelta2 T cell, a Vγ2Vδ2 T cell, a Vgamma2Vdelta2 T cell or further as a GD T cell. The term "gamma delta T cell activation" refers to any measurable biological phenomenon associated with a gamma delta T cell that is representative of such T cell being activated. Non-limiting examples of such a biological phenomenon include an increase of cytokine production, changes in the qualitative or quantitative composition of cell surface proteins, an increase in T cell proliferation, and/or an increase in T cell effector function, such as killing a target cell or assisting another effector cell to kill a target cell.

As used herein, the term "F-Tase" refers to farnesyl transferase.

As used herein, the term "GGPP" refers to geranylgeranyl pyrophosphate, and may also be referred to herein as geranylgeranyl diphosphate.

As used herein, the terms "GGDPS," "GGPPS," "GGDPS1," "GGPS1" and "GGPPS1" refer to geranylgeranyl diphosphate synthase 1, and may also be referred to herein as geranylgeranyl pyrophosphate synthase or geranylgeranyl-diphosphate synthase.

As used herein, the term "HER-2" refers to human epidermal growth factor receptor 2.

As used herein, cytokines such as "interleukin 2" may also be referred to as "IL-2," "IL2" and the like. IL-2 can also include reference to SEQ ID NO: 56. In a related manner, "interleukin 15" can also include reference to SEQ ID NO: 57. In a related manner, "interleukin 18" can also include reference to SEQ ID NO: 58. In a related manner, "interleukin 23" can also include reference to SEQ ID NO: 60. In a related manner, "interleukin 36" can also include reference to any of SEQ ID NOs: 61-63. In general, the prefix "IL" refers to an interleukin.

As used herein, the term "IDI1" refers to isopentenyl-diphosphate delta isomerase 1.

As used herein, the term "IFN" refers to interferon, and the terms IFN-gamma and IFN-γ refer to interferon-gamma.

As used herein, the terms "individual," "subject," and "patient" are used interchangeably herein, and refer to any individual mammal subject, e.g., bovine, canine, feline, equine, and/or human.

As used herein, the term "IPP" refers to isopentenyl pyrophosphate.

As used herein, the term "M2-PK" refers to pyruvate kinase isoenzyme type M2.

As used herein, the term "MHC" refers to a major histocompatibility complex.

As used herein, the term "miRNA" refers to a microRNA, and also may be referred to herein as "miR".

As used herein, the term "NK cell" or "NK receptor family" refers to a "natural killer cell" or "natural killer cell receptor family", respectively.

As used herein, the term "packaging cell line" refers to any cell line that can be used to express a lentiviral particle.

As used herein, the term "PBMC" refers to peripheral blood mononuclear cells.

As used herein, the term "homology" refers to the percentage number of amino acids, nucleic acids, or analogs thereof, that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

As used herein, the term "sequence identity," which also may appear in the non-limiting context of "a sequence 50% identical to," and "having at least 80%, or at least 85%, or at least 90%, or at least 95% identity with" a given sequence, as similar pharasings, as used herein, refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile. Phe. Tyr. Trp, Lys, Arg. His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

As used here, the term "percent identity," which may be used interchangeably with the term "sequence identity", in the context of two or more nucleic acid or polypeptide sequences, refer to two or more sequences or subsequences that have a specified percentage of nucleotides or amino acid residues that are the same, when compared and aligned for maximum 25 correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

Suitable algorithms for determining percent sequence identity include the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, (J. Mol. Biol. (48): 444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, word-length =3 to obtain amino acid sequences homologous to the protein molecules of the disclosure. To obtain gapped alignments for comparison purposes, Gapped BLAST can be utilized as described in Altschul et al. Nucleic Acids Res. 25 (17): 3389-3402 (1997). When utilizing BLAST and Gapped BLAST programs, the default parameters of the respective programs (e.g., XBLAST and NBLAST) can be used. See www.ncbi.nlm.nih.gov.

As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. J Pharm Sci 66:1-19) (1977).

As used herein, the term "pharmaceutically acceptable salt" refers to derivatives of compounds or other active ingredients, wherein the parent compound or active ingredient is modified by converting an existing acid or base moiety to its salt form. Non-limiting examples of pharmaceutically acceptable salts include, but are not limited to, mineral or organic acid salts of basic residues such as amines: alkali or organic salts of acidic residues such as carboxylic acids: alkali metal, alkaline metal, ammonium, and mono-, di, tri-, or tetra-C1-C30-alkyl-substituted ammonium; and the like. The pharmaceutically acceptable salts of various embodiments include the conventional non-toxic salts of the compound or active ingredient formed, for example, from nontoxic inorganic or organic acids. Suitable organic acids are, e.g., carboxylic acids or sulfonic acids, such as acetic acid, succinic acid, fumaric acid or methansulfonic acid. The pharmaceutically acceptable salts herein can be synthesized from the parent compound or active ingredient which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two: generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "PSA" refers to prostate-specific antigen.

As used herein, the term "RANTES" is synonymous with chemokine (C-C motif) ligand 5, which is also synonymous with CCL5.

As used herein, the term "SEQ ID NO" is synonymous with the term "Sequence ID No."

As used herein, "small RNA" refers to non-coding RNA that are generally about 200 nucleotides or less in length and possess a silencing or interference function. In embodiments, the small RNA is about 175 nucleotides or less, about 150) nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). In embodiments, "small RNA" are capable of inhibiting or knocking-down gene expression of a target gene, generally through pathways that result in the inhibition or destruction of the target gene mRNA.

As used herein, the term "TCR" refers to a T cell receptor, and the term "TCRs" refers to the plural form thereof.

As used herein, the term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

Figure 2:
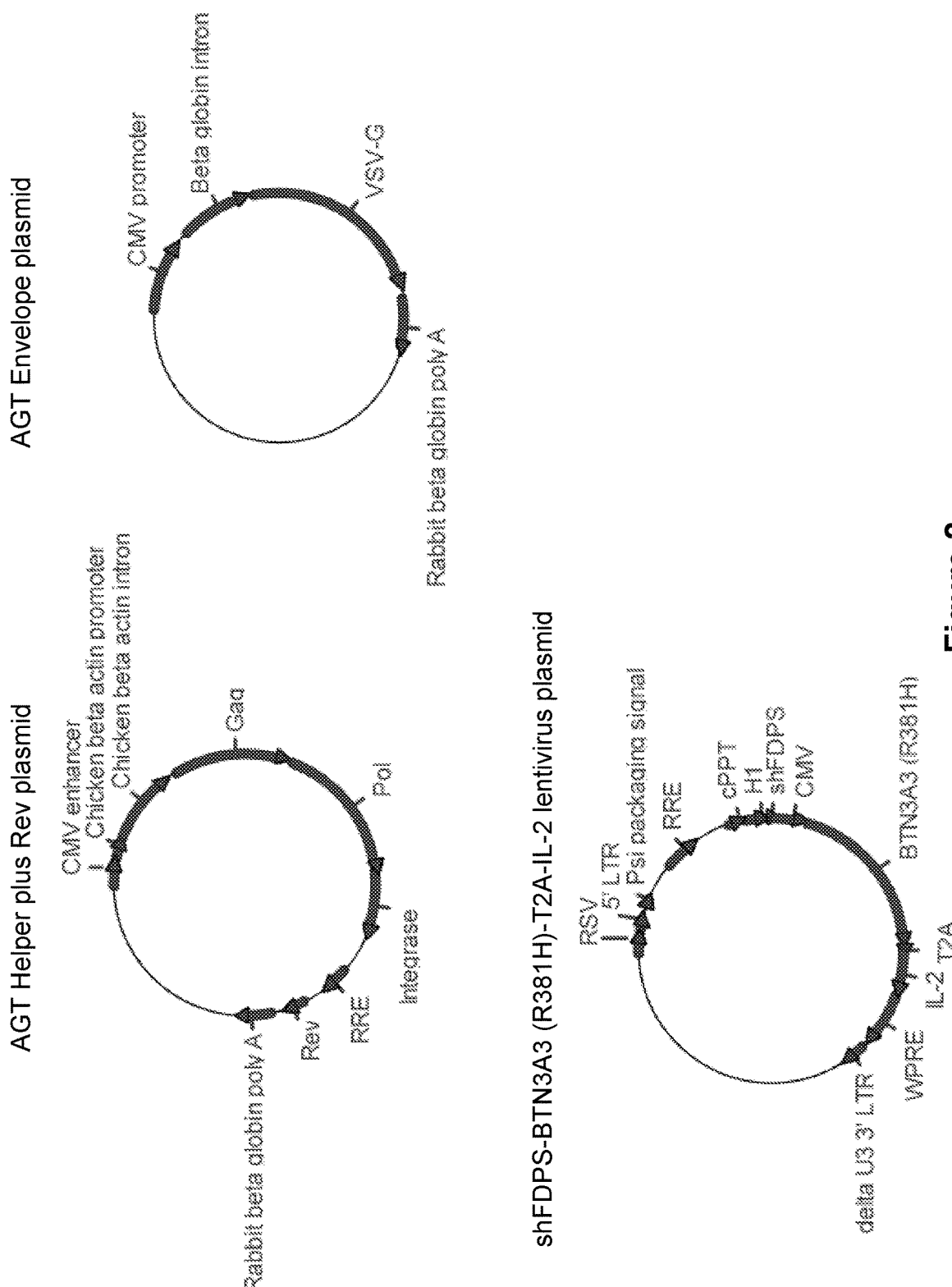
FIG. 2 depicts an exemplary 3-vector lentiviral vector system in a circularized form.
Figure 3:
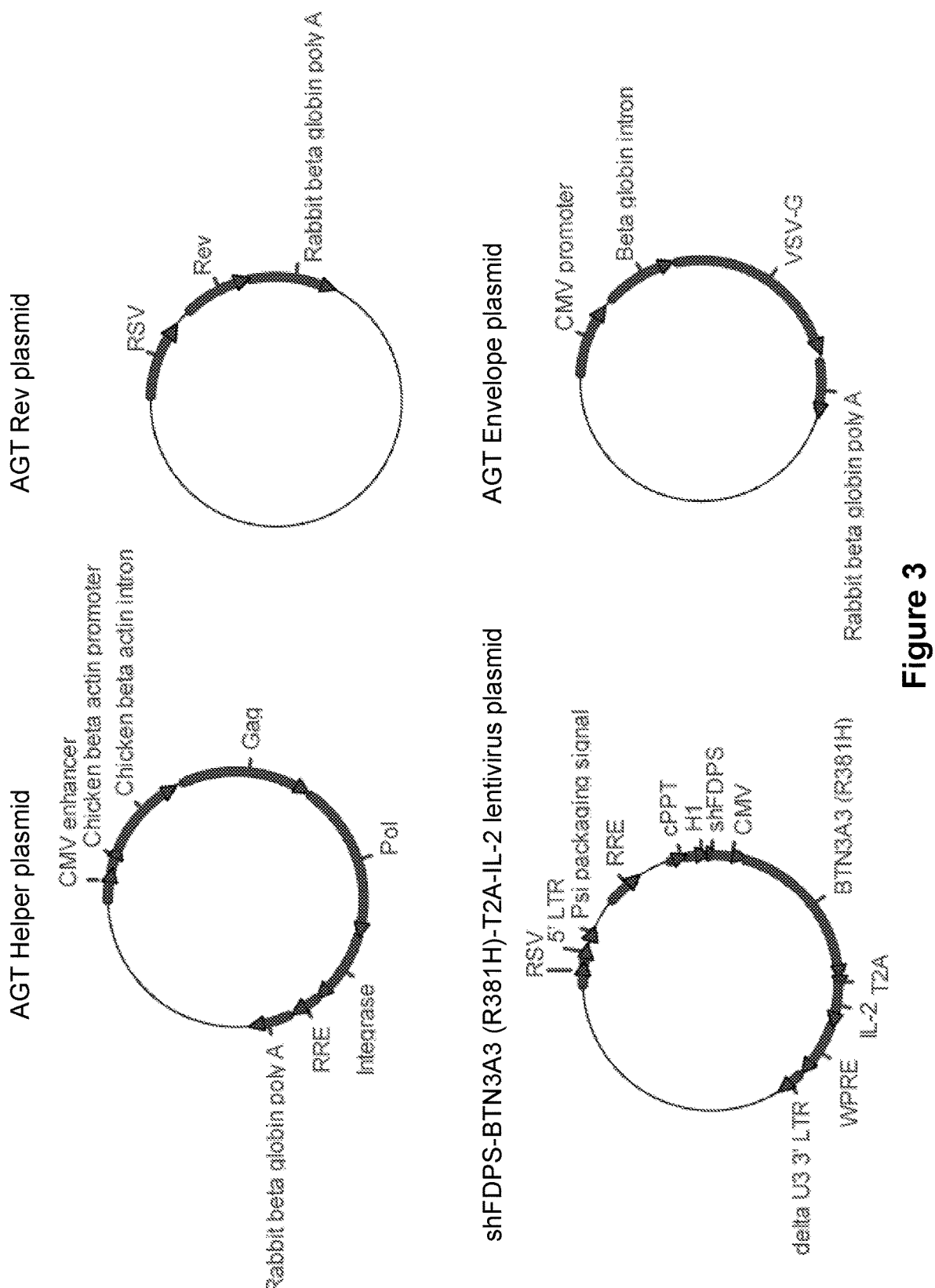
FIG. 3 depicts an exemplary 4-vector lentiviral vector system in a circularized form.

As used herein, the term "therapeutic vector" includes, without limitation, reference to a lentiviral vector, and a lentivirus plasmid as mentioned, for example in FIGS. 2 and 3 herein.

As used herein, the term "TNF" refers to tumor necrosis factor, and reference to TNF-alpha or TNF-α refers to tumor necrosis factor-alpha.

As used herein, the terms "treatment" and "treating" refer to the intended targeting of a disease state and combatting of it, i.e., ameliorating or preventing the disease state. A particular treatment thus will depend on the disease state to be targeted and the current or future state of medicinal therapies and therapeutic approaches. A treatment may have associated toxicities.

As used herein, the terms "treatment" or "treating" generally refer to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

As used herein, the term "VSVG" or "VSV-G" refers to vesicular stomatitis virus G envelope glycoprotein.

DESCRIPTION OF ASPECTS OF THE DISCLOSURE

In an aspect of the disclosure, a viral vector comprising first and second encoded genetic elements is disclosed. The first encoded genetic element comprises a small RNA capable of inhibiting production of an enzyme involved in the mevalonate pathway, and the second encoded genetic element comprises one of a butyrophilin family member, a cytokine, or a chemokine. In embodiments, the viral vector includes a third encoded genetic element, wherein the third encoded genetic element comprises one of a butyrophilin family member, a cytokine, or a chemokine. In embodiments, the viral vector includes a fourth encoded genetic element, wherein the fourth encoded genetic element comprises one of a butyrophilin family member, a cytokine, or a chemokine. In embodiments, the enzyme is farnesyl diphosphate synthase (FDPS) or a functional variant thereof. In embodiments, the first encoded genetic element comprises a microRNA or a shRNA. In embodiments, the shRNA comprises a sequence having at least 80%, at least 81%, at least 82%, at least 83%, at least 84%, at least 85%, at least 86%, at least 87%, at least 88%, at least 89%, at least 90%, at least 95% percent identity or more with

```
                                           (SEQ ID NO: 1)
GTCCTGGAGTACAATGCCATTCTCGAGAATGGCATTGTACTCCAGGACTT
TTT;
```

```
                                           (SEQ ID NO: 2)
GCAGGATTTCGTTCAGCACTTCTCGAGAAGTGCTGAACGAAATCCTGCTT
TTT;
```

```
                                           (SEQ ID NO: 3)
GCCATGTACATGGCAGGAATTCTCGAGAATTCCTGCCATGTACATGGCTT
TTT;
or
```

```
                                           (SEQ ID NO: 4)
GCAGAAGGAGGCTGAGAAAGTCTCGAGACTTTCTCAGCCTCCTTCTGCTT
TTT.
```

In embodiments, the shRNA comprises:

```
                                           (SEQ ID NO: 1)
GTCCTGGAGTACAATGCCATTCTCGAGAATGGCATTGTACTCCAGGACTT
TTT;
```

```
                                           (SEQ ID NO: 2)
GCAGGATTTCGTTCAGCACTTCTCGAGAAGTGCTGAACGAAATCCTGCTT
TTT;
```

```
                                           (SEQ ID NO: 3)
GCCATGTACATGGCAGGAATTCTCGAGAATTCCTGCCATGTACATGGCTT
TTT;
or
```

```
                                           (SEQ ID NO: 4)
GCAGAAGGAGGCTGAGAAAGTCTCGAGACTTTCTCAGCCTCCTTCTGCTT
TTT.
```

In embodiments, the shRNA comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity with SEQ ID NO: 64, SEQ ID NO: 65, SEQ ID NO: 66, or SEQ ID NO: 67.

In embodiments, the miRNA comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity with SEQ ID NO: 68 or SEQ ID NO: 69.

In embodiments, the enzyme is GGPS1 or a functional variant thereof. In embodiments, the shRNA comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity with SEQ ID NO: 70, SEQ ID NO: 71, or SEQ ID NO: 72.

In embodiments, the enzyme is IDI1 or a functional variant thereof. In embodiments, the shRNA comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity with SEQ ID NO: 76.

In embodiments, the enzyme is F-Tase, or squalene synthase, or functional variants thereof.

In embodiments, the butyrophilin family member comprises BTN3A3, BTN3A3, or BTN3A1. In embodiments, the butyrophilin family member comprises BTN3A3 (R381H). In embodiments, the butyrophilin family member comprises a butyrophilin-like molecule. In embodiments, the butyrophilin-like molecule comprises BTNL3 or BTNL8. In embodiments, the cytokine comprises IL-1, IL-1B, IL-2, IL-4, IL-7, IL-12, IL-15, IL-17, IL-18, IL-23, IL-33, IL-36, TNF-α, or interferon-γ.

In embodiments, the chemokine comprises a CC chemokine, a CXC chemokine, a CX3C chemokine, a C chemokine, or a XC chemokine. In further embodiments, the CC chemokine comprises RANTES. In embodiments, the viral vector is a lentiviral vector. In further embodiments, the C chemokine comprises XCL1 (Lymphotactin).

In another aspect, a lentiviral vector system for expressing a lentiviral particle is disclosed. The system includes a lentiviral vector as detailed herein: at least one envelope plasmid for expressing an envelope protein optimized for infecting a target cell; and at least one helper plasmid for expressing gag, pol, and rev genes, or functional variants thereof, wherein when the lentiviral vector, the at least one envelope plasmid, and the at least one helper plasmid are transfected into a packaging cell, a lentiviral particle is produced by the packaging cell, wherein the lentiviral particle is capable of infecting the target cell and inhibiting an enzyme involved in the mevalonate pathway within the target cell.

In embodiments, the lentiviral particle is capable of causing increased levels of a first product of the mevalonate pathway. In embodiments, the first product comprises IPP. In embodiments, the lentiviral particle is capable of causing decreased levels of a second product of the mevalonate pathway. In embodiments, the second product comprises GGPP. In embodiments, the lentiviral product increases the first product and decreases the second product.

In embodiments, the lentiviral particle encodes a small RNA capable of targeting a first target of the mevalonate pathway. In embodiments, the lentiviral particle further encodes a small RNA capable of targeting a second target of the mevalonate pathway. In embodiments, at least one of the first target and the second target is an enzyme. In embodiments, at least one of the first target and the second target is FDPS, GGPSI, IDII, F-Tase, or squalene synthase.

In embodiments, targeting of the first target by the small RNA causes an increase in the presence, level, or concentration of a first product of the mevalonate pathway. In embodiments, the presence, level, or concentration of the first product of the mevalonate pathway is increased by up to 10% over a first product control, wherein the first product control can mean the presence, level, or concentration of the first product when the first target is not targeted by the small RNA. In embodiments, the presence, level, or concentration of the first product of the mevalonate pathway is increased by up to 10% to up to 20% over the first product control, as described herein. In embodiments, the presence, level, or concentration of the first product of 30) the mevalonate pathway is increased by up to 20% to up to 30% over the first product control, as described herein. In embodiments, the presence, level, or concentration of the first product of the mevalonate pathway is increased by up to 30% to up to 40% over the first product control, as described herein. In embodiments, the presence, level, or concentration of the first product of the mevalonate pathway is increased by up to 40% to up to 50% over the first product control, as described herein. In embodiments, the presence, level, or concentration of the first product of the mevalonate pathway is increased by more than 50% over the first product control, as described herein. In embodiments, the first product of the mevalonate pathway comprises IPP.

In embodiments, targeting of the second target by the small RNA causes a decrease in the presence, level, or concentration of a second product of the mevalonate pathway. In embodiments, the presence, level, or concentration of the second product of the mevalonate pathway is decreased by up to 10% of a second product control, wherein the second product control can mean the presence, level, or concentration of the second product when the second target is not targeted by the small RNA. In embodiments, the presence, level, or concentration of the second product of the mevalonate pathway is decreased by up to 10% to up to 20% of the second product control, as described herein. In embodiments, the presence, level, or concentration of the second product of the mevalonate pathway is decreased by up to 20% to up to 30% of the second product control, as described herein. In embodiments, the presence, level, or concentration of the second product of the mevalonate pathway is decreased by up to 30% to up to 40% of the second product control, as described herein. In embodiments, the presence, level, or concentration of the second product of the mevalonate pathway is decreased by up to 40% to up to 50% of the second product control, as described herein. In embodiments, the presence, level, or concentration of the second product of the mevalonate pathway is decreased by more than 50% of the second product control, as described herein. In embodiments, the second product of the mevalonate pathway comprises GGPP.

In embodiments, the increase in the presence, level, or concentration of the first product of the mevalonate pathway causes an increase in gamma delta (GD) T cell activation. In embodiments, GD T cell activation is increased by up to 10% over a first activation control, wherein the first activation control can mean the level of GD T cell activation when the first target is not targeted by the small RNA. In embodiments, GD T cell activation caused by modulation of the first product is increased by up to 10% to up to 20% over the first activation control, as described herein. In embodiments, GD T cell activation caused by modulation of the first product is increased by up to 20% to up to 30% over the first activation control, as described herein. In embodiments, GD T cell activation caused by modulation of the first product is increased by up to 30% to up to 40% over the first activation control, as described herein. In embodiments, GD T cell activation caused by modulation of the first product is increased by up to 40% to up to 50% over the first activation control, as described herein. In embodiments, GD T cell activation caused by modulation of the first product is increased by 50% or more over first activation control, as described herein.

In embodiments, the decrease in the presence, level, or concentration of the second product of the mevalonate pathway causes an increase in gamma delta (GD) T cell activation. In embodiments. GD T cell activation caused by modulation of the second product is increased by up to 10% over a second activation control, wherein the second activation control can mean the level of GD T cell activation when the second target is not targeted by the small RNA. In embodiments. GD T cell activation caused by modulation of the second product is increased by up to 10% to up to 20% over the second activation control, as described herein. In embodiments. GD T cell activation caused by modulation of the second product is increased by up to 20% to up to 30% over the second activation control, as described herein. In embodiments. GD T cell activation caused by modulation of the second product is increased by up to 30% to up to 40% over the second activation control, as described herein. In embodiments. GD T cell activation caused by modulation of the second product is increased by up to 40% to up to 50% over the second activation control, as described herein. In embodiments. GD T cell activation caused by modulation of the second product is increased by 50% or more over the second activation control, as described herein.

In another aspect, a lentiviral particle capable of infecting a target cell is disclosed. The lentiviral particle comprises an envelope protein optimized for infecting the target cell, and a lentiviral vector as detailed herein. In embodiments, the target cell is a cancer cell.

In another aspect, a method of activating a gamma delta (GD) T cell is disclosed. The method includes infecting, in the presence of the GD T cell, a target cell with a lentiviral particle, wherein the lentiviral particle comprises a viral vector comprising first and second encoded genetic elements wherein the first encoded genetic element comprises a small RNA capable of inhibiting production of an enzyme involved in the mevalonate pathway, and the second encoded genetic element comprises one of a butyrophilin family member, a cytokine, or a chemokine, wherein when the enzyme is inhibited in the target cell, the target cell activates the GD T cell. In embodiments, the enzyme comprises at least one of FDPS. GGPS1. IDII. F-Tase, and/or squalene synthase, or functional variants thereof.

In embodiments, the target cell is a cancer cell. In embodiments, the method further comprises contacting the target cell and the GD T cell with an amount of an amino-bisphosphonate drug. In embodiments, the aminobisphos-phonate drug is zoledronic acid.

In another aspect, a method of treating cancer in a subject is disclosed. The method includes administering to the subject a therapeutically effective amount of a lentiviral particle wherein the lentiviral particle comprises a viral vector comprising first and second encoded genetic elements, wherein the first encoded genetic element comprises a small RNA capable of inhibiting production of an enzyme involved in the mevalonate pathway, and the second encoded genetic element comprises one of a butyrophilin family member, a cytokine, or a chemokine, wherein when the enzyme is inhibited in a cancer cell in the presence of a GD T cell, the target cell activates the GD T cell, to thereby treat the cancer. In embodiments, the enzyme comprises at least one of FDPS, GGPSI, IDII, F-Tase, squalene synthase, and/or functional variants thereof.

In embodiments, the method further comprises contacting the target cell and the GD T cell with an amount of an aminobisphosphonate drug. In embodiments, the method includes administering to the subject a therapeutically effective amount of a lentiviral particle wherein the lentiviral particle comprises a viral vector comprising first, second and third encoded genetic elements wherein the first encoded genetic element comprises a small RNA or RNAs capable of inhibiting production of an enzyme or enzymes involved in the mevalonate pathway. the second encoded genetic element comprises a butyrophilin family member, and the third genetic element encodes a cytokine or a chemokine, wherein when the enzyme is inhibited in a cancer cell in the presence of a GD T cell, the target cell activates the GD T cell, the butyrophilin increases efficiency of activating GD T cells, the cytokine increases GD T cell activation and proliferation, and the chemokine increases the presence of the GD T cells at a tumor site to thereby treat the cancer. In embodiments, the method further comprises exposure of the target cell and the GD T cell with an amount of an aminobisphosphonate drug. In embodiments, the aminobisphosphonate drug is zoledronic acid.

In embodiments, the butyrophilin family member includes BTN3A3 (SEQ ID NO: 17) or BTN3A3 (R381H) (SEQ ID NO: 54). In embodiments, the cytokine includes IL-2, IL-12, IL-15, IL-18, IL-23, or IL-36 but can also include other cytokines which are known to activate immune cells, such as T cells. In embodiments, the chemokine may include chemokine (C-C motif) ligand 5 encoded by the CCL5 gene, or other chemokines known to be recognized by GD T cell receptors and known to be capable of attracting GD T cells to sites of tumor growth.

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell, and can also include a cancer cell population from any of the foregoing, and can be associated with one or more of carcinomas, sarcomas, myelomas, leukemias, lymphomas, mixed types or mixtures of the foregoing. In still a further aspect cancer includes, but is not limited to astrocytoma, acute myeloid leukemia, anaplastic large cell lymphoma, acute lymphoblastic leukemia, angiosarcoma, B-cell lymphoma, Burkitt's lymphoma, breast carcinoma, bladder carcinoma, carcinoma of the head and neck, cervical carcinoma, chronic lymphoblastic leukemia, chronic myeloid leukemia, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leukemia, leiomyosarcoma, lipoma, liposarcoma, melanoma, mantle cell lymphoma, medulloblastoma, mesothelioma, myxofibrosarcoma, myeloid leukemia, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, esophageal carcinoma, osteosarcoma, pancreatic carcinoma, pheochromocytoma, prostate carcinoma, renal cell carcinoma, retinoblastoma, rhabdomyosarcoma, salivary gland tumor, schwanomma, small cell lung cancer, squamous cell carcinoma of the head and neck, testicular tumor, thyroid carcinoma, urothelial carcinoma, and Wilms tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Infectious Diseases

The compositions and methods disclosed herein can be used to treat infectious diseases. The term "infectious disease" includes any disease that is caused by an infectious agent. An "infectious agent" includes any exogenous pathogen including, without limitation, bacteria, fungi, viruses, mycoplasma, and parasites. Infectious agents that may be treated with compositions provided for in this disclosure include any art-recognized infectious organisms that cause pathogenesis in an animal, including such organisms as bacteria that are gram-negative or gram-positive cocci or bacilli, DNA and RNA viruses, including, but not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picomaviruses, paramyxoviruses, reoviruses, retroviruses, and rhabdoviruses. Examples of fungi that may be treated with the compositions and methods of the disclosure include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidio-idomycosis, and candidiasis. Compositions and methods provided for herein may be utilized to treat parasitic infections including, but not limited to, infections caused by somatic tapeworms, blood flukes, tissue roundworms, ameba, and *Plasmodium. Trypanosoma. Leishmania*, and *Toxoplasma* species.

Methods of GD T Cell Activation

Provided herein are compositions and methods for activating GD T cells in an individual, as well as methods for treating tumors and infectious diseases. For instance, in embodiments, the compositions and methods provided herein can be used in methods to treat all known cancers because activated GD T cells comprise a natural mechanism for immune surveillance of tumors (See for e.g.: Pauza et al. Frontiers in Immunol. 5:687 (2014). Likewise, in embodiments, the compositions and methods provided herein can be used to treat infectious diseases, including but not limited to flavivirus, influenza virus, human retrovirus, mycobacteria, plasmodia and a variety of other viral, fungal and bacterial infections. (See for e.g.: Pauza and Cairo, 2015 Cell Immunol. 296 (1).

In general, a vector system is administered to an individual to transfect or transduce a target cell population with the disclosed constructs for decreasing expression of FDPS and, in other embodiments, increasing expression of chemokines or cytokines. Administration and transfection/transduction can occur in vivo or ex vivo, with the transfected cells later administered back into the subject in the latter scenario.

Administration of the disclosed vectors and transfection or transduction of the disclosed constructs into a subject's cells result in decreased expression of FDPS, increased expression of cytokines or chemokines, accumulation of IPP and in many cases, reduced growth rates for genetically modified tumor cells. All of these features work together to activate and co-localize GD T cells to the site of a tumor or infection.

The disclosed methods can also increase the capacity of NK cells to recognize and destroy tumor cells and/or infected cells. Crosstalk between GD T cells and NK cells is an important aspect of regulating the immune and inflammatory responses. Further. GD T cells can trigger dendritic cell maturation, recruit B cells and macrophages, and participate in a variety of cytolytic activities, such as secretion of interferon-γ and TNF-α.

In embodiments, the disclosed compositions and methods provided herein comprise a form of gene therapy for activating GD T cells at the site of tumor. In an aspect. the compositions and methods provided herein activate GD T cells and support their proliferation. differentiation, and functional capacities by promoting the production of specific cytokines needed for cytolytic activity capable of killing cancer cells or treating infectious diseases.

In embodiments, the gene therapy sequences (e.g., FDPS shRNAs, FDPS miRNAs, GGPSI shRNAs, IDII shRNAs, F-Tase small RNAs, or squalene synthase small RNAs) are carried by therapeutic vectors, including but not limited to viral vectors such as lentiviruses or adeno-associated viruses, although other viral vectors can also be suitable. Gene therapy constructs may also be delivered in the form of DNA or RNA, including but not limited to plasmid forms. In embodiments, the disclosed gene therapy constructs may also be delivered in the form of protein-nucleic acid complexes or lipid nucleic acid complexes and mixtures of these formulations. For instance, a protein-nucleic acid complex can comprise nucleic acids of interest in a complex with cationic peptides such as lysine and arginine. Lipid-nucleic acids complexes can comprise lipid emulsions, micelles, liposomes, and/or mixtures of neutral and cationic lipids such as DOTMA, DOSPA, DOTAP, and DMRIE.

In embodiments, therapeutic vectors may comprise a single construct or at least two, at least three, at least four, or at least five different constructs. When more than one construct is present in a vector the constructs may be identical, or they may be different. For instance, the constructs may vary in terms of their promoters, the presence or absence of integrating elements, and/or their sequences.

In embodiments, a therapeutic vector will comprise at least one construct that encodes a small RNA capable of knocking down the expression of at least one of FDPS. GGPSI. IDII. F-Tase, squalene synthase, and/or functional variants thereof. In embodiments, the therapeutic 30) vector will also encode a specific cytokine(s) and/or chemokine(s), including but not limited to TNF-α, interferon-γ, IL-1, IL-1B, IL-2, IL-4, IL-7, IL-12, IL-15, IL-17, IL-18, IL-23, IL-33, IL-36, or RANTES. In embodiments, a single construct may encode both small RNAs capable of knocking down the expression of FDPS and specific cytokines or chemokines. including but not limited to TNF-α, interferon-γ, IL-1, IL-1B, IL-2, IL-4, IL-7, IL-12, IL-15, IL-17, IL-18, IL-23, IL-33, IL-36, or RANTES.

In embodiments, viral vectors may introduce nucleic acid constructs that become integrated into the host chromosome. Alternately, transient delivery vectors may be used to prevent chromosomal integration and limit the lifespan of gene therapy constructs.

In embodiments, the disclosed constructs and vectors comprise short hairpin RNA ("shRNA"), micro RNA ("miRNA"), or siRNA capable of reducing or knocking down expression of FDPS, geranyl pyrophosphate synthase ("GPPS"), farnesyl transferase ("F-Tase"), IDII, and/or squalene synthase genes. By down regulating these genes, which control steroid and isoprenoid synthesis, isopentenyl pyrophosphate ("IPP") levels are elevated and/or GGPP levels are decreased. Elevation and accumulation of IPP is a mechanism for increasing GD T cells activation. Further, down regulation of these pyrophosphate synthase genes removes an important negative regulator of inflammasome function that in turn results in increased expression of cytokines that are important for GD T cell activation and effector cell function. BTN3A3 on the cancer cell surface and higher cytoplasmic levels of IPP potently stimulate Vgamma9Vdelta2 T cells (also referred to herein as Vγ9Vδ2 T cells).

In embodiments, the disclosed constructs are regulated by specific promoters that are capable of producing interleukin-2 and/or interleukin-15 to sustain GD T cell proliferation. However, as noted herein, other cytokines including IL-18, IL-23, and IL-36 can also be selected and used. In addition, the disclosed constructs may be regulated by specific promoters that are capable of producing interleukin-1 beta and/or interleukin-18 and/or interferon-gamma required for GD T cell differentiation and acquisition of all effector cell function. Desirable effector cell functions include the capacity for direct cytotoxic cell killing of tumors and/or infected cells, secretion of beneficial cytokines and/or chemokines, increased expression of NK receptors required to recognize cancerous or cells, and increased expression of Fc receptors needed to bind targeting antibodies in order to co-localize GD T cells with cancerous or infected cell targets.

In embodiments, the disclosed methods activate GD T cells, resulting in the indirect effect of increasing the capacity for NK cells to attack and destroy cancerous cells, tumors, or infected cells. The activation of NK cells requires GD T cells that are stimulated to proliferate 30) and differentiate, and to express 4-1BBL costimulatory ligand needed to engage the 4-1BB costimulatory receptor on NK cells. This form of crosstalk is known as an important mechanism for activating NK cells and is achieved here through the action of the disclosed methods and compositions.

In another aspect, crosstalk between GD T cells and NK cells is an important mechanism for eliminating inflammatory dendritic cells that accumulate in diseased tissues. Alone, neither GD T cells nor NK cells are capable of destroying dendritic cells, but once the aforementioned crosstalk interactions have occurred, NK cells are altered to become cytotoxic against inflammatory dendritic cells. This immuno-regulatory mechanism depends on strong activation and proliferation of GD T cells.

In embodiments, the disclosed methods for activation of GD T cells further comprise a step of suppressing pathologic inflammatory responses that may include cellular proliferation leading to atherosclerosis, chronic immune activation that stimulates tumor growth, autoimmune diseases including psoriasis and other presentations in the epidermis, inflammatory diseases of the central nervous system, and arthritis and other diseases of unregulated immune responses.

In embodiments, therapeutic vectors are administered concurrently with bisphosphonate drugs to achieve synergistic activation of gamma delta T cells. The synergism can allow alternate, modified or reduced doses of bisphosphonate drugs and may decrease adverse reactions to bisphosphonates including acute inflammatory responses and chronic diseases.

In embodiments, therapeutic vectors are administered in combination with bisphosphonate drugs. In various embodiments, such combinations achieve synergistic, positive or heightened activation of gamma delta T cells. Such positive activation may allow alternate, modified or reduced doses of bisphosphonates and may decrease adverse reactions to bisphosphonates including acute inflammatory responses and chronic diseases. Combinations of therapeutic vectors with bisphosphonates may be together or separate, with or without instructions for combined use or to combination products. The therapeutic vectors and/or bisphosphonates may be administered entirely separately and may be formulated in entirely distinct pharmaceutical dosage forms. The therapeutic vectors and/or bisphosphonates may be sold independently of each other, with or without label instructions concerning the possibility of a combined use. Such instructions also may be provided in the package equipment, e.g., leaflet or the like, or in other information e.g., provided to physicians and medical staff (e.g., oral communications, communications in writing or the like). Such labels 30) or other instructions can refer to either a fixed combination in one dosage unit form, or a non-fixed combination as a kit of parts for the combined administration where the therapeutic vector may be administered independently of the bisphosphonate drug, at the same time, or separately within time intervals. In various embodiments, the combination exhibits a cooperative or joint effect, or a decrease in toxicity or complications of treatment. In one embodiment the effect of the combination is synergistic. A synergistic effect is achieved when the active ingredients used together is greater than the sum of the effects that results from using the compounds separately. A synergistic effect may be attained when the active ingredients are: (1) co-formulated and administered or delivered simultaneously in a combined, unit dosage formulation: (2) delivered by alternation or in parallel as separate formulations: or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together, albeit subject to potential variances in timing as detailed herein.

The combinations herein may be manufactured and/or formulated by the same or different manufacturers. The active ingredients may be brought together into a combination therapy: (i) prior to release of the combination product to physicians (e.g., in the case of a kit comprising the compound of the disclosure and the other therapeutic agent): (ii) by the treating physician (or under the guidance of a physician) shortly before administration: (iii) in the actual patient, e.g., during sequential administration of the active ingredients disclosed herein.

In embodiments, a therapeutically effective amount of each of the combinations may be administered simultaneously or sequentially and in any order, and the components may be 20) administered together or separate. For example, the method of treating a proliferative disease according to the disclosure may comprise (i) administration of a first agent such as a therapeutic vector that forms part of a lentiviral particle and/or (ii) administration of a second agent such as a bisphosphonate drug in free or pharmaceutically acceptable salt form. The administration of agents (i), and/or (ii) may be simultaneous or sequential in any order, in therapeutically effective amounts, preferably in cooperative, jointly effective, and/or synergistically effective, amounts, e.g., in daily or intermittent dosages corresponding to the amounts described herein. The combinations may be administered separately at different times during the course of therapy or concurrently in divided or single drug forms.

Furthermore, the term "administering" also encompasses the use of a pro-drug of a combination partner that converts in vivo to the combination partner as such. The instant disclosure is therefore to be understood as embracing all such regimens of simultaneous or alternating treatment and the term "administering" is to be interpreted accordingly.

In embodiments, agents (i) and (ii) can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation For example, a therapeutic vector and/or bisphosphonate drug may be administered intravenously. Further, agents (i) and (ii) can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. For example, a bisphosphonate drug may be formulated into a tablet and administered orally.

A combination therapy according to the disclosure can besides or in addition be administered especially for cancer therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemo-preventive therapy, for example in patients at risk.

Constructs for GD T Cell Activation

Inhibition of FDPS, GGPS1, IDII, and/or functional variants thereof may result in IPP accumulation and/or diminished GGPP levels, resulting in activation of Vdelta2+GD T cells and expression of interferon-gamma, TNF-alpha, and IL-18, which are also important in activating GD T cells. Inhibition of farnesyl transferase and/or squalene synthase results in decreased prenylation of proteins. The disclosed constructs can be transfected or transduced into specific target cells, like tumor cells or infected cells, where they can express RNA sequences (i.e., siRNA, shRNA or microRNA) that will inhibit translation of FDPS, GGPS1, IDII, F-Tase, squalene synthase, and/or functional variants thereof, as well as encode and express cytotoxic cytokines or chemokines.

Disclosed herein are constructs for decreasing expression of FDPS, GGPSI, IDII, F-Tase, squalene synthase, and/or functional variants thereof, increasing expression of cytokines, and increasing expression of chemokines including RANTES. For instance, in embodiments the constructs may encode for interferon-gamma, IL-1, IL-1B, IL-2, IL-4, IL-7, IL-12, IL-15, IL-17, IL-18, IL-23, IL-33, IL-36, or TNF-$\alpha$.

Expression of cytokines and chemokines, like those listed above, will result in localized cytotoxic destruction of tumor cells or cells infected with pathogenic organisms. Accordingly, expression of such constructs by a tumor cell can result in the tumor cells assisting in their own destruction and activating an immune mechanism capable of destroying other tumor cells not genetically modified by the lentivirus vector. The capacity for genetically modified cells to activate GD T cells involves the GD T cell receptor, butyrophilin recognition, and the activation of GD T cell receptors for common gamma chain cytokines. Killing of tumor cells relies on a family of GD T cell surface receptors generally described as members of the NK receptor family that distinguish tumor cells from normal cells and provide for selectivity in the cell killing process. Consequently, a small number of genetically modified tumor cells can activate a sufficient number of GD T cells to achieve broad destruction of tumors including killing of both genetically-modified and non-modified cells in the same or distant tumors. Accordingly, expression of such constructs by a tumor cell or an infected cell will result in the unwanted cells assisting in its own destruction.

Likewise, if the disclosed constructs are expressed in a tumor cell or infected cell, decreasing the expression of FDPS, GGPS1, IDI1, F-Tase, squalene synthase, and/or functional variants thereof may result in activation and recruitment of GD T cells to the tumor site of site of cell infection. Increasing expression of RANTES will further attract GD T cells to intended tissue location. Because GD T cells can kill a broad range of tumors of epithelial origin as well as many leukemias and lymphomas, and are further able to produce high levels of the anti-tumor cytokine, IFNγ, recruitment of GD T cells to the site of a tumor can be a particularly effective means of inducing anti-tumor immunity.

Decreased expression of FDPS, GGPSI, IDII, F-Tase, squalene synthase, and/or functional variants thereof can be achieved via shRNA, microRNA, siRNA, or other means known in the art. For instance, shRNAs according to SEQ ID NOs: 1, 2, 3, or 4, or variants thereof can be used in the disclosed constructs and methods, although this example is not limiting, shRNAs according to SEQ ID NOs: 64-67, 70-72, 76, or variants thereof can be used in the disclosed constructs and methods, although this example is not limiting. miRNAs according to SEQ ID NOs: 68 or 69, or variants thereof can be used in the disclosed constructs and methods, although this example is not limiting. The coding regions for RNAs to decrease expression of FDPS, GGPSI, IDII, F-Tase, squalene synthase, and/or functional variants thereof, and the coding regions of cytokine and chemokines may be in the same construct or on different constructs.

The classical approach for the production of recombinant polypeptides or gene regulatory molecules including small RNA is the use of stable expression constructs. These constructs are based upon chromosomal integration of a transduced expression plasmid (or at least a portion thereof) into the genome of the host cell, short-duration plasmid transfection, or non-integrating viral vectors also with limited half-life. The sites of gene integration are generally random, and the number and ratio of genes integrating at any particular site are often unpredictable: likewise, non-integrating plasmids or viral vectors also generate nuclear DNA but these species usually lack sequences required for DNA replication and continuous maintenance. Thus, constructs that rely on chromosomal integration result in permanent maintenance of the recombinant gene that may exceed the therapeutic interval.

An alternative to stable expression constructs for gene expression are transient expression constructs. The expression of the latter gene expression construct is based on non-integrated plasmids, and hence the expression is typically lost as the cell undergoes division or the plasmid vectors are destroyed by endogenous nucleases.

The disclosed constructs are preferably episomal constructs that are transiently expressed. Episomal constructs are degraded or diluted over time such that they do not make permanent changes to a subject's genome, nor are they incorporated into the chromosome of a target cell. The process of episomal replication typically incorporates both host cell replication machinery and viral trans-acting factors.

Avoiding chromosomal integration reduces certain barriers to in vivo gene delivery. However, even integration-defective constructs can have a background frequency of integration, and any DNA molecule can find rare homologies to recombine with host sequences: but these rates of integration are exceptionally rare and generally not clinically significant.

Thus, in embodiments, the disclosed vectors support active gene and/or small RNA delivery over a period of about 1, about 2, about 3, about 4, about 5, about 6, about 7, about 8, about 9, about 10, about 11, or about 12 weeks. In embodiments, the disclosed vectors support active gene and/or small RNA delivery over a period of about 1 month, 2 months, 3 months, 4 months, 5 months, 6 months, 7 months, 8 months, 9 months, 10 months, 11 months, 12 months, or longer. Any combination of these time periods can also be used in the methods of the invention, e.g., 1 month and I week, or 3 months and 2 weeks.

However, in embodiments, the constructs comprise integrating elements that depend on a retroviral integrase gene, such that the construct becomes integrated into the subject's 30) chromosome. Retrotransposition and transposition are additional examples of mechanisms whereby mobile genetic elements become integrated or inserted into the chromosome. Plasmids may become integrated into the chromosome by recombination, and gene editing technologies including CRISPR and TALEN utilize guide RNA sequences and alter chromosomal loci by gene deletion or gene conversion mechanisms.

Constructs may comprise specific promoters for expressing cytokines involved in the maintenance of GD T cells (i.e., IL-2, IL-7, IL-12, IL-15, IL-17, IL-18, IL-23, or IL-36). For example, promoters that may be incorporated into the disclosed constructs include but are not limited to TATA-box promoters, CpG-box promoters, CCAAT-box promoters, TTGACA-box promoters, BRE-box promoters, INR-box promoters, AT-based promoters, CG-based promoters, ATCG-compact promoters, ATCG-balanced promoters, ATCG-middle promoters, ATCG-less promoters, AT-less promoters, CG-less promoters, AT-spike promoters, and CG-spike promoters. See, for e.g.: Gagniuc and Ionescu-Tirgoviste, Eukaryotic genomes may exhibit up to 10 generic classes of gene promoters, BMC GENOMICS 13:512 (2012).

Therapeutic Vectors

The construct can be delivered via known transfection and/or transduction vectors, including but not limited to lentiviral vectors, adeno-associated virus, poxvirus, herpesvirus vectors, protein and/or lipid complexes, liposomes, micelles, bacterially-produced vesicles, eukaryotic cell-produced vesicles, exosomes and the like.

Viral vectors can be preferentially targeted to cell types that are useful for the disclosed methods (i.e., tumor cells or myeloid cells, or lymphocytes). Viral vectors can be used to transduce genes into target cells owing to specific virus envelope-host cell receptor interactions and viral mechanisms for gene expression. As a result, viral vectors have been used as vehicles for the transfer of genes into many different cell types including whole embryos, fertilized eggs, isolated tissue samples, tissue targets in situ, and cultured cell lines. The ability to introduce and express foreign genes in a cell is useful for the study of gene expression, and the elucidation of cell lineages as well as providing the potential for therapeutic interventions such as gene therapy, somatic cell reprogramming of induced pluripotent stem cells, and various types of immunotherapy. Viral components from viruses like Papovaviridae (e.g., bovine papillomavirus or BPV) or Herpesviridae (e.g. Epstein Barr Virus or EBV) or Hepadnaviridae (e.g., Hepatitis B Virus or HBV) or pox vectors including vaccinia may be used in the disclosed vectors.

Lentiviral vectors are a preferred type of vector for the disclosed compositions and methods, although the disclosure is not specifically limited to lentiviral vectors. Lentivirus is a genus of viruses that can deliver a significant amount of viral nucleic acid into a host cell. Lentiviruses are characterized as having a unique ability to infect/transduce non-dividing cells, and following transduction, lentiviruses integrate their nucleic acid into the host cell's chromosomes.

Infectious lentiviruses have three main genes coding for the virulence proteins gag, pol, and env, and two regulatory genes including tat and rev. Depending on the specific serotype and virus, there may be additional accessory genes that code for proteins involved in regulation, synthesis, and/or processing viral nucleic acids and other replicative functions.

Moreover, lentiviruses contain long terminal repeat (LTR) regions, which may be approximately 600 nt long. LTRs may be segmented into U3, R, and U5 regions. LTRs can mediate integration of retroviral DNA into the host chromosome via the action of integrase. Alternatively, without functioning integrase, the LTRs may be used to circularize the viral nucleic acid.

Viral proteins involved in early stages of lentivirus replication include reverse transcriptase and integrase. Reverse transcriptase is the virally encoded, RNA-dependent DNA polymerase. The enzyme uses a viral RNA genome as a template for the synthesis of a complementary DNA copy. Reverse transcriptase also has RNaseH activity for destruction of the RNA-template. Integrase binds both the viral cDNA generated by reverse transcriptase and the host DNA. Integrase processes the LTR before inserting the viral genome into the host DNA. Tat acts as a trans-activator during transcription to enhance initiation and elongation. The rev responsive element acts post-transcriptionally, regulating mRNA splicing and transport to the cytoplasm.

Viral vectors, in general, comprise glycoproteins and the various glycoproteins may provide specific affinities. For instance, Vesicular Stomatitis Virus G (VSVG) peptides can increase transfection into myeloid cells. Alternatively, viral vectors can also have targeting moieties, such as antibodies, attached to their shell peptides. Targeting antibodies can be specific for antigens that are overexpressed on a tumor, for instance, like HER-2, PSA, CEA, M2-PK, and CA19-9.

Other viral vector specificities are also known in the art and can be used to target particular populations of cells. For example, poxvirus and herpesvirus vectors target to macrophages, dendritic cells and epithelial cells, measles virus vectors may target to B cells, rabies viral vectors may target to neural cells.

Lentiviral Vector System

A lentiviral virion (particle) is expressed by a vector system encoding the necessary viral proteins to produce a virion (viral particle). There is at least one vector containing a nucleic acid sequence encoding the lentiviral pol proteins necessary for reverse transcription and integration, operably linked to a promoter. In another embodiment, the pol proteins are expressed by multiple vectors. There is also a vector containing a nucleic acid sequence encoding the lentiviral gag proteins necessary for forming a viral capsid operably linked to a promoter. In an embodiment, this gag nucleic acid sequence is on a separate vector than at least some of the pol nucleic acid sequence. In another embodiment, the gag nucleic acid is on a separate vector from all the pol nucleic acid sequences that encode pol proteins.

Numerous modifications can be made to the vectors, which are used to create the particles to further minimize the chance of obtaining wild type revertants. These include, but are not limited to deletions of the U3 region of the LTR, tat deletions and matrix (MA) deletions.

The gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In embodiments, the env nucleic acid sequence encodes a lentiviral envelope protein. In another embodiment the envelope protein is not from the lentivirus, but from a different virus. The resultant particle is referred to as a pseudotyped particle. By appropriate selection of envelopes one can "infect" virtually any cell. For example, one can use an en gene that encodes an envelope protein that targets an endocytic compartment such as that of the influenza virus, VSV-G, alpha viruses (Semliki forest virus. Sindbis virus), arenaviruses (lymphocytic choriomeningitis virus), flaviviruses (tick-borne encephalitis virus, Dengue virus, hepatitis C virus. GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E. MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and GP: glycoproteins. In another embodiment, one can use different lentiviral capsids with a pseudotyped envelope (for example, FIV or SHIV [U.S. Pat. No. 5,654,195]). A SHIV pseudotyped vector can readily be used in animal models such as monkeys.

As detailed herein, a lentiviral vector system typically includes at least one helper plasmid comprising at least one of a gag, pol, or rev gene, or functional variants thereof. Each of the gag, pol and rev genes, or functional variants thereof, may be provided on individual plasmids, or one or more genes may be provided together on the same plasmid. In one embodiment, the gag, pol, and rev genes are provided on the same plasmid (e.g., FIG. 2). In another embodiment, the gag and pol genes are provided on a first plasmid and the rev gene is provided on a second plasmid (e.g., FIG. 3). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, or functional variants thereof, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

In another aspect, and as detailed in FIG. 2, the lentiviral vector, which is also referred to herein as a therapeutic vector, can include the following elements: hybrid 5' long terminal repeat (RSV/5' LTR) (SEQ ID NOs: 5-6), Psi sequence (RNA packaging site) (SEQ ID NO: 7), RRE (Rev-response element) (SEQ ID NO: 8), cPPT (polypurine tract) (SEQ ID NO: 9), H1 promoter (SEQ ID NO: 10), shFDPS (SEQ ID NOs: 1, 2, 3, 4), CMV (SEQ ID NO: 19), BTN3A3 (R381H)-T2A-IL-2 (collectively, SEQ ID NO: 55), Woodchuck Post-Transcriptional Regulatory Element (WPRE) (SEQ ID NO: 11), and 3' Delta LTR (SEQ ID NO: 12). In another aspect, sequence variation, by way of substitution, deletion, addition, or mutation can be used to modify the sequences references herein.

In another aspect, and as detailed herein, a helper plasmid has been designed to include the following elements: a CMV (CAG) enhancer (SEQ ID NO: 21); a Chicken beta actin (CAG) promoter (SEQ ID NO: 13); a chicken beta actin intron (SEQ ID NO: 22); a HIV gag (SEQ ID NO: 14); a HIV Pol (SEQ ID NO: 15); a HIV Int (SEQ ID NO: 16); a HIV RRE (SEQ ID NO: 8); a HIV Rev (SEQ ID NO: 18); and a rabbit beta globin poly A (SEQ ID NO: 23). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein, an envelope plasmid has been designed to include the following elements being from left to right: RNA polymerase II promoter (CMV) (SEQ ID NO: 19) and vesicular stomatitis virus G glycoprotein (VSV-G) (SEQ ID NO: 20). In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, MD), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

The disclosed vectors allow for short, medium, or long-term expression of genes or sequences of interest and episomal maintenance of the disclosed vectors. Accordingly, dosing regimens may vary based upon the condition being treated and the method of administration.

In one embodiment, transduction vectors may be administered to a subject in need in varying doses. Specifically, a subject may be administered about $\geq 10^6$ infectious doses (where 1 dose is needed on average to transduce 1 target cell). More specifically, a subject may be administered about $\geq 10^7$, about $\geq 10^8$, about $\geq 10^9$, or about $\geq 10^{10}$ infectious doses, or any number of doses in-between these values. Upper limits of transduction vector dosing will be determined for each disease indication and will depend on toxicity/safety profiles for each individual product or product lot.

Additionally, a vector of the present disclosure may be administered periodically, such as once or twice a day, or any other suitable time period. For example, vectors may be administered to a subject in need once a week, once every other week, once every three weeks, once a month, every other month, every three months, every six months, every nine months, once a year, every eighteen months, every two years, every thirty months, or every three years.

In one embodiment, the disclosed vectors are administered as a pharmaceutical composition. In embodiments, the pharmaceutical composition comprising the disclosed vectors can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition comprising a vector can also be formulated for injection, insufflation, infusion, or intradermal exposure. For instance, an injectable formulation may comprise the disclosed vectors in an aqueous or non-aqueous solution at a suitable pH and tonicity.

The disclosed vectors may be administered to a subject via direct injection into a tumor site or at a site of infection. In embodiments, the vectors can be administered systemically. In embodiments, the vectors can be administered via guided cannulation to tissues immediately surrounding the sites of tumor or infection.

The disclosed vector compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed vector compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the composition may be a controlled release formulation, sustained release formulation, immediate release formulation, or any combination thereof. Further, the composition may be a transdermal delivery system. In embodiments, the pharmaceutical composition comprising a vector can be formulated in a solid dosage form for oral administration, and the solid dosage form can be powders, granules, capsules, tablets or pills. In embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In embodiments, the oral dosage form can be immediate release, or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a vector can be formulated as a sublingual or buccal dosage form. Such dosage forms comprise sublingual tablets or solution compositions that are administered under the tongue and buccal tablets that are placed between the cheek and gum.

In embodiments, the pharmaceutical composition comprising a vector can be formulated as a nasal dosage form. Such dosage forms of the present invention comprise solution, suspension, and gel compositions for nasal delivery.

In embodiments, the pharmaceutical composition comprising a vector can be formulated in a liquid dosage form for oral administration, such as suspensions, emulsions or syrups. In embodiments, the liquid dosage form can include, in addition to commonly used simple diluents such as water and liquid paraffin, various excipients such as humectants, sweeteners, aromatics or preservatives. In particular embodiments, the composition comprising vectors can be formulated to be suitable for administration to a pediatric patient.

In embodiments, the pharmaceutical composition can be formulated in a dosage form for parenteral administration, such as sterile aqueous solutions, suspensions, emulsions, non-aqueous solutions or suppositories. In embodiments, the solutions or suspensions can include propylene glycol, polyethylene glycol, vegetable oils such as olive oil or injectable esters such as ethyl oleate.

The dosage of the pharmaceutical composition can vary depending on the patient's weight, age, gender, administration time and mode, excretion rate, and the severity of disease.

In embodiments, the treatment of cancer is accomplished by guided direct injection of the disclosed vector constructs into tumors, using needle, or intravascular cannulation. In embodiments, the disclosed vectors are administered into the cerebrospinal fluid, blood or lymphatic circulation by venous or arterial cannulation or injection, intradermal delivery, intramuscular delivery or injection into a draining organ near the site of disease. The following examples are given to illustrate the present invention. It should be understood, however, that the invention is not to be limited to the specific conditions or details described in these examples. All printed publications referenced herein are specifically incorporated by reference.

EXAMPLES

Example 1—Development of a Lentiviral Vector System

A lentiviral vector system was developed as summarized in FIGS. 2 and 3 (circularized forms shown). Lentiviral particles were produced in 293T/17 HEK cells (purchased from American Type Culture Collection, Manassas, VA) following transfection 10 with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-vector system (i.e., a 2-vector lentiviral packaging system) was designed for the production of lentiviral particles. A schematic of the 3-vector system is shown in FIG. 2. Briefly, and with reference to FIG. 2, the top-most vector is a helper plasmid, which, in this case, includes Rev. The vector appearing in the middle of FIG. 2 is the envelope plasmid. The bottom-most vector is the therapeutic vector, as described herein.

Referring more specifically to FIG. 2, the Helper plus Rev plasmid includes a CMV (CAG) enhancer (SEQ ID NO: 21); a Chicken beta actin (CAG) promoter (SEQ ID NO: 13); a chicken beta actin intron (SEQ ID NO: 22); a HIV gag (SEQ ID NO: 14); a HIV Pol (SEQ ID NO: 15); a HIV Int (SEQ ID NO: 16); a HIV RRE (SEQ ID NO: 8); a HIV Rev (SEQ ID NO: 18); and a rabbit beta globin poly A (SEQ ID NO: 23).

The Envelope plasmid includes a CMV promoter (SEQ ID NO: 19); a beta globin intron (SEQ ID NO: 24); a VSV-G (SEQ ID NO: 20); and a rabbit beta globin poly A (SEQ ID NO: 25).

Synthesis of a 2-Vector Lentiviral Packaging System Including Helper (Plus Rev) and Envelope Plasmids.

Materials and Methods:

Construction of the helper plasmid: The helper plasmid was constructed by initial PCR 5 amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3.1 plasmid (Invitrogen). The forward primer was (5'-TAAGCAGAATTC ATGAATTTGCCAG-GAAGAT-3') (SEQ ID NO: 26) and reverse primer was (5'-CCATACAAT-GAATGGACACTAGGCGGCCGCACGAAT-3') (SEQ ID NO: 27).

The sequence for the Gag, Pol, Integrase fragment was as follows:

```
                                              (SEQ ID NO: 28)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC

ATAATTGGAAGAAATCTGTTGACTCAGATTGGCTGCACTTTAAATTTTCC
```

CATTAGTCCTATTGAGACTGTACCAGTAAAATTAAAGCCAGGAATGGATG

GCCCAAAAGTTAAACAATGGCCATTGACAGAAGAAAAAATAAAAGCATTA

GTAGAAATTTGTACAGAAATGGAAAAGGAAGGAAAAATTTCAAAAATTGG

GCCTGAAAATCCATACAATACTCCAGTATTTGCCATAAAGAAAAAAGACA

GTACTAAATGGAGAAAATTAGTAGATTTCAGAGAACTTAATAAGAGAACT

CAAGATTTCTGGGAAGTTCAATTAGGAATACCACATCCTGCAGGGTTAAA

ACAGAAAAAATCAGTAACAGTACTGGATGTGGGCGATGCATATTTTTCAG

TTCCCTTAGATAAAGACTTCAGGAAGTATACTGCATTTACCATACCTAGT

ATAAACAATGAGACACCAGGGATTAGATATCAGTACAATGTGCTTCCACA

GGGATGGAAAGGATCACCAGCAATATTCCAGTGTAGCATGACAAAAATCT

TAGAGCCTTTTAGAAAACAAAATCCAGACATAGTCATCTATCAATACATG

GATGATTTGTATGTAGGATCTGACTTAGAAATAGGGCAGCATAGAACAAA

AATAGAGGAACTGAGACAACATCTGTTGAGGTGGGGATTTACCACACCAG

ACAAAAAACATCAGAAAGAACCTCCATTCCTTTGGATGGGTTATGAACTC

CATCCTGATAAATGGACAGTACAGCCTATAGTGCTGCCAGAAAAGGACAG

CTGGACTGTCAATGACATACAGAAATTAGTGGGAAAATTGAATTGGGCAA

GTCAGATTTATGCAGGGATTAAAGTAAGGCAATTATGTAAACTTCTTAGG

GGAACCAAAGCACTAACAGAAGTAGTACCACTAACAGAAGAAGCAGAGCT

AGAACTGGCAGAAAACAGGGAGATTCTAAAAGAACCGGTACATGGAGTGT

ATTATGACCCATCAAAAGACTTAATAGCAGAAATACAGAAGCAGGGGCAA

GGCCAATGGACATATCAAATTTATCAAGAGCCATTTAAAAAATCTGAAAAC

AGGAAAGTATGCAAGAATGAAGGGTGCCCACACTAATGATGTGAAACAAT

TAACAGAGGCAGTACAAAAAATAGCCACAGAAAGCATAGTAATATGGGGA

AAGACTCCTAAATTTAAATTACCCATACAAAAGGAAACATGGGAAGCATG

GTGGACAGAGTATTGGCAAGCCACCTGGATTCCTGAGTGGGAGTTTGTCA

ATACCCCTCCCTTAGTGAAGTTATGGTACCAGTTAGAGAAAGAACCCATA

ATAGGAGCAGAAACTTTCTATGTAGATGGGGCAGCCAATAGGGAAACTAA

ATTAGGAAAAGCAGGATATGTAACTGACAGAGGAAGACAAAAAGTTGTCC

CCCTAACGGACACAACAAATCAGAAGACTGAGTTACAAGCAATTCATCTA

GCTTTGCAGGATTCGGGATTAGAAGTAAACATAGTGACAGACTCACAATA

TGCATTGGGAATCATTCAAGCACAACCAGATAAGAGTGAATCAGAGTTAG

TCAGTCAAATAATAGAGCAGTTAATAAAAAAGGAAAAAGTCTACCTGGCA

TGGGTACCAGCACACAAAGGAATTGGAGGAAATGAACAAGTAGATAAATT

GGTCAGTGCTGGAATCAGGAAAGTACTATTTTTAGATGGAATAGATAAGG

CCCAAGAAGAACATGAGAAATATCACAGTAATTGGAGAGCAATGGCTAGT

GATTTTAACCTACCACCTGTAGTAGCAAAAGAAATAGTAGCCAGCTGTGA

TAAATGTCAGCTAAAAGGGGAAGCCATGCATGGACAAGTAGACTGTAGCC

CAGGAATATGGCAGCTAGATTGTACACATTTAGAAGGAAAAGTTATCTTG

GTAGCAGTTCATGTAGCCAGTGGATATATAGAAGCAGAAGTAATTCCAGC

AGAGACAGGGCAAGAAACAGCATACTTCCTCTTAAAATTAGCAGGAAGAT

GGCCAGTAAAAACAGTACATACAGACAATGGCAGCAATTTCACCAGTACT

ACAGTTAAGGCCGCCTGTTGGTGGGCGGGGATCAAGCAGGAATTTGGCAT

TCCCTACAATCCCCAAAGTCAAGGAGTAATAGAATCTATGAATAAAGAAT

TAAAGAAAATTATAGGACAGGTAAGAGATCAGGCTGAACATCTTAAGACA

GCAGTACAAATGGCAGTATTCATCCACAATTTTAAAAGAAAAGGGGGGAT

TGGGGGGTACAGTGCAGGGGAAAGAATAGTAGACATAATAGCAACAGACA

TACAAACTAAAGAATTACAAAAACAAATTACAAAAATTCAAAATTTTCGG

GTTTATTACAGGGACAGCAGAGATCCAGTTTGGAAAGGACCAGCAAAGCT

CCTCTGGAAAGGTGAAGGGGCAGTAGTAATACAAGATAATAGTGACATAA

AAGTAGTGCCAAGAAGAAAAGCAAAGATCATCAGGGATTATGGAAAACAG

ATGGCAGGTGATGATTGTGTGGCAAGTAGACAGGATGAGGATTAA

Next, a DNA fragment containing the Rev, RRE, and rabbit beta globin poly A sequence with XbaI and XmaI flanking restriction sites was synthesized by Eurofins Genomics. The DNA fragment was then inserted into the plasmid at the XbaI and XmaI restriction sites The DNA sequence was as follows: IDC-28 DNA M (SEQ ID NO: 29)
TCTAGAATGGCAGGAAGAAGCGGAGACAGCGACGAAGAGCTCATCAGAAC

AGTCAGACTCATCAAGCTTCTCTATCAAAGCAACCCACCTCCCAATCCCG

AGGGGACCCGACAGGCCCGAAGGAATAGAAGAAGAAGGTGGAGAGAGAGA

CAGAGACAGATCCATTCGATTAGTGAACGGATCCTTGGCACTTATCTGGG

ACGATCTGCGGAGCCTGTGCCTCTTCAGCTACCACCGCTTGAGAGACTTA

CTCTTGATTGTAACGAGGATTGTGGAACTTCTGGGACGCAGGGGGTGGGA

AGCCCTCAAATATTGGTGGAATCTCCTACAATATTGGAGTCAGGAGCTAA

AGAATAGAGGAGCTTTGTTCCTTGGGTTCTTGGGAGCAGCAGGAAGCACT

ATGGGCGCAGCGTCAATGACGCTGACGGTACAGGCCAGACAATTATTGTC

TGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGA

ATCCTGGCTGTGGAAAGATACCTAAAGGATCAACAGCTCCTAGATCTTTT

TCCCTCTGCCAAAAATTATGGGGACATCATGAAGCCCCTTGAGCATCTGA

CTTCTGGCTAATAAAGGAAATTTATTTTCATTGCAATAGTGTGTTGGAAT

TTTTTGTGTCTCTCACTCGGAAGGACATATGGGAGGGCAAATCATTTAAA

ACATCAGAATGAGTATTTGGTTTAGAGTTTGGCAACATATGCCATATGCT

GGCTGCCATGAACAAAGGTGGCTATAAAGAGGTCATCAGTATATGAAACA

GCCCCCTGCTGTCCATTCCTTATTCCATAGAAAAGCCTTGACTTGAGGTT

AGATTTTTTTTATATTTTGTTTTGTGTTATTTTTTTCTTTAACATCCCTA

AAATTTTCCTTACATGTTTTACTAGCCAGATTTTTCCTCCTCTCCTGACT

ACTCCCAGTCATAGCTGTCCCTCTTCTCTTATGAAGATCCCTCGACCTGC

AGCCCAAGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

-continued

```
TCACTGCCCGCTTTCCAGTCGGGAAACCTGTCGTGCCAGCGGATCCGCAT

CTCAATTAGTCAGCAACCATAGTCCCGCCCCTAACTCCGCCCATCCCGCC

CCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCAGCGGCCGCCCCGGG
```

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by Eurofins Genomics. The DNA fragment was then inserted into the plasmid at the MluI and EcoRI restriction sites. The DNA sequence was as follows:

```
                                          (SEQ ID NO: 30)
ACGCGTTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGACTATT

TACGGTAAACTGCCCACTTGGCAGTACATCAAGTGTATCATATGCCAAGT

ACGCCCCCTATTGACGTCAATGACGGTAAATGGCCCGCCTGGCATTATGC

CCAGTACATGACCTTATGGGACTTTCCTACTTGGCAGTACATCTACGTAT

TAGTCATCGCTATTACCATGGGTCGAGGTGAGCCCCACGTTCTGCTTCAC

TCTCCCCATCTCCCCCCCCTCCCCACCCCCAATTTTGTATTTATTTATTT

TTTAATTATTTTGTGCAGCGATGGGGGCGGGGGGGGGGGGGGGCGCGCGCC

AGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGG

GACGGCCCTTCTCCTCCGGGCTGTAATTAGCGCTTGGTTTAATGACGGCT

CGTTTCTTTTCTGTGGCTGCGTGAAAGCCTTAAAGGGCTCCGGGAGGGCC

CTTTGTGCGGGGGGAGCGGCTCGGGGGGTGCGTGCGTGTGTGTGTGCGT

GGGGAGCGCCGCGTGCGGCCCGCGCTGCCCGGCGGCTGTGAGCGCTGCGG

GCGCGGCGCGGGGCTTTGTGCGCTCCGCGTGTGCGCGAGGGGAGCGCGGC

CGGGGGCGGTGCCCCGCGGTGCGGGGGGGCTGCGAGGGGAACAAAGGCTG

CGTGCGGGGTGTGTGCGTGGGGGGGTGAGCAGGGGGTGTGGGCGCGGCGG

TCGGGCTGTAACCCCCCCCTGCACCCCCCTCCCCGAGTTGCTGAGCACGG

CCCGGCTTCGGGTGCGGGGCTCCGTGCGGGGCGTGGCGCGGGGCTCGCCG

TGCCGGGCGGGGGGTGGCGGCAGGTGGGGGTGCCGGGCGGGGCGGGGCCG

CCTCGGGCCGGGGAGGGCTCGGGGGAGGGGCGCGGCGGCCCCGGAGCGCC
```

-continued

```
GGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAA

ATCTGGGAGGCGCCGCCGCACCCCCTCTAGCGGGCGCGGGCGAAGCGGTG

CGGCGCCGGCAGGAAGGAAATGGGCGGGGAGGGCCTTCGTGCGTCGCCGC

GCCGCCGTCCCCTTCTCCATCTCCAGCCTCGGGGCTGCCGCAGGGGGACG

GCTGCCTTCGGGGGGGGACGGGGCAGGGCGGGGTTCGGCTTCTGGCGTGTG

ACCGGCGGGAATTC
```

Construction of the VSV-G Envelope Plasmid:

The vesicular stomatitis Indiana virus glycoprotein (VSV-G) sequence was synthesized by Eurofins Genomics with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

```
                                          (SEQ ID NO: 31)
GAATTCATGAAGTGCCTTTTGTACTTAGCCTTTTTATTCATTGGGGTGAA

TTGCAAGTTCACCATAGTTTTTCCACACAACCAAAAAGGAAACTGGAAAA

ATGTTCCTTCTAATTACCATTATTGCCCGTCAAGCTCAGATTTAAATTGG

CATAATGACTTAATAGGCACAGCCTTACAAGTCAAAATGCCCAAGAGTCA

CAAGGCTATTCAAGCAGACGGTTGGATGTGTCATGCTTCCAAATGGGTCA

CTACTTGTGATTTCCGCTGGTATGGACCGAAGTATATAACACATTCCATC

CGATCCTTCACTCCATCTGTAGAACAATGCAAGGAAAGCATTGAACAAAC

GAAACAAGGAACTTGGCTGAATCCAGGCTTCCCTCCTCAAAGTTGTGGAT

ATGCAACTGTGACGGATGCCGAAGCAGTGATTGTCCAGGTGACTCCTCAC

CATGTGCTGGTTGATGAATACACAGGAGAATGGGTTGATTCACAGTTCAT

CAACGGAAAATGCAGCAATTACATATGCCCCACTGTCCATAACTCTACAA

CCTGGCATTCTGACTATAAGGTCAAAGGGCTATGTGATTCTAACCTCATT

TCCATGGACATCACCTTCTTCTCAGAGGACGGAGAGCTATCATCCCTGGG

AAAGGAGGGCACAGGGTTCAGAAGTAACTACTTTGCTTATGAAACTGGAG

GCAAGGCCTGCAAAATGCAATACTGCAAGCATTGGGGAGTCAGACTCCCA

TCAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACCT

CAGTGGATGTAAGTCTAATTCAGGACGTTGAGAGGATCTTGGATTATTCC

CTCTGCCAAGAAACCTGGAGCAAAATCAGAGCGGGTCTTCCAATCTCTCC

AGTGGATCTCAGCTATCTTGCTCCTAAAAACCCAGGAACCGGTCCTGCTT

TCACCATAATCAATGGTACCCTAAAATACTTTGAGACCAGATACATCAGA

GTCGATATTGCTGCTCCAATCCTCTCAAGAATGGTCGGAATGATCAGTGG

AACTACCACAGAAAGGGAACTGTGGGATGACTGGGCACCATATGAAGACG

TGGAAATTGGACCCAATGGAGTTCTGAGGACCAGTTCAGGATATAAGTTT

CCTTTATACATGATTGGACATGGTATGTTGGACTCCGATCTTCATCTTAG

CTCAAAGGCTCAGGTGTTCGAACATCCTCACATTCAAGACGCTGCTTCGC

AACTTCCTGATGATGAGAGTTTATTTTTTTGGTGATACTGGGCTATCCAAA
```

-continued

```
AATCCAATCGAGCTTGTAGAAGGTTGGTTCAGTAGTTGGAAAAGCTCTAT

TGCCTCTTTTTTCTTTATCATAGGGTTAATCATTGGACTATTCTTGGTTC

TCCGAGTTGGTATCCATCTTTGCATTAAATTAAAGCACACCAAGAAAAGA

CAGATTTATACAGACATAGAGATGAGAATTC
```

A 4-vector system (i.e., a 3-vector lentiviral packaging system) has also been designed and produced using the methods and materials described herein. A schematic of the 4-vector system is shown in FIG. 3. Briefly, and with reference to FIG. 3, the top-most vector is a helper plasmid, which, in this case, does not include Rev. The vector second from the top is a separate Rev plasmid. The vector second from the bottom is the envelope plasmid. The bottom-most vector is the previously described therapeutic vector.

Referring, in part, to FIG. 3, the Helper plasmid includes a CMV (CAG) enhancer (SEQ ID NO: 21); a Chicken beta actin (CAG) promoter (SEQ ID NO: 13); a chicken beta actin intron (SEQ ID NO: 22); a HIV gag (SEQ ID NO: 14); a HIV Pol (SEQ ID NO: 15); a HIV Int (SEQ ID NO: 16); a HIV RRE (SEQ ID NO: 8); and a rabbit beta globin poly A (SEQ ID NO: 23).

The Rev plasmid includes a RSV promoter and a HIV Rev (SEQ ID NO: 33); and a rabbit beta globin poly A (SEQ ID NO: 23).

The Envelope plasmid includes a CMV promoter (SEQ ID NO: 19); a beta globin intron (SEQ ID NO: 24); a VSV-G (SEQ ID NO: 20); and a rabbit beta globin poly A (SEQ ID NO: 23).

Synthesis of a 3-Vector Lentiviral Packaging System Including Helper, Rev, and Envelope Plasmids.

Materials and Methods:

Construction of the Helper Plasmid without Rev:

The Helper plasmid without Rev was constructed by inserting a DNA fragment containing the RRE and rabbit beta globin poly A sequence. This sequence was synthesized by Eurofins Genomics with flanking XbaI and XmaI restriction sites. The RRE/rabbit poly A beta globin sequence was then inserted into the Helper plasmid at the XbaI and XmaI restriction sites. The DNA sequence is as follows:

```
                                       (SEQ ID NO: 32)
TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA

GATTTTTTTTATATTTTGTTTTGTGTTATTTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA
```

-continued

```
GCCCAAGCTTGGCGTAATCATGGTCATAGCTGTTTCCTGTGTGAAATTGT

TATCCGCTCACAATTCCACACAACATACGAGCCGGAAGCATAAAGTGTAA

AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG
```

Construction of the Rev Plasmid:

The RSV promoter and HIV Rev sequence was synthesized as a single DNA fragment by Eurofins Genomics with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                       (SEQ ID NO: 33)
CAATTGCGATGTACGGGCCAGATATACGCGTATCTGAGGGGACTAGGGTG

TGTTTAGGCGAAAAGCGGGGCTTCGGTTGTACGCGGTTAGGAGTCCCCTC

AGGATATAGTAGTTTCGCTTTTGCATAGGGAGGGGGAAATGTAGTCTTAT

GCAATACACTTGTAGTCTTGCAACATGGTAACGATGAGTTAGCAACATGC

CTTACAAGGAGAGAAAAAGCACCGTGCATGCCGATTGGTGGAAGTAAGGT

GGTACGATCGTGCCTTATTAGGAAGGCAACAGACAGGTCTGACATGGATT

GGACGAACCACTGAATTCCGCATTGCAGAGATAATTGTATTTAAGTGCCT

AGCTCGATACAATAAACGCCATTTGACCATTCACCACATTGGTGTGCACC

TCCAAGCTCGAGCTCGTTTAGTGAACCGTCAGATCGCCTGGAGACGCCAT

CCACGCTGTTTTGACCTCCATAGAAGACACCGGGACCGATCCAGCCTCCC

CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA
```

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 34), phosphoglycerate kinase (PGK) (SEQ ID NO: 35), and ubiquitin C (UbC) (SEQ ID NO: 36) can replace the CMV (SEQ ID NO: 19) or Chicken beta actin (CAG) promoter (SEQ ID NO: 13). These sequences can also be further varied by addition, substitution, deletion or mutation.

Poly A sequences: SV40 poly A (SEQ ID NO: 37) and bGH poly A (SEQ ID NO: 38) can replace the rabbit beta globin poly A (SEQ ID NO: 23). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 14); HIV Pol (SEQ ID NO: 15); and HIV Int (SEQ ID NO: 16) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD 114) (SEQ ID NO: 39), gibbon ape leukemia virus (GALV) (SEQ ID NO: 40), Rabies (FUG) (SEQ ID NO: 41), lymphocytic choriomeningitis virus (LCMV) (SEQ ID NO: 42), influenza A fowl plague virus (FPV) (SEQ ID NO: 43), Ross River alphavirus (RRV) (SEQ ID NO: 44), murine leukemia virus 10A1 (MLV) (SEQ ID NO: 45), or Ebola virus (EboV) (SEQ ID NO: 46). Sequences for these envelopes are identified in the 25 sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV, 5'LTR, Psi Packaging Signal, RRE, cPPT, H1, shFDPS, CMV, BTN3A3 (R381H) T2A IL-2, WPRE, and 3'6 LTR. The 4-vector lentiviral vector system contains: 1.

Helper plasmid: HIV Gag, Pol, and Integrase; 2. Rev plasmid: Rev; 3. Envelope plasmid: VSV-G/FUG envelope; and 4. Therapeutic vector: RSV, 5'LTR, Psi Packaging Signal, RRE, cPPT, H1, shFDPS, CMV, BTN3A3 (R381H) T2A IL-2, WPRE, and 3'6 LTR. Sequences corresponding with the above elements are identified in the sequence listings portion herein.

Example 2—Development of a Lentiviral Vector that Inhibits FDPS

The purpose of this Example was to develop an FDPS-inhibiting lentivirus vector, which is also referred to herein as LV-shFDPS.

Inhibitory RNA Design: The sequence of *Homo sapiens* Farnesyl diphosphate synthase (FDPS)(NM_002004.3) mRNA was used to search for potential siRNA or shRNA candidates to knockdown FDPS levels in human cells. Potential RNA interference sequences were identified by siRNA or shRNA design programs such as from GPP Web Portal hosted by the Broad Institute (portals.broadinstitute-.org/gpp/public/) or the BLOCK-iT RNAi Designer from Thermo Scientific (maidesigner.thermofisher.com/maiexpress/). Individual selected shRNA sequences were inserted into a lentiviral vector immediately 3 prime to a RNA polymerase III promoter such as H1 (SEQ ID NO: 10), U6 (SEQ ID NO: 47), or 7SK (SEQ ID NO: 48) to regulate shRNA expression. These lentivirus shRNA constructs were used to transduce cells and measure the change in specific mRNA levels. The shRNA most potent for reducing mRNA levels were embedded individually within a microRNA backbone to allow for expression by either the EF-1alpha or CMV RNA polymerase II promoters. The microRNA backbone was selected from mirbase.org. RNA sequences were also synthesized as synthetic siRNA oligonucleotides and introduced directly into cells without using a lentiviral vector.

Lentiviral Vector Construction: For FDPS shRNA, oligonucleotide sequences containing BamHI and EcoRI restriction sites were synthesized by Eurofins Genomics. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the lentiviral vector was verified by DNA sequencing using a specific primer for the promoter used to regulate shRNA expression. Using the following target sequences, exemplary shRNA sequences were determined to knock-down FDPS:

```
          (FDPS target sequence #1; SEQ ID NO: 49)
GTCCTGGAGTACAATGCCATT;

(FDPS shRNA sequence #1; SEQ ID NO: 1)
GTCCTGGAGTACAATGCCATTCTCGAGAATGGCATTGTACTCCAGGACTT
TTT;

(FDPS target sequence #2; SEQ ID NO: 50)
GCAGGATTTCGTTCAGCACTT;

(FDPS shRNA sequence #2; SEQ ID NO: 2)
GCAGGATTTCGTTCAGCACTTCTCGAGAAGTGCTGAACGAAATCCTGCTT
TTT;

(FDPS target sequence #3; SEQ ID NO: 51)
GCCATGTACATGGCAGGAATT;

(FDPS shRNA sequence #3; SEQ ID NO: 3)
GCCATGTACATGGCAGGAATTCTCGAGAATTCCTGCCATGTACATGGCTT
TTT;

(FDPS target sequence #4; SEQ ID NO: 52)
GCAGAAGGAGGCTGAGAAAGT;
and (FDPS shRNA sequence #4; SEQ ID NO: 4)
GCAGAAGGAGGCTGAGAAAGTCTCGAGACTTTCTCAGCCTCCTTCTGCTT
TTT.
```

Figure 4:
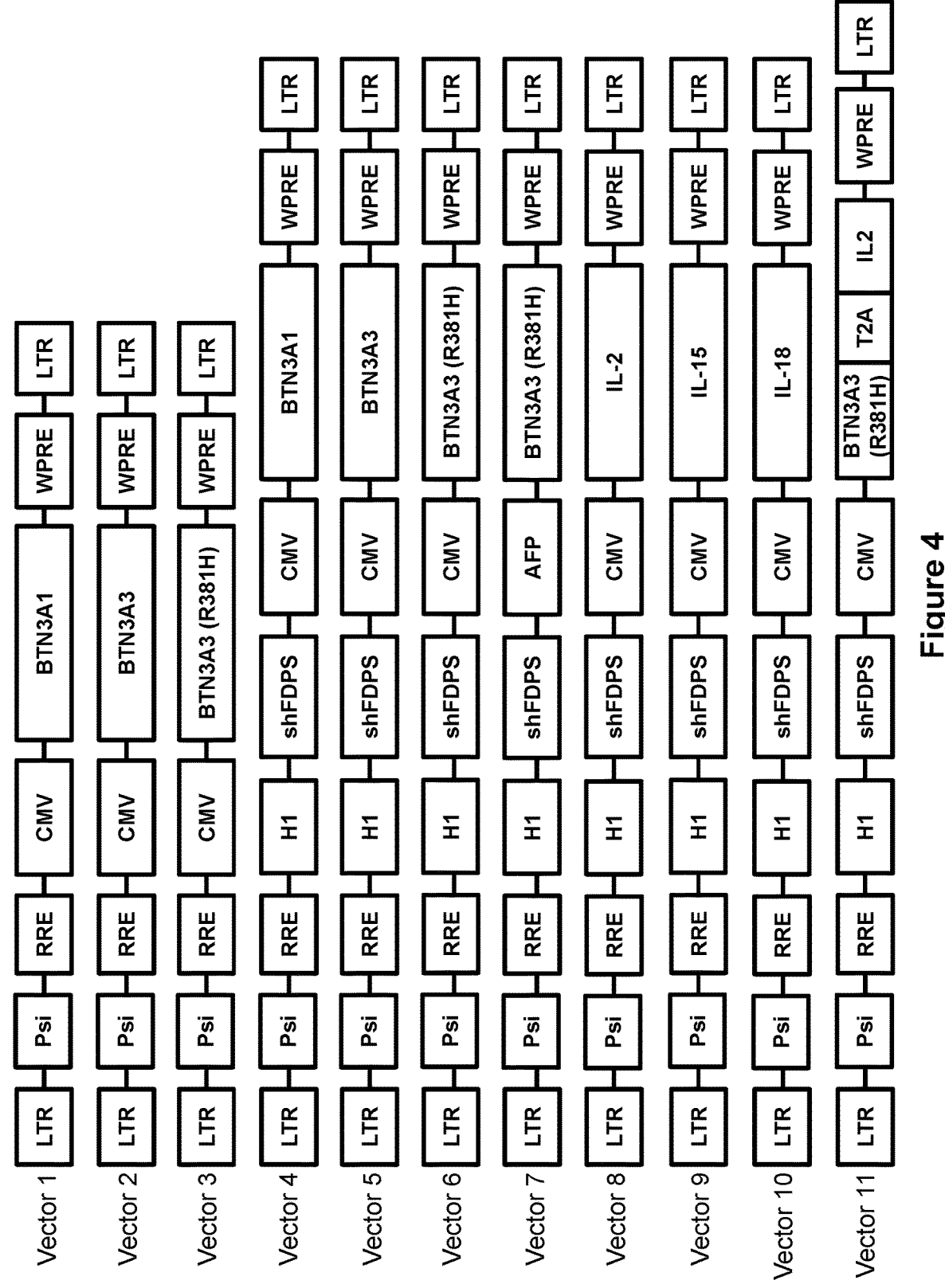
FIG. 4 depicts various linear maps of lentiviral vectors expressing a FDPS shRNA targeting sequence in combination with BTN3A3 and/or IL-2, IL-15, and IL-18.

Without limiting any of the foregoing, therapeutic vectors (which are also referred to herein as lentiviral plasmids) can be constructed as detailed in FIGS. 2-4. With continued reference to FIG. 4:

Vector 1 includes from left to right, a 5' LTR sequence; a Psi sequence; a RRE sequence; a CMV sequence; a BTN3A1 sequence; a WPRE sequence; and a 3' LTR sequence.

Vector 2 includes from left to right, a 5' LTR sequence; a Psi sequence; a RRE sequence; a CMV sequence; a BTN3A3 sequence; a WPRE sequence; and a 3' LTR sequence.

Vector 3 includes from left to right, a 5' LTR sequence; a Psi sequence; a RRE sequence; a CMV sequence; a BTN3A3 (R381H) sequence; a WPRE sequence; and a 3' LTR sequence.

Vector 4 includes from left to right, a 5' LTR sequence; a Psi sequence; a RRE sequence; a H1 sequence; a shFDPS sequence; a CMV sequence; a BTN3A1 sequence; a WPRE sequence; and a 3' LTR sequence.

Vector 5 includes from left to right, a 5' LTR sequence; a Psi sequence; a RRE sequence; a H1 sequence; a shFDPS sequence; a CMV sequence; a BTN3A3 sequence; a WPRE sequence; and a 3' LTR sequence.

Vector 6 includes from left to right, a 5' LTR sequence; a Psi sequence; a RRE sequence; a H1 sequence; a shFDPS sequence; a CMV sequence; a BTN3A3 (R381H) sequence; a WPRE sequence; and a 3' LTR sequence.

Vector 7 includes from left to right, a 5' LTR sequence; a Psi sequence; a RRE sequence; a H1 sequence; a shFDPS sequence; an AFP sequence; a BTN3A3 (R381H) sequence, a WPRE sequence; and a 3' LTR sequence.

Vector 8 includes from left to right, a 5' LTR sequence; a Psi sequence; a RRE sequence; a H1 sequence; a shFDPS sequence; a CMV sequence; an IL-2 sequence; a WPRE sequence; and a 3' LTR sequence.

Vector 9 includes from left to right, a 5' LTR sequence; a Psi sequence; a RRE sequence; a H1 sequence; a shFDPS sequence; a CMV sequence; an IL-15 sequence; a WPRE sequence; and a 3' LTR sequence.

Vector 10 includes from left to right, a 5' LTR sequence; a Psi sequence; a RRE 20 sequence; a H1 sequence; a shFDPS sequence; a CMV sequence; an IL-18 sequence; a WPRE sequence; and a 3' LTR sequence.

Vector 11 includes from left to right, a 5' LTR sequence; a Psi sequence; a RRE sequence; a H1 sequence; a shFDPS sequence; a CMV sequence; a BTN3A3 (R381H) sequence; a T2A sequence; an IL-2 sequence; a WPRE sequence; and a 3' LTR sequence.

Figure 5:
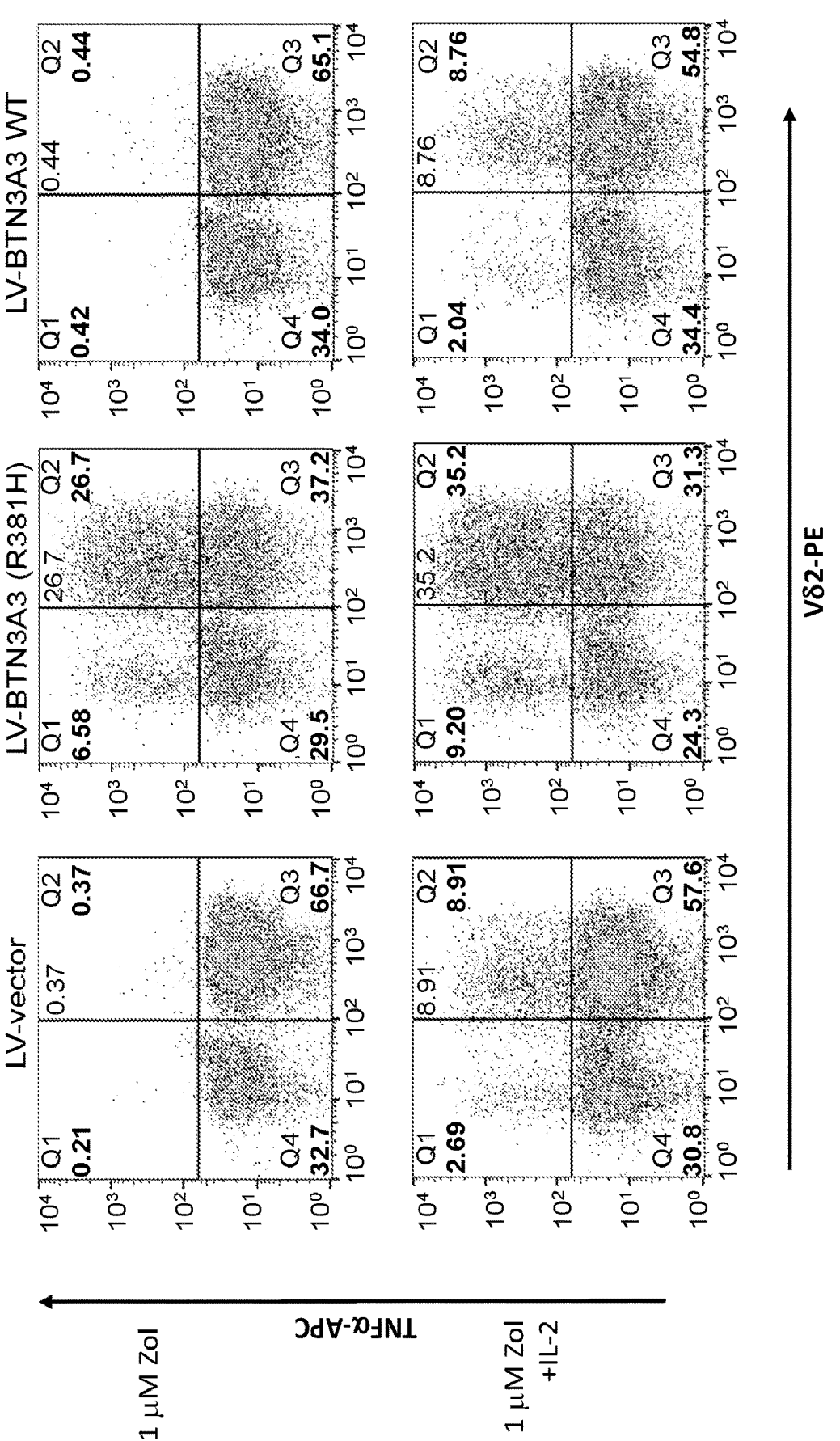
FIG. 5 depicts FACS data demonstrating activation of Vδ2+ T cells by PC3 prostate carcinoma cells with a lentivirus expressing BTN3A3 (R381H) or BTN3A3 (WT), as described herein.

Example 3—Expression of BTN3A3 (R381H) or BTN3A3 (WT) in PC3 Prostate Carcinoma Cells This Example illustrates that expression of BTN3A3 (R381H) or BTN3A3 (WT) in PC3 cells by lentiviral (LV)-expressing BTN3A3 (R381H) or BTN3A3 (WT) stimulates TNF-a expression in GD T cells, as shown in FIG. 5.

PC3 cells were transduced with either LV-vector, LV-BTN3A3 (R381H), or LV-BTN3A3 (WT). Three days after transduction, cells were treated with or without 1 μM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, the percent of TNF-α expressing Vγ9Vδ2 T cells was 0.37% with LV-vector, 26.7% with BTN3A3 (R381H), and 0.44% with LV-BTN3A3 (WT). With zoledronic acid, the percent of TNF-α expressing Vγ9Vδ2 T cells was 8.91% with LV-vector, 35.2% with BTN3A3 (R381H), and 8.76% with LV-BTN3A3 (WT).

Example 4—Expression of BTN3A3 (R381H) and Knock-Down of FDPS in HepG2 Liver Carcinoma Cells by shRNA #4

Figure 6:
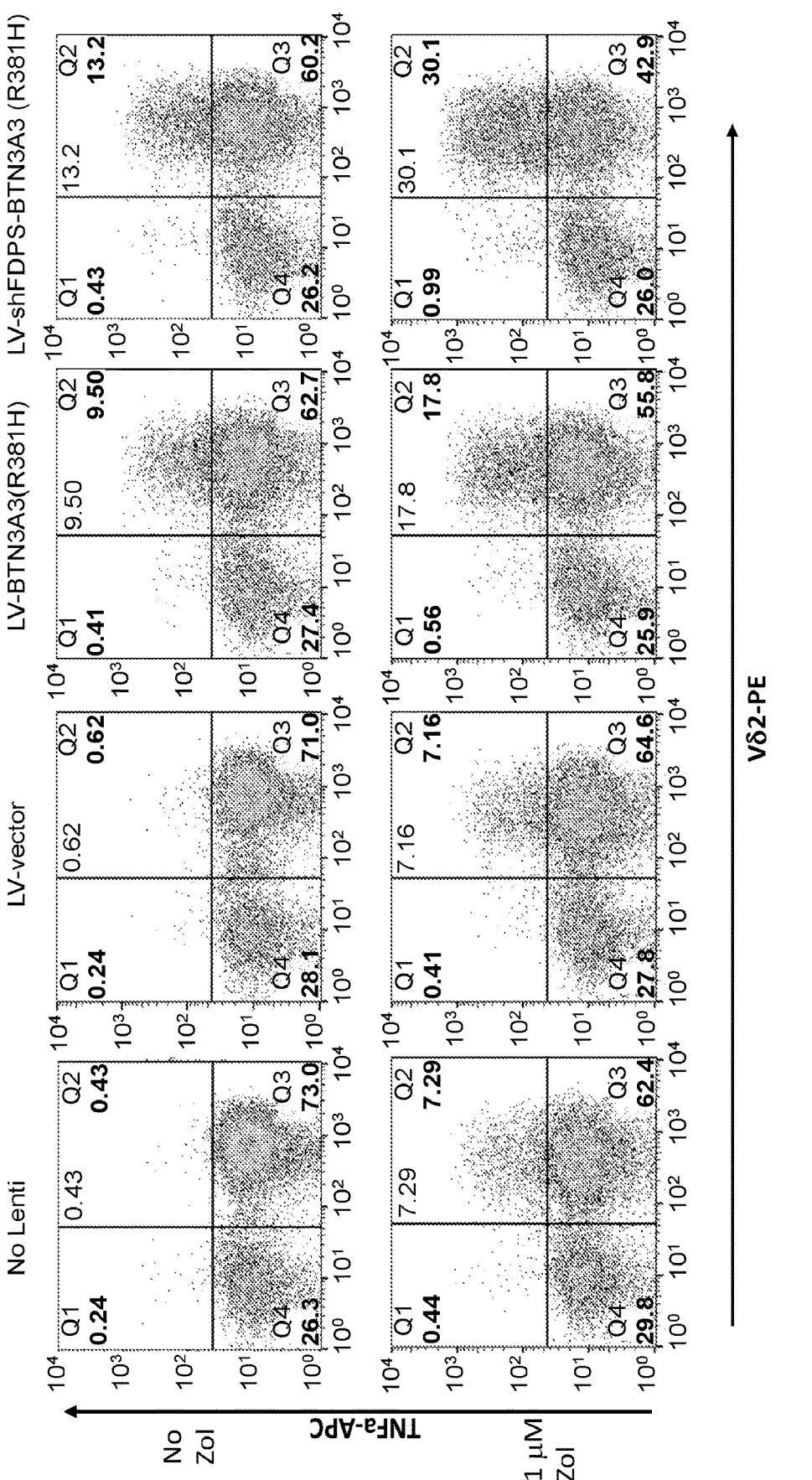
FIG. 6 depicts FACS data demonstrating activation of Vδ2+ T cells HepG2 cells with a lentivirus expressing BTN3A3 (R381H) or both BTN3A3 (R381H) and shRNA #4, as described herein.

This Example illustrates that expression of BTN3A3 (R381H) and knock-down of FDPS cells by lentiviral (LV)-expressing BTN3A3 (R381H) and FDPS shRNA #4 stimulates TNF-α expression in GD T cells, as shown in FIG. 6.

HepG2 cells were transduced with LV-vector, LV-BTN3A3 (R381H), or LV-shFDPS-BTN3A3 (R381H). Three days after transduction, cells were treated with or without 1 μM zoledronic acid. After 24 hours, the transduced HepG2 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+cells were selected on a dot blot. The activated cytotoxic Vγ9Vδ2 T cells appeared in the upper right quadrant of flow cytograms. Without zoledronic acid, the percent of TNF-α expressing Vγ9Vδ2 T cells was 0.6% with LV-vector, 9.5% with BTN3A3 (R381H), and 13.2% with the combination of LV-shFDPS-BTN3A3 (R381H). With zoledronic acid, the percent of TNF-α expressing Vγ9Vδ2 T cells was 7.2% with LV-vector, 17.8% with BTN3A3 (R381H), and 30.1% with the combination of LV-shFDPS-BTN3A3 (R381H).

Example 5—Expression of BTN3A3 (R381H) and Knock-Down of FDPS in PC3 Prostate Carcinoma Cells by shRNA #4

Figure 7:
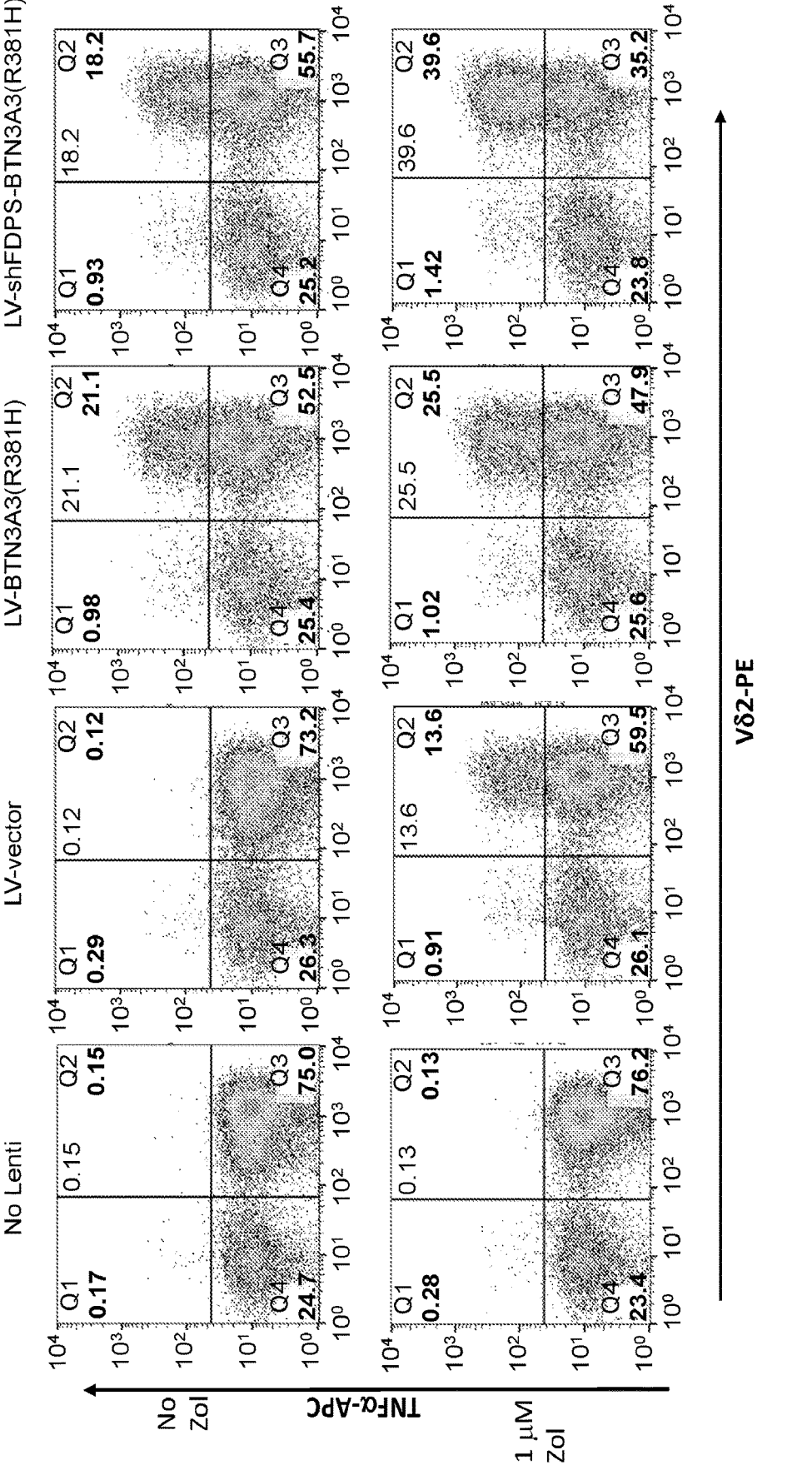
FIG. 7 depicts FACS data demonstrating activation of Vδ2+ T cells by PC3 prostate carcinoma cells with a lentivirus expressing BTN3A3 (R381H) or both BTN3A3 (R381H) and shRNA #4, as described herein.

This Example illustrates that expression of BTN3A3 (R381H) and knock-down of FDPS cells by lentiviral (LV)-expressing BTN3A3 (R381H) and FDPS shRNA #4 stimulates TNF-α expression in GD T cells, as shown in FIG. 7.

PC3 cells were transduced with LV-vector, LV-BTN3A3 (R381H), or LV-shFDPS-BTN3A3 (R381H). Three days after transduction, cells were treated with or without 1 μM zoledronic acid. After 24 hours, the transduced PC3 cells were co-cultured with $5\times10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, the percent of TNF-α expressing Vγ9Vδ2 T cells was 0.1% with LV-vector, 21.1% with BTN3A3 (R381H), and 18.2% with the combination of LV-shFDPS-BTN3A3 (R381H). With zoledronic acid, the percent of TNF-α expressing Vγ9Vδ2 T cells was 13.6% with LV-vector, 25.5% with BTN3A3 (R381H), and 39.6% with the combination of LV-shFDPS-BTN3A3 (R381H).

Example 6—Expression of IL-2 and Knock-Down of FDPS in HepG2 Liver Carcinoma Cells by shRNA #4

Figure 8:
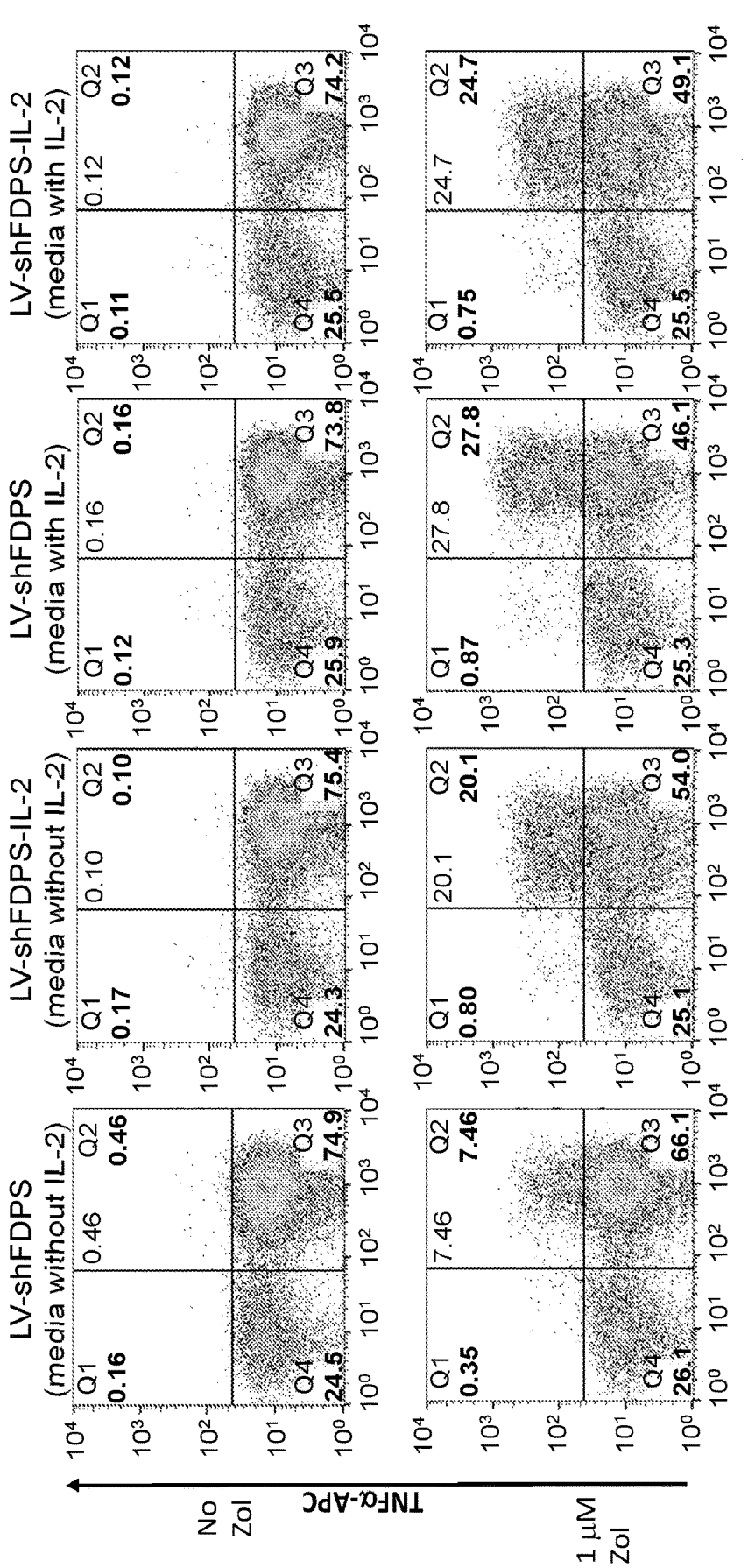
FIG. 8 depicts FACS data demonstrating activation of Vδ2+ T cells by HepG2 cells with a lentivirus expressing shFDPS-IL-2, as described herein.

This Example illustrates that expression of IL-2 and knock-down of FDPS cells by lentiviral (LV)-expressing IL-2 and FDPS shRNA #4 stimulates TNF-α expression in GD T cells, as shown in FIG. 8.

HepG2 cells were transduced with LV-shFDPS or LV-shFDPS-IL-2. Three days after transduction, cells were treated with or without 1 μM zoledronic acid. After 24 hours, the transduced HepG2 cells were co-cultured with 5×10⁵ PBMC cells and with or without IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. With only zoledronic acid, the percent of TNF-α expressing Vγ9Vδ2 T cells was 7.5% with LV-shFDPS and 20.1% with LV-shFDPS-IL-2. With zoledronic acid and IL-2, the percent of TNF-α expressing Vγ9Vδ2 T cells was 27.8% with LV-shFDPS and 24.7% with LV-shFDPS-IL-2.

Example 7—Expression of IL-2 and Knock-Down of FDPS in PC3 Carcinoma Cells by shRNA #4

Figure 9:
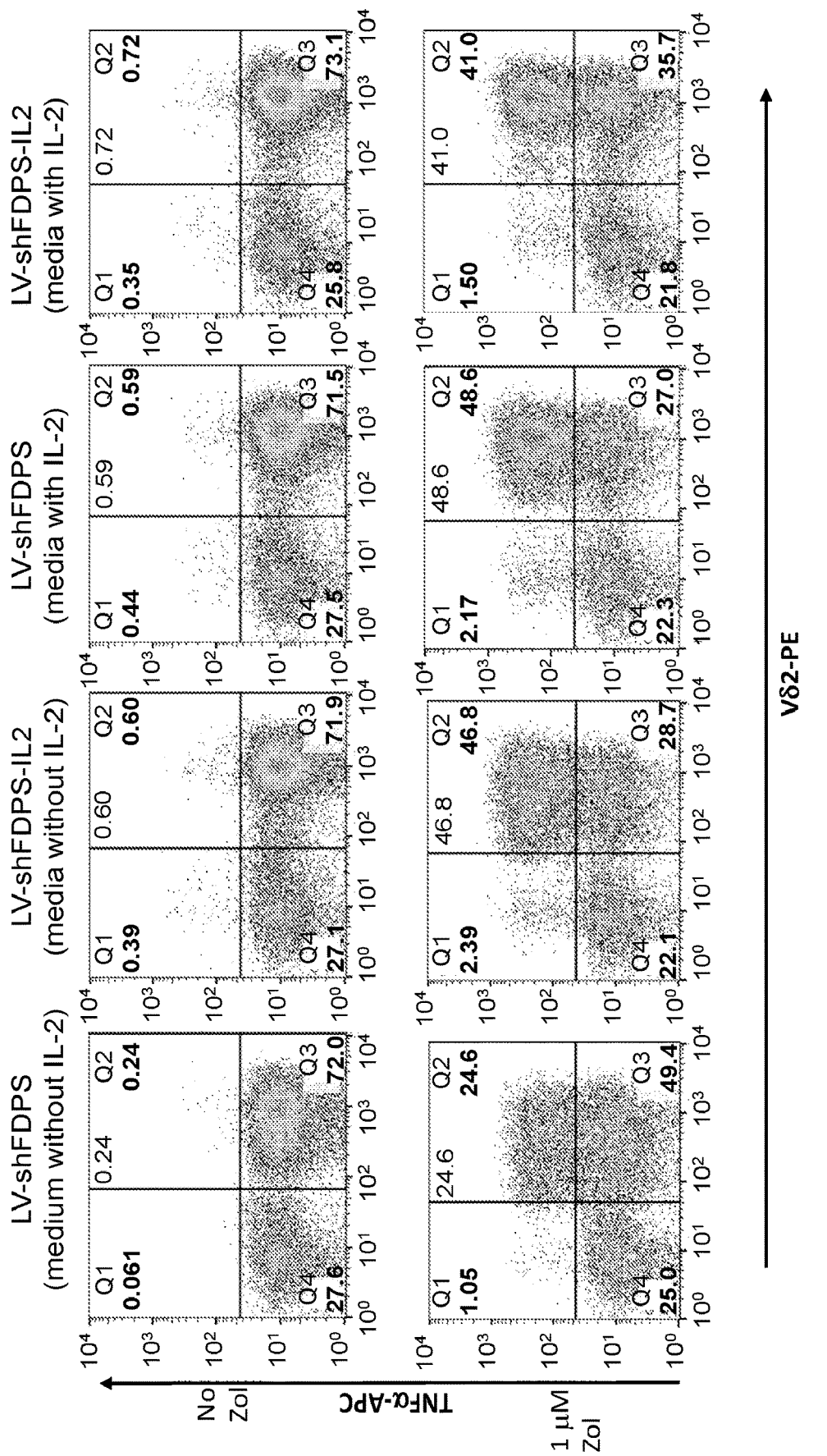
FIG. 9 depicts FACS data demonstrating activation of Vδ2+ T cells by PC3 cells with a lentivirus expressing shFDPS-IL-2, as described herein.

This Example illustrates that expression of IL-2 and knock-down of FDPS cells by lentiviral (LV)-expressing IL-2 and FDPS shRNA #4 stimulates TNF-α expression in GD T cells, as shown in FIG. 9.

PC3 cells were transduced with LV-shFDPS or LV-shFDPS-IL-2. Three days after transduction, cells were treated with or without 1 μM zoledronic acid. After 24 hours, the transduced PC3 cells were co-cultured with 5×10⁵ PBMC cells and with or without IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. With only zoledronic acid, the percent of TNF-α expressing Vγ9Vδ2 T cells was 24.6% with LV-shFDPS and 46.8% with LV-shFDPS-IL-2. With zoledronic acid and IL-2, the percent of TNF-α expressing Vγ9Vδ2 T cells was 48.6% with LV-shFDPS and 41% with LV-shFDPS-IL-2.

Example 8—Expression of IL-15 and Knock-Down of FDPS in PC3 Carcinoma Cells by shRNA #4

Figure 10:
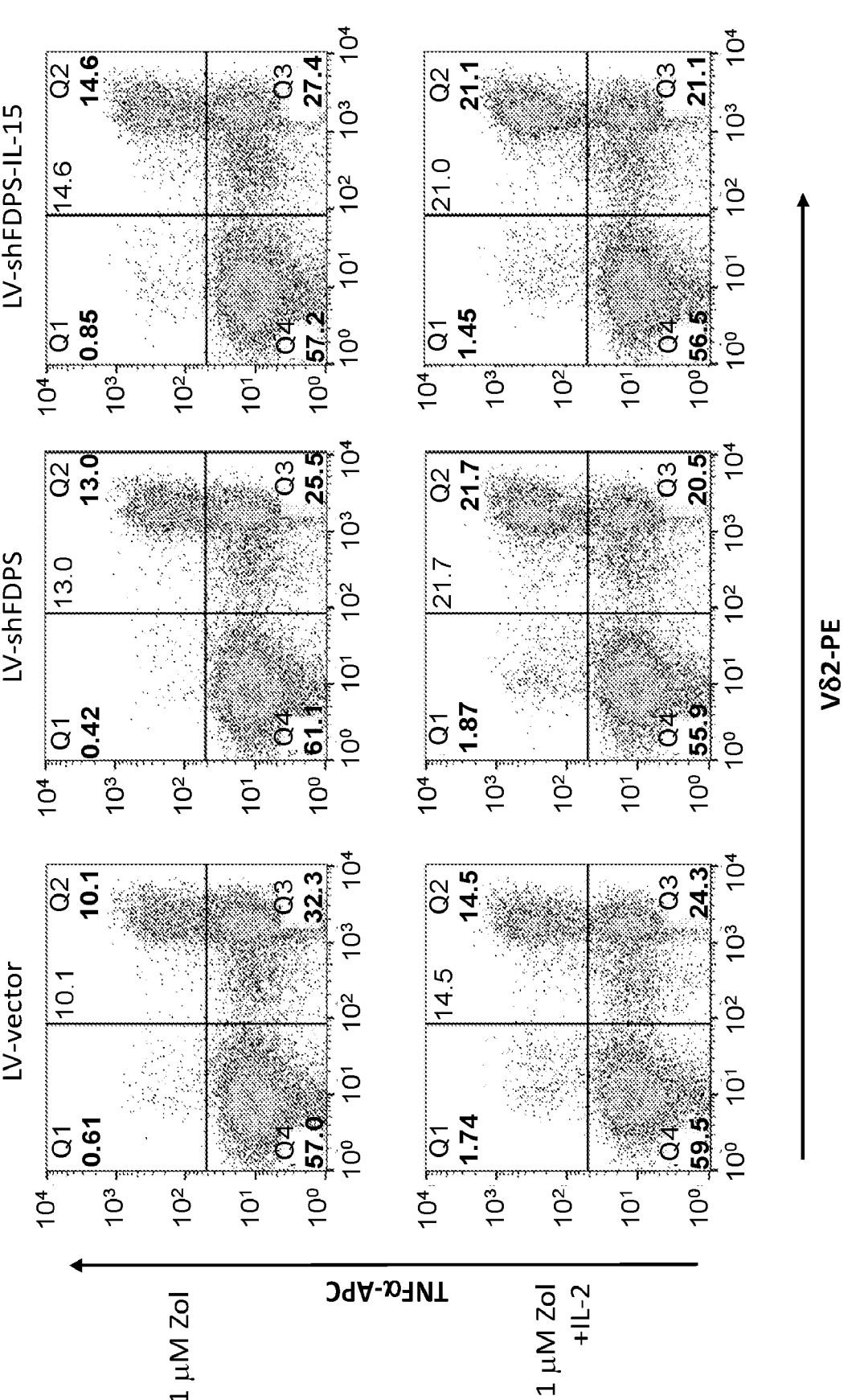
FIG. 10 depicts FACS data demonstrating activation of Vδ2+ T cells by PC3 cells with a lentivirus expressing shFDPS-IL-15, as described herein.

This Example illustrates that expression of IL-15 and knock-down of FDPS cells by lentiviral (LV)-expressing IL-15 and FDPS shRNA #4 stimulates TNF-α expression in GD T cells, as shown in FIG. 10.

PC3 cells were transduced with LV-vector, LV-shFDPS, or LV-shFDPS-IL-15. Three days after transduction, cells were treated with or without 1 μM zoledronic acid. After 24 hours, the transduced PC3 cells were co-cultured with 5×10⁵ PBMC cells and with or without IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. With only zoledronic acid, the percent of TNF-α expressing Vγ9Vδ2 T cells was 10% with LV-vector, 13% with LV-shFDPS, and 14.6% with LV-shFDPS-IL-15. With zoledronic acid and IL-2, the percent of TNF-α expressing Vγ9Vδ2 T cells was 14.5% with LV-vector, 21.7% with LV-shFDPS, and 21% with LV-shFDPS-IL-15.

Example 9—Expression of BTN3A3 in PC3 and HepG2 Carcinoma Cells by LV-BTN3A3 (R381H) and LV-shFDPS-BTN3A3 (R381H)

Figure 11:
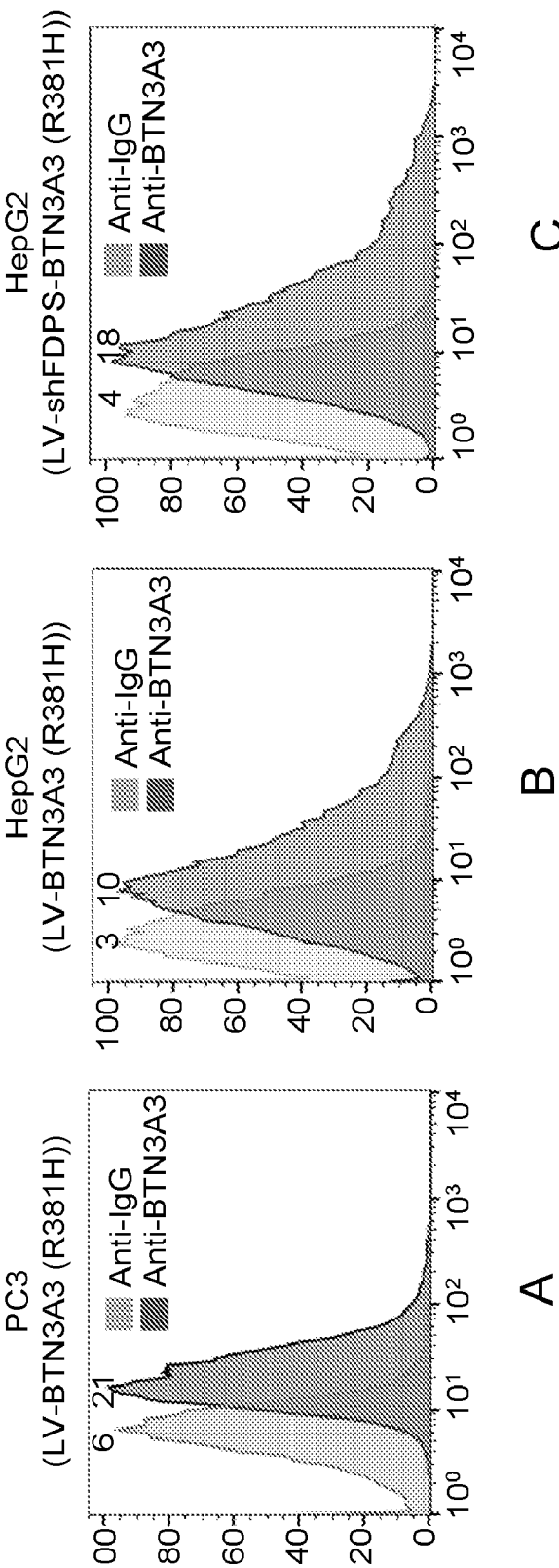
FIG. 11 depicts data demonstrating the extracellular expression of BTN3A3 in PC3 and HepG2 cells with a lentivirus expressing BTN3A3 (R381H) or BTN3A3 (R381H) and shFDPS.

This Example illustrates that lentivirus (LV)-expressing BTN3A3 (R381H) alone and with shFDPS increases BTN3A3 expression in PC3 and HepG2 carcinoma cells as shown in FIG. 11.

PC3 prostate or HepG2 liver carcinoma cells were transduced with LV-vector or LV-BTN3A3 (R381H) for 3 days, as shown in FIGS. 11A and 11B. After staining for BTN3A3 using a fluorophore-conjugated anti BTN3A3 (CD277) antibody, cells were analyzed via flow cytometry. There was an increase in the mean fluorescence intensity (MFI) from 6 to 21 and from 3 to 10 in PC3 and HepG2 cells, respectively. HepG2 liver carcinoma cells were transduced with LV-vector or LV-shFDPS-BTN3A3 (R381H) for 3 days, as shown in FIG. 11C. There was an increase in the mean fluorescence intensity (MFI) from 4 to 18.

Figure 12:
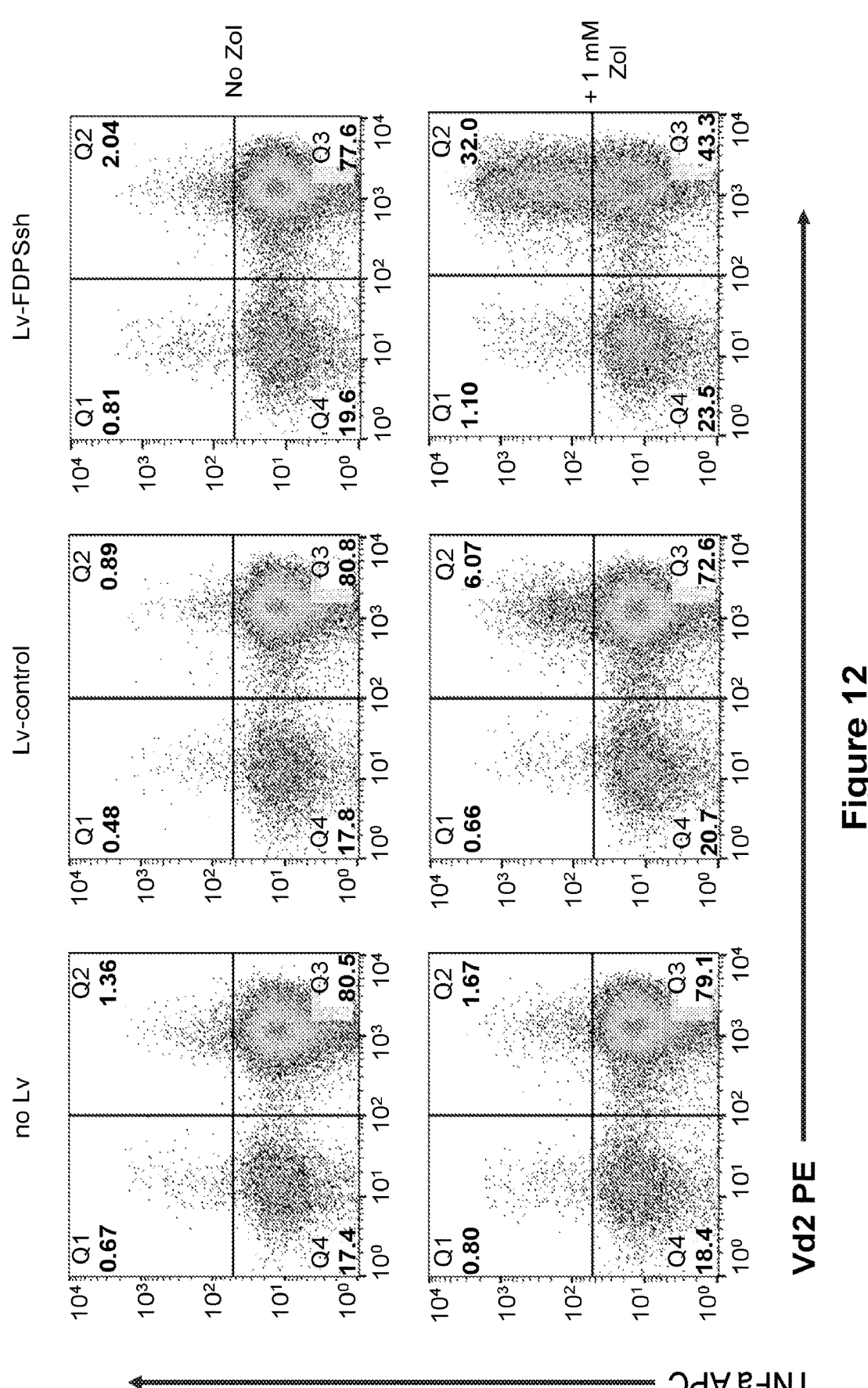
FIG. 12 depicts FACS data demonstrating activation of Vδ2+ T cells by HepG2 cells transduced with a lentivirus expressing Lv-shFDPS, as described herein.

Example 10—Stimulation of Cytotoxic Vγ2Vδ2 Cells by Lv-shFDPS Transduced Cells and Zoledronic Acid This Example illustrates that activation of cytotoxic Vγ2Vδ2 cells is increased by treatment with lentivirus expressing shFDPS (LV-shFDPS) and zoledronic acid, as shown in FIG. 12.

HepG2 liver carcinoma cells were transduced with Lv-shFDPS, Lv-FDPS-IL-15 (expressing both shRNAFDPS and the human cytokine interleukin 15) or Lv-control and cultured for 72 hours. Zoledronic acid (1 μM) was added to (1) cells transduced with Lv-shFDPS, (2) cells transduced with Lv-FDPS-IL-15, and (3) HepG2 cells transduced with Lv-control. Treated cells were cultured for 24 hours. Lv-shFDPS transduced cells, Lv-FDPS-IL-15 transduced cells, and Lv-control transduced cells were co-cultured with PBMC enriched for Vγ9Vδ2 cells plus a protein transport inhibitor (BD GolgiStop) for 4 hours. After 4 hours of stimulation, cells were collected and labeled with Vδ2 phycoerythrin (PE) and TNFαallophycocyanin (APC), and the labeled cells were analyzed by flow cytometry.

Results showed that the frequency of responding Vγ9Vδ2 T cells (expressing TNF-α measured by intracellular cytokine staining) in the presence of 1 M zoledronic acid, was higher in Lv-FDPS than in Lv-control and was increased further by Lv-FDPS-IL-15. Adding 100 Units/ml of interleukin-2 (IL-2) increased activation of Vγ9Vδ2 T cells by HepG2 transduced with Lv-FDPS compared to Lv-control, but IL-2 substitute for IL-15 and reduced the differences between Lv-FDPS and Lv-FDPS-IL-15 treated HepG2 for activating Vγ9Vδ2 T cells.

Figure 13:
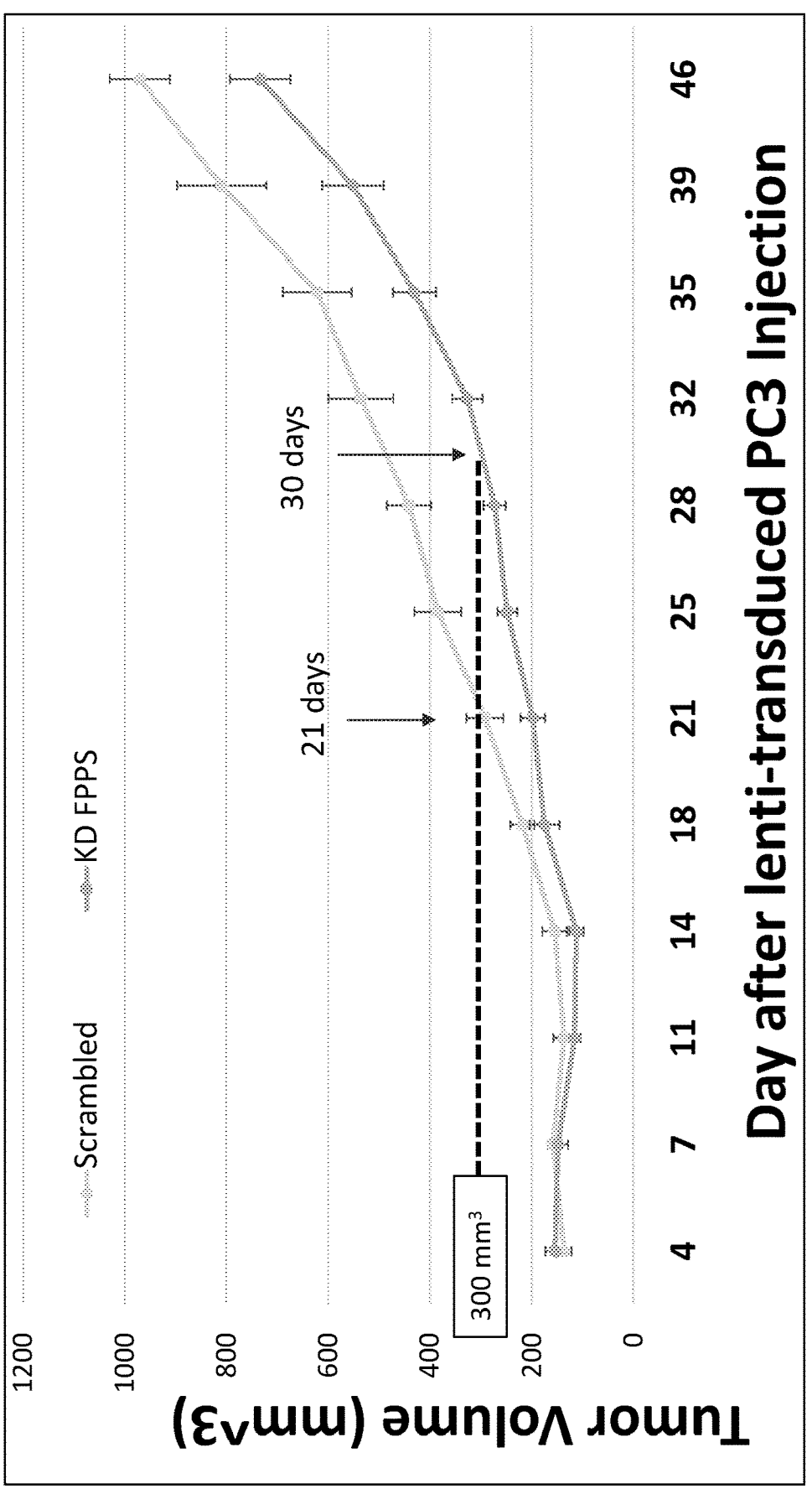
FIG. 13 depicts data demonstrating delayed growth of tumors in mice injected with PC3 cells transduced with a lentivirus expressing Lv-shFDPS, as described herein.

Example 11—Growth Curve of Lv-shFDPS Versus Lv-control Transduced PC3 Tumors in Mice This Example illustrates that the rate of human prostate cancer (PC3) cell tumor growth in mice is slowed after treatment with Lv-shFDPS, as shown in FIG. 13.

NSG™ mice were subcutaneously injected with Matrigel® and 3 million PC3 cells that were transduced with one of Lv-shFDPS or Lv-control. Tumors were monitored and measured twice a week. Tumor size was determined by measuring the perpendicular diameter of each tumor with calipers. Tumor volume ($mm^3$) was calculated with the following formula: $d^2x$ (D/2), where d=the shortest diameter, and D=the longest diameter.

Xenografted PC3 tumors treated and/or transduced with Lv-shFDPS showed slower growth compared to the growth of xenografted PC3 tumors treated and/or transduced with Lv-control. For example, it took 21 days for Lv-control xenografted PC3 tumors to grow to 300 $mm^3$, but it took 30 day for Lv-shFDPS xenografted PC3 tumors to grow to 300 $mm^3$.

Example 12—Tumor Growth and Survival of Mice Xenografted with Lv-FDPS or Lv-Control Transduced PC3 Tumors when Treated with or without Vγ9Vδ2 T Cells and/or Zoledronic Acid This Example illustrates that treatment of xenografted PC3 tumors transduced with Lv-shFDPS and subsequently treated with Vγ9Vδ2 T cells, slows tumor growth and increases survival, with or without zoledronic acid treatment.

Figure 14:
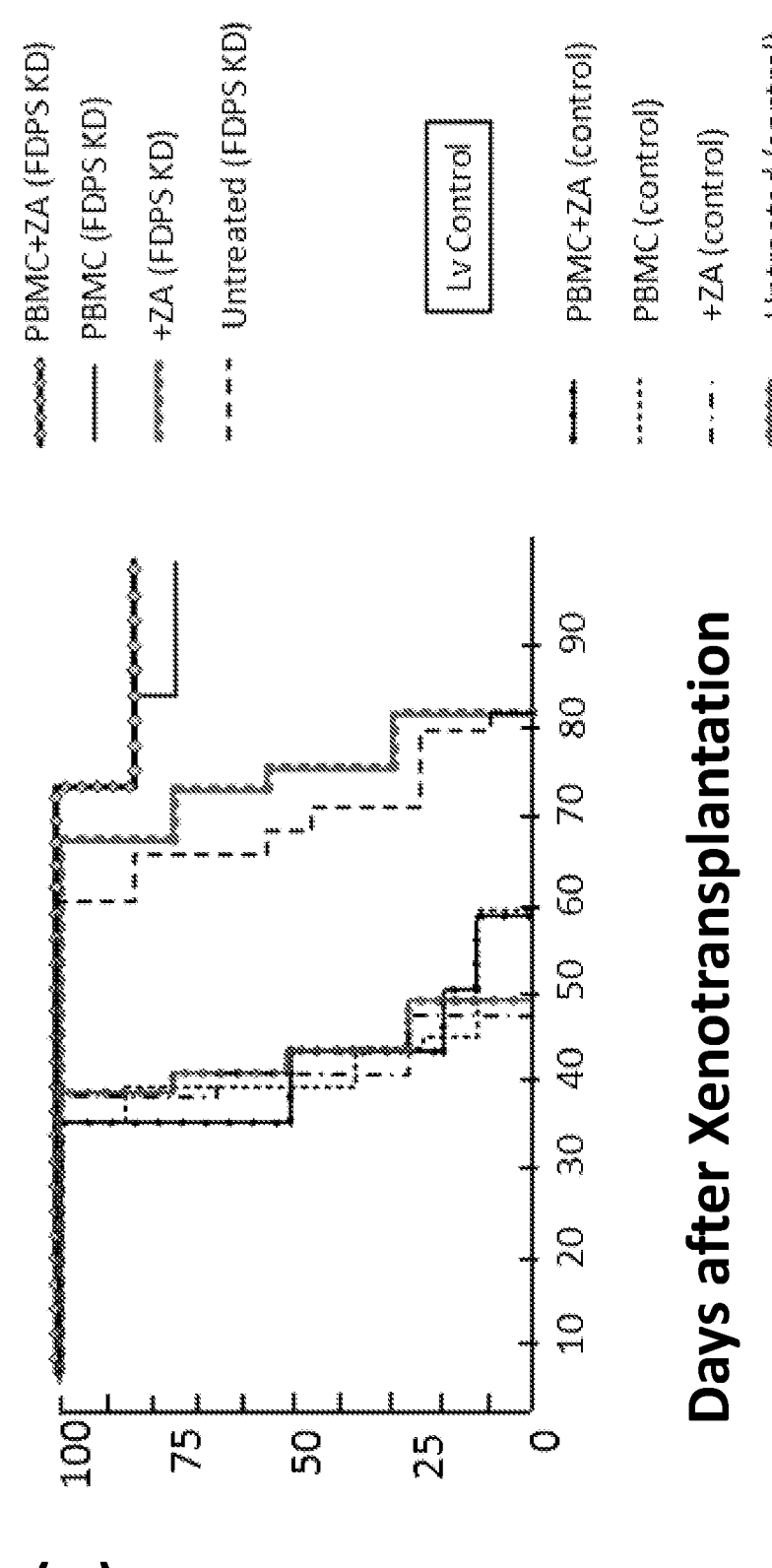
FIG. 14 depicts data demonstrating survival of mice injected with a lentivirus expressing Lv-shFDPS and subsequently treated with PBMC and/or zoledronic acid.
Figure 15:
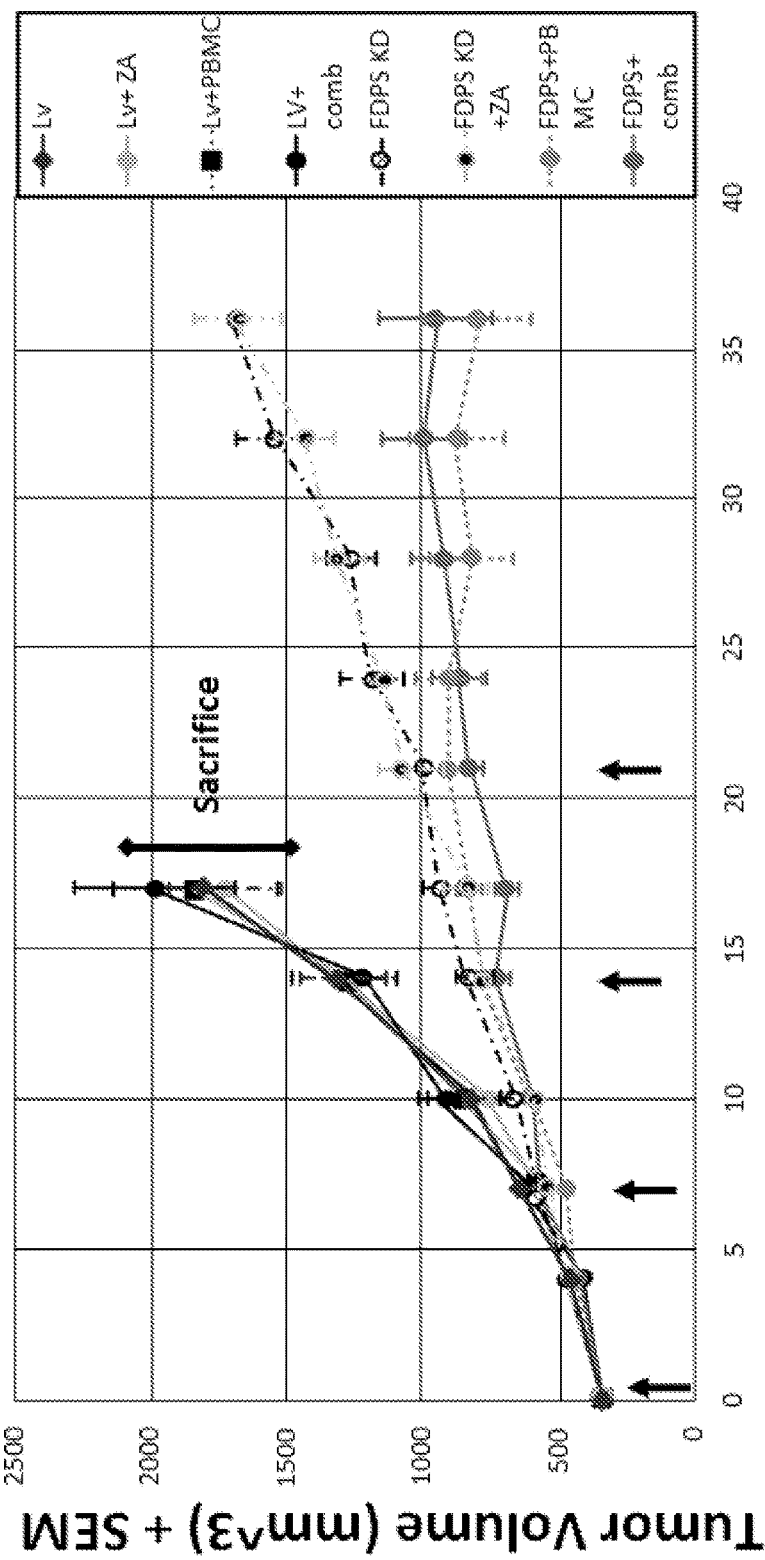
FIG. 15 depicts data demonstrating tumor volume of mice injected with a lentivirus expressing Lv-shFDPS and subsequently treated with PBMC and/or zoledronic acid.

NSG™ mice were subcutaneously injected in the right flank with Matrigel® and 3 million PC3 cells transduced with one of Lv-shFDPS (also referred to in FIGS. 14 and 15 as FDPS knockdown or "FDPS KD") or Lv-control (also referred to in FIGS. 14 and 15 as "Lv" or "control"). Tumors were monitored and measured until the tumor size reached about 300 $mm^3$. Tumor size was determined by measuring the perpendicular diameter of each tumor with calipers. Tumor volume ($mm^3$) was calculated with the following formula: $d^2$ x (D/2), where d=the shortest diameter, and D=the longest diameter.

When the resulting tumors reached a size of 300 $mm^3$, the mice were randomized and grouped into eight groups: four groups of Lv-shFDPS-transduced mice and four groups of Lv-control-transduced mice. One group from each of the Lv-shFDPS-transduced mice and the Lv-control-transduced mice were treated with intraperitoneal injections of PBMCs once per week for 4 weeks. One group from each of the Lv-shFDPS-transduced mice and the Lv-control-transduced mice were treated with 100 µg/kg of zoledronic acid. One group from each of the Lv-shFDPS-transduced mice and the Lv-control-transduced mice were treated with a combination of PBMCs and zoledronic acid. One group from each of the Lv-shFDPS-transduced mice and the Lv-control-transduced mice were treated with intraperitoneal injections of PBS once per week for 4 weeks (control). Mouse survival was observed for the shorter of 95 days or when the tumor size reached 2000 $mm^3$. Tumors were excised and observed at the end of the study.

As shown in FIG. 14, a Kaplan Meier survival curve showed a significant survival advantage achieved by Lv-shFDPS PC3 xenografted mice compared to Lv-control PC3 xenografted (scramble) mice. The survival rate of Lv-shFDPS xenografted mice treated with PBMCs (many of which were Vγ9Vδ2 cells) was greater than the survival rate of Lv-shFDPS xenografted mice not treated with PBMCs. Treatment of Lv-control PC3 xenografted mice with PBMCs did not substantially affect survival.

As shown in FIG. 15, gross observation of Lv-shFDPS xenografted PC3 tumors showed smaller tumor volumes compare to that of Lv-control xenografted PC3 tumors.

Tumor volume of Lv-shFDPS xenografted PC3 tumors treated with PBMCs (many of which were Vγ9Vδ2 cells) was largely decreased as compare to the tumor volume of Lv-shFDPS PC3 tumors not treated with PBMCs. No significant difference was observed between Lv-control xenografted mice treated or untreated with PBMCs, and the constituents of these groups were sacrificed when tumors reached a size of 2000 $mm^3$. Treatment Lv-shFDPS-transduced mice and Lv-control-transduced mice with 100 µg/kg of zoledronic acid showed no obvious effect on tumor size or survival.

Figure 16:
FIG. 16 depicts the gross appearance of Lv-shFDPS PC3 xenografted tumors treated and untreated with PBMC.

As shown in FIG. 16, gross observation of the appearance of Lv-shFDPS xenografted PC3 tumors showed that the volume of tumors treated with PBMCs was largely decreased compare to that of Lv-shFDPS PC3 tumors untreated with PBMCs. Some Lv-shFDPS PC3 tumors treated with PBMCs showed unmeasurable tumors.

Example 13—Development of Lentiviral Vectors that Inhibit FDPS, GGPS1, and IDI1

Figure 17:
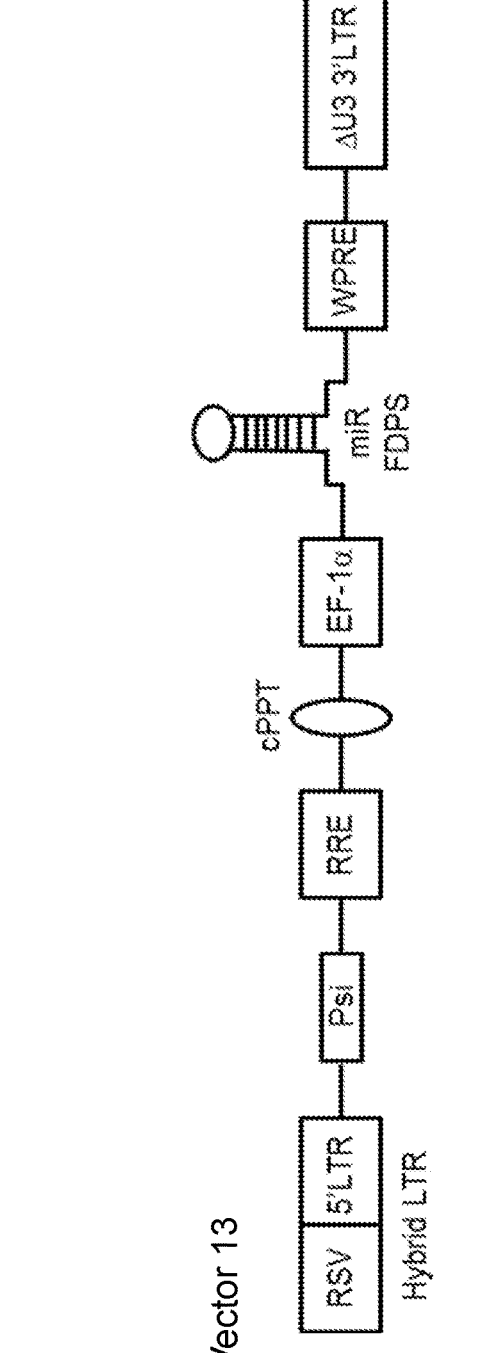
FIG. 17 depicts a lentiviral vector containing a H1 promoter with a synthetic shRNA sequence targeting FDPS. GGPSI, or IDI1, and a lentiviral vector containing an elongation factor 1 alpha promoter with a synthetic microRNA having a FDPS targeting sequence.

This Example illustrates development of lentiviral vectors that inhibit FDPS, GGPS1, and IDI1, as shown in FIG. 17.

Cloning of shRNA sequences: Potential RNA interference sequences were identified with the shRNA design program from the Broad institute (portals.broadinstitute.org/gpp/public/seq/search) of the BLOCK-iT RNAi Designer (maidesigner.thermofisher.com/maiexpress/) from Thermo Scientific. Short-hairpin oligonucleotide sequences containing BamHI and EcoRI restriction sites or microRNA sequences containing BsrGI and EcoRI restriction sites were synthesized by Eurofins Genomics. Oligonucleotide sequences were annealed by incubating at 70 degrees Celsius then cooling to room temperature for 1 hour. In parallel, the lentiviral vectors were digested with the restriction enzymes BamHI and EcoRI or BsrGI and EcoRI for one hour at 37 degrees Celsius. The digested lentiviral vectors were purified by agarose gel electrophoresis and extracted from the gel using a DNA gel extraction kit (Thermo Scientific). The DNA concentration was determined for each and 50 ng of vector were added to 2 microliters of annealed oligo. The ligation reactions were done with T4 DNA ligase for 30 minutes at room temperature. 2.5 microliters of the ligation mix were added to 25 microliters of StbI3 competent bacterial cells. Transformations were done with a heat-shock step at 42 degrees Celsius. Bacterial cells were streaked onto agar plates containing ampicillin and selected colonies were expanded in LB broth. To check for insertion of the oligo sequences, plasmid DNA were extracted from harvested bacterial cultures with a DNA mini prep kit (Thermo Scientific). Insertions of the shRNA sequence in the lentiviral vector were verified by DNA sequencing using H1 or EF-1 primers. Lentiviral vectors containing correct shRNA sequences were used to package lentiviral particles for testing their ability to knock-down mRNA. Cells were transduced with lentiviral particles and collected after 3 days; both protein and mRNA were analyzed.

Identification of FDPS shRNA sequences. The sequence of *Homo sapiens* farnesyl diphosphate synthase (FDPS) (NM_002004.3) mRNA were used to search for potential shRNA candidates to reduce FDPS levels in human cells. In addition to FDPS shRNA sequences #1-4, as discussed above, the following exemplary shRNA and microRNA sequences were determined to knock down FDPS:

```
                (FDPS shRNA sequence #4A; SEQ ID NO: 64)
ACTTTCTCAGCCTCCTTCTGCCTCGAGGCAGAAGGAGGCTGAGAAAGTTT
TTT;

(FPDS shRNA sequence #4R; SEQ ID NO: 65)
GCAGAAGGAGGCTGAGAAAGTGAGCTCACTTTCTCAGCCTCCTTCTG;

(FDPS shRNA sequence #4TT; SEQ ID NO: 66)
GCAGAAGGAGGCTGAGAAAGTTTACTTTCTCAGCCTCCTTCTGCTTTTT;

(FDPS shRNA sequence #4L; SEQ ID NO: 67)
GCAGAAGGAGGCTGAGAAAGTACTTTCTCAGCCTCCTTCTGCTTTTT;

(FDPS miR30 sequence #1; SEQ ID NO: 68)
AAGGTATATTGCTGTTGACAGTGAGCGACACTTTCTCAGCCTCCTTCTGC
GTGAAGCCACAGATGGCAGAAGGAGGCTGAGAAAGTGCTGCCTACTGCCT
CGGACTTCAAGGGGCT;

(FDPS miR30 sequence #3; SEQ ID NO: 69)
AAGGTATATTGCTGTTGACAGTGAGCGACACTTTCTCAGCCTCCTTCTGC
GTGAAGCCACAGATGGCAGAAGGGCTGAGAAAGTGCTGCCTACTGCCTCG
GACTTCAAGGGGCT.
```

Identification of GGPS1 shRNA sequences. The sequences of *Homo sapiens* geranylgeranyl pyrophosphate synthase (GGPS1) (NM_001037277.1) mRNA were used to search for potential shRNA candidates to reduce GGPS1 in human cells. Using the following target sequences, exemplary shRNA sequences were determined to knock-down GGPS1:

```
                (GGPS1 target sequence #1; SEQ ID NO: 73)
GCTTGAAGCTAAAGCCTATAA;

(GGPS1 shRNA sequence #1; SEQ ID NO: 70)
GCTTGAAGCTAAAGCCTATAACTCGAGTTATAGGCTTTAGCTTCAAGCTT
TTT;

(GGPS1 target sequence #2; SEQ ID NO: 74)
GTACATTATCTTGAGGATGTA;

(GGPS1 shRNA sequence #2; SEQ ID NO: 71)
GTACATTATCTTGAGGATGTACTCGAGTACATCCTCAAGATAATGTACTT
TTT;

(GGPS1 target sequence #3; SEQ ID NO: 75)
CCTGAGCTAGTAGCCTTAGTA;
and (GGPS1 shRNA sequence #3; SEQ ID NO: 72)
CCTGAGCTAGTAGCCTTAGTACTCGAGTACTAAGGCTACTAGCTCAGGTT
TTT.
```

Identification of IDI1 shRNA sequences. The sequence of *Homo sapiens* isopentenyl-diphosphate delta-isomerase 1 (IDI1) (NM_004508.3) mRNA was used to search for potential shRNA candidates to reduce IDI1 levels in human cells. Using the following target sequence, an exemplary shRNA sequence was determined to knock-down IDI1:

```
                (IDI1 target sequence; SEQ ID NO: 77)
GCCAGTGGTGAAATTAAGATA;
and (IDI1 shRNA sequence; SEQ ID NO: 76)
GCCAGTGGTGAAATTAAGATACTCGAGTATCTTAATTTCACCACTGGCTT
TTT.
```

Example 14—FDPS RNA and Protein Expression in HepG2 Hepatocellular Carcinoma Cells Transduced with Lentiviruses Expressing shFDPS This Example illustrates reduction of FDPS RNA and protein expression by shFDPS in HepG2 cells.

Figure 18:
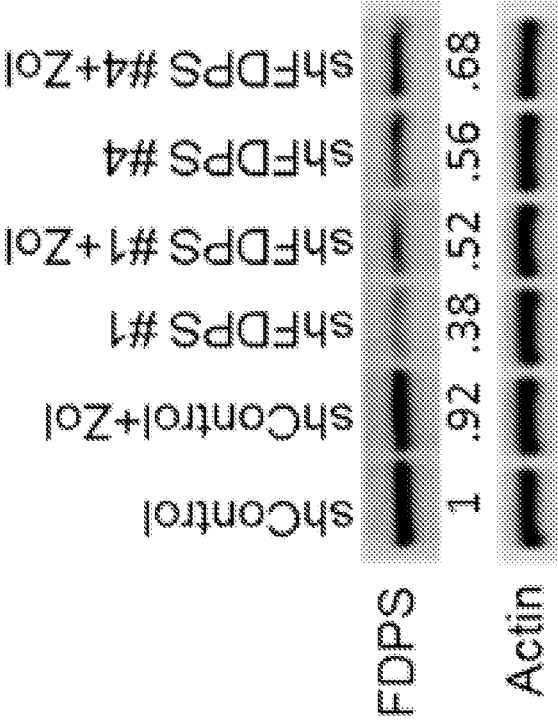
FIG. 18 depicts data demonstrating reduction of FDPS protein expression in HepG2 cells transduced with lentivirus expressing shFDPS #1 (SEQ ID NO: 1) or shFDPS #4 (SEQ ID NO: 4) and treated with or without zoledronic acid, as described herein.

FIG. 18 shows that FDPS protein expression is reduced by shFDPS. HepG2 cells were infected at 5 MOI with lentiviral vectors containing either shCon or two different FDPS shRNA sequences, LV-shFDPS #1 (SEQ ID NO: 1) or LV-shFDPS #4 (SEQ ID NO: 4). After 48 hours, the cells were treated with or without 1 µM zoledronic acid (Zol). After 72 hours, 10 cells were lysed and an immunoblot was performed using an anti-FDPS and an anti-actin antibody as a protein loading control. The densitometry of the immunoblot bands were quantified and LV-shControl was set as 1 (100%). There was a 62% (LV-shFDPS #1 (SEQ ID NO: 1)), 48% (LV-shFDPS #1+Zol (SEQ ID NO: 1)), 44% (LV-shFDPS #4 (SEQ ID NO: 4)), and 32% (LV-shFDPS #4+Zol (SEQ ID NO: 4)) reduction of FDPS protein expression.

Example 15—FDPS Protein Expression in PC3 Prostate Carcinoma Cells Transduced with Lentiviruses Expressing shFDPS Hairpin-Loop Variations This Example illustrates that shFDPS hairpin-loop variations; A (antisense-loop-sense), R (sense-reverse loop-antisense), TT (sense-TT-antisense), and L (sense-antisense) are effective in reducing FDPS protein expression in PC3 cells.

PC3 cells were infected, at 5 MOI, with lentiviral vectors containing a non-targeting sequence (shCon) or different variations of shFDPS, namely, shFDPS #4 (SEQ ID NO: 4), shFDPS-A (SEQ ID NO: 64), shFDPS-R (SEQ ID NO: 65), shFDPS-TT (SEQ ID NO: 66), or shFDPS-L (SEQ ID NO: 67). After 72 hours, cells were lysed and RNA was extracted using the RNeasy mini kit. cDNA was synthesized from RNA using the SuperScript VILO cDNA synthesis kit. PCR reactions were performed using the TaqMan® Fast Advanced Master Mix and the samples were then analyzed by quantitative PCR (qPCR) using an Applied Biosystems QuantStudio3™ qPCR machine (Thermo Scientific).

Figure 19B:
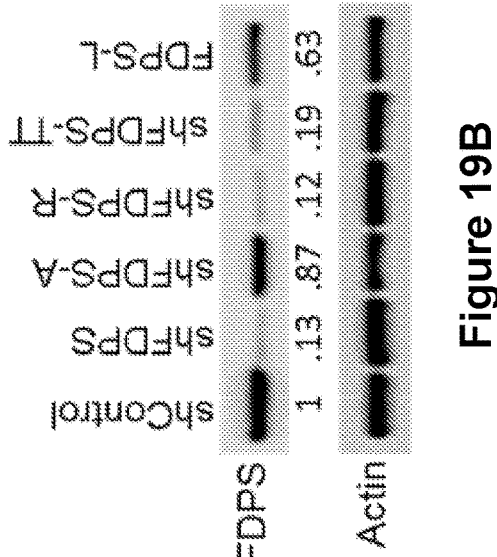
FIGS. 19A and 19B depict data demonstrating reduction of FDPS RNA (FIG. 19A) and protein expression (FIG. 19B) in PC3 cells transduced with lentivirus expressing shFDPS-A (SEQ ID NO: 64), shFDPS-R (SEQ ID NO: 65). shFDPS-TT (SEQ ID NO: 66). and shFDPS-L (SEQ ID NO: 67), as described herein.
Figure 19A:
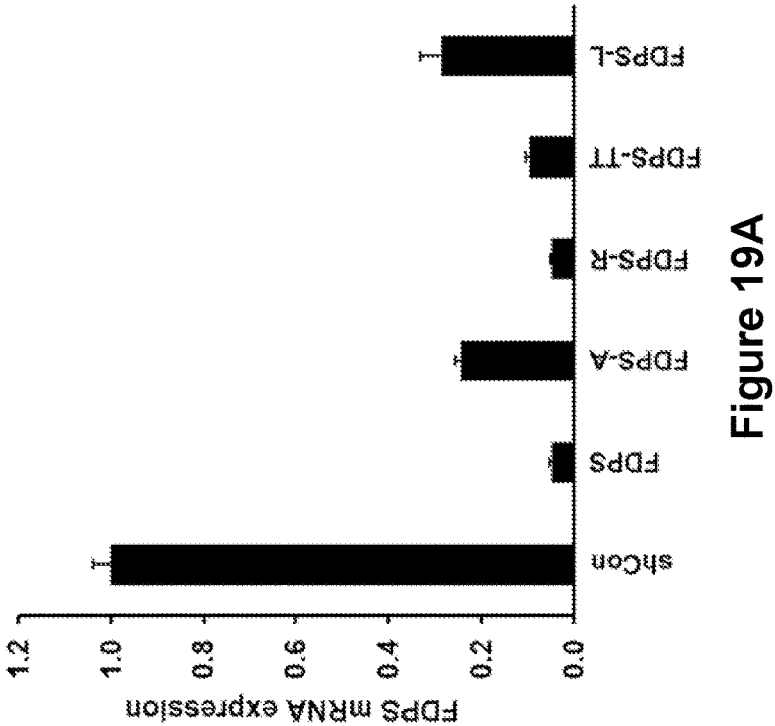

Expression of FDPS cDNA was determined by quantitative PCR using a TaqMan® FDPS probe and FDPS primers. For FIG. 19A, FDPS expression was detected with Fam-labeled TaqMan® probe (5'-TAGCATCTCC-TATCTCTGGGTGCCC-3') (SEQ ID NO: 78), using the FDPS forward primer (5'-GTGCTGACTGAGGAT-GAGATG-3') (SEQ IF NO: 79) and reverse primer (5'-CCGGTTATACTTGCCTCCAAT-3') (SEQ ID NO: 80). The samples were normalized to actin expression. Actin was detected with a Fam-labeled TaqMan® probe (5'-AGCGG-GAAATCGTGCGTGAC-3') (SEQ ID NO: 81) using the Actin forward primer (5'-GGACCTGACTGACTACCT-CAT-3') (SEQ ID NO: 82) and reverse primer (5'-CGTAGCACAGCTTCTCCTTAAT-3') (SEQ ID NO: 83). The relative FDPS RNA expression of the shCon sample is set at 100%. There was a 95% (shFDPS #4 (SEQ ID NO: 4)), 75% (shFDPS-A (SEQ ID NO: 64)), 95% (shFDPS-R (SEQ ID NO: 65)), 90% (shFDPS-TT (SEQ ID NO: 66)) and a 72% (FDPS-L (SEQ ID NO: 67)) decrease in FDPS expression, as shown in FIG. 19A.

To examine the effects of the shFDPS variations on protein expression, PC3 cells were infected at 5 MOI with lentiviral vectors containing either shControl or variations of shFDPS 10 #4. After 72 hours, cells were lysed and an immunoblot was performed using an anti-FDPS and an anti-actin antibody as a protein loading control. The densitometry of the immunoblot bands were quantified and LV-shControl was set as 1 (100%). As shown in FIG. 19B, there was an 87% (LV-shFDPS #4 (SEQ ID NO: 4)), 13% (LV-shFDPS-A (SEQ ID NO: 64)), 88% (LV-shFDPS-R (SEQ ID NO: 65)), 81% (LV-FDPS-TT (SEQ ID NO: 66)), and 37% (LV-FDPS-L (SEQ ID NO: 67)) reduction of FDPS protein expression.

Example 16—FDPS Protein Expression in HepG2 Hepatocellular Carcinoma Cells Transduced with Lentiviruses Expressing miR30-FDPS This Example illustrates decrease in FDPS protein expression in cells transduced with lentiviruses expressing miR30-FDPS.

Figure 20:
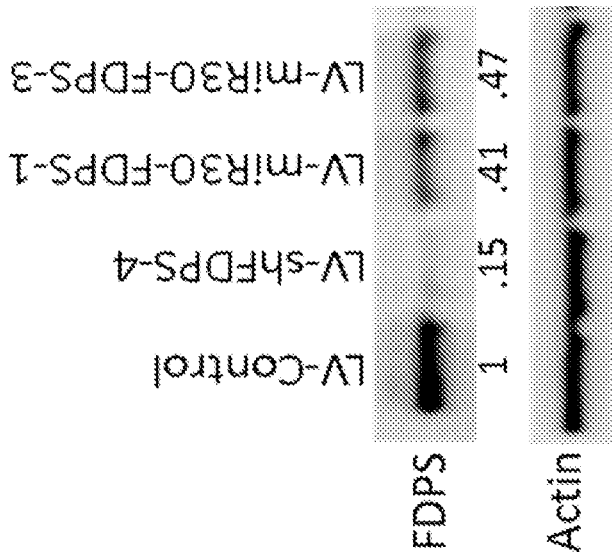
FIG. 20 depicts reduction of FDPS protein expression in HepG2 cells transduced with lentivirus expressing shFDPS-4 (SEQ ID NO: 4), miR30-FDPS-1 (SEQ ID NO: 68) and miR30-FDPS-3 (SEQ ID NO: 69), as described herein.

To measure FDPS protein expression, HepG2 human hepatocellular carcinoma cells were infected, at 5 MOI, with lentiviral vectors containing either a shControl, shFDPS #3 (SEQ ID NO: 3), miR30-FDPS #1 (SEQ ID NO: 68), or miR30-FDPS #3 (SEQ ID NO: 69). After 72 hours, cells were lysed with NP-40 lysis buffer and proteins were measured with the Bio-Rad protein assay reagent. Protein samples at 50 micrograms were electrophoresed on 4-12% Bis-Tris gels (Thermo Scientific) and transferred to PVDF membranes. The blots were blocked in 5% blotting grade blocker. An immunoblot was performed using an anti-FDPS antibody (Bethyl Laboratories) and an anti-actin antibody (Millipore Sigma) as a protein loading control. Antibodies were bound with HRP-conjugated secondary antibodies (Thermo Scientific) and detected with a Licor c-DiGit Blot scanner using the Immobilon Western ECL reagent (Millipore Sigma). The densitometry of the immunoblot bands were quantified with the NIH image software, and LV-Control was set as 1 (100%). As shown in FIG. 20, there was an 85% (LV-shFDPS #4 (SEQ ID NO: 4)), 59% (LV-miR30-FDPS #1 (SEQ ID NO: 68)), and 53% (LV-miR30-FDPS #3 (SEQ ID NO: 69)) reduction of FDPS protein expression, respectively.

Example 17—Activation of Vγ9Vδ2 T Cells by THP-1 Monocytic Leukemia Carcinoma Cells Transduced with a Lentivirus Expressing miR30-FDPS #1

Figure 21:
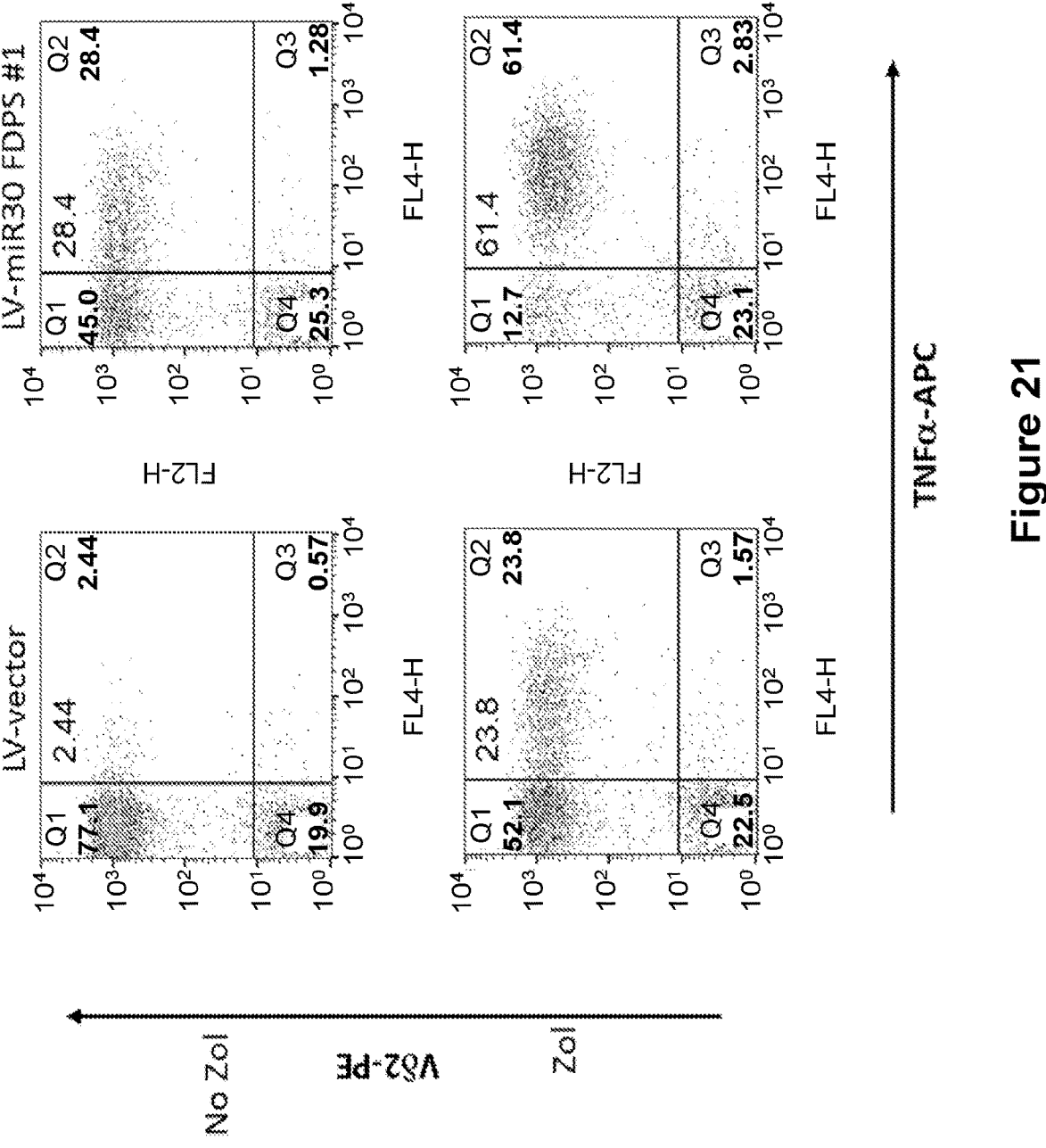
FIG. 21 depicts FACS data demonstrating activation of Vδ2+ T cells by THP-1 cells transduced with a lentivirus expressing miR30-FDPS #1 (SEQ ID NO: 68) and treated with or without zoledronic acid, as described herein.

This Example illustrates that knock-down of FDPS for 7 days in THP-1 monocytic leukemia carcinoma cells by LV-expressing miR30-FDPS miRNA #1 (SEQ ID NO: 68) and treatment with or without zoledronic acid stimulates TNF-α expression in Vγ9Vδ2 T cells, as shown in FIG. 21.

THP-1 cells ($2 \times 10^5$ cells) were transduced with LV-control or LV-miR30 FDPS #1 (SEQ ID NO: 68) for 7 days. Cells were treated with or without 1 μM zoledronic acid. After 24 hours, the transduced THP-1 cells were co-cultured for 4 hours with $2 \times 10^5$ PBMC cells in 5 mL round-bottom tubes. The PBMC cells had been pre-stimulated with zoledronic acid plus IL-2 for at least 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. Without zoledronic acid, LV-control stimulated 2.44% of TNF-α expressing Vγ9Vδ2 T cells and LV-miR30 FDPS #1 (SEQ ID NO: 68) stimulated 28.4%. With zoledronic acid treatment, LV-control stimulated 23.8% of TNF-α expressing Vγ9Vδ2 T cells and LV-miR30 FDPS #1 (SEQ ID NO: 68) stimulated 61.4%.

Example 18—GGPS1 Protein Expression in HeLa Cervical Carcinoma Cells Transduced with Lentiviruses Expressing shGGPS1

Figure 22:
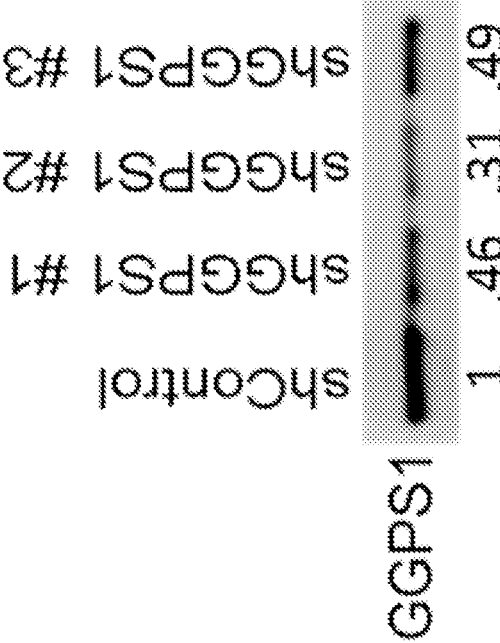
FIG. 22 depicts reduction of GGPSI protein expression in Hela cells transduced with lentivirus expressing shGGPS1 #1 (SEQ ID NO: 70), shGGPS1 #2 (SEQ ID NO: 71), and shGGPS1 #3 (SEQ ID NO: 73), as described herein.

HeLa cells were infected at 5 MOI with lentiviral vectors containing either a shControl or three different GGPS1 shRNA sequences, namely LV-shGGPS1 #1 (SEQ ID NO: 70), LV-shGGPS1 #2 (SEQ ID NO: 71), or LV-shGGPS1 #3 (SEQ ID NO: 73). After 72 hours, cells were lysed and an immunoblot was performed using an anti-GGPS1 antibody from Santa Cruz Biotechnology (Cat. No. sc-271680) and an anti-actin antibody as a protein loading control. The densitometry of the immunoblot bands were quantified, and LV-shControl was set as 1 (100%). As shown in FIG. 22, there was a 54% (LV-shGGPS1 #1 (SEQ ID NO: 70)), 69% (LV-shGGPS1 #2 (SEQ ID NO: 71)), and 51% (LV-shGGPS1 #3 (SEQ ID NO: 72)) reduction of FDPS protein expression, respectively.

Figure 23:
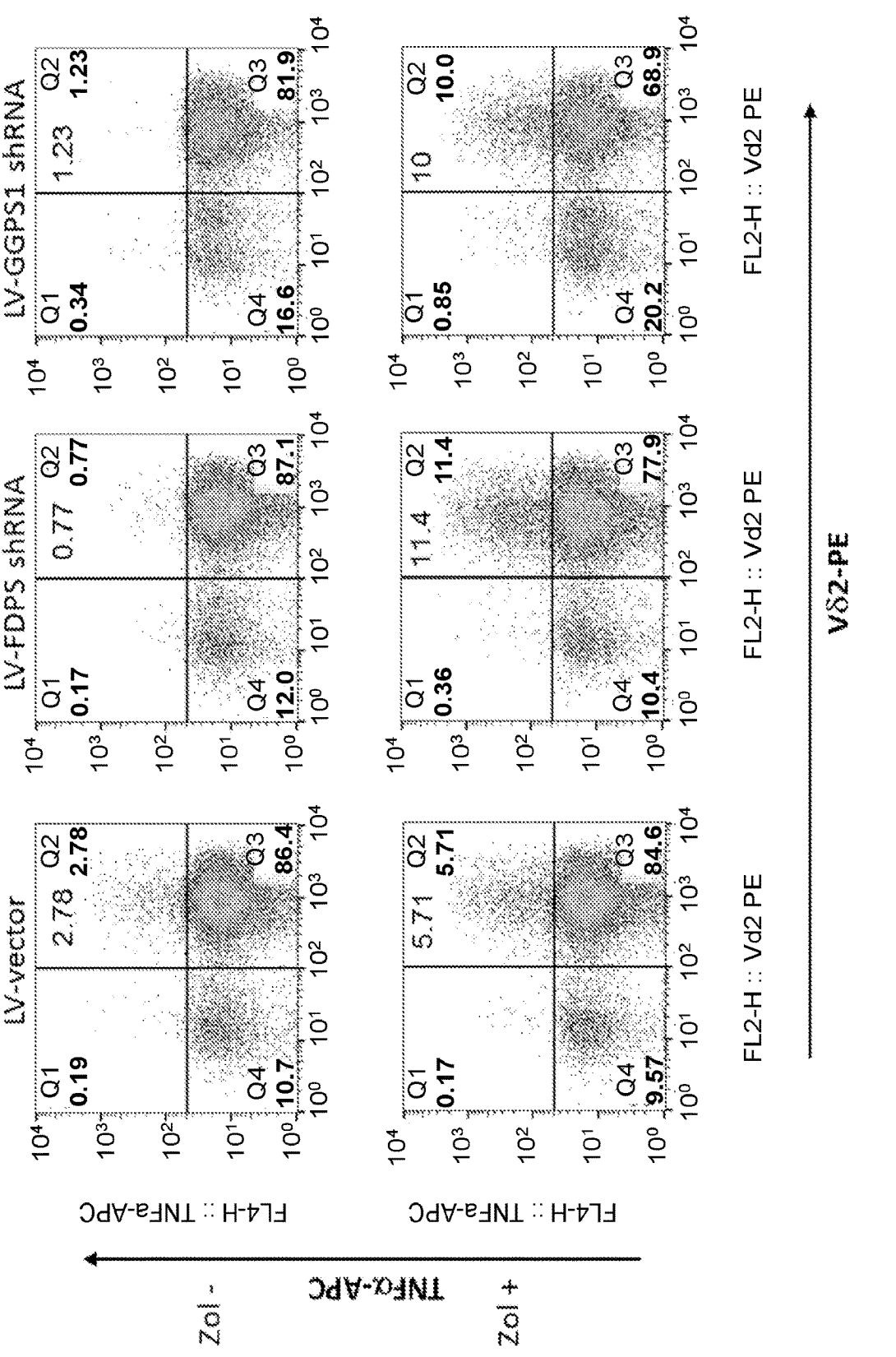
FIG. 23 depicts FACS data demonstrating activation of Vδ2+ T cells by PC3 cells transduced with a lentivirus expressing shFDPS sequence #4 (SEQ ID NO: 4) or shGGPS1 sequence #1 (SEQ ID NO: 70) and treated with or without zoledronic acid, as described herein.

Example 19—Activation of Vγ9Vδ2 T Cells by PC3 Prostate Carcinoma Cells Transduced with a Lentivirus Expressing shFDPS or shGGPS1 and Treated with Zoledronic Acid This Example illustrates that knock-down of FDPS or GGPS1 for 3 days in PC3 cells transduced with LV-expressing FDPS shRNA #4 (SEQ ID NO: 4) or GGPS1 shRNA #1 (SEQ ID NO: 1) and treatment with zoledronic acid stimulates TNF-α expression in Vγ9Vδ2 T cells, as shown in FIG. 23.

PC3 cells were transduced with LV-control or LV-FDPS shRNA #4 (SEQ ID NO: 4) or LV-GGPS1 shRNA #1 (SEQ ID NO: 70) for 3 days. Two days after transduction, cells were treated with or without 1 μM zoledronic acid. After 24 hours, the transduced PC3 cells were co-cultured for 4 hours with $5 \times 10^5$ PBMC cells in a round bottom 96 well plate. The PBMC cells had been pre-stimulated with zoledronic acid plus IL-2 for at least 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. Without zoledronic acid, LV-control stimulated 2.78% of TNF-α expressing Vγ9Vδ2 T cells whereas LV-FDPS shRNA #4 (SEQ ID NO: 4) stimulated 0.77% and LV-GGPS1 #1 shRNA (SEQ ID NO: 70) stimulated 1.23%. With zoledronic acid treatment, LV-control stimulated 5.71% of TNF-α expressing Vγ9Vδ2 T cells, whereas LV-FDPS shRNA #4 (SEQ ID NO: 4) stimulated 11.4% and LV-GGPS1 #1 shRNA (SEQ ID NO: 70) stimulated 10%.

Figure 24:
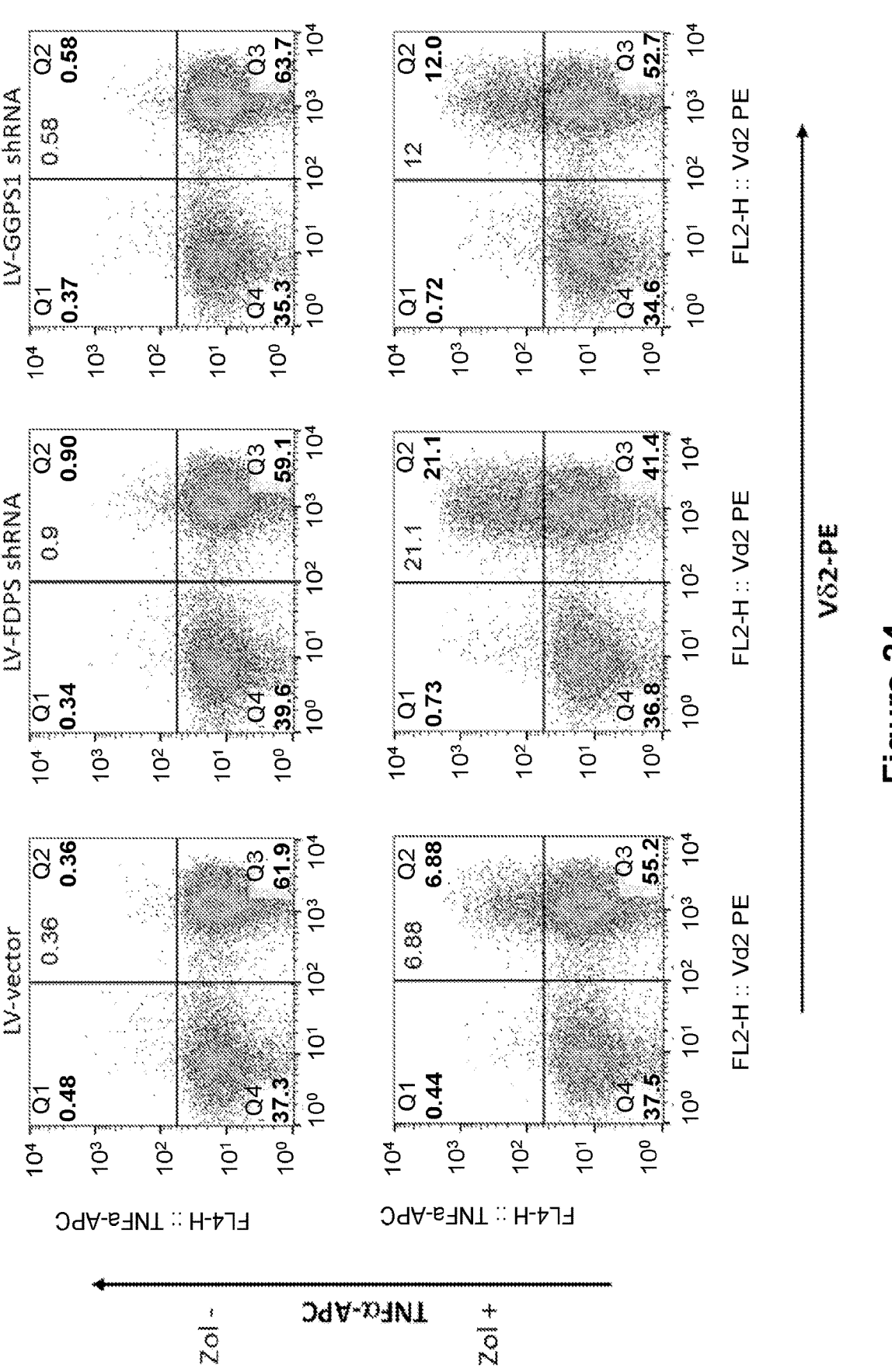
FIG. 24 depicts FACS data demonstrating activation of Vδ2+ T cells by HepG2 cells transduced with a lentivirus expressing shFDPS sequence #4 (SEQ ID NO: 4) or shGGPS1 sequence #1 (SEQ ID NO: 70) and treated with or without zoledronic acid, as described herein.

Example 20—Activation of VS2+T Cells by HepG2 Hepatocellular Carcinoma Cells Transduced with a Lentivirus Expressing shFDPS or shGGPS1 and Treated with Zoledronic Acid This Example illustrates that knock-down of FDPS or GGPS1 for 3 days in HepG2 cells transduced with LV-expressing FDPS shRNA #4 (SEQ ID NO: 4) or GGPS1 shRNA #1 (SEQ ID NO: 70) and treatment with zoledronic acid stimulates TNF-α expression in Vγ9Vδ2 T cells, as shown in FIG. 24.

HepG2 cells were transduced with LV-control or LV-FDPS shRNA #4 (SEQ ID NO: 4) or LV-GGPS1 shRNA #1 (SEQ ID NO: 70) for 3 days. Two days after transduction, cells were treated with or without 1 μM zoledronic acid. After 24 hours, the transduced HepG2 cells were co-cultured for 4 hours with $5 \times 10^5$ PBMC cells in a round bottom 96 well plate. The PBMC cells had been pre-stimulated with zoledronic acid plus IL-2 for at least 11 days to expand Vγ9Vδ2 T cells. After staining for Vγ9Vδ2 and TNF-α using fluorophore-conjugated anti TCR-Vδ2 and anti-TNF-α anti-body, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. Without zole-dronic acid, LV-control stimulated 0.36% of TNF-α express-ing Vγ9Vδ2 T cells whereas LV-FDPS shRNA #4 (SEQ ID NO: 4) stimulated 0.9% and LV-GGPS1 #1 (SEQ ID NO: 70) shRNA stimulated 0.58%. With zoledronic acid treat-ment, LV-control stimulated 6.88% of TNF-α expressing Vγ9Vδ2 T cells, whereas LV-FDPS shRNA #4 (SEQ ID NO: 4) stimulated 21.1% and LV-GGPS1 #1 shRNA (SEQ ID NO: 70) stimulated 12%.

Figure 25:
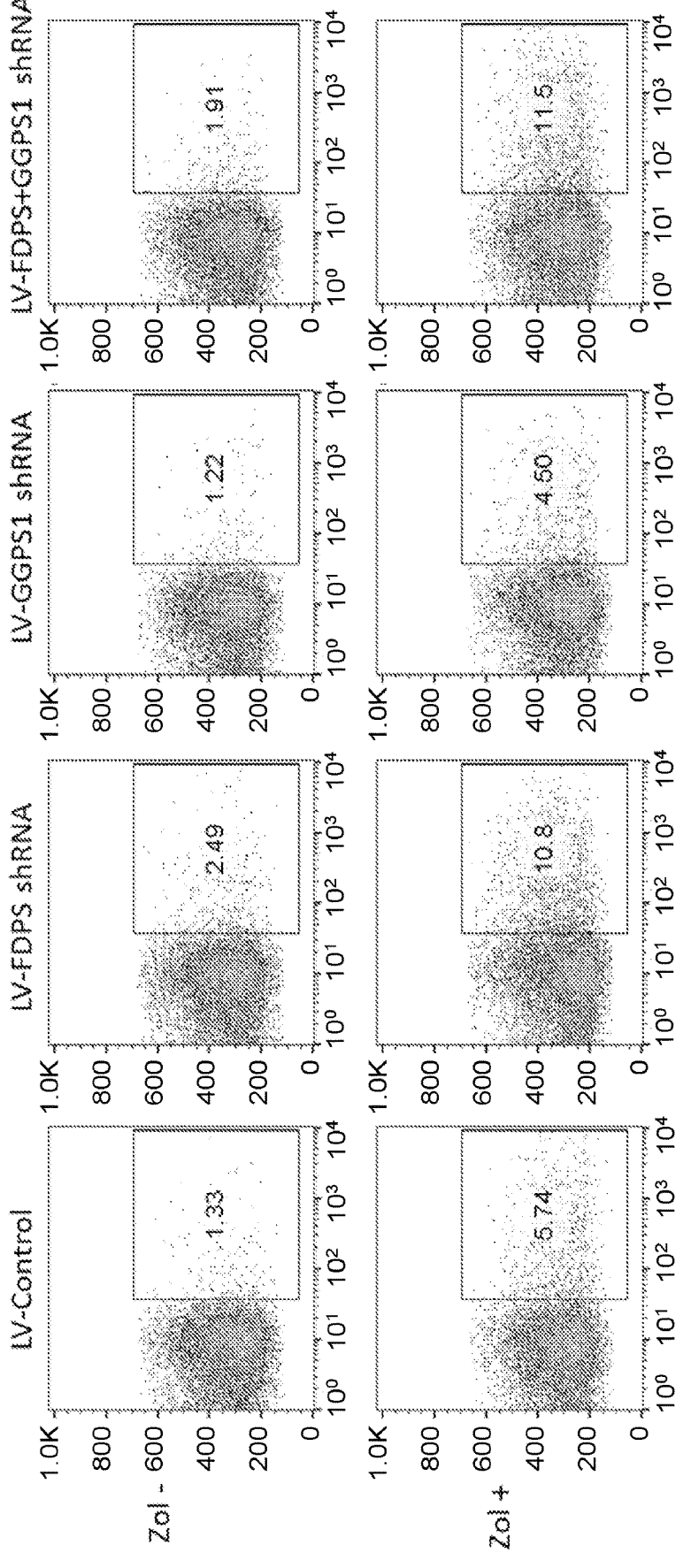
FIG. 25 depicts FACS data demonstrating activation of Vδ2+ T cells by THP-1 cells transduced with a lentivirus expressing shFDPS sequence #4 (SEQ ID NO: 4) and/or shGGPS1 sequence #1 (SEQ ID NO: 70) and treated with or without zoledronic acid, as described herein.

Example 21—Activation of Vγ9Vδ2 T Cells by THP-1 Cells Transduced with a Lentivirus Expressing shFDPS or shGGPS1 and Treated with Zoledronic Acid This Example illustrates that knock-down of FDPS or GGPS1 for 3 days in THP-1 cells transduced with Lv-expressing FDPS shRNA #4 (SEQ ID NO: 4) and/or GGPS1 shRNA #1 (SEQ ID NO: 70) and treatment with zoledronic acid stimulates TNF-α expression in Vγ9Vδ2 T cells, as shown in FIG. 25.

THP-1 cells were transduced with LV-control or LV-FDPS shRNA #4 (SEQ ID NO: 4) or Lv-GGPS1 shRNA #1 (SEQ ID NO: 70) for 3 days. Two days after transduction, cells were treated with or without 1 μM zoledronic acid. After 24 hours, the transduced THP-1 cells were co-cultured for 4 hours with 5×10⁵ PBMC cells in a round bottom 96 well plate. The PBMC cells had been pre-stimulated with zoledronic acid plus IL-2 for at least 11 days to expand Vγ9Vδ2 T cells. After staining for Vγ9Vδ2 and TNF-α using fluorophore-conjugated anti TCR-Vδ2 and anti-TNF-α anti-body, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. Without zole-dronic acid, LV-control stimulated 1.33% of TNF-α express-ing Vγ9Vδ2 T cells whereas Lv-FDPS shRNA #4 (SEQ ID NO: 4) stimulated 2.49%, Lv-GGPS1 #1 shRNA (SEQ ID NO: 70) stimulated 1.22%, and both combined stimulated 1.91%. With zoledronic acid treatment, Lv-control stimu-lated 5.74% of TNF-α expressing Vγ9Vδ2 T cells, whereas Lv-FDPS shRNA #4 (SEQ ID NO: 4) stimulated 10.8%, Lv-GGPS1 shRNA #1 (SEQ ID NO: 70) stimulated 4.5%, and both combined stimulated 11.5%.

Example 22—IDI1 Protein Expression in PC3 Prostate Carcinoma Cells Transduced with Lentiviruses Expressing shIDI1

This Example illustrates the effects of transduction with a lentiviral vector encoding the IDI1 shRNA sequence on IDI1 expression, as determined by immunoblot analyses.

Figure 26:
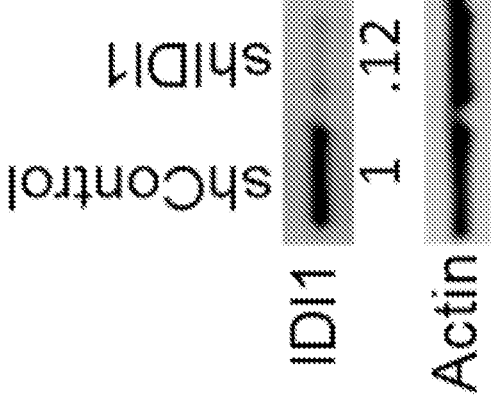
FIG. 26 depicts reduction of IDII protein expression in PC3 cells transduced with lentivirus expressing shIDI1 (SEQ ID NO: 76), as described herein.

PC3 cells were infected, at 5 MOI, with lentiviral vectors containing either a shControl or an IDI1 shRNA sequence (SEQ ID NO: 76). After 72 hours, cells were lysed and an 5 immunoblot was performed using an anti-IDI1 antibody from Thermo Fisher (Cat. No. PA5-44207) and an anti-actin antibody as a protein loading control. The densitometry of the immunoblot bands were quantified, and Lv-shControl was set as 1 (100%). As shown in FIG. 26, there was an 88% reduction of IDI1 protein expression.

Figure 27:
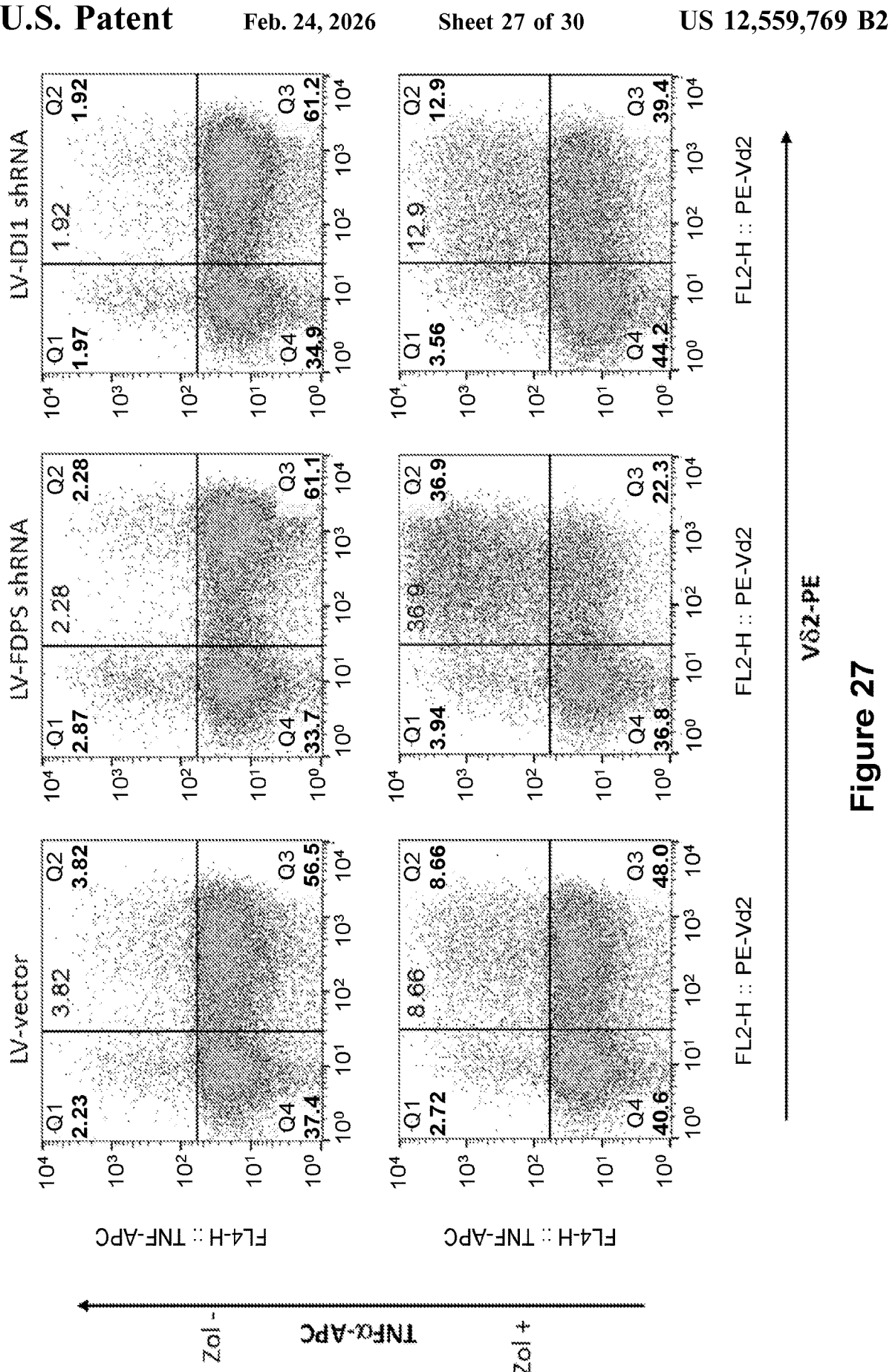
FIG. 27 depicts FACS data demonstrating activation of Vδ2+ T cells by PC3 cells transduced with a lentivirus expressing shFDPS sequence #4 (SEQ ID NO: 1) or shIDI1 sequence #1 (SEQ ID NO: 76), as described herein.

Example 23—Activation of Vγ9Vδ2 T Cells by PC3 Prostate Carcinoma Cells Transduced with a Lentivirus Expressing shFDPS or shIDI1 and Treated with Zoledronic Acid This Example illustrates that knock-down of FDPS or IDI1 for 3 days in PC3 cells transduced with Lv-expressing FDPS shRNA #4 (SEQ ID NO: 4) or IDI1 shRNA #1 (SEQ ID NO: 76) and treatment with zoledronic acid stimulates TNF-α expression in Vγ9Vδ2 T cells, as shown in FIG. 27.

PC3 cells were transduced with Lv-control or Lv-FDPS shRNA #4 (SEQ ID NO: 4) or LV-IDI1 shRNA #1 (SEQ ID NO: 76) for 3 days. Two days after transduction, cells were treated with or without 1 μM zoledronic acid. After 24 hours, the transduced PC3 cells were co-cultured for 4 hours with 5×10⁵ PBMC cells in a round bottom 96 well plate. The PBMC cells had been pre-stimulated with zoledronic acid plus IL-2 for at least 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. Without zoledronic acid, LV-control stimulated 3.82% of TNF-α expressing Vγ9Vδ2 T cells whereas LV-FDPS shRNA #4 (SEQ ID NO: 4) stimulated 2.28% and LV-IDI1 shRNA #1 (SEQ ID NO: 76) stimulated 1.92%. With zoledronic acid treatment, LV-control stimulated 8.66% of TNF-α expressing Vγ9Vδ2 T cells, whereas LV-FDPS shRNA #4 (SEQ ID NO: 4) stimu-lated 36.9% and LV-IDI1 shRNA #1 (SEQ ID NO: 76) stimulated 12.9%.

Example 24—Activation of Vγ9Vδ2 T Cells by THP-1 Acute Monocytic Leukemia Cells Treated with Zoledronic Acid (Zol), FTI277 (FTI), or Zaragozic Acid (ZA)

Figure 28:
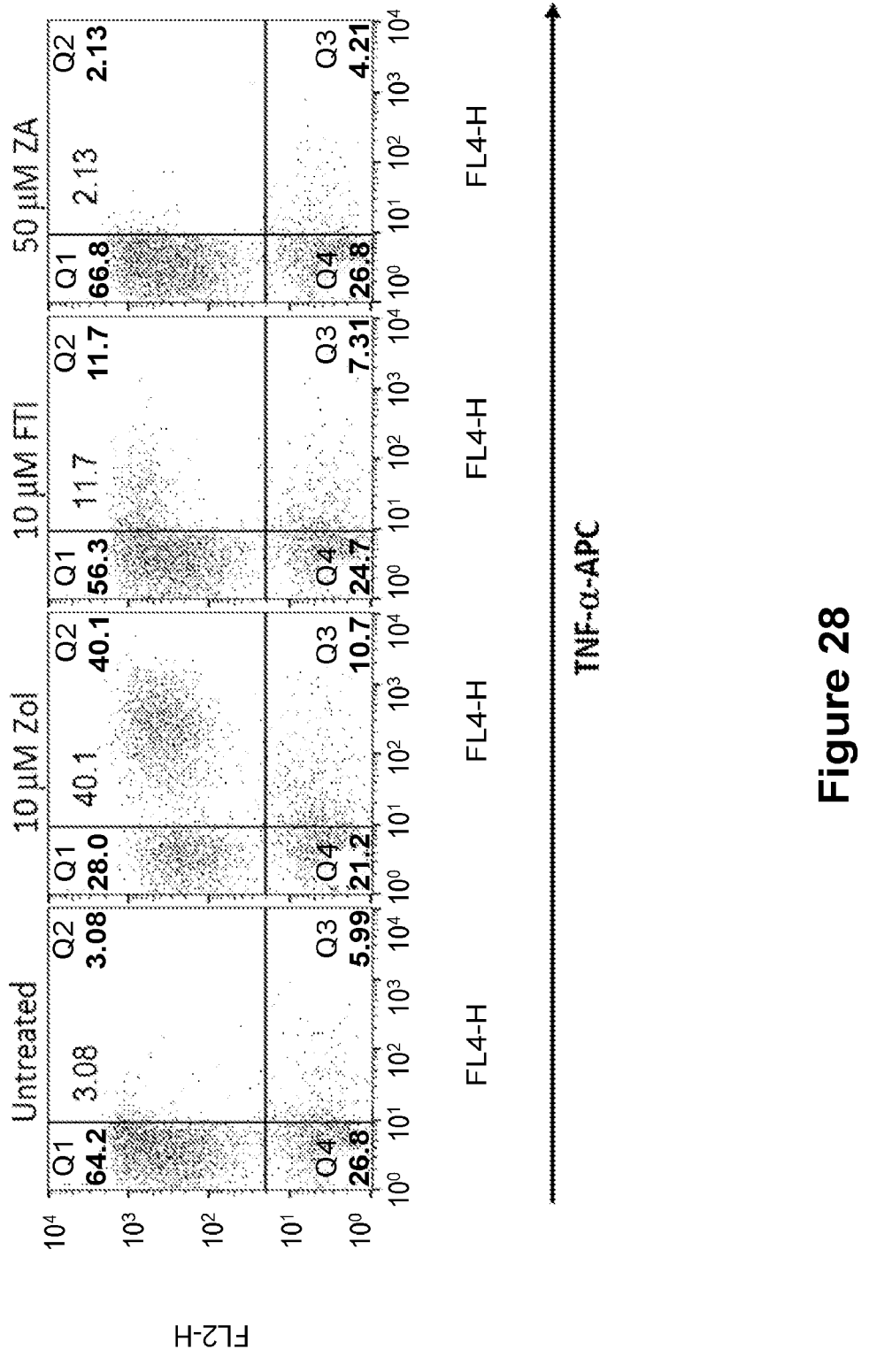
FIG. 28 depicts data demonstrating activation of Vδ2+ T cells by THP-1 cells treated with zoledronic acid, FTI277, or zaragozic acid, as described herein.

This Example illustrates that treatment with zoledronic acid stimulates TNF-α expression in Vγ9Vδ2 T cells, as shown in FIG. 28.

ZA is a small molecule inhibitor of squalene synthase in the pathway committed to sterol synthesis. THP-1 cells were treated with either the FDPS inhibitor Zol (10 μM), the famesyl transferase inhibitor FTI (10 μM), or ZA (50 μM) for 24 hours. THP-1 cells (2.5×10⁵) were co-cultured with 2.5×10⁵ PBMC cells in a round bottom 96 well plate for 5 hours. The PBMC cells had been pre-stimulated with zole-dronic acid plus IL-2 for at least 11 days to expand Vγ9Vδ2 T cells. After staining for Vγ9Vδ2 and TNF-α using fluo-rophore-conjugated anti TCR-Vδ2 and anti-TNF-α anti-body, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. Untreated cells stimulated 3.08% of TNF-α expressing Vγ9Vδ2 T cells, whereas zoledronic acid treatment stimulated 40.1%, FT1277 treatment stimulated 11.7%, and zaragozic acid stimulated 2.13%.

Example 25—Activation of Vγ9Vδ2 T Cells by PC3 Prostate Carcinoma Cells Transduced with a Lentivirus Expressing shFDPS and Treated with Zoledronic Acid (Zol), FTI277 (FTI), or Zaragozic Acid (ZA)

Figure 29:
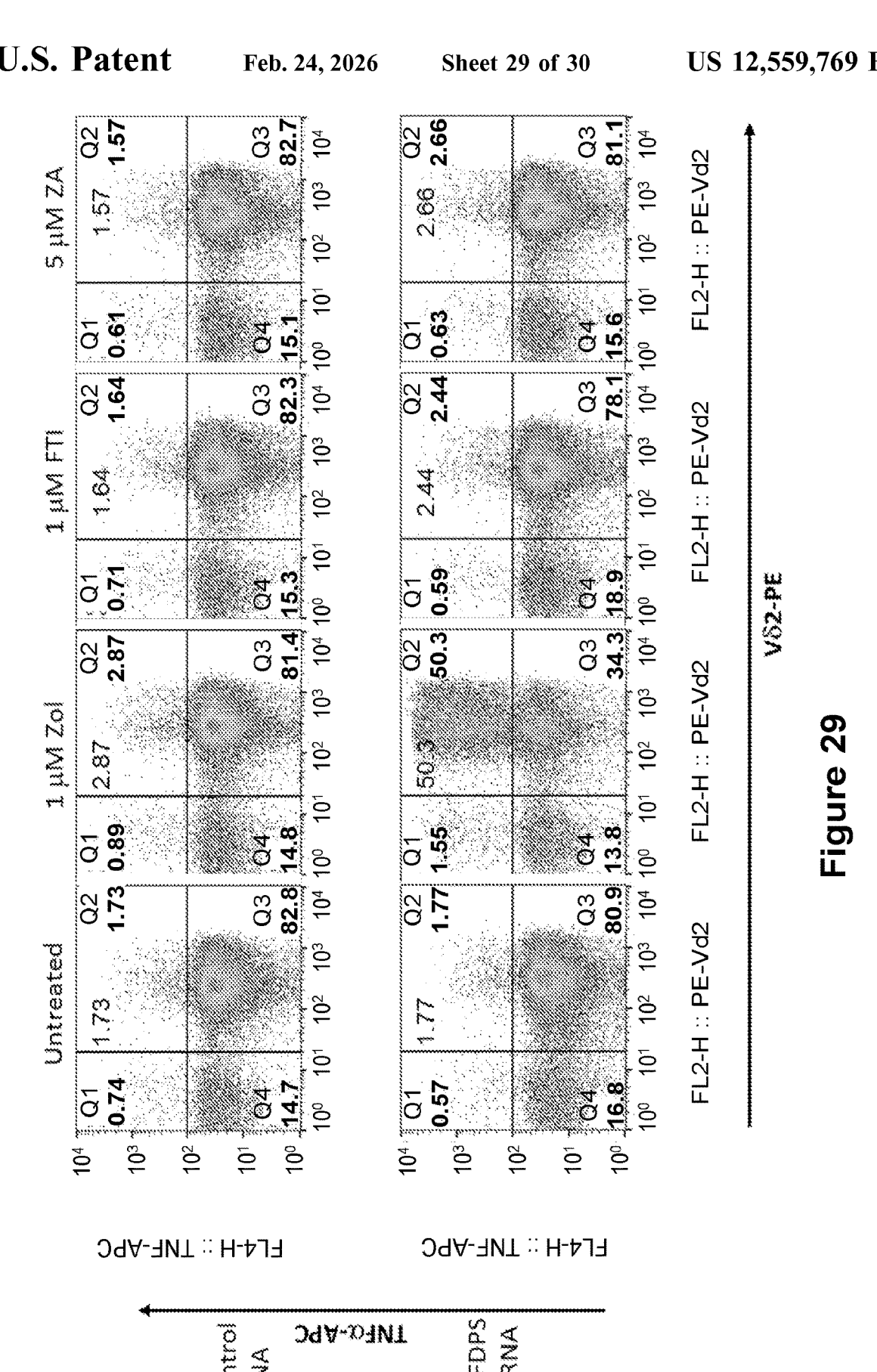
FIG. 29 depicts FACS data demonstrating activation of Vδ2+ T cells by PC3 cells transduced with a lentivirus expressing shFDPS sequence #4 (SEQ ID NO: 4) and treated with zoledronic acid, FTI277, or zaragozic acid, as described herein.

This Example illustrates that treatment of PC3 cells transduced with LV-expressing FDPS shRNA #4, with zole-dronic acid stimulates TNF-α expression in Vγ9Vδ2 T cells, as shown in FIG. 29.

PC3 cells were transduced with LV-control or LV-FDPS shRNA #4 (SEQ ID NO: 4) for 3 days. Two days after transduction, cells were treated with or without 1 μM zoledronic acid, 1 μM FT1277, or 5 μM zaragozic acid. After 24 hours, the transduced PC3 cells were co-cultured for 4 hours with 5×10⁵ PBMC cells in a round bottom 96 well plate. The PBMC cells had been pre-stimulated with zoledronic acid plus IL-2 for at least 11 days to expand Vγ9Vδ2 T cells. After staining for Vγ9Vδ2 and TNF-α using fluorophore-conjugated anti TCR-Vδ2 25 and anti-TNF-α antibody, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. In LV-control transduced cells, untreated cells stimulated 1.73% of TNF-α expressing Vγ9Vδ2 T cells, whereas zoledronic acid treatment stimulated 2.87%, FT1277 stimulated 1.64%, and zaragozic acid stimulated 1.57%. In LV-FDPS shRNA #4 (SEQ ID NO: 4) transduced cells, untreated cells stimulated 1.77% of TNF-α expressing Vγ9Vδ2 T cells, whereas zoledronic acid stimulated 50.3%, FT1277 stimulated 2.44% and zaragozic acid stimulated 2.66%.

Example 26—Activation of Vγ9Vδ2 T Cells by HepG2 Hepatocellular Carcinoma Cells Transduced with a Lentivirus Expressing shFDPS and Treated with Zoledronic Acid (Zol), FTI277 (FTI), or Zaragozic Acid (ZA)

Figure 30:
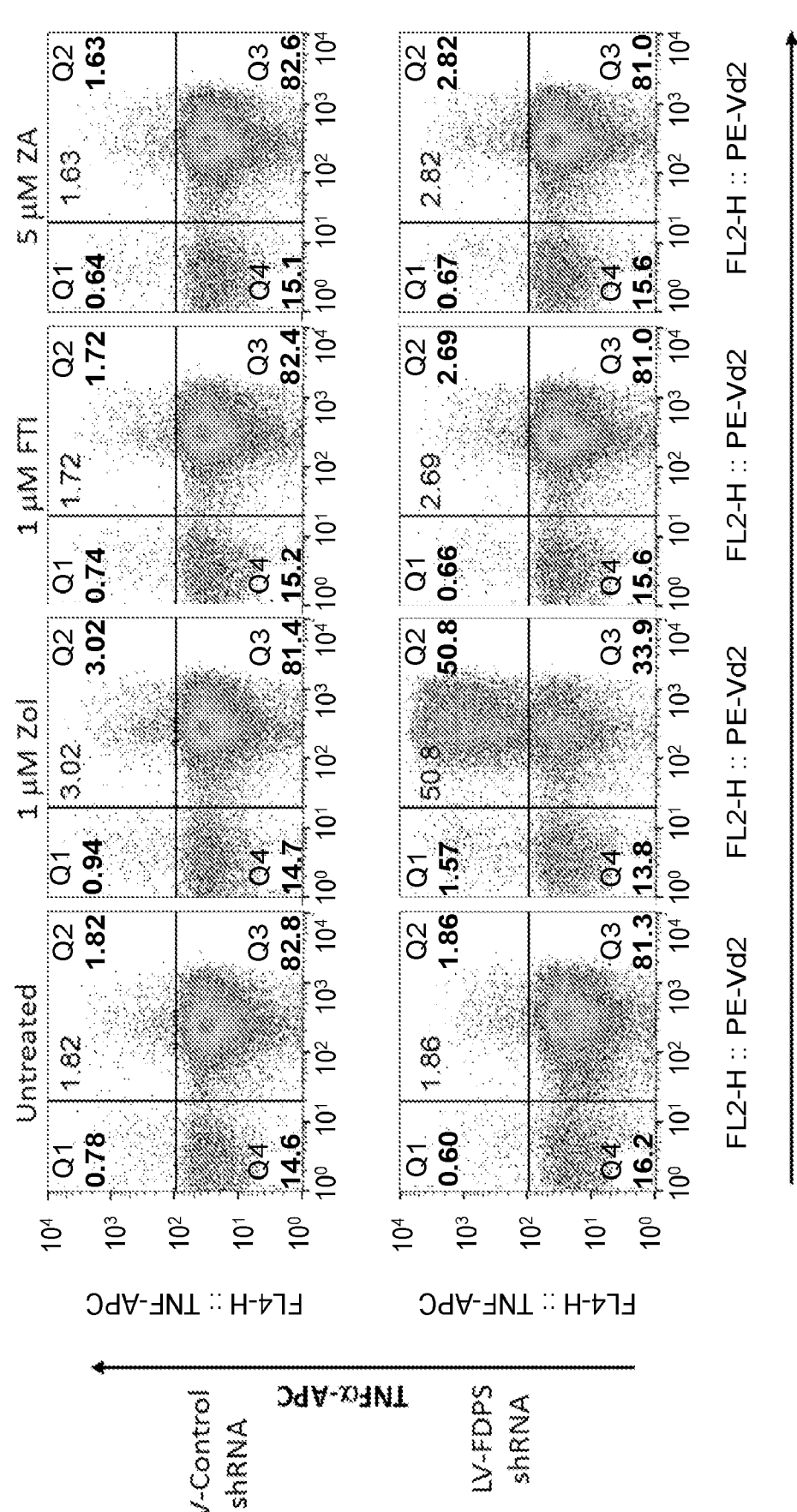
FIG. 30 depicts FACS data demonstrating activation of Vδ2+ T cells by HepG2 cells transduced with a lentivirus expressing shFDPS sequence #4 (SEQ ID NO: 4) and treated with zoledronic acid, FTI277, or zaragozic acid, as described herein.

This Example illustrates that treatment of HepG2 cells transduced with LV-expressing FDPS shRNA #4, with zoledronic acid stimulates TNF-α expression in Vγ9Vδ2 T cells, as shown in FIG. 30.

HepG2 cells were transduced with LV-control or LV-FDPS shRNA #4 (SEQ ID NO: 4) for 3 days. Two days after transduction, cells were treated with or without 1 μM zoledronic acid, 1 μM FT1277, or 5 μM zaragozic acid. After 24 hours, the transduced HepG2 cells were co-cultured for 4 hours with 5×10⁵ PBMC cells in a round bottom 96 well plate. The PBMC cells had been pre-stimulated with zoledronic acid plus IL-2 for at least 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated; Vδ2+ and TNF-α+ cells were identified on a dot blot. The activated cytotoxic Vγ9Vδ2 T cells appeared in the upper right quadrant of the flow cytograms. In LV-control transduced cells, untreated cells stimulated 1.82% of TNF-α expressing Vγ9Vδ2 T cells, whereas zoledronic acid treatment stimulated 3.02%, FT1277 stimulated 1.72%, and zaragozic acid stimulated 1.63%. In LV-FDPS shRNA #4 (SEQ ID NO: 4) transduced cells, untreated cells stimulated 1.86% of TNF-α expressing Vγ9Vδ2 T cells, whereas zoledronic acid stimulated 50.8%, FT1277 stimulated 2.69% and zaragozic acid stimulated 2.82%.

While certain preferred embodiments of the present disclosure have been described and specifically exemplified above, it is not intended that any invention be limited to such embodiments.

Sequences

The following sequences are referred to herein and, as such, are incorporated into this disclosure:

| SEQ ID NO: | Description | Sequence |
|---|---|---|
| 1 | FDPS shRNA sequence #1 | GTCCTGGAGTACAATGCCATTCTCGAGAATGGCATTGTAC TCCAGGACTTTTT |
| 2 | FDPS shRNA sequence #2 | GCAGGATTTCGTTCAGCACTTCTCGAGAAGTGCTGAACG AAATCCTGCTTTTT |
| 3 | FDPS shRNA sequence #3 | GCCATGTACATGGCAGGAATTCTCGAGAATTCCTGCCAT GTACATGGCTTTTT |
| 4 | FDPS shRNA sequence #4 | GCAGAAGGAGGCTGAGAAAGTCTCGAGACTTTCTCAGCC TCCTTCTGCTTTTT |
| 5 | Rous Sarcoma virus (RSV) promoter | GTAGTCTTATGCAATACTCTTGTAGTCTTGCAACATGGTA ACGATGAGTTAGCAACATGCCTTACAAGGAGAGAAAAAG CACCGTGCATGCCGATTGGTGGAAGTAAGGTGGTACGAT CGTGCCTTATTAGGAAGGCAACAGACGGGTCTGACATGG ATTGGACGAACCACTGAATTGCCGCATTGCAGAGATATT GTATTTAAGTGCCTAGCTCGATACAATAAACG |
| 6 | 5′ Long terminal repeat (LTR) | GGTCTCTCTGGTTAGACCAGATCTGAGCCTGGGAGCTCTC TGGCTAACTAGGGAACCCACTGCTTAAGCCTCAATAAAG CTTGCCTTGAGTGCTTCAAGTAGTGTGTGCCCGTCTGTTG TGTGACTCTGGTAACTAGAGATCCCTCAGACCCTTTTAGT CAGTGTGGAAAATCTCTAGCA |
| 7 | Psi Packaging signal | TACGCCAAAAATTTTGACTAGCGGAGGCTAGAAGGAGAG AG |
| 8 | Rev response element (RRE) | AGGAGCTTTGTTCCTTGGGTTCTTGGGAGCAGCAGGAAG CACTATGGGCGCAGCCTCAATGACGCTGACGGTACAGGC CAGACAATTATTGTCTGGTATAGTGCAGCAGCAGAACAA TTTGCTGAGGGCTATTGAGGCGCAACAGCATCTGTTGCA ACTCACAGTCTGGGGCATCAAGCAGCTCCAGGCAAGAAT CCTGGCTGTGGAAAGATACCTAAAGGATCAACAGCTCC |

-continued

| SEQ ID NO: | Description | Sequence |
|---|---|---|
| 9 | Central polypurine tract (cPPT) | TTTTAAAAGAAAAGGGGGGATTGGGGGGTACAGTGCAGG GGAAAGAATAGTAGACATAATAGCAACAGACATACAAA CTAAAGAATTACAAAAACAAATTACAAAATTCAAAATTT TA |
| 10 | Polymerase III shRNA promoters; H1 promoter | GAACGCTGACGTCATCAACCCGCTCCAAGGAATCGCGGG CCCAGTGTCACTAGGCGGGAACACCCAGCGCGCGTGCGC CCTGGCAGGAAGATGGCTGTGAGGGACAGGGGAGTGGC GCCCTGCAATATTTGCATGTCGCTATGTGTTCTGGGAAAT CACCATAAACGTGAAATGTCTTTGGATTTGGGAATCTTAT AAGTTCTGTATGAGACCACTT |
| 11 | Long WPRE sequence | AATCAACCTCTGATTACAAAATTTGTGAAAGATTGACTG GTATTCTTAACTATGTTGCTCCTTTTACGCTATGTGGATAC GCTGCTTTAATGCCTTTGTATCATGCTATTGCTTCCCGTAT GGCTTTCATTTTCTCCTCCTTGTATAAATCCTGGTTGCTGT CTCTTTATGAGGAGTTGTGGCCCGTTGTCAGGCAACGTGG CGTGGTGTGCACTGTGTTTGCTGACGCAACCCCCACTGGT TGGGGCATTGCCACCACCTGTCAGCTCCTTTCCGGGACTT TCGCTTTCCCCCTCCCTATTGCCACGGCGGAACTCATCGC CGCCTGCCTTGCCCGCTGCTGGACAGGGGCTCGGCTGTTG GGCACTGACAATTCCGTGGTGTTGTCGGGGAAATCATCG TCCTTTCCTTGGCTGCTCGCCTGTGTTGCCACCTGGATTCT GCGCGGGACGTCCTTCTGCTACGTCCCTTCGGCCCTCAAT CCAGCGGACCTTCCTTCCCGCGGCCTGCTGCCGGCTCTGC GGCCTCTTCCGCGTCTTCGCCTTCGCCCTCAGACGAGTCG GATCTCCCTTTGGGCCGCCTCCCCGCCT |
| 12 | 3' delta LTR | TGGAAGGGCTAATTCACTCCCAACGAAGATAAGATCTGC TTTTTGCTTGTACTGGGTCTCTCTGGTTAGACCAGATCTG AGCCTGGGAGCTCTCTGGCTAACTAGGGAACCCACTGCT TAAGCCTCAATAAAGCTTGCCTTGAGTGCTTCAAGTAGTG TGTGCCCGTCTGTTGTGTGACTCTGGTAACTAGAGATCCC TCAGACCCTTTTAGTCAGTGTGGAAAATCTCTAGCAGTAG TAGTTCATGTCA |
| 13 | Helper/Rev; Chicken beta actin (CAG) promoter; Transcription | GCTATTACCATGGGTCGAGGTGAGCCCCACGTTCTGCTTC ACTCTCCCCATCTCCCCCCCCTCCCCACCCCCAATTTTGTA TTTATTTATTTTTTAATTATTTTGTGCAGCGATGGGGGCG GGGGGGGGGGGGGGCGCGCGCCAGGCGGGCGGGGCGGG GCGAGGGGCGGGGCGGGGCGAGGCGGAGAGGTGCGGCG GCAGCCAATCAGAGCGGCGCGCTCCGAAAGTTTCCTTTT ATGGCGAGGCGGCGGCGGCGGCGGCGGCCCTATAAAAAGCG AAGCGCGCGGCGGGCG |
| 14 | Helper/Rev; HIV Gag; Viral capsid | ATGGGTGCGAGAGCGTCAGTATTAAGCGGGGGAGAATTA GATCGATGGGAAAAAATTCGGTTAAGGCCAGGGGGAAA GAAAAAATATAAATTAAAACATATAGTATGGGCAAGCAG GGAGCTAGAACGATTCGCAGTTAATCCTGGCCTGTTAGA AACATCAGAAGGCTGTAGACAAATACTGGGACAGCTACA ACCATCCCTTCAGACAGGATCAGAAGAACTTAGATCATT ATATAATACAGTAGCAACCCTCTATTGTGTGCATCAAAG GATAGAGATAAAAGACACCAAGGAAGCTTTAGACAAGA TAGAGGAAGAGCAAAACAAAAGTAAGAAAAAAGCACAG CAAGCAGCAGCTGACACAGGACACAGCAATCAGGTCAGC CAAAATTACCCTATAGTGCAGAACATCCAGGGGCAAATG GTACATCAGGCCATATCACCTAGAACTTTAAATGCATGG GTAAAAGTAGTAGAAGAGAAGGCTTTCAGCCCAGAAGTG ATACCCATGTTTTCAGCATTATCAGAAGGAGCCACCCCAC AAGATTTAAACACCATGCTAAACACAGTGGGGGGACATC AAGCAGCCATGCAAATGTTAAAAGAGACCATCAATGAGG AAGCTGCAGAATGGGATAGAGTGCATCCAGTGCATGCAG GGCCTATTGCACCAGGCCAGATGAGAGAACCAAGGGGA AGTGACATAGCAGGAACTACTAGTACCCTTCAGGAACAA ATAGGATGGATGACACATAATCCACCTATCCCAGTAGGA GAAATCTATAAAAGATGGATAATCCTGGGATTAAATAAA ATAGTAAGAATGTATAGCCCTACCAGCATTCTGGACATA AGACAAGGACCAAAGGAACCCTTTAGAGACTATGTAGAC CGATTCTATAAAACTCTAAGAGCCGAGCAAGCTTCACAA GAGGTAAAAAATTGGATGACAGAAACCTTGTTGGTCCAA AATGCGAACCCAGATTGTAAGACTATTTTAAAAGCATTG GGACCAGGAGCGACACTAGAAGAAATGATGACAGCATG TCAGGGAGTGGGGGGACCCGGCCATAAAGCAAGAGTTTT GGCTGAAGCAATGAGCCAAGTAACAAATCCAGCTACCAT AATGATACAGAAAGGCAATTTTAGGAACCAAAGAAAGA |

-continued

| SEQ ID NO: | Description | Sequence |
|---|---|---|
| | | CTGTTAAGTGTTTCAATTGTGGCAAAGAAGGGCACATAG |
| | | CCAAAAATTGCAGGGCCCCTAGGAAAAAGGGCTGTTGGA |
| | | AATGTGGAAAGGAAGGACACCAAATGAAAGATTGTACTG |
| | | AGAGACAGGCTAATTTTTTAGGGAAGATCTGGCCTTCCC |
| | | ACAAGGGAAGGCCAGGGAATTTTCTTCAGAGCAGACCAG |
| | | AGCCAACAGCCCCACCAGAAGAGAGCTTCAGGTTTGGGG |
| | | AAGAGACAACAACTCCCTCTCAGAAGCAGGAGCCGATAG |
| | | ACAAGGAACTGTATCCTTTAGCTTCCCTCAGATCACTCTT |
| | | TGGCAGCGACCCCTCGTCACAATAA |
| 15 | Helper/Rev; HIV Pol; Protease and reverse transcriptase | ATGAATTTGCCAGGAAGATGGAAACCAAAAATGATAGGG |
| | | GGAATTGGAGGTTTTATCAAAGTAGGACAGTATGATCAG |
| | | ATACTCATAGAAATCTGCGGACATAAAGCTATAGGTACA |
| | | GTATTAGTAGGACCTACACCTGTCAACATAATTGGAAGA |
| | | AATCTGTTGACTCAGATTGGCTGCACTTTAAATTTTCCCA |
| | | TTAGTCCTATTGAGACTGTACCAGTAAAATTAAAGCCAG |
| | | GAATGGATGGCCCAAAAGTTAAACAATGGCCATTGACAG |
| | | AAGAAAAAATAAAAGCATTAGTAGAAATTTGTACAGAAA |
| | | TGGAAAAGGAAGGAAAAATTTCAAAAATTGGGCCTGAA |
| | | AATCCATACAATACTCCAGTATTTGCCATAAAGAAAAAA |
| | | GACAGTACTAAATGGAGAAAATTAGTAGATTTCAGAGAA |
| | | CTTAATAAGAGAACTCAAGATTTCTGGGAAGTTCAATTA |
| | | GGAATACCACATCCTGCAGGGTTAAAACAGAAAAAATCA |
| | | GTAACAGTACTGGATGTGGGCGATGCATATTTTTCAGTTC |
| | | CCTTAGATAAAGACTTCAGGAAGTATACTGCATTTACCAT |
| | | ACCTAGTATAAACAATGAGACACCAGGGATTAGATATCA |
| | | GTACAATGTGCTTCCACAGGGATGGAAAGGATCACCAGC |
| | | AATATTCCAGTGTAGCATGACAAAAATCTTAGAGCCTTTT |
| | | AGAAAACAAAATCCAGACATAGTCATCTATCAATACATG |
| | | GATGATTTGTATGTAGGATCTGACTTAGAAATAGGGCAG |
| | | CATAGAACAAAAATAGAGGAACTGAGACAACATCTGTTG |
| | | AGGTGGGGATTTACCACACCAGACAAAAAACATCAGAAA |
| | | GAACCTCCATTCCTTTGGATGGGTTATGAACTCCATCCTG |
| | | ATAAATGGACAGTACAGCCTATAGTGCTGCCAGAAAAGG |
| | | ACAGCTGGACTGTCAATGACATACAGAAATTAGTGGGAA |
| | | AATTGAATTGGGCAAGTCAGATTTATGCAGGGATTAAAG |
| | | TAAGGCAATTATGTAAACTTCTTAGGGGAACCAAAGCAC |
| | | TAACAGAAGTAGTACCACTAACAGAAGAAGCAGAGCTA |
| | | GAACTGGCAGAAAACAGGGAGATTCTAAAAGAACCGGT |
| | | ACATGGAGTGTATTATGACCCATCAAAAGACTTAATAGC |
| | | AGAAATACAGAAGCAGGGGCAAGGCCAATGGACATATC |
| | | AAATTTATCAAGAGCCATTTAAAAATCTGAAAACAGGAA |
| | | AATATGCAAGAATGAAGGGTGCCCACACTAATGATGTGA |
| | | AACAATTAACAGAGGCAGTACAAAAAATAGCCACAGAA |
| | | AGCATAGTAATATGGGGAAAGACTCCTAAATTTAAATTA |
| | | CCCATACAAAAGGAAACATGGGAAGCATGGTGGACAGA |
| | | GTATTGGCAAGCCACCTGGATTCCTGAGTGGGAGTTTGTC |
| | | AATACCCCTCCCTTAGTGAAGTTATGGTACCAGTTAGAGA |
| | | AAGAACCCATAATAGGAGCAGAAACTTTCTATGTAGATG |
| | | GGGCAGCCAATAGGGAAACTAAATTAGGAAAAGCAGGA |
| | | TATGTAACTGACAGAGGAAGACAAAAAGTTGTCCCCCTA |
| | | ACGGACACAACAAATCAGAAGACTGAGTTACAAGCAATT |
| | | CATCTAGCTTTGCAGGATTCGGGATTAGAAGTAAACATA |
| | | GTGACAGACTCACAATATGCATTGGGAATCATTCAAGCA |
| | | CAACCAGATAAGAGTGAATCAGAGTTAGTCAGTCAAATA |
| | | ATAGAGCAGTTAATAAAAAAGGAAAAAGTCTACCTGGCA |
| | | TGGGTACCAGCACACAAAGGAATTGGAGGAAATGAACA |
| | | AGTAGATGGGTTGGTCAGTGCTGGAATCAGGAAAGTACT |
| | | A |
| 16 | Helper Rev; HIV Integrase; Integration of viral RNA | TTTTTAGATGGAATAGATAAGGCCCAAGAAGAACATGAG |
| | | AAATATCACAGTAATTGGAGAGCAATGGCTAGTGATTTT |
| | | AACCTACCACCTGTAGTAGCAAAAGAAATAGTAGCCAGC |
| | | TGTGATAAATGTCAGCTAAAAGGGGAAGCCATGCATGGA |
| | | CAAGTAGACTGTAGCCCAGGAATATGGCAGCTAGATTGT |
| | | ACACATTTAGAAGGAAAAGTTATCTTGGTAGCAGTTCAT |
| | | GTAGCCAGTGGATATATAGAAGCAGAAGTAATTCCAGCA |
| | | GAGACAGGGCAAGAAACAGCATACTTCCTCTTAAAATTA |
| | | GCAGGAAGATGGCCAGTAAAAACAGTACATACAGACAA |
| | | TGGCAGCAATTTCACCAGTACTACAGTTAAGGCCGCCTGT |
| | | TGGTGGGCGGGGATCAAGCAGGAATTTGGCATTCCCTAC |
| | | AATCCCCAAAGTCAAGGAGTAATAGAATCTATGAATAAA |
| | | GAATTAAAGAAAATTATAGGACAGGTAAGAGATCAGGCT |
| | | GAACATCTTAAGACAGCAGTACAAATGGCAGTATTCATC |
| | | CACAATTTTAAAAGAAAAGGGGGGATTGGGGGGTACAGT |
| | | GCAGGGGAAAGAATAGTAGACATAATAGCAACAGACAT |

-continued

| SEQ ID NO: | Description | Sequence |
|---|---|---|
| | | ACAAACTAAAGAATTACAAAAACAAATTACAAAAATTCA<br>AAATTTTCGGGTTTATTACAGGGACAGCAGAGATCCAGT<br>TTGGAAAGGACCAGCAAAGCTCCTCTGGAAAGGTGAAGG<br>GGCAGTAGTAATACAAGATAATAGTGACATAAAAGTAGT<br>GCCAAGAAGAAAAGCAAAGATCATCAGGGATTATGGAA<br>AACAGATGGCAGGTGATGATTGTGTGGCAAGTAGACAGG<br>ATGAGGATTAA |
| 17 | Lenti-BTN3A3 ("BTN3A3") | ATGAAAATGGCAAGTTCCCTGGCTTTCCTTCTGCTCAACT<br>TTCATGTCTCCCTCTTCTTGGTCCAGCTGCTCACTCCTTGC<br>TCAGCTCAGTTTTCTGTGCTTGGACCCTCTGGGCCCATCC<br>TGGCCATGGTGGGTGAAGACGCTGATCTGCCCTGTCACCT<br>GTTCCCGACCATGAGTGCAGAGACCATGGAGCTGAGGTG<br>GGTGAGTTCCAGCCTAAGGCAGGTGGTGAACGTGTATGC<br>AGATGGAAAGGAAGTGGAAGACAGGCAGAGTGCACCGT<br>ATCGAGGGAGAACTTCGATTCTGCGGGATGGCATCACTG<br>CAGGGAAGGCTGCTCTCCGAATACACAACGTCACAGCCT<br>CTGACAGTGGAAAGTACTTGTGTTATTTCCAAGATGGTGA<br>CTTCTACGAAAAAGCCCTGGTGGAGCTGAAGGTTGCAGC<br>ATTGGGTTCTGATCTTCACATTGAAGTGAAGGGTTATGAG<br>GATGGAGGGATCCATCTGGAGTGCAGGTCCACTGGCTGG<br>TACCCCCAACCCCAAATAAAGTGGAGCGACGCCAAGGGA<br>GAGAACATCCCGGCTGTGGAAGCACCTGTGGTTGCAGAT<br>GGAGTGGGCCTGTATGCAGTAGCAGCATCTGTGATCATG<br>AGAGGCAGCTCTGGTGGGGGTGTATCCTGCATCATCAGA<br>AATTCCCTCCTCGGCCTGGAAAAGACAGCCAGCATATCC<br>ATCGCAGACCCCTTCTTCAGGAGCGCCCAGCCCTGGATC<br>GCGGCCCTGGCAGGGACCCTGCCTATCTCGTTGCTGCTTC<br>TCGCAGGAGCCAGTTACTTCTTGTGGAGACAACAGAAGG<br>AAAAAATTGCTCTGTCCAGGGAGACAGAAAGAGAGCGA<br>GAGATGAAAGAAATGGGATACGCTGCAACAGAGCAAGA<br>AATAAGCCTAAGAGAGAAGCTCCAGGAGGAACTCAAGT<br>GGAGGAAAATCCAGTACATGGCTCGTGGAGAGAAGTCTT<br>TGGCCTATCATGAATGGAAAATGGCCCTCTTCAAACCTGC<br>GGATGTGATTCTGGATCCAGACACGGCAAACGCCATCCT<br>CCTTGTTTCTGAGGACCAGAGGAGTGTGCAGCGTGCTGA<br>AGAGCCGCGGGATCTGCCAGACAACCCTGAGAGATTTGA<br>ATGGCGTTACTGTGTCCTTGGCTGTGAAAAACTTCACATCA<br>GGGAGACATTACTGGGAGGTGGAAGTGGGGGGACAGAAA<br>AGAGTGGCATATTGGGGTATGTAGTAAGAACGTGGAGAG<br>GAAAAAAGGTTGGGTCAAAATGACACCGGAGAACGGAT<br>ACTGGACTATGGGCCTGACTGATGGGAATAAGTATCGGG<br>CTCTCACTGAGCCCAGAACCAACCTGAAACTTCCTGAGC<br>CTCCTAGGAAAGTGGGGATCTTCCTGGACTATGAGACTG<br>GAGAGATCTCGTTCTATAATGCCACAGATGGATCTCATAT<br>CTACACCTTTCCGCACGCCTCTTTCTCTGAGCCTCTATATC<br>CTGTTTTCAGAATTTTGACCTTGGAGCCCACTGCCCTGAC<br>CATTTGCCCAATACCAAAAGAAGTAGAGAGTTCCCCCGA<br>TCCTGACCTAGTGCCTGATCATTCCCTGGAGACACCACTG<br>ACCCCGGGCTTAGCTAATGAAAGTGGGGAGCCTCAGGCT<br>GAAGTAACATCTCTGCTTCTCCCTGCCCACCCTGGAGCTG<br>AGGTCTCCCCTTCTGCAACAACCAATCAGAACCATAAGC<br>TACAGGCACGCACTGAAGCACTTTACTGA |
| 18 | Helper/Rev; HIV Rev; Nuclear export and stabilize viral mRNA | ATGGCAGGAAGAAGCGGAGACAGCGACGAAGAACTCCT<br>CAAGGCAGTCAGACTCATCAAGTTTCTCTATCAAAGCAA<br>CCCACCTCCCAATCCCGAGGGGACCCGACAGGCCCGAAG<br>GAATAGAAGAAGAAGGTGGAGAGAGAGACAGAGACAGA<br>TCCATTCGATTAGTGAACGGATCCTTAGCACTTATCTGGG<br>ACGATCTGCGGAGCCTGTGCCTCTTCAGCTACCACCGCTT<br>GAGAGACTTACTCTTGATTGTAACGAGGATTGTGGAACTT<br>CTGGGACGCAGGGGGTGGGAAGCCCTCAAATATTGGTGG<br>AATCTCCTACAATATTGGAGTCAGGAGCTAAAGAATAG |
| 19 | Envelope; CMV promoter; Transcription | ACATTGATTATTGACTAGTTATTAATAGTAATCAATTACG<br>GGGTCATTAGTTCATAGCCCATATATGGAGTTCCGCGTTA<br>CATAACTTACGGTAAATGGCCCGCCTGGCTGACCGCCCA<br>ACGACCCCCGCCCATTGACGTCAATAATGACGTATGTTCC<br>CATAGTAACGCCAATAGGGACTTTCCATTGACGTCAATG<br>GGTGGAGTATTTACGGTAAACTGCCCACTTGGCAGTACA<br>TCAAGTGTATCATATGCCAAGTACGCCCCCTATTGACGTC<br>AATGACGGTAAATGGCCCGCCTGGCATTATGCCCAGTAC<br>ATGACCTTATGGGACTTTCCTACTTGGCAGTACATCTACG<br>TATTAGTCATCGCTATTACCATGGTGATGCGGTTTTGGCA<br>GTACATCAATGGGCGTGGATAGCGGTTTGACTCACGGGG<br>ATTTCCAAGTCTCCACCCCATTGACGTCAATGGGAGTTTG |

| SEQ ID NO: | Description | Sequence |
|---|---|---|
| | | TTTTGGCACCAAAATCAACGGGACTTTCCAAAATGTCGTA ACAACTCCGCCCCATTGACGCAAATGGGCGGTAGGCGTG TACGGTGGGAGGTCTATATAAGC |
| 20 | Envelope; VSV-G; Glycoprotein envelope-cell entry | ATGAAGTGCCTTTTGTACTTAGCCTTTTTATTCATTGGGGT GAATTGCAAGTTCACCATAGTTTTTCCACACAACCAAAA AGGAAACTGGAAAAATGTTCCTTCTAATTACCATTATTGC CCGTCAAGCTCAGATTTAAATTGGCATAATGACTTAATAG GCACAGCCTTACAAGTCAAAATGCCCAAGAGTCACAAGG CTATTCAAGCAGACGGTTGGATGTGTCATGCTTCCAAATG GGTCACTACTTGTGATTTCCGCTGGTATGGACCGAAGTAT ATAACACATTCCATCCGATCCTTCACTCCATCTGTAGAAC AATGCAAGGAAAGCATTGAACAAACGAAACAAGGAACT TGGCTGAATCCAGGCTTCCCTCCTCAAAGTTGTGGATATG CAACTGTGACGGATGCCGAAGCAGTGATTGTCCAGGTGA CTCCTCACCATGTGCTGGTTGATGAATACACAGGAGAAT GGGTTGATTCACAGTTCATCAACGGAAAATGCAGCAATT ACATATGCCCCACTGTCCATAACTCTACAACCTGGCATTC TGACTATAAGGTCAAAGGGCTATGTGATTCTAACCTCATT TCCATGGACATCACCTTCTTCTCAGAGGACGGAGAGCTAT CATCCCTGGGAAAGGAGGGCACAGGGTTCAGAAGTAACT ACTTTGCTTATGAAACTGGAGGCAAGGCCTGCAAAATGC AATACTGCAAGCATTGGGGAGTCAGACTCCCATCAGGTG TCTGGTTCGAGATGGCTGATAAGGATCTCTTTGCTGCAGC CAGATTCCCTGAATGCCCAGAAGGGTCAAGTATCTCTGCT CCATCTCAGACCTCAGTGGATGTAAGTCTAATTCAGGAC GTTGAGAGGATCTTGGATTATTCCCTCTGCCAAGAAACCT GGAGCAAAATCAGAGCGGGTCTTCCAATCTCTCCAGTGG ATCTCAGCTATCTTGCTCCTAAAAACCCAGGAACCGGTCC TGCTTTCACCATAATCAATGGTACCCTAAAATACTTTGAG ACCAGATACATCAGAGTCGATATTGCTGCTCCAATCCTCT CAAGAATGGTCGGAATGATCAGTGGAACTACCACAGAAA GGGAACTGTGGGATGACTGGGCACCATATGAAGACGTGG AAATTGGACCCAATGGAGTTCTGAGGACCAGTTCAGGAT ATAAGTTTCCTTTATACATGATTGGACATGGTATGTTGGA CTCCGATCTTCATCTTAGCTCAAAGGCTCAGGTGTTCGAA CATCCTCACATTCAAGACGCTGCTTCGCAACTTCCTGATG ATGAGAGTTTATTTTTTGGTGATACTGGGCTATCCAAAAA TCCAATCGAGCTTGTAGAAGGTTGGTTCAGTAGTTGGAA AAGCTCTATTGCCTCTTTTTTTCTTTATCATAGGGTTAATCA TTGGACTATTCTTGGTTCTCCGAGTTGGTATCCATCTTTGC ATTAAATTAAAGCACACCAAGAAAAGACAGATTTATACA GACATAGAGATGA |
| 21 | Helper/Rev; CMV early (CAG) enhancer; Enhance Transcription | TAGTTATTAATAGTAATCAATTACGGGGTCATTAGTTCAT AGCCCATATATGGAGTTCCGCGTTACATAACTTACGGTAA ATGGCCCGCCTGGCTGACCGCCCAACGACCCCCGCCCAT TGACGTCAATAATGACGTATGTTCCCATAGTAACGCCAAT AGGGACTTTCCATTGACGTCAATGGGTGGACTATTTACGG TAAACTGCCCACTTGGCAGTACATCAAGTGTATCATATGC CAAGTACGCCCCCTATTGACGTCAATGACGGTAAATGGC CCGCCTGGCATTATGCCCAGTACATGACCTTATGGGACTT TCCTACTTGGCAGTACATCTACGTATTAGTCATC |
| 22 | Helper/Rev; Chicken beta actin intron; Enhance gene expression | GGAGTCGCTGCGTTGCCTTCGCCCCGTGCCCCGCTCCGCG CCGCCTCGCGCCGCCCGCCCCGGCTCTGACTGACCGCGTT ACTCCCACAGGTGAGCGGGCGGGACGGCCCTTCTCCTCC GGGCTGTAATTAGCGCTTGGTTTAATGACGGCTCGTTTCT TTTCTGTGGCTGCGTGAAAGCCTTAAAGGGCTCCGGGAG GGCCCTTTGTGCGGGGGGGAGCGGCTCGGGGGGTGCGTG CGTGTGTGTGTGCGTGGGGAGCGCCGCGTGCGGCCCGCG CTGCCCGGCGGCTGTGAGCGCTGCGGGCGCGGCGCGGGG CTTTGTGCGCTCCGCGTGTGCGCGAGGGGAGCGCGGCCG GGGGCGGTGCCCCGCGGTGCGGGGGGGCTGCGAGGGGA ACAAAGGCTGCGTGCGGGGTGTGTGCGTGGGGGGGTGAG CAGGGGGTGTGGGCGCGGCGGTCGGGCTGTAACCCCCCC CTGCACCCCCCTCCCCGAGTTGCTGAGCACGGCCCGGCTT CGGGTGCGGGGCTCCGTACGGGGCGTGGCGCGGGGCTCG CCGTGCCGGGCGGGGGGTGGCGGCAGGTGGGGGTGCCG GGCGGGGCGGGGCCGCCTCGGGCCGGGGAGGGCTCGGG GGAGGGGCGCGGCGGCCCCGGAGCGCCGGCGGCTGTCG AGGCGCGGCGAGCCGCAGCCATTGCCTTTTATGGTAATC GTGCGAGAGGGCGCAGGGACTTCCTTTGTCCCAAATCTG GCGGAGCCGAAATCTGGGAGGCGCCGCCGCACCCCCTCT AGCGGGCGCGGGCGAAGCGGTGCGGCGCCGGCAGGAAG GAAATGGGCGGGGAGGGCCTTCGTGCGTCGCCGCGCCGC |

-continued

| SEQ ID NO: | Description | Sequence |
|---|---|---|
| | | CGTCCCCTTCTCCATCTCCAGCCTCGGGGCTGCCGCAGGG GGACGGCTGCCTTCGGGGGGGACGGGGCAGGGCGGGGTT CGGCTTCTGGCGTGTGACCGGCGG |
| 23 | Helper/Rev; Rabbit beta globin poly A; RNA stability | AGATCTTTTTCCCTCTGCCAAAAATTATGGGGACATCATG AAGCCCCTTGAGCATCTGACTTCTGGCTAATAAAGGAAA TTTATTTTCATTGCAATAGTGTGTTGGAATTTTTTGTGTCT CTCACTCGGAAGGACATATGGGAGGGCAAATCATTTAAA ACATCAGAATGAGTATTTGGTTTAGAGTTTGGCAACATAT GCCATATGCTGGCTGCCATGAACAAAGGTGGCTATAAAG AGGTCATCAGTATATGAAACAGCCCCCTGCTGTCCATTCC TTATTCCATAGAAAAGCCTTGACTTGAGGTTAGATTTTTT TTATATTTTGTTTTGTGTTATTTTTTTCTTTAACATCCCTAA AATTTTCCTTACATGTTTTACTAGCCAGATTTTTCCTCCTC TCCTGACTACTCCCAGTCATAGCTGTCCCTCTTCTCTTATG AAGATC |
| 24 | Envelope; Beta globin intron; Enhance gene expression | GTGAGTTTGGGGACCCTTGATTGTTCTTTCTTTTTCGCTAT TGTAAAATTCATGTTATATGGAGGGGGCAAAGTTTTCAG GGTGTTGTTTAGAATGGGAAGATGTCCCTTGTATCACCAT GGACCCTCATGATAATTTTGTTTCTTTCACTTTCTACTCTG TTGACAACCATTGTCTCCTCTTATTTTCTTTTCATTTTCTG TAACTTTTTCGTTAAACTTTAGCTTGCATTTGTAACGAATT TTTAAATTCACTTTTGTTTATTTGTCAGATTGTAAGTACTT TCTCTAATCACTTTTTTTTTCAAGGCAATCAGGGTATATTA TATTGTACTTCAGCACAGTTTTAGAGAACAATTGTTATAA TTAAATGATAAGGTAGAATATTTCTGCATATAAATTCTGG CTGGCGTGGAAATATTCTTATTGGTAGAAACAACTACAC CCTGGTCATCATCCTGCCTTTCTCTTTATGGTTACAATGAT ATACACTGTTTGAGATGAGGATAAAATACTCTGAGTCCA AACCGGGCCCCTCTGCTAACCATGTTCATGCCTTCTTCTC TTTCCTACAG |
| 25 | Envelope; Rabbit beta globin poly A; RNA stability | AGATCTTTTTCCCTCTGCCAAAAATTATGGGGACATCATG AAGCCCCTTGAGCATCTGACTTCTGGCTAATAAAGGAAA TTTATTTTCATTGCAATAGTGTGTTGGAATTTTTTGTGTCT CTCACTCGGAAGGACATATGGGAGGGCAAATCATTTAAA ACATCAGAATGAGTATTTGGTTTAGAGTTTGGCAACATAT GCCCATATGCTGGCTGCCATGAACAAAGGTTGGCTATAA AGAGGTCATCAGTATATGAAACAGCCCCCTGCTGTCCATT CCTTATTCCATAGAAAAGCCTTGACTTGAGGTTAGATTTT TTTTATATTTTGTTTTGTGTTATTTTTTTCTTTAACATCCCT AAAATTTTCCTTACATGTTTTACTAGCCAGATTTTTCCTCC TCTCCTGACTACTCCCAGTCATAGCTGTCCCTCTTCTCTTA TGGAGATC |
| 26 | Primer | TAAGCAGAATTCATGAATTTGCCAGGAAGAT |
| 27 | Primer | CCATACAATGAATGGACACTAGGCGGCCGCACGAAT |
| 28 | Gag, Pol, Integrase fragment | GAATTCATGAATTTGCCAGGAAGATGGAAACCAAAAATG ATAGGGGGAATTGGAGGTTTTATCAAAGTAAGACAGTAT GATCAGATACTCATAGAAATCTGCGGACATAAAGCTATA GGTACAGTATTAGTAGGACCTACACCTGTCAACATAATT GGAAGAAATCTGTTGACTCAGATTGGCTGCACTTTAAATT TTCCCATTAGTCCTATTGAGACTGTACCAGTAAAATTAAA GCCAGGAATGGATGGCCCAAAAGTTAAACAATGGCCATT GACAGAAGAAAAAATAAAAGCATTAGTAGAAATTTGTAC AGAAATGGAAAAGGAAGGAAAAATTTCAAAAATTGGGC CTGAAAATCCATACAATACTCCAGTATTTGCCATAAAGA AAAAAGACAGTACTAAATGGAGAAAATTAGTAGATTTCA GAGAACTTAATAAGAGAACTCAAGATTTCTGGGAAGTTC AATTAGGAATACCACATCCTGCAGGGTTAAAACAGAAAA AATCAGTAACAGTACTGGATGTGGGCGATGCATATTTTTC AGTTCCCTTAGATAAAGACTTCAGGAAGTATACTGCATTT ACCATACCTAGTATAAACAATGAGACACCAGGGATTAGA TATCAGTACAATGTGCTTCCACAGGGATGGAAAGGATCA CCAGCAATATTCCAGTGTAGCATGACAAAAATCTTAGAG CCTTTTAGAAAACAAAATCCAGACATAGTCATCTATCAAT ACATGGATGATTTGTATGTAGGATCTGACTTAGAAATAG GGCAGCATAGAACAAAAATAGAGGGAACTGAGACAACAT CTGTTGAGGTGGGGATTTACCACACCAGACAAAAAACAT CAGAAAGAACCTCCATTCCTTTGGATGGGTTATGAACTCC ATCCTGATAAATGGACAGTACAGCCTATAGTGCTGCCAG AAAAGGACAGCTGGACTGTCAATGACATACAGAAATTAG TGGGAAAATTGAATTGGGCAAGTCAGATTTATGCAGGGA |

-continued

| SEQ ID NO: | Description | Sequence |
|---|---|---|
|  |  | TTAAAGTAAGGCAATTATGTAAACTTCTTAGGGGAACCA |
|  |  | AAGCACTAACAGAAGTAGTACCACTAACAGAAGAAGCA |
|  |  | GAGCTAGAACTGGCAGAAAACAGGGAGATTCTAAAAGA |
|  |  | ACCGGTACATGGAGTGTATTATGACCCATCAAAAGACTT |
|  |  | AATAGCAGAAATACAGAAGCAGGGGCAAGGCCAATGGA |
|  |  | CATATCAAATTTATCAAGAGCCATTTAAAAATCTGAAAA |
|  |  | CAGGAAAGTATGCAAGAATGAAGGGTGCCCACACTAATG |
|  |  | ATGTGAAACAATTAACAGAGGCAGTACAAAAAATAGCCA |
|  |  | CAGAAAGCATAGTAATATGGGGAAAGACTCCTAAATTTA |
|  |  | AATTACCCATACAAAAGGAAACATGGGAAGCATGGTGGA |
|  |  | CAGAGTATTGGCAAGCCACCTGGATTCCTGAGTGGGAGT |
|  |  | TTGTCAATACCCCTCCCTTAGTGAAGTTATGGTACCAGTT |
|  |  | AGAGAAAGAACCCATAATAGGAGCAGAAACTTTCTATGT |
|  |  | AGATGGGGCAGCCAATAGGGAAACTAAATTAGGAAAAG |
|  |  | CAGGATATGTAACTGACAGAGGAAGACAAAAAGTTGTCC |
|  |  | CCCTAACGGACACAACAAATCAGAAGACTGAGTTACAAG |
|  |  | CAATTCATCTAGCTTTGCAGGATTCGGGATTAGAAGTAA |
|  |  | ACATAGTGACAGACTCACAATATGCATTGGGAATCATTC |
|  |  | AAGCACAACCAGATAAGAGTGAATCAGAGTTAGTCAGTC |
|  |  | AAATAATAGAGCAGTTAATAAAAAAGGAAAAAGTCTACC |
|  |  | TGGCATGGGTACCAGCACACAAAGGAATTGGAGGAAATG |
|  |  | AACAAGTAGATAAATTGGTCAGTGCTGGAATCAGGAAAG |
|  |  | TACTATTTTTAGATGGAATAGATAAGGCCCAAGAAGAAC |
|  |  | ATGAGAAATATCACAGTAATTGGAGAGCAATGGCTAGTG |
|  |  | ATTTTAACCTACCACCTGTAGTAGCAAAAGAAATAGTAG |
|  |  | CCAGCTGTGATAAATGTCAGCTAAAAGGGGAAGCCATGC |
|  |  | ATGGACAAGTAGACTGTAGCCCAGGAATATGGCAGCTAG |
|  |  | ATTGTACACATTTAGAAGGAAAAGTTATCTTGGTAGCAG |
|  |  | TTCATGTAGCCAGTGGATATATAGAAGCAGAAGTAATTC |
|  |  | CAGCAGAGACAGGGCAAGAAACAGCATACTTCCTCTTAA |
|  |  | AATTAGCAGGAAGATGGCCAGTAAAAACAGTACATACAG |
|  |  | ACAATGGCAGCAATTTCACCAGTACTACAGTTAAGGCCG |
|  |  | CCTGTTGGTGGGCGGGGATCAAGCAGGAATTTGGCATTC |
|  |  | CCTACAATCCCCAAAGTCAAGGAGTAATAGAATCTATGA |
|  |  | ATAAAGAATTAAAGAAAATTATAGGACAGGTAAGAGATC |
|  |  | AGGCTGAACATCTTAAGACAGCAGTACAAATGGCAGTAT |
|  |  | TCATCCACAATTTTAAAAGAAAAGGGGGGATTGGGGGGT |
|  |  | ACAGTGCAGGGGAAAGAATAGTAGACATAATAGCAACA |
|  |  | GACATACAAACTAAAGAATTACAAAAACAAATTACAAAA |
|  |  | ATTCAAAATTTTCGGGTTTATTACAGGGACAGCAGAGAT |
|  |  | CCAGTTTGGAAAGGACCAGCAAAGCTCCTCTGGAAAGGT |
|  |  | GAAGGGGCAGTAGTAATACAAGATAATAGTGACATAAA |
|  |  | AGTAGTGCCAAGAAGAAAAGCAAAGATCATCAGGGATT |
|  |  | ATGGAAAACAGATGGCAGGTGATGATTGTGTGGCAAGTA |
|  |  | GACAGGATGAGGATTAA |
| 29 | DNA Fragment containing Rev, RRE and rabbit beta globin poly A | TCTAGAATGGCAGGAAGAAGCGGAGACAGCGACGAAGA |
|  |  | GCTCATCAGAACAGTCAGACTCATCAAGCTTCTCTATCAA |
|  |  | AGCAACCCACCTCCCAATCCCGAGGGGACCCGACAGGCC |
|  |  | CGAAGGAATAGAAGAAGAAGGTGGAGAGAGAGACAGAG |
|  |  | ACAGATCCATTCGATTAGTGAACGGATCCTTGGCACTTAT |
|  |  | CTGGGACGATCTGCGGAGCCTGTGCCTCTTCAGCTACCAC |
|  |  | CGCTTGAGAGACTTACTCTTGATTGTAACGAGGATTGTGG |
|  |  | AACTTCTGGGACGCAGGGGGTGGGAAGCCCTCAAATATT |
|  |  | GGTGGAATCTCCTACAATATTGGAGTCAGGAGCTAAAGA |
|  |  | ATAGAGGAGCTTTGTTCCTTGGGTTCTTGGGAGCAGCAG |
|  |  | GAAGCACTATGGGCGCAGCGTCAATGACGCTGACGGTAC |
|  |  | AGGCCAGACAATTATTGTCTGGTATAGTGCAGCAGCAGA |
|  |  | ACAATTTGCTGAGGGCTATTGAGGCGCAACAGCATCTGT |
|  |  | TGCAACTCACAGTCTGGGGCATCAAGCAGCTCCAGGCAA |
|  |  | GAATCCTGGCTGTGGAAAGATACCTAAAGGATCAACAGC |
|  |  | TCCTAGATCTTTTTCCCTCTGCCAAAAATTATGGGGACAT |
|  |  | CATGAAGCCCCTTGAGCATCTGACTTCTGGCTAATAAAG |
|  |  | GAAATTTATTTTCATTGCAATAGTGTGTTGGAATTTTTTGT |
|  |  | GTCTCTCACTCGGAAGGACATATGGGAGGGCAAATCATT |
|  |  | TAAAACATCAGAATGAGTATTTGGTTTAGAGTTTGGCAA |
|  |  | CATATGCCATATGCTGGCTGCCATGAACAAAGGTGGCTA |
|  |  | TAAAGAGGTCATCAGTATATGAAACAGCCCCCTGCTGTC |
|  |  | CATTCCTTATTCCATAGAAAAGCCTTGACTTGAGGTTAGA |
|  |  | TTTTTTTTATATTTTGTTTTGTGTTATTTTTTTCTTTAACAT |
|  |  | CCCTAAAATTTTCCTTACATGTTTTACTAGCCAGATTTTTC |
|  |  | CTCCTCTCCTGACTACTCCCAGTCATAGCTGTCCCTCTTCT |
|  |  | CTTATGAAGATCCCTCGACCTGCAGCCCAAGCTTGGCGTA |
|  |  | ATCATGGTCATAGCTGTTTCCTGTGTGAAATTGTTATCCG |
|  |  | CTCACAATTCCACACAACATACGAGCCGGAAGCATAAAG |
|  |  | TGTAAAGCCTGGGGTGCCTAATGAGTGAGCTAACTCACA |

| SEQ ID NO: | Description | Sequence |
|---|---|---|
| | | TTAATTGCGTTGCGCTCACTGCCCGCTTTCCAGTCGGGAA<br>ACCTGTCGTGCCAGCGGATCCGCATCTCAATTAGTCAGCA<br>ACCATAGTCCCGCCCCTAACTCCGCCCATCCCGCCCCTAA<br>CTCCGCCCAGTTCCGCCCATTCTCCGCCCCATGGCTGACT<br>AATTTTTTTTATTTATGCAGAGGCCGAGGCCGCCTCGGCC<br>TCTGAGCTATTCCAGAAGTAGTGAGGAGGCTTTTTTGGAG<br>GCCTAGGCTTTTGCAAAAAGCTAACTTGTTTATTGCAGCT<br>TATAATGGTTACAAATAAAGCAATAGCATCACAAATTTC<br>ACAAATAAAGCATTTTTTTCACTGCATTCTAGTTGTGGTT<br>TGTCCAAACTCATCAATGTATCTTATCAGCGGCCGCCCCG<br>GG |
| 30 | DNA fragment containing the CAG enhancer/promoter/ intron sequence | ACGCGTTAGTTATTAATAGTAATCAATTACGGGGTCATTA<br>GTTCATAGCCCATATATGGAGTTCCGCGTTACATAACTTA<br>CGGTAAATGGCCCGCCTGGCTGACCGCCCAACGACCCCC<br>GCCCATTGACGTCAATAATGACGTATGTTCCCATAGTAAC<br>GCCAATAGGGACTTTCCATTGACGTCAATGGGTGGACTA<br>TTTACGGTAAACTGCCCACTTGGCAGTACATCAAGTGTAT<br>CATATGCCAAGTACGCCCCCTATTGACGTCAATGACGGT<br>AAATGGCCCGCCTGGCATTATGCCCAGTACATGACCTTAT<br>GGGACTTTCCTACTTGGCAGTACATCTACGTATTAGTCAT<br>CGCTATTACCATGGGTCGAGGTGAGCCCCACGTTCTGCTT<br>CACTCTCCCCATCTCCCCCCCCTCCCCACCCCCAATTTTGT<br>ATTTATTTATTTTTTAATTATTTTGTGCAGCGATGGGGGC<br>GGGGGGGGGGGGGGGCGCGCGCCAGGCGGGGCGGGGCGG<br>GGCGAGGGGCGGGGCGGGGCGAGGCGGAGAGGTGCGGC<br>GGCAGCCAATCAGAGCGGCGCGCTCCGAAAGTTTCCTTT<br>TATGGCGAGGCGGCGGCGGCGGCGGCCCTATAAAAAGCG<br>AAGCGCGCGGCGGGCGGGAGTCGCTGCGTTGCCTTCGCC<br>CCGTGCCCCGCTCCGCGCCGCCTCGCGCCGCCCGCCCCG<br>GCTCTGACTGACCGCGTTACTCCCACAGGTGAGCGGGCG<br>GGACGGCCCTTCTCCTCCGGGCTGTAATTAGCGCTTGGTT<br>TAATGACGGCTCGTTTCTTTTCTGTGGCTGCGTGAAAGCC<br>TTAAAGGGCTCCGGGAGGGCCCTTTGTGCGGGGGGGAGC<br>GGCTCGGGGGGTGCGTGCGTGTGTGTGTGCGTGGGGGAGC<br>GCCGCGTGCGGCCCGCGCTGCCCGGCGGCTGTGAGCGCT<br>GCGGGCGCGGCGCGGGGCTTTGTGCGCTCCGCGTGTGCG<br>CGAGGGGAGCGCGGCCGGGGGCGGTGCCCCGCGGTGCG<br>GGGGGGCTGCGAGGGGAACAAAGGCTGCGTGCGGGGTG<br>TGTGCGTGGGGGGGTGAGCAGGGGGTGTGGGCGCGGCG<br>GTCGGGCTGTAACCCCCCCCTGCACCCCCCTCCCCGAGTT<br>GCTGAGCACGGCCCGGCTTCGGGTGCGGGGCTCCGTGCG<br>GGGCGTGGCGCGGGGCTCGCCGTGCCGGGCGGGGGGTGG<br>CGGCAGGTGGGGGTGCCGGGCGGGGCGGGGCCGCCTCG<br>GGCCGGGGAGGGCTCGGGGGAGGGGCGCGGCGGCCCCG<br>GAGCGCCGGCGGCTGTCGAGGCGCGGCGAGCCGCAGCCA<br>TTGCCTTTTATGGTAATCGTGCGAGAGGGCGCAGGGACTT<br>CCTTTGTCCCAAATCTGGCGGAGCCGAAATCTGGGAGGC<br>GCCGCCGCACCCCCTCTAGCGGGCGCGGGCGAAGCGGTG<br>CGGCGCCGGCAGGAAGGAAATGGGCGGGGAGGGCCTTC<br>GTGCGTCGCCGCGCCGCCGTCCCCTTCTCCATCTCCAGCC<br>TCGGGGCTGCCGCAGGGGGACGGCTGCCTTCGGGGGGGA<br>CGGGGCAGGGCGGGGTTCGGCTTCTGGCGTGTGACCGGC<br>GGGAATTC |
| 31 | DNA fragment containing VSV-G | GAATTCATGAAGTGCCTTTTGTACTTAGCCTTTTTATTCAT<br>TGGGGTGAATTGCAAGTTCACCATAGTTTTTCCACACAAC<br>CAAAAAGGAAACTGGAAAAATGTTCCTTCTAATTACCAT<br>TATTGCCCGTCAAGCTCAGATTTAAATTGGCATAATGACT<br>TAATAGGCACAGCCTTACAAGTCAAAATGCCCAAGAGTC<br>ACAAGGCTATTCAAGCAGACGGTTGGATGTGTCATGCTT<br>CCAAATGGGTCACTACTTGTGATTTCCGCTGGTATGGACC<br>GAAGTATATAACACATTCCATCCGATCCTTCACTCCATCT<br>GTAGAACAATGCAAGGAAAGCATTGAACAAACGAAACA<br>AGGAACTTGGCTGAATCCAGGCTTCCCTCCTCAAAGTTGT<br>GGATATGCAACTGTGACGGATGCCGAAGCAGTGATTGTC<br>CAGGTGACTCCTCACCATGTGCTGGTTGATGAATACACA<br>GGAGAATGGGTTGATTCACAGTTCATCAACGGAAAATGC<br>AGCAATTACATATGCCCCACTGTCCATAACTCTACAACCT<br>GGCATTCTGACTATAAGGTCAAAGGGCTATGTGATTCTA<br>ACCTCATTTCCATGGACATCACCTTCTTCTCAGAGGACGG<br>AGAGCTATCATCCCTGGGAAAGGAGGGCACAGGGTTCAG<br>AAGTAACTACTTTGCTTATGAAACTGGAGGCAAGGCCTG<br>CAAAATGCAATACTGCAAGCATTGGGGAGTCAGACTCCC<br>ATCAGGTGTCTGGTTCGAGATGGCTGATAAGGATCTCTTT<br>GCTGCAGCCAGATTCCCTGAATGCCCAGAAGGGTCAAGT |

-continued

| SEQ ID NO: | Description | Sequence |
|---|---|---|
| | | ATCTCTGCTCCATCTCAGACCTCAGTGGATGTAAGTCTAA |
| | | TTCAGGACGTTGAGAGGATCTTGGATTATTCCCTCTGCCA |
| | | AGAAACCTGGAGCAAAATCAGAGCGGGTCTTCCAATCTC |
| | | TCCAGTGGATCTCAGCTATCTTGCTCCTAAAAACCCAGGA |
| | | ACCGGTCCTGCTTTCACCATAATCAATGGTACCCTAAAAT |
| | | ACTTTGAGACCAGATACATCAGAGTCGATATTGCTGCTCC |
| | | AATCCTCTCAAGAATGGTCGGAATGATCAGTGGAACTAC |
| | | CACAGAAAGGGAACTGTGGGATGACTGGGCACCATATGA |
| | | AGACGTGGAAATTGGACCCAATGGAGTTCTGAGGACCAG |
| | | TTCAGGATATAAGTTTCCTTTATACATGATTGGACATGGT |
| | | ATGTTGGACTCCGATCTTCATCTTAGCTCAAAGGCTCAGG |
| | | TGTTCGAACATCCTCACATTCAAGACGCTGCTTCGCAACT |
| | | TCCTGATGATGAGAGTTTATTTTTTGGTGATACTGGGCTA |
| | | TCCAAAAATCCAATCGAGCTTGTAGAAGGTTGGTTCAGT |
| | | AGTTGGAAAAGCTCTATTGCCTCTTTTTTCTTTATCATAG |
| | | GGTTAATCATTGGACTATTCTTGGTTCTCCGAGTTGGTAT |
| | | CCATCTTTGCATTAAATTAAAGCACACCAAGAAAAGACA |
| | | GATTTATACAGACATAGAGATGAGAATTC |
| 32 | DNA fragment of Helper plasmid without Rev containing RRE and rabbit beta globin poly A | TCTAGAAGGAGCTTTGTTCCTTGGGTTCTTGGGAGC |
| | | AGCAGGAAGCACTATGGGCGCAGCGTCAATGACGC |
| | | TGACGGTACAGGCCAGACAATTATTGTCTGGTATAG |
| | | TGCAGCAGCAGAACAATTTGCTGAGGGCTATTGAGG |
| | | CGCAACAGCATCTGTTGCAACTCACAGTCTGGGGCA |
| | | TCAAGCAGCTCCAGGCAAGAATCCTGGCTGTGGAAA |
| | | GATACCTAAAGGATCAACAGCTCCTAGATCTTTTTC |
| | | CCTCTGCCAAAAATTATGGGGACATCATGAAGCCCC |
| | | TTGAGCATCTGACTTCTGGCTAATAAAGGAAATTTA |
| | | TTTTCATTGCAATAGTGTGTTGGAATTTTTTGTGTCT |
| | | CTCACTCGGAAGGACATATGGGAGGGCAAATCATTT |
| | | AAAACATCAGAATGAGTATTTGGTTTAGAGTTTGGC |
| | | AACATATGCCATATGCTGGCTGCCATGAACAAAGGT |
| | | GGCTATAAAGAGGTCATCAGTATATGAAACAGCCCC |
| | | CTGCTGTCCATTCCTTATTCCATAGAAAAGCCTTGAC |
| | | TTGAGGTTAGATTTTTTTTATATTTTGTTTTGTGTTAT |
| | | TTTTTTCTTTAACATCCCTAAAATTTTCCTTACATGTT |
| | | TTACTAGCCAGATTTTTCCTCCTCTCCTGACTACTCC |
| | | CAGTCATAGCTGTCCCTCTTCTCTTATGAAGATCCCT |
| | | CGACCTGCAGCCCAAGCTTGGCGTAATCATGGTCAT |
| | | AGCTGTTTCCTGTGTGAAATTGTTATCCGCTCACAAT |
| | | TCCACACAACATACGAGCCGGAAGCATAAAGTGTA |
| | | AAGCCTGGGGTGCCTAATGAGTGAGCTAACTCACAT |
| | | TAATTGCGTTGCGCTCACTGCCCGCTTTCCAGTCGGG |
| | | AAACCTGTCGTGCCAGCGGATCCGCATCTCAATTAG |
| | | TCAGCAACCATAGTCCCGCCCCTAACTCCGCCCATC |
| | | CCGCCCCTAACTCCGCCCAGTTCCGCCCATTCTCCGC |
| | | CCCATGGCTGACTAATTTTTTTTATTTATGCAGAGGC |
| | | CGAGGCCGCCTCGGCCTCTGAGCTATTCCAGAAGTA |
| | | GTGAGGAGGCTTTTTTGGAGGCCTAGGCTTTTGCAA |
| | | AAAGCTAACTTGTTTATTGCAGCTTATAATGGTTACA |
| | | AATAAAGCAATAGCATCACAAATTTCACAAATAAAG |
| | | CATTTTTTTCACTGCATTCTAGTTGTGGTTTGTCCAA |
| | | ACTCATCAATGTATCTTATCACCCGGG |
| 33 | RSV promoter and HIV Rev | CAATTGCGATGTACGGGCCAGATATACGCGTATCTGAGG |
| | | GGACTAGGGTGTGTTTAGGCGAAAAGCGGGGCTTCGGTT |
| | | GTACGCGGTTAGGAGTCCCCTCAGGATATAGTAGTTTCGC |
| | | TTTTGCATAGGGAGGGGGAAATGTAGTCTTATGCAATAC |
| | | ACTTGTAGTCTTGCAACATGGTAACGATGAGTTAGCAAC |
| | | ATGCCTTACAAGGAGAGAAAAAGCACCGTGCATGCCGAT |
| | | TGGTGGAAGTAAGGTGGTACGATCGTGCCTTATTAGGAA |
| | | GGCAACAGACAGGTCTGACATGGATTGGACGAACCACTG |
| | | AATTCCGCATTGCAGAGATAATTGTATTTAAGTGCCTAGC |
| | | TCGATACAATAAACGCCATTTGACCATTCACCACATTGGT |
| | | GTGCACCTCCAAGCTCGAGCTCGTTTAGTGAACCGTCAG |
| | | ATCGCCTGGAGACGCCATCCACGCTGTTTTGACCTCCATA |
| | | GAAGACACCGGGACCGATCCAGCCTCCCCTCGAAGCTAG |
| | | CGATTAGGCATCTCCTATGGCAGGAAGAAGCGGAGACAG |
| | | CGACGAAGAACTCCTCAAGGCAGTCAGACTCATCAAGTT |
| | | TCTCTATCAAAGCAACCCACCTCCCAATCCCGAGGGGAC |
| | | CCGACAGGCCCGAAGGAATAGAAGAAGAAGGTGGAGAG |
| | | AGAGACAGAGACAGATCCATTCGATTAGTGAACGGATCC |
| | | TTAGCACTTATCTGGGACGATCTGCGGAGCCTGTGCCTCT |

-continued

| SEQ ID NO: | Description | Sequence |
| --- | --- | --- |
| | | TCAGCTACCACCGCTTGAGAGACTTACTCTTGATTGTAAC<br>GAGGATTGTGGAACTTCTGGGACGCAGGGGGTGGGAAGC<br>CCTCAAATATTGGTGGAATCTCCTACAATATTGGAGTCAG<br>GAGCTAAAGAATAGTCTAGA |
| 34 | Elongation Factor-<br>1 alpha (EF1-<br>alpha) promoter | CCGGTGCCTAGAGAAGGTGGCGCGGGGTAAACTGGGAA<br>AGTGATGTCGTGTACTGGCTCCGCCTTTTTCCCGAGGGTG<br>GGGGAGAACCGTATATAAGTGCAGTAGTCGCCGTGAACG<br>TTCTTTTTCGCAACGGGTTTGCCGCCAGAACACAGGTAAG<br>TGCCGTGTGTGGTTCCCGCGGGCCTGGCCTCTTTACGGGT<br>TATGGCCCTTGCGTGCCTTGAATTACTTCCACGCCCCTGG<br>CTGCAGTACGTGATTCTTGATCCCGAGCTTCGGGTTGGAA<br>GTGGGTGGGAGAGTTCGAGGCCTTGCGCTTAAGGAGCCC<br>CTTCGCCTCGTGCTTGAGTTGAGGCCTGGCCTGGGCGCTG<br>GGGCCGCCGCGTGCGAATCTGGTGGCACCTTCGCGCCTG<br>TCTCGCTGCTTTCGATAAGTCTCTAGCCATTTAAAATTTTT<br>GATGACCTGCTGCGACGCTTTTTTTCTGGCAAGATAGTCT<br>TGTAAATGCGGGCCAAGATCTGCACACTGGTATTTCGGTT<br>TTTGGGGCCGCGGGCGGCGACGGGGCCCGTGCGTCCCAG<br>CGCACATGTTCGGCGAGGCGGGGCCTGCGAGCGCGGCCA<br>CCGAGAATCGGACGGGGGTAGTCTCAAGCTGGCCGGCCT<br>GCTCTGGTGCCTGGCCTCGCGCCGCCGTGTATCGCCCCGC<br>CCTGGGCGGCAAGGCTGGCCCGGTCGGCACCAGTTGCGT<br>GAGCGGAAAGATGGCCGCTTCCCGGCCCTGCTGCAGGGA<br>GCTCAAAATGGAGGACGCGGCGCTCGGGAGAGCGGGCG<br>GGTGAGTCACCCACACAAAGGAAAAGGGCCTTTCCGTCC<br>TCAGCCGTCGCTTCATGTGACTCCACGGAGTACCGGGCG<br>CCGTCCAGGCACCTCGATTAGTTCTCGAGCTTTTGGAGTA<br>CGTCGTCTTTAGGTTGGGGGGAGGGGTTTTATGCGATGG<br>AGTTTCCCCACACTGAGTGGGTGGAGACTGAAGTTAGGC<br>CAGCTTGGCACTTGATGTAATTCTCCTTGGAATTTGCCCT<br>TTTTGAGTTTGGATCTTGGTTCATTCTCAAGCCTCAGACA<br>GTGGTTCAAAGTTTTTTTCTTCCATTTCAGGTGTCGTGA |
| 35 | Promoter; PGK | GGGGTTGGGGTTGCGCCTTTTCCAAGGCAGCCCTGGGTTT<br>GCGCAGGGACGCGGCTGCTCTGGGCGTGGTTCCGGGAAA<br>CGCAGCGGCGCCGACCCTGGGTCTCGCACATTCTTCACGT<br>CCGTTCGCAGCGTCACCCGGATCTTCGCCGCTACCCTTGT<br>GGGCCCCCCGGCGACGCTTCCTGCTCCGCCCCTAAGTCGG<br>GAAGGTTCCTTGCGGTTCGCGGCGTGCCGGACGTGACAA<br>ACGGAAGCCGCACGTCTCACTAGTACCCTCGCAGACGGA<br>CAGCGCCAGGGAGCAATGGCAGCGCGCCGACCGCGATG<br>GGCTGTGGCCAATAGCGGCTGCTCAGCAGGGCGCGCCGA<br>GAGCAGCGGCCGGGAAGGGGCGGTGCGGGAGGCGGGGT<br>GTGGGGCGGTAGTGTGGGCCCTGTTCCTGCCCGCGCGGT<br>GTTCCGCATTCTGCAAGCCTCCGGAGCGCACGTCGGCAG<br>TCGGCTCCCTCGTTGACCGAATCACCGACCTCTCTCCCCA<br>G |
| 36 | Promoter; UbC | GCGCCGGGTTTTGGCGCCTCCCGCGGGCGCCCCCCTCCTC<br>ACGGCGAGCGCTGCCACGTCAGACGAAGGGCGCAGGAG<br>CGTTCCTGATCCTTCCGCCCGGACGCTCAGGACAGCGGCC<br>CGCTGCTCATAAGACTCGGCCTTAGAACCCCAGTATCAG<br>CAGAAGGACATTTTAGGACGGGACTTGGGTGACTCTAGG<br>GCACTGGTTTTCTTTCCAGAGAGCGGAACAGGCGAGGAA<br>AAGTAGTCCCTTCTCGGCGATTCTGCGGAGGGATCTCCGT<br>GGGGCGGTGAACGCCGATGATTATATAAGGACGCGCCGG<br>GTGTGGCACAGCTAGTTCCGTCGCAGCCGGGATTTGGGT<br>CGCGGTTCTTGTTTGTGGATCGCTGTGATCGTCACTTGGT<br>GAGTTGCGGGCTGCTGGGCTGGCCGGGGCTTTCGTGGCC<br>GCCGGGCCGCTCGGTGGGACGGAAGCGTGTGGAGAGACC<br>GCCAAGGGCTGTAGTCTGGGTCCGCGAGCAAGGTTGCCC<br>TGAACTGGGGGTTGGGGGGAGCGCACAAAATGGCGGCTG<br>TTCCCGAGTCTTGAATGGAAGACGCTTGTAAGGCGGGCT<br>GTGAGGTCGTTGAAACAAGGTGGGGGGCATGGTGGGCGG<br>CAAGAACCCAAGGTCTTGAGGCCTTCGCTAATGCGGGAA<br>AGCTCTTATTCGGGTGAGATGGGCTGGGGCACCATCTGG<br>GGACCCTGACGTGAAGTTTGTCACTGACTGGAGAACTCG<br>GGTTTGTCGTCTGGTTGCGGGGGCGGCAGTTATGCGGTGC<br>CGTTGGGCAGTGCACCCGTACCTTTGGGAGCGCGCGCCT<br>CGTCGTGTCGTGACGTCACCCGTTCTGTTGGCTTATAATG<br>CAGGGTGGGGCCACCTGCCGGTAGGTGTGCGGTAGGCTT<br>TTCTCCGTCGCAGGACGCAGGGTTCGGGCCTAGGGTAGG<br>CTCTCCTGAATCGACAGGCGCCGGACCTCTGGTGAGGGG<br>AGGGATAAGTGAGGCGTCAGTTTCTTTGGTCGGTTTTATG<br>TACCTATCTTCTTAAGTAGCTGAAGCTCCGGTTTTGAACT |

-continued

| SEQ ID NO: | Description | Sequence |
|---|---|---|
| | | ATGCGCTCGGGGTTGGCGAGTGTGTTTTGTGAAGTTTTTT AGGCACCTTTTGAAATGTAATCATTTGGGTCAATATGTAA TTTTCAGTGTTAGACTAGTAAA |
| 37 | Poly A; SV40 | GTTTATTGCAGCTTATAATGGTTACAAATAAAGCAATAGC ATCACAAATTTCACAAATAAAGCATTTTTTTCACTGCATT CTAGTTGTGGTTTGTCCAAACTCATCAATGTATCTTATCA |
| 38 | Poly A; bGH | GACTGTGCCTTCTAGTTGCCAGCCATCTGTTGTTTGCCCC TCCCCCGTGCCTTCCTTGACCCTGGAAGGTGCCACTCCCA CTGTCCTTTCCTAATAAAATGAGGAAATTGCATCGCATTG TCTGAGTAGGTGTCATTCTATTCTGGGGGGTGGGGTGGG GCAGGACAGCAAGGGGGAGGATTGGGAAGACAATAGCA GGCATGCTGGGGATGCGGTGGGCTCTATGG |
| 39 | Envelope; RD114 | TTAGGTTACTCCAGATGTCCAATTTTAGCCTTGCCCAAGA TTGTTGGCTCTGTTTAAAACTAGGTACCCCTACCCCTCTT GCGATACCCACTCCCTCTTTAACCTACTCCCTAGCAGACT CCCTAGCGAATGCCTCCTGTCAGATTATACCTCCCCTCTT GGTTCAACCGATGCAGTTCTCCAACTCGTCCTGTTTATCT TCCCCTTTCATTAACGATACGGAACAAATAGACTTAGGTG CAGTCACCTTTACTAACTGCACCTCTGTAGCCAATGTCAG TAGTCCTTTATGTGCCCTAAACGGGTCAGTCTTCCTCTGT GGAAATAACATGGCATACACCTATTTACCCCAAAACTGG ACAGGACTTTGCGTCCAAGCCTCCCTCCTCCCCGACATTG ACATCATCCCGGGGGATGAGCCAGTCCCCATTCCTGCCAT TGATCATTATATACATAGACCTAAACGAGCTGTACAGTTC ATCCCTTTACTAGCTGGACTGGGAATCACCGCAGCATTCA CCACCGGAGCTACAGGCCTAGGTGTCTCCGTCACCCAGT ATACAAAATTATCCCATCAGTTAATATCTGATGTCCAAGT CTTATCCGGTACCATACAAGATTTACAAGACCAGGTAGA CTCGTTAGCTGAAGTAGTTCTCCAAAATAGGAGGGGACT GGACCTACTAACGGCAGAACAAGGAGGAATTTGTTTAGC CTTACAAGAAAAATGCTGTTTTTATGCTAACAAGTCAGG AATTGTGAGAAACAAAATAAGAACCCTACAAGAAGAATT ACAAAAACGCAGGGAAAGCCTGGCATCCAACCCTCTCTG GACCGGGCTGCAGGGCTTTCTTCCGTACCTCCTACCTCTC CTGGGACCCCTACTCACCCTCCTACTCATACTAACCATTG GGCCATGCGTTTTCAATCGATTGGTCCAATTTGTTAAAGA CAGGATCTCAGTGGTCCAGGCTCTGGTTTTGACTCAGCAA TATCACCAGCTAAAACCCATAGAGTACGAGCCATGA |
| 40 | Envelope; GALV | ATGCTTCTCACCTCAAGCCCGCACCACCTTCGGCACCAGA TGAGTCCTGGGAGCTGGAAAAGACTGATCATCCTCTTAAG CTGCGTATTCGGAGACGGCAAAACGAGTCTGCAGAATAA GAACCCCCACCAGCCTGTGACCCTCACCTGGCAGGTACTG TCCCAAACTGGGGACGTTGTCTGGGACAAAAAGGCAGTC CAGCCCCTTTGGACTTGGTGGCCCTCTCTTACACCTGATG TATGTGCCCTGGCGGCCGGTCTTGAGTCCTGGGATATCCC GGGATCCGATGTATCGTCCTCTAAAAGAGTTAGACCTCCT GATTCAGACTATACTGCCGCTTATAAGCAAATCACCTGGG GAGCCATAGGGTGCAGCTACCCTCGGGCTAGGACCAGGA TGGCAAATTCCCCCTTCTACGTGTGTCCCCGAGCTGGCCG AACCCATTCAGAAGCTAGGAGGTGTGGGGGGCTAGAATC CCTATACTGTAAAGAATGGAGTTGTGAGACCACGGGTAC CGTTTATTGGCAACCCAAGTCCTCATGGGACCTCATAACT GTAAAATGGGACCAAAATGTGAAATGGGAGCAAAAATTT CAAAAGTGTGAACAAACCGGCTGGTGTAACCCCCTCAAG ATAGACTTCACAGAAAAAGGAAAACTCTCCAGAGATTGG ATAACGGAAAAAACCTGGGAATTAAGGTTCTATGTATAT GGACACCCAGGCATACAGTTGACTATCCGCTTAGAGGTC ACTAACATGCCGGTTGTGGCAGTGGGCCCAGACCCTGTCC TTGCGGAACAGGGACCTCCTAGCAAGCCCCTCACTCTCCC TCTCTCCCCACGGAAAGCGCCGCCCACCCCTCTACCCCCG GCGGCTAGTGAGCAAACCCCTGCGGTGCATGGAGAAACT GTTACCCTAAACTCTCCGCCTCCCACCAGTGGCGACCGAC TCTTTGGCCTTGTGCAGGGGGCCTTCCTAACCTTGAATGC TACCAACCCAGGGGCCACTAAGTCTTGCTGGCTCTGTTTG GGCATGAGCCCCCCTTATTATGAAGGGATAGCCTCTTCAG GAGAGGTCGCTTATACCTCCAACCATACCCGATGCCACTG GGGGGCCCAAGGAAAGCTTACCCTCACTGAGGTCTCCGG ACTCGGGTCATGCATAGGGAAGGTGCCTCTTACCCATCAA CATCTTTGCAACCAGACCTTACCCATCAATTCCTCTAAAA ACCATCAGTATCTGCTCCCCTCAAACCATAGCTGGTGGGC CTGCAGCACTGGCCTCACCCCCTGCCTCTCCACCTCAGTT TTTAATCAGTCTAAAGACTTCTGTGTCCAGGTCCAGCTGA |

-continued

| SEQ ID NO: | Description | Sequence |
|---|---|---|
| | | TCCCCCGCATCTATTACCATTCTGAAGAAACCTTGTTACA<br>AGCCTATGACAAATCACCCCCCAGGTTTAAAAGAGAGCC<br>TGCCTCACTTACCCTAGCTGTCTTCCTGGGGTTAGGGATT<br>GCGGCAGGTATAGGTACTGGCTCAACCGCCCTAATTAAA<br>GGGCCCATAGACCTCCAGCAAGGCCTAACCAGCCTCCAA<br>ATCGCCATTGACGCTGACCTCCGGGCCCTTCAGGACTCAA<br>TCAGCAAGCTAGAGGACTCACTGACTTCCCTATCTGAGGT<br>AGTACTCCAAAATAGGAGAGGCCTTGACTTACTATTCCTT<br>AAAGAAGGAGGCCTCTGCGCGGCCCTAAAAGAAGAGTGC<br>TGTTTTTATGTAGACCACTCAGGTGCAGTACGAGACTCCA<br>TGAAAAAACTTAAAGAAAGACTAGATAAAAGACAGTTAG<br>AGCGCCAGAAAAACCAAAACTGGTATGAAGGGTGGTTCA<br>ATAACTCCCCTTGGTTTACTACCCTACTATCAACCATCGCT<br>GGGCCCCTATTGCTCCTCCTTTTGTTACTCACTCTTGGGCC<br>CTGCATCATCAATAAATTAATCCAATTCATCAATGATAGG<br>ATAAGTGCAGTCAAAATTTTAGTCCTTAGACAGAAATATC<br>AGACCCTAGATAACGAGGAAAACCTTTAA |
| 41 | Envelope; FUG | ATGGTTCCGCAGGTTCTTTTGTTTGTACTCCTTCTGGGTTT<br>TTCGTTGTGTTTCGGGAAGTTCCCCATTTACACGATACCA<br>GACGAACTTGGTCCCTGGAGCCCTATTGACATACACCATC<br>TCAGCTGTCCAAATAACCTGGTTGTGGAGGATGAAGGAT<br>GTACCAACCTGTCCGAGTTCTCCTACATGGAACTCAAAGT<br>GGGATACATCTCAGCCATCAAAGTGAACGGGTTCACTTGC<br>ACAGGTGTTGTGACAGAGGCAGAGACCTACACCAACTTT<br>GTTGGTTATGTCACAACCACATTCAAGAGAAAGCATTTCC<br>GCCCCACCCCAGACGCATGTAGAGCCGCGTATAACTGGA<br>AGATGGCCGGTGACCCCAGATATGAAGAGTCCCTACACA<br>ATCCATACCCCGACTACCACTGGCTTCGAACTGTAAGAAC<br>CACCAAAGAGTCCCTCATTATCATATCCCCAAGTGTGACA<br>GATTTGGACCCATATGACAAATCCCTTCACTCAAGGGTCT<br>TCCCTGGCGGAAAGTGCTCAGGAATAACGGTGTCCTCTAC<br>CTACTGCTCAACTAACCATGATTACACCATTTGGATGCCC<br>GAGAATCCGAGACCAAGGACACCTTGTGACATTTTTACCA<br>ATAGCAGAGGGAAGAGAGCATCCAACGGGAACAAGACTT<br>GCGGCTTTGTGGATGAAAGAGGCCTGTATAAGTCTCTAAA<br>AGGAGCATGCAGGCTCAAGTTATGTGGAGTTCTTGGACTT<br>AGACTTATGGATGGAACATGGGTCGCGATGCAAACATCA<br>GATGAGACCAAATGGTGCCCTCCAGATCAGTTGGTGAATT<br>TGCACGACTTTCGCTCAGACGAGATCGAGCATCTCGTTGT<br>GGAGGAGTTAGTTAAGAAAAGAGAGGAATGTCTGGATGC<br>ATTAGAGTCCATCATGACCACCAAGTCAGTAAGTTTCAGA<br>CGTCTCAGTCACCTGAGAAAACTTGTCCCAGGGTTTGGAA<br>AAGCATATACCATATTCAACAAAACCTTGATGGAGGCTG<br>ATGCTCACTACAAGTCAGTCCGGACCTGGAATGAGATCAT<br>CCCCTCAAAAGGGTGTTTGAAAGTTGGAGGAAGGTGCCA<br>TCCTCATGTGAACGGGGTGTTTTTCAATGGTATAATATTA<br>GGGCCTGACGACCATGTCCTAATCCCAGAGATGCAATCAT<br>CCCTCCTCCAGCAACATATGGAGTTGTTGGAATCTTCAGT<br>TATCCCCCTGATGCACCCCCTGGCAGACCCTTCTACAGTT<br>TTCAAAGAAGGTGATGAGGCTGAGGATTTTGTTGAAGTTC<br>ACCTCCCCGATGTGTACAAACAGATCTCAGGGGTTGACCT<br>GGGTCTCCCGAACTGGGGAAAGTATGTATTGATGACTGC<br>AGGGGCCATGATTGGCCTGGTGTTGATATTTTCCCTAATG<br>ACATGGTGCAGAGTTGGTATCCATCTTTGCATTAAATTAA<br>AGCACACCAAGAAAAGACAGATTTATACAGACATAGAGA<br>TGAACCGACTTGGAAAGTAA |
| 42 | Envelope; LCMV | ATGGGTCAGATTGTGACAATGTTTGAGGCTCTGCCTCACA<br>TCATCGATGAGGTGATCAACATTGTCATTATTGTGCTTAT<br>CGTGATCACGGGTATCAAGGCTGTCTACAATTTTGCCACC<br>TGTGGGATATTCGCATTGATCAGTTTCCTACTTCTGGCTG<br>GCAGGTCCTGTGGCATGTACGGTCTTAAGGGACCCGACAT<br>TTACAAAGGAGTTTACCAATTTAAGTCAGTGGAGTTTGAT<br>ATGTCACATCTGAACCTGACCATGCCCAACGCATGTTCAG<br>CCAACAACTCCCACCATTACATCAGTATGGGGACTTCTGG<br>ACTAGAATTGACCTTCACCAATGATTCCATCATCAGTCAC<br>AACTTTTGCAATCTGACCTCTGCCTTCAACAAAAAGACCT<br>TTGACCACACACTCATGAGTATAGTTTCGAGCCTACACCT<br>CAGTATCAGAGGGAACTCCAACTATAAGGCAGTATCCTG<br>CGACTTCAACAATGGCATAACCATCCAATACAACTTGACA<br>TTCTCAGATCGACAAAGTGCTCAGAGCCAGTGTAGAACCT<br>TCAGAGGTAGAGTCCTAGATATGTTTAGAACTGCCTTCGG<br>GGGGAAATACATGAGGAGTGGCTGGGGCTGGACAGGCTC<br>AGATGGCAAGACCACCTGGTGTAGCCAGACGAGTTACCA<br>ATACCTGATTATACAAAATAGAACCTGGGAAAACCACTG |

-continued

| SEQ ID NO: | Description | Sequence |
|---|---|---|

CACATATGCAGGTCCTTTTGGGATGTCCAGGATTCTCCTT
TCCCAAGAGAAGACTAAGTTCTTCACTAGGAGACTAGCG
GGCACATTCACCTGGACTTTGTCAGACTCTTCAGGGGTGG
AGAATCCAGGTGGTTATTGCCTGACCAAATGGATGATTCT
TGCTGCAGAGCTTAAGTGTTTCGGGAACACAGCAGTTGCG
AAATGCAATGTAAATCATGATGCCGAATTCTGTGACATGC
TGCGACTAATTGACTACAACAAGGCTGCTTTGAGTAAGTT
CAAAGAGGACGTAGAATCTGCCTTGCACTTATTCAAAAC
AACAGTGAATTCTTTGATTTCAGATCAACTACTGATGAGG
AACCACTTGAGAGATCTGATGGGGGTGCCATATTGCAATT
ACTCAAAGTTTTGGTACCTAGAACATGCAAAGACCGGCG
AAACTAGTGTCCCCAAGTGCTGGCTTGTCACCAATGGTTC
TTACTTAAATGAGACCCACTTCAGTGATCAAATCGAACAG
GAAGCCGATAACATGATTACAGAGATGTTGAGGAAGGAT
TACATAAAGAGGCAGGGGAGTACCCCCCTAGCATTGATG
GACCTTCTGATGTTTTCCACATCTGCATATCTAGTCAGCAT
CTTCCTGCACCTTGTCAAAATACCAACACACAGGCACATA
AAAGGTGGCTCATGTCCAAAGCCACACCGATTAACCAAC
AAAGGAATTTGTAGTTGTGGTGCATTTAAGGTGCCTGGTG
TAAAAACCGTCTGGAAAAGACGCTGA

| 43 | Envelope; FPV | ATGAACACTCAAATCCTGGTTTTCGCCCTTGTGGCAGTCA |

TCCCCACAAATGCAGACAAAATTTGTCTTGGACATCATGC
TGTATCAAATGGCACCAAAGTAAACACACTCACTGAGAG
AGGAGTAGAAGTTGTCAATGCAACGGAAACAGTGGAGCG
GACAAACATCCCCAAAATTTGCTCAAAAGGGAAAAGAAC
CACTGATCTTGGCCAATGCGGACTGTTAGGGACCATTACC
GGACCACCTCAATGCGACCAATTTCTAGAATTTTTCAGCTG
ATCTAATAATCGAGAGACGAGAAGGAAATGATGTTTGTT
ACCCGGGGAAGTTTGTTAATGAAGAGGCATTGCGACAAA
TCCTCAGAGGATCAGGTGGGATTGACAAAGAAACAATGG
GATTCACATATAGTGGAATAAGGACCAACGGAACAACTA
GTGCATGTAGAAGATCAGGGTCTTCATTCTATGCAGAAAT
GGAGTGGCTCCTGTCAAATACAGACAATGCTGCTTTCCCA
CAAATGACAAAATCATACAAAAACACAAGGAGAGAATCA
GCTCTGATAGTCTGGGGAATCCACCATTCAGGATCAACCA
CCGAACAGACCAAACTATATGGGAGTGGAAATAAACTGA
TAACAGTCGGGAGTTCCAAATATCATCAATCTTTTGTGCC
GAGTCCAGGAACACGACCGCAGATAAATGGCCAGTCCGG
ACGGATTGATTTTCATTGGTTGATCTTGGATCCCAATGAT
ACAGTTACTTTTAGTTTCAATGGGGCTTTCATAGCTCCAA
ATCGTGCCAGCTTCTTGAGGGGAAAGTCCATGGGGATCC
AGAGCGATGTGCAGGTTGATGCCAATTGCGAAGGGGAAT
GCTACCACAGTGGAGGGACTATAACAAGCAGATTGCCTT
TTCAAAACATCAATAGCAGAGCAGTTGGCAAATGCCCAA
GATATGTAAAACAGGAAAGTTTATTATTGGCAACTGGGA
TGAAGAACGTTCCCGAACCTTCCAAAAAAAAGGAAAAAAA
GAGGCCTGTTTGGCGCTATAGCAGGGTTTATTGAAAATGG
TTGGGAAGGTCTGGTCGACGGGTGGTACGGTTTCAGGCAT
CAGAATGCACAAGGAGAAGGAACTGCAGCAGACTACAA
AAGCACCCAATCGGCAATTGATCAGATAACCGGAAAGTT
AAATAGACTCATTGAGAAAACCAACCAGCAATTTGAGCT
AATAGATAATGAATTCACTGAGGTGGAAAAGCAGATTGG
CAATTTAATTAACTGGACCAAAGACTCCATCACAGAAGT
ATGGTCTTACAATGCTGAACTTCTTGTGGCAATGGAAAAC
CAGCACACTATTGATTTGGCTGATTCAGAGATGAACAAGC
TGTATGAGCGAGTGAGGAAACAATTAAGGGAAAATGCTG
AAGAGGATGGCACTGGTTGCTTTGAAATTTTTCATAAATG
TGACGATGATTGTATGGCTAGTATAAGGAACAATACTTAT
GATCACAGCAAATACAGAGAAGAAGCGATGCAAAATAG
AATACAAATTGACCCAGTCAAATTGAGTAGTGGCTACAA
AGATGTGATACTTTGGTTTAGCTTCGGGGCATCATGCTTT
TTGCTTCTTGCCATTGCAATGGGCCTTGTTTTCATATGTGT
GAAGAACGGAAACATGCGGTGCACTATTTGTATATAA

| 44 | Envelope; RRV | AGTGTAACAGAGCACTTTAATGTGTATAAGGCTACTAGAC |

CATACCTAGCACATTGCGCCGATTGCGGGGACGGGTACTT
CTGCTATAGCCCAGTTGCTATCGAGGAGATCCGAGATGA
GGCGTCTGATGGCATGCTTAAGATCCAAGTCTCCGCCCAA
ATAGGTCTGGACAAGGCAGGCACCCACGCCCACACGAAG
CTCCGATATATGGCTGGTCATGATGTTCAGGAATCTAAGA
GAGATTCCTTGAGGGTGTACACGTCCGCAGCGTGCTCCAT
ACATGGGACGATGGGACACTTCATCGTCGCACACTGTCCA
CCAGGCGACTACCTCAAGGTTTCGTTCGAGGACGCAGATT
CGCACGTGAAGGCATGTAAGGTCCAATACAAGCACAATC
CATTGCCGGTGGGTAGAGAGAAGTTCGTGGTTAGACCAC

-continued

| SEQ ID NO: | Description | Sequence |
|---|---|---|
| | | ACTTTGGCGTAGAGCTGCCATGCACCTCATACCAGCTGAC |
| | | AACGGCTCCCACCGACGAGGAGATTGACATGCATACACC |
| | | GCCAGATATACCGGATCGCACCCTGCTATCACAGACGGC |
| | | GGGCAACGTCAAAATAACAGCAGGCGGCAGGACTATCAG |
| | | GTACAACTGTACCTGCGGCCGTGACAACGTAGGCACTAC |
| | | CAGTACTGACAAGACCATCAACACATGCAAGATTGACCA |
| | | ATGCCATGCTGCCGTCACCAGCCATGACAAATGGCAATTT |
| | | ACCTCTCCATTTGTTCCCAGGGCTGATCAGACAGCTAGGA |
| | | AAGGCAAGGTACACGTTCCGTTCCCTCTGACTAACGTCAC |
| | | CTGCCGAGTGCCGTTGGCTCGAGCGCCGGATGCCACCTAT |
| | | GGTAAGAAGGAGGTGACCCTGAGATTACACCCAGATCAT |
| | | CCGACGCTCTTCTCCTATAGGAGTTTAGGAGCCGAACCGC |
| | | ACCCGTACGAGGAATGGGTTGACAAGTTCTCTGAGCGCA |
| | | TCATCCCAGTGACGGAAGAAGGGATTGAGTACCAGTGGG |
| | | GCAACAACCCGCCGGTCTGCCTGTGGGCGCAACTGACGA |
| | | CCGAGGGCAAACCCCATGGCTGGCCACATGAAATCATTC |
| | | AGTACTATTATGGACTATACCCCGCCGCCACTATTGCCGC |
| | | AGTATCCGGGGCGAGTCTGATGGCCCTCCTAACTCTGGCG |
| | | GCCACATGCTGCATGCTGGCCACCGCGAGGAGAAAGTGC |
| | | CTAACACCGTACGCCCTGACGCCAGGAGCGGTGGTACCG |
| | | TTGACACTGGGGCTGCTTTGCTGCGCACCGAGGGCGAATG |
| | | CA |
| 45 | Envelope; MLV 10A1 | ATGGAAGGTCCAGCGTTCTCAAAACCCCTTAAAGATAAG |
| | | ATTAACCCGTGGAAGTCCTTAATGGTCATGGGGGTCTATT |
| | | TAAGAGTAGGGATGGCAGAGAGCCCCCATCAGGTCTTTA |
| | | ATGTAACCTGGAGAGTCACCAACCTGATGACTGGGCGTA |
| | | CCGCCAATGCCACCTCCCTTTTAGGAACTGTACAAGATGC |
| | | CTTCCCAAGATTATATTTTGATCTATGTGATCTGGTCGGA |
| | | GAAGAGTGGGGACCCTTCAGACCAGGAACCATATGTCGGG |
| | | TATGGCTGCAAATACCCCGGAGGGAGAAAGCGGACCCGG |
| | | ACTTTTGACTTTTACGTGTGCCCTGGGCATACCGTAAAAT |
| | | CGGGGTGTGGGGGGCCAAGAGAGGGCTACTGTGGTGAAT |
| | | GGGGTTGTGAAACCACCGGACAGGCTTACTGGAAGCCCA |
| | | CATCATCATGGGACCTAATCTCCCTTAAGCGCGGTAACAC |
| | | CCCCTGGGACACGGGATGCTCCAAAATGGCTTGTGGCCCC |
| | | TGCTACGACCTCTCCAAAGTATCCAATTCCTTCCAAGGGG |
| | | CTACTCGAGGGGGCAGATGCAACCCTCTAGTCCTAGAATT |
| | | CACTGATGCAGGAAAAAAGGCTAATTGGGACGGGCCCAA |
| | | ATCGTGGGGACTGAGACTGTACCGGACAGGAACAGATCC |
| | | TATTACCATGTTCTCCCTGACCCGCCAGGTCCTCAATATA |
| | | GGGCCCCGCATCCCCATTGGGCCTAATCCCGTGATCACTG |
| | | GTCAACTACCCCCCTCCCGACCCGTGCAGATCAGGCTCCC |
| | | CAGGCCTCCTCAGCCTCCTCCTACAGGCGCAGCCTCTATA |
| | | GTCCCTGAGACTGCCCCACCTTCTCAACAACCTGGGACGG |
| | | GAGACAGGCTGCTAAACCTGGTAGAAGGAGCCTATCAGG |
| | | CGCTTAACCTCACCAATCCCGACAAGACCCAAGAATGTTG |
| | | GCTGTGCTTAGTGTCGGGACCTCCTTATTACGAAGGAGTA |
| | | GCGGTCGTGGGCACTTATACCAATCATTCTACCGCCCCGG |
| | | CCAGCTGTACGGCCACTTCCCAACATAAGCTTACCCTATC |
| | | TGAAGTGACAGGACAGGGCCTATGCATGGGAGCACTACC |
| | | TAAAACTCACCAGGCCTTATGTAACACCACCCAAAGTGCC |
| | | GGCTCAGGATCCTACTACCTTGCAGCACCCGCTGGAACAA |
| | | TGTGGGCTTGTAGCACTGGATTGACTCCCTGCTTGTCCAC |
| | | CACGATGCTCAATCTAACCACAGACTATTGTGTATTAGTT |
| | | GAGCTCTGGCCCAGAATAATTTACCACTCCCCCGATTATA |
| | | TGTATGGTCAGCTTGAACAGCGTACCAAATATAAGAGGG |
| | | AGCCAGTATCGTTGACCCTGGCCCTTCTGCTAGGAGGATT |
| | | AACCATGGGAGGGATTGCAGCTGGAATAGGGACGGGGAC |
| | | CACTGCCCTAATCAAAACCCAGCAGTTTGAGCAGCTTCAC |
| | | GCCGCTATCCAGACAGACCTCAACGAAGTCGAAAAATCA |
| | | ATTACCAACCTAGAAAAGTCACTGACCTCGTTGTCTGAAG |
| | | TAGTCCTACAGAACCGAAGAGGCCTAGATTTGCTCTTCCT |
| | | AAAAGAGGGAGGTCTCTGCGCAGCCCTAAAAGAAGAATG |
| | | TTGTTTTTATGCAGACCACACGGGACTAGTGAGAGACAGC |
| | | ATGGCCAAACTAAGGGAAAGGCTTAATCAGAGACAAAAA |
| | | CTATTTGAGTCAGGCCAAGGTTGGTTCGAAGGGCAGTTTA |
| | | ATAGATCCCCCTGGTTTACCACCTTAATCTCCACCATCAT |
| | | GGGACCTCTAATAGTACTCTTACTGATCTTACTCTTTGGA |
| | | CCCTGCATTCTCAATCGATTGGTCCAATTTGTTAAAGACA |
| | | GGATCTCAGTGGTCCAGGCTCTGGTTTTGACTCAACAATA |
| | | TCACCAGCTAAAACCTATAGAGTACGAGCCATGA |
| 46 | Envelope; Ebola | ATGGGTGTTACAGGAATATTGCAGTTACCTCGTGATCGAT |
| | | TCAAGAGGACATCATTCTTTCTTTGGGTAATTATCCTTTTC |
| | | CAAAGAACATTTTCCATCCCACTTGGAGTCATCCACAATA |

-continued

| SEQ ID NO: | Description | Sequence |
|---|---|---|
| | | GCACATTACAGGTTAGTGATGTCGACAAACTGGTTTGCCG<br>TGACAAACTGTCATCCACAAATCAATTGAGATCAGTTGGA<br>CTGAATCTCGAAGGGAATGGAGTGGCAACTGACGTGCCA<br>TCTGCAACTAAAAGATGGGGCTTCAGGTCCGGTGTCCCAC<br>CAAAGGTGGTCAATTATGAAGCTGGTGAATGGGCTGAAA<br>ACTGCTACAATCTTGAAATCAAAAAACCTGACGGGAGTG<br>AGTGTCTACCAGCAGCGCCAGACGGGATTCGGGGCTTCC<br>CCCGGTGCCGGTATGTGCACAAAGTATCAGGAACGGGAC<br>CGTGTGCCGGAGACTTTGCCTTCCACAAAGAGGGTGCTTT<br>CTTCCTGTATGACCGACTTGCTTCCACAGTTATCTACCGA<br>GGAACGACTTTCGCTGAAGGTGTCGTTGCATTTCTGATAC<br>TGCCCCAAGCTAAGAAGGACTTCTTCAGCTCACACCCCTT<br>GAGAGAGCCGGTCAATGCAACGGAGGACCCGTCTAGTGG<br>CTACTATTCTACCACAATTAGATATCAAGCTACCGGTTTT<br>GGAACCAATGAGACAGAGTATTTGTTCGAGGTTGACAAT<br>TTGACCTACGTCCAACTTGAATCAAGATTCACACCACAGT<br>TTCTGCTCCAGCTGAATGAGACAATATATACAAGTGGGA<br>AAAGGAGCAATACCACGGGAAAACTAATTTGGAAGGTCA<br>ACCCCGAAATTGATACAACAATCGGGGAGTGGGCCTTCT<br>GGGAAACTAAAAAAACCTCACTAGAAAAATTCGCAGTGA<br>AGAGTTGTCTTTCACAGCTGTATCAAACAGAGCCAAAAA<br>CATCAGTGGTCAGAGTCCGGCGCGAACTTCTTCCGACCCA<br>GGGACCAACACAACAACTGAAGACCACAAAATCATGGCT<br>TCAGAAAATTCCTCTGCAATGGTTCAAGTGCACAGTCAAG<br>GAAGGGAAGCTGCAGTGTCGCATCTGACAACCCTTGCCA<br>CAATCTCCACGAGTCCTCAACCCCCCACAACCAAACCAG<br>GTCCGGACAACAGCACCCACAATACACCCGTGTATAAAC<br>TTGACATCTCTGAGGCAACTCAAGTTGAACAACATCACCG<br>CAGAACAGACAACGACAGCACAGCCTCCGACACTCCCCC<br>CGCCACGACCGCAGCCGGACCCCTAAAAGCAGAGAACAC<br>CAACACGAGCAAGGGTACCGACCTCCTGGACCCCGCCAC<br>CACAACAAGTCCCCAAAACCACAGCGAGACCGCTGGCAA<br>CAACAACACTCATCACCAAGATACCGGAGAAGAGAGTGC<br>CAGCAGCGGGAAGCTAGGCTTAATTACCAATACTATTGCT<br>GGAGTCGCAGGACTGATCACAGGCGGGAGGAGAGCTCGA<br>AGAGAAGCAATTGTCAATGCTCAACCCAAATGCAACCCT<br>AATTTACATTACTGGACTACTCAGGATGAAGGTGCTGCAA<br>TCGGACTGGCCTGGATACCATATTTCGGGCCAGCAGCCGA<br>GGGAATTTACATAGAGGGGCTGATGCACAATCAAGATGG<br>TTTAATCTGTGGGTTGAGACAGCTGGCCAACGAGACGACT<br>CAAGCTCTTCAACTGTTCCTGAGAGCCACAACCGAGCTAC<br>GCACCTTTTCAATCCTCAACCGTAAGGCAATTGATTTCTT<br>GCTGCAGCGATGGGGCGGCACATGCCACATTTTGGGACC<br>GGACTGCTGTATCGAACCACATGATTGGACCAAGAACAT<br>AACAGACAAAATTGATCAGATTATTCATGATTTTGTTGAT<br>AAAACCCTTCCGGACCAGGGGGACAATGACAATTGGTGG<br>ACAGGATGGAGACAATGGATACCGGCAGGTATTGGAGTT<br>ACAGGCGTTATAATTGCAGTTATCGCTTTATTCTGTATAT<br>GCAAATTTGTCTTTTAG |
| 47 | Polymerase III<br>shRNA promoters;<br>U6 promoter | TTTCCCATGATTCCTTCATATTTGCATATACGATACAAGG<br>CTGTTAGAGAGATAATTGGAATTAATTTGACTGTAAACAC<br>AAAGATATTAGTACAAAATACGTGACGTAGAAAGTAATA<br>ATTTCTTGGGTAGTTTGCAGTTTTAAAATTATGTTTTAAAA<br>TGGACTATCATATGCTTACCGTAACTTGAAAGTATTTCGA<br>TTTCTTGGCTTTATATATCTTGTGGAAAGGACGAAAC |
| 48 | Polymerase III<br>shRNA promoters;<br>7SK promoter | CTGCAGTATTTAGCATGCCCCACCCATCTGCAAGGCATTC<br>TGGATAGTGTCAAAACAGCCGGAAATCAAGTCCGTTTATC<br>TCAAACTTTAGCATTTTGGGAATAAATGATATTTGCTATG<br>CTGGTTAAATTAGATTTTAGTTAAATTTCCTGCTGAAGCT<br>CTAGTACGATAAGCAACTTGACCTAAGTGTAAAGTTGAG<br>ATTTCCTTCAGGTTTATATAGCTTGTGCGCCGCCTGGCTAC<br>CTC |
| 49 | FDPS target<br>sequence #1 | GTCCTGGAGTACAATGCCATT |
| 50 | FDPS target<br>sequence #2 | GCAGGATTTCGTTCAGCACTT |
| 51 | FDPS target<br>sequence #3 | GCCATGTACATGGCAGGAATT |
| 52 | FDPS target<br>sequence #4 | GCAGAAGGAGGCTGAGAAAGT |

-continued

| SEQ ID NO: | Description | Sequence |
|---|---|---|
| 53 | Lenti-BTN3A1 ("LV-BTN3A1, lentivirus expressing BTN3A1") | ATGAAAATGGCAAGTTTCCTGGCCTTCCTTCTGCTCAACT TTCGTGTCTGCCTCCTTTTGCTTCAGCTGCTCATGCCTCAC TCAGCTCAGTTTTCTGTGCTTGGACCCTCTGGGCCCATCCT GGCCATGGTGGGTGAAGACGCTGATCTGCCCTGTCACCTG TTCCCGACCATGAGTGCAGAGACCATGGAGCTGAAGTGG GTGAGTTCCAGCCTAAGGCAGGTGGTGAACGTGTATGCA GATGGAAAGGAAGTGGAAGACAGGCAGAGTGCACCGTAT CGAGGGAGAACTTCGATTCTGCGGGATGGCATCACTGCA GGGAAGGCTGCTCTCCGAATACACAACGTCACAGCCTCT GACAGTGGAAAGTACTTGTGTTATTTCCAAGATGGTGACT TCTATGAAAAAGCCCTGGTGGAGCTGAAGGTTGCAGCAC TGGGTTCTGATCTTCACGTTGATGTGAAGGGTTACAAGGA TGGAGGGATCCATCTGGAGTGCAGGTCCACTGGCTGGTA CCCCCAACCCCAAATACAGTGGAGCAACAACAAGGGAGA GAACATCCCGACTGTGGAAGCACCTGTGGTTGCAGACGG AGTGGGCCTGTATGCAGTAGCAGCATCTGTGATCATGAG AGGCAGCTCTGGGGAGGGTGTATCCTGTACCATCAGAAG TTCCCTCCTCGGCCTGGAAAAGACAGCCAGCATTTCCATC GCAGACCCCTTCTTCAGGAGCGCCCAGAGGTGGATCGCC GCCCTGGCAGGGACCCTGCCTGTCTTGCTGCTGCTTCTTG GGGGAGCCGGTTACTTCCTGTGGCAACAGCAGGAGGAAA AAAAGACTCAGTTCAGAAAGAAAAAGAGAGAGCAAGAG TTGAGAGAAATGGCATGGAGCACAATGAAGCAAGAACAA AGCACAAGAGTGAAGCTCCTGGAGGAACTCAGATGGAGA AGTATCCAGTATGCATCTCGGGGAGAGAGACATTCAGCC TATAATGAATGGAAAAAGGCCCTCTTCAAGCCTGCGGAT GTGATTCTGGATCCAAAAACAGCAAACCCCATCCTCCTTG TTTCTGAGGACCAGAGGAGTGTGCAGCGTGCCAAGGAGC CCCAGGATCTGCCAGACAACCCTGAGAGATTTAATTGGC ATTATTGTGTTCTCGGCTGTGAGAGCTTCATATCAGGGAG ACATTACTGGGAGGTGGAGGTAGGGGACAGGAAAGAGTG GCATATAGGGGTGTGCAGTAAGAATGTGCAGAGAAAAGG CTGGGGTCAAAATGACACCTGAGAATGGATTCTGGACTAT GGGGCTGACTGATGGGAATAAGTATCGGACTCTAACTGA GCCCAGAACCAACCTGAAACTTCCTAAGCCCCCTAAGAA AGTGGGGGTCTTCCTGGACTATGAGACTGGAGATATCTCA TTCTACAATGCTGTGGATGGATCGCATATTCATACTTTCCT GGACGTCTCCTTCTCTGAGGCTCTATATCCTGTTTTCAGAA TTTTGACCTTGGAGCCCACGGCCCTGACTATTTGTCCAGC GTGA |
| 54 | Lenti-BTN3A3 (R381H) | ATGAAAATGGCAAGTTCCCTGGCTTTCCTTCTGCTCAACT TTCATGTCTCCCTCTTCTTGGTCCAGCTGCTCACTCCTTGC TCAGCTCAGTTTTCTGTGCTTGGACCCTCTGGGCCCATCCT GGCCATGGTGGGTGAAGACGCTGATCTGCCCTGTCACCTG TTCCCGACCATGAGTGCAGAGACCATGGAGCTGAGGTGG GTGAGTTCCAGCCTAAGGCAGGTGGTGAACGTGTATGCA GATGGAAAGGAAGTGGAAGACAGGCAGAGTGCACCGTAT CGAGGGAGAACTTCGATTCTGCGGGATGGCATCACTGCA GGGAAGGCTGCTCTCCGAATACACAACGTCACAGCCTCT GACAGTGGAAAGTACTTGTGTTATTTCCAAGATGGTGACT TCTACGAAAAAGCCCTGGTGGAGCTGAAGGTTGCAGCAT TGGGTTCTGATCTTCACATTGAAGTGAAGGGTTATGAGGA TGGAGGGATCCATCTGGAGTGCAGGTCCACTGGCTGGTA CCCCCAACCCCAAATAAAGTGGAGCGACACCAAGGGAGA GAACATCCCGGCTGTGGAAGCACCTGTGGTTGCAGATGG AGTGGGCCTGTATGCAGTAGCAGCATCTGTGATCATGAG AGGCAGCTCTGGTGGGGGTGTATCCTGCATCATCAGAAAT TCCCTCCTCGGCCTGGAAAAGACAGCCAGCATATCCATCG CAGACCCCTTCTTCAGGAGCGCCCAGCCCTGGATCGCGGC CCTGGCAGGGACCCTGCCTATCTCGTTGCTGCTTCTCGCA GGAGCCAGTTACTTCTTGTGGAGACAACAGAAGGAAAAA ATTGCTCTGTCCAGGGAGACAGAAAGAGAGCGAGAGATG AAAGAAATGGGATACGCTGCAACAGAGCAAGAAATAAG CCTAAGAGAGAAGCTCCAGGAGGAACTCAAGTGGAGGAA AATCCAGTACATGGCTCGTGGAGAGAAGTCTTTGGCCTAT CATGAATGGAAAATGGCCCTCTTCAAACCTGCGGATGTG ATTCTGGATCCAGACACGGCAAACGCCATCCTCCTTGTTT CTGAGGACCAGAGGAGTGTGCAGCGTGCTGAAGAGCCGC GGGATCTGCCAGACAACCCTGAGAGATTTGAATGGCACT ACTGTGTCCTTGGCTGTGAAAACTTCACATCAGGGAGACA TTACTGGGAGGTGGAAGTGGGGGACAGAAAGAGTGGCA TATTGGGGTATGTAGTAAGAACGTGGAGAGGAAAAAAGG TTGGGTCAAAATGACACCGGAGAACGGATACTGGACTAT GGGCCTGACTGATGGGAATAAGTATCGGGCTCTCACTGA |

-continued

| SEQ ID NO: | Description | Sequence |
|---|---|---|
| | | GCCCAGAACCAACCTGAAACTTCCTGAGCCTCCTAGGAA |
| | | AGTGGGGATCTTCCTGGACTATGAGACTGGAGAGATCTC |
| | | GTTCTATAATGCCACAGATGGATCTCATATCTACACCTTT |
| | | CCGCACGCCTCTTTCTCTGAGCCTCTATATCCTGTTTTCAG |
| | | AATTTTGACCTTGGAGCCCACTGCCCTGACCATTTGCCCA |
| | | ATACCAAAAGAAGTAGAGAGTTCCCCCGATCCTGACCTA |
| | | GTGCCTGATCATTCCCTGGAGACACCACTGACCCCGGGCT |
| | | TAGCTAATGAAAGTGGGGAGCCTCAGGCTGAAGTAACAT |
| | | CTCTGCTTCTCCCTGCCCACCCTGGAGCTGAGGTCTCCCCT |
| | | TCTGCAACAACCAATCAGAACCATAAGCTACAGGCACGC |
| | | ACTGAAGCACTTTACTGA |
| 55 | BTN3A3-FDPSsh-IL-2 ("BTN3A3 (R381H) T2A IL-2") | ATGAAAATGGCAAGTTCCCTGGCTTTCCTTCTGCTCAACT |
| | | TTCATGTCTCCCTCTTCTTGGTCCAGCTGCTCACTCCTTGC |
| | | TCAGCTCAGTTTTCTGTGCTTGGACCCTCTGGGCCCATCCT |
| | | GGCCATGGTGGGTGAAGACGCTGATCTGCCCTGTCACCTG |
| | | TTCCCGACCATGAGTGCAGAGACCATGGAGCTGAGGTGG |
| | | GTGAGTTCCAGCCTAAGGCAGGTGGTGAACGTGTATGCA |
| | | GATGGAAAGGAAGTGGAAGACAGGCAGAGTGCACCGTAT |
| | | CGAGGGAGAACTTCGATTCTGCGGGATGGCATCACTGCA |
| | | GGGAAGGCTGCTCTCCGAATACACAACGTCACAGCCTCT |
| | | GACAGTGGAAAGTACTTGTGTTATTTCCAAGATGGTGACT |
| | | TCTACGAAAAAGCCCTGGTGGAGCTGAAGGTTGCAGCAT |
| | | TGGGTTCTGATCTTCACATTGAAGTGAAGGGTTATGAGGA |
| | | TGGAGGGATCCATCTGGAGTGCAGGTCCACTGGCTGGTA |
| | | CCCCCAACCCCAAATAAAGTGGAGCGACACCAAGGGAGA |
| | | GAACATCCCGGCTGTGGAAGCACCTGTGGTTGCAGATGG |
| | | AGTGGGCCTGTATGCAGTAGCAGCATCTGTGATCATGAG |
| | | AGGCAGCTCTGGTGGGGGTGTATCCTGCATCATCAGAAAT |
| | | TCCCTCCTCGGCCTGGAAAAGACAGCCAGCATATCCATCG |
| | | CAGACCCCTTCTTCAGGAGCGCCCAGCCCTGGATCGCGGC |
| | | CCTGGCAGGGACCCTGCCTATCTCGTTGCTGCTTCTCGCA |
| | | GGAGCCAGTTACTTCTTGTGGAGACAACAGAAGGAAAAA |
| | | ATTGCTCTGTCCAGGGAGACAGAAAGAGAGCGAGAGATG |
| | | AAAGAAATGGGATACGCTGCAACAGAGCAAGAAATAAG |
| | | CCTAAGAGAGAAGCTCCAGGAGGAACTCAAGTGGAGGAA |
| | | AATCCAGTACATGGCTCGTGGAGAGAAGTCTTTGGCCTAT |
| | | CATGAATGGAAAATGGCCCTCTTCAAACCTGCGGATGTG |
| | | ATTCTGGATCCAGACACGGCAAACGCCATCCTCCTTGTTT |
| | | CTGAGGACCAGAGGAGTGTGTGCAGCGTGCTGAAGAGCCGC |
| | | GGGATCTGCCAGACAACCCTGAGAGATTTGAATGGCACT |
| | | ACTGTGTCCTTGGCTGTGAAAACTTCACATCAGGGAGACA |
| | | TTACTGGGAGGTGGAAGTGGGGGACAGAAAAGAGTGGCA |
| | | TATTGGGGTATGTAGTAAGAACGTGGAGAGGAAAAAAGG |
| | | TTGGGTCAAAATGACACCGGAGAACGGATACTGGACTAT |
| | | GGGCCTGACTGATGGGAATAAGTATCGGGCTCTCACTGA |
| | | GCCCAGAACCAACCTGAAACTTCCTGAGCCTCCTAGGAA |
| | | AGTGGGGATCTTCCTGGACTATGAGACTGGAGAGATCTC |
| | | GTTCTATAATGCCACAGATGGATCTCATATCTACACCTTT |
| | | CCGCACGCCTCTTTCTCTGAGCCTCTATATCCTGTTTTCAG |
| | | AATTTTGACCTTGGAGCCCACTGCCCTGACCATTTGCCCA |
| | | ATACCAAAAGAAGTAGAGAGTTCCCCCGATCCTGACCTA |
| | | GTGCCTGATCATTCCCTGGAGACACCACTGACCCCGGGCT |
| | | TAGCTAATGAAAGTGGGGAGCCTCAGGCTGAAGTAACAT |
| | | CTCTGCTTCTCCCTGCCCACCCTGGAGCTGAGGTCTCCCCT |
| | | TCTGCAACAACCAATCAGAACCATAAGCTACAGGCACGC |
| | | ACTGAAGCACTTTACCGTAGACGAAAGCGCGGAAGCGGA |
| | | GAGGGCAGAGGAAGTCTGCTAACATGCGGTGACGTCGAG |
| | | GAGAATCCTGGACCTATGTACAGGATGCAACTCCTGTCTT |
| | | GCATTGCACTAAGTCTTGCACTTGTCACAAACAGTGCACC |
| | | TACTTCAAGTTCTACAAAGAAAACACAGCTACAACTGGA |
| | | GCATTTACTGCTGGATTTACAGATGATTTTGAATGGAATT |
| | | AATAATTACAAGAATCCCAAACTCACCAGGATGCTCACA |
| | | TTTAAGTTTTACATGCCCAAGAAGGCCACAGAACTGAAA |
| | | CATCTTCAGTGTCTAGAAGAAGAACTCAAACCTCTGGAG |
| | | GAAGTGCTAAATTTAGCTCAAAGCAAAAACTTTCACTTAA |
| | | GACCCAGGGACTTAATCAGCAATATCAACGTAATAGTTCT |
| | | GGAACTAAAGGGATCTGAAACAACATTCATGTGTGAATA |
| | | TGCTGATGAGACAGCAACCATTGTAGAATTTCTGAACAG |
| | | ATGGATTACCTTTTGTCAAAGCATCATCTCAACACTGACT |
| | | TGA |
| 56 | Cytokine IL-2 ("IL-2, or IL2") | ATGTACAGGATGCAACTCCTGTCTTGCATTGCACTAAGTC |
| | | TTGCACTTGTCACAAACAGTGCACCTACTTCAAGTTCTAC |
| | | AAAGAAAACACAGCTACAACTGGAGCATTTACTGCTGGA |
| | | TTTACAGATGATTTTGAATGGAATTAATAATTACAAGAAT |

-continued

| SEQ ID NO: | Description | Sequence |
|---|---|---|
| | | CCCAAACTCACCAGGATGCTCACATTTAAGTTTTACATGC |
| | | CCAAGAAGGCCACAGAACTGAAACATCTTCAGTGTCTAG |
| | | AAGAAGAACTCAAACCTCTGGAGGAAGTGCTAAATTTAG |
| | | CTCAAAGCAAAAACTTTCACTTAAGACCCAGGGACTTAAT |
| | | CAGCAATATCAACGTAATAGTTCTGGAACTAAAGGGATC |
| | | TGAAACAACATTCATGTGTGAATATGCTGATGAGACAGC |
| | | AACCATTGTAGAATTTCTGAACAGATGGATTACCTTTTGT |
| | | CAAAGCATCATCTCAACACTGACTTGA |
| 57 | Cytokine IL-15 ("IL15", or "IL-15") | ATGAGAATTTCGAAACCACATTTGAGAAGTATTTCCATCC |
| | | AGTGCTACTTGTGTTTACTTCTAAACAGTCATTTTCTAACT |
| | | GAAGCTGGCATTCATGTCTTCATTTTGGGCTGTTTCAGTG |
| | | CAGGGCTTCCTAAAACAGAAGCCAACTGGGTGAATGTAA |
| | | TAAGTGATTTGAAAAAATTGAAGATCTTATTCAATCTAT |
| | | GCATATTGATGCTACTTTATATACGGAAAGTGATGTTCAC |
| | | CCCAGTTGCAAAGTAACAGCAATGAAGTGCTTTCTCTTGG |
| | | AGTTACAAGTTATTTCACTTGAGTCCGGAGATGCAAGTAT |
| | | TCATGATACAGTAGAAAATCTGATCATCCTAGCAAACAA |
| | | CAGTTTGTCTTCTAATGGGAATGTAACAGAATCTGGATGC |
| | | AAAGAATGTGAGGAACTGGAGGAAAAAAATATTAAAGA |
| | | ATTTTTGCAGAGTTTTGTACATATTGTCCAAATGTTCATCA |
| | | ACACTTCTTGA |
| 58 | Cytokine IL-18 ("IL-18", or "IL18") | CTGGACAGTCAGCAAGGAATTGTCTCCCAGTGCATTTTGC |
| | | CCTCCTGGCTGCCAACTCTGGCTGCTAAAGCGGCTGCCAC |
| | | CTGCTGCAGTCTACACAGCTTCGGGAAGAGGAAAGGAAC |
| | | CTCAGACCTTCCAGATCGCTTCCTCTCGCAACAAACTATT |
| | | TGTCGCAGGAATAAAGATGGCTGCTGAACCAGTAGAAGA |
| | | CAATTGCATCAACTTTGTGGCAATGAAATTTATTGACAAT |
| | | ACGCTTTACTTTATAGCTGAAGATGATGAAAACCTGGAAT |
| | | CAGATTACTTTGGCAAGCTTGAATCTAAATTATCAGTCAT |
| | | AAGAAATTTGAATGACCAAGTTCTCTTCATTGACCAAGGA |
| | | AATCGGCCTCTATTTGAAGATATGACTGATTCTGACTGTA |
| | | GAGATAATGCACCCCGGACCATATTTATTATAAGTATGTA |
| | | TAAAGATAGCCAGCCTAGAGGTATGGCTGTAACTATCTCT |
| | | GTGAAGTGTGAGAAAATTTCAACTCTCTCCTGTGAGAACA |
| | | AAATTATTTCCTTTAAGGAAATGAATCCTCCTGATAACAT |
| | | CAAGGATACAAAAAGTGACATCATATTCTTTCAGAGAAG |
| | | TGTCCCAGGACATGATAATAAGATGCAATTTGAATCTTCA |
| | | TCATACGAAGGATACTTTCTAGCTTGTGAAAAAGAGAGA |
| | | GACCTTTTTAAACTCATTTTGAAAAAAGAGGATGAATTGG |
| | | GGGATAGATCTATAATGTTCACTGTTCAAAACGAAGACTA |
| | | G |
| 59 | Lenti-AFP tumor-specific promoter (BTN3A3) [LTSP-AFP BTN3A3"] | CGATAGTTTGAGGAGAATATTTGTTATATTTGCAAAATAA |
| | | AATAAGTTTGCAAGTTTTTTTTTTCTGCCCCAAAGAGCTCT |
| | | GTGTCCTTGAACATAAAATACAAATAACCGCTATGCTGTT |
| | | AATTATTGGCAAATGTCCCATTTTCAACCTAAGGAAATAC |
| | | CATAAAGTAACAGATATACCAACAAAAGGTTACTAGTTA |
| | | ACAGGCATTGCCTGAAAAGAGTATAAAAGAATTTCAGCA |
| | | TGATTTTCCATATTGTGCTTCCACCACTGCCAATAACACG |
| 60 | Cytokine IL-23 ("IL-23", or "IL23") alpha subunit p19 | AGAGCCAGCCAGATTTGAGAAGAAGGCAAAAAGATGCTG |
| | | GGGAGCAGAGCTGTAATGCTGCTGTTGCTACTGCCCTGGA |
| | | CAGCTCAGGGCAGAGCTGTGCCTGGGGGCAGCAGCCCTG |
| | | CCTGGACTCAGTGCCAGCAGCTTTCACAGAAGCTCTGCAC |
| | | ACTGGCCTGGAGTGCACATCCACTAGTGGGACACATGGA |
| | | TCTAAGAGAAGAGGGAGATGAAGAGACTACAAATGATGT |
| | | TCCCCATATCCAGTGTGGAGATGGCTGTGACCCCCAAGGA |
| | | CTCAGGGACAACAGTCAGTTCTGCTTGCAAAGGATCCACC |
| | | AGGGTCTGATTTTTTTATGAGAAGCTGCTAGGATCGGATAT |
| | | TTTCACAGGGGAGCCTTCTCTGCTCCCTGATAGCCCTGTG |
| | | GGCCAGCTTCATGCCTCCCTACTGGGCCTCAGCCAACTCC |
| | | TGCAGCCTGAGGGTCACCACTGGGAGACTCAGCAGATTC |
| | | CAAGCCTCAGTCCCAGCCAGCCATGGCAGCGTCTCCTTCT |
| | | CCGCTTCAAGATCCTTCGCAGCCTCCAGGCCTTTGTGGCC |
| | | GTAGCCGCCCGGGTCTTTGCCCATGGAGCAGCAACCCTGA |
| | | GTCCCTAAAGGCAGCAGCTCAAG |
| 61 | Cytokine IL-36A ("IL-36A", or "IL36A") alpha | AAAACCCAAGTGCAGTAGAAGCCATTGTTCATAATGGTA |
| | | GGGATACAGGGTCCTTCGTAACAGATTATCAGTGTGGCCT |
| | | ATGCTGGAAAGTCTGGTGACCTCTGATTTTTTTTGCTTCCA |
| | | GGTCTTTGGCCTTGGCACTCTTTGTCATATTAGAGTTCCTG |
| | | GGTCTAGGCCTGGGCAGGATTCATAGGTGCAGCTGCTTCT |
| | | GCTGGAGGTAGACTGCATCCAACAAAGTAAGGGTGCTGG |
| | | GTGAGTTCTGGGAGTATAGATTCTGACTGGGGTCACTGCT |

-continued

| SEQ ID NO: | Description | Sequence |
|---|---|---|
|  |  | GGGCTGGCCGCCAGTCTTTCATCTGACCCAGGGTTAAACT |
|  |  | GTGGCTTGGGACTGACTCAGGTCCTCTCTTGGGGTCGGTC |
|  |  | TGCACATAAAAGGACTCCTATCCTTGGCAGTTCTGAAACA |
|  |  | ACACCACCACAATGGAAAAAGCATTGAAAATTGACACAC |
|  |  | CTCAGCAGGGGAGCATTCAGGATATCAATCATCGGGTGT |
|  |  | GGGTTCTTCAGGACCAGACGCTCATAGCAGTCCCGAGGA |
|  |  | AGGACCGTATGTCTCCAGTCACTATTGCCTTAATCTCATG |
|  |  | CCGACATGTGGAGACCCTTGAGAAAGACAGAGGGAACCC |
|  |  | CATCTACCTGGGCCTGAATGGACTCAATCTCTGCCTGATG |
|  |  | TGTGCTAAAGTCGGGGACCAGCCCACACTGCAGCTGAAG |
|  |  | GAAAAGGATATAATGGATTTGTACAACCAACCCGAGCCT |
|  |  | GTGAAGTCCTTTCTCTTCTACCACAGCCAGAGTGGCAGG |
|  |  | AACTCCACCTTCGAGTCTGTGGCTTTCCCTGGCTGGTTCAT |
|  |  | CGCTGTCAGCTCTGAAGGAGGCTGTCCTCTCATCCTTACC |
|  |  | CAAGAACTGGGGAAAGCCAACACTACTGACTTTGGG |
|  |  | TTAACTATGCTGTTTTAA |
| 62 | Cytokine IL-36B ("IL-36B", or "IL36B") beta | CACGGGTTCCTCCCCACTCTGTCTTTCTCACCTCTCCTTCA |
|  |  | CTTTTCCTAGCCTCCTCACCACCATCTGATCTATCTTGTTC |
|  |  | TCTTCACAAAAGGCTCTGAAGACATCATGAACCCACAAC |
|  |  | GGGAGGCAGCACCCAAATCCTATGCTATTCGTGATTCTCG |
|  |  | ACAGATGGTGTGGGTCCTGAGTGGAAATTCTTTAATAGCA |
|  |  | GCTCCTCTTAGCCGCAGCATTAAGCCTGTCACTCTTCATTT |
|  |  | AATAGCCTGTAGAGACACAGAATTCAGTGACAAGGAAAA |
|  |  | GGGTAATATGGTTTACCTGGGAATCAAGGGAAAAGATCT |
|  |  | CTGTCTCTTCTGTGCAGAAATTCAGGGCAAGCCTACTTTG |
|  |  | CAGCTTAAGCTTCAGGGCTCCCAAGATAACATAGGGAAG |
|  |  | GACACTTGCTGGAAACTAGTTGGAATTCACACATGCATAA |
|  |  | ACCTGGATGTGAGAGAGAGCTGCTTCATGGGAACCCTTG |
|  |  | ACCAATGGGGAATAGGAGTGGGTAGAAAGAAGTGGAAG |
|  |  | AGTTCCTTTCAACATCACCATCTCAGGAAGAAGGACAAA |
|  |  | GATTTCTCATCCATGCGGACCAACATAGGAATGCCAGGA |
|  |  | AGGATGTAGAAATAAGGGGAGGAAGATTCCCATCTCTAC |
|  |  | AATCTTTGAGTGGGTTTGCTATCAATGAAATGCTACAAAT |
|  |  | GGAATAAGTTGCAGAAATTTTTCTCTTTTCTTGGGTTCTGG |
|  |  | AGAGTTTGTAAAACAAGGACACTATGTATTTTTAAAGAGT |
|  |  | TGGTAAATCTTACCTGTAAAGCTAGAGAAGGTCGGAGTCT |
|  |  | TTTTAGGAGTAGATTTGGACTACATAACCTGTAAATGTGT |
|  |  | TTTGTCCAGTCCTTAGAGTGTTTTTTAAAAAATTGT |
|  |  | AAAGTCAAGGTTTTCATGAAAAATGGGAAGATCAGACAA |
|  |  | CATTGCTCCTGAATTCCCACAGAGCAGCAAGCTACTAGAG |
|  |  | CTCAATCTGTTATTTCTTTTCCTGATGTACAGGGGTTAAGT |
|  |  | CCTATGGAAGAAACAGCAGAATTATTCAAAATTATTTACA |
|  |  | TAATGTGCAATTATTCACTAGAGCATGAGGAGTGAAACG |
|  |  | CTCTGTTTAGTATGTATAACTTAAAAGGAACACATACAAT |
|  |  | TAAAAGTAATTGAAAGACATTTCTTCTTAAAAATTCTATA |
|  |  | ATCTTACACTGGTAAAATAAACTAGTTTTTCCCATGT |
| 63 | Cytokine IL-36G ("IL-36G", or "IL-36G") gamma | GAAGCTGCTGGAGCCACGATTCAGTCCCCTGGACTGTAG |
|  |  | ATAAAGACCCTTTCTTGCCAGGTGCTGAGACAACCACACT |
|  |  | ATGAGAGGCACTCCAGGAGACGCTGATGGTGGAGGAAGG |
|  |  | GCCGTCTATCAATCAATCACTGTTGCTGTTATCACATGCA |
|  |  | AGTATCCAGAGGCTCTTGAGCAAGGCAGAGGGGATCCCA |
|  |  | TTTATTTGGGAATCCAGAATCCAGAAATGTGTTTGTATTG |
|  |  | TGAGAAGGTTGGAGAACAGCCCACATTGCAGCTAAAAGA |
|  |  | GCAGAAGATCATGGATCTGTATGGCCAACCCGAGCCCGT |
|  |  | GAAACCCTTCCTTTTCTACCGTGCCAAGACTGGTAGGACC |
|  |  | TCCACCCTTGAGTCTGTGGCCTTCCCGGACTGGTTCATTG |
|  |  | CCTCCTCCAAGAGAGACCAGCCCATCATTCTGACTTCAGA |
|  |  | ACTTGGGAAGTCATACAACACTGCCTTTGAATTAAATATA |
|  |  | AATGACTGAACTCAGCCTAGAGGTGGCAGCTTGGTCTTTG |
|  |  | TCTTAAAGTTTCTGGTTCCCAATGTGTTTTCGTCTACATTT |
|  |  | TCTTAGTGTCATTTTCACGCTGGTGCTGAGACAGGGGCAA |
|  |  | GGCTGCTGTTATCATCTCATTTTATAATGAAGAAGAAGCA |
|  |  | ATTACTTCATAGCAACTGAAGAACAGGATGTGGCCTCAG |
|  |  | AAGCAGGAGAGCTGGGTGGTATAAGGCTGTCCTCTCAAG |
|  |  | CTGGTGCTGTGTAGGCCACAAGGCATCTGCATGAGTGACT |
|  |  | TTAAGACTCAAAGACCAAACACTGAGCTTTCTTCTAGGGG |
|  |  | TGGGTATGAAGATGCTTCAGAGCTCATGCGCGTTACCCAC |
|  |  | GATGGCATGACTAGCACAGAGCTGATCTCTGTTTCT |
|  |  | GTTTTGCTTTATTCCCTCTTGGGATGATATCATCCAGTCTT |
|  |  | TATATGTTGCCAATATACCTCATTGTGTGTAATAGAACCT |
|  |  | TCTTAGCATTAAGACCTTGTAAACAAAAATAATTCTTGTG |
|  |  | TTAAGTTAAATCATTTTTGTCCTAATTGTAATGTGTAATCT |
|  |  | TAAAGTTAAATAAACTTTGTGTATTTATATAATAATAAAG |
|  |  | CTAAAACTGATATAAAATAAAGAAAGAGTAAACTG |

-continued

| SEQ ID NO: | Description | Sequence |
|---|---|---|
| 64 | FDPS shRNA sequence #4A | ACTTTCTCAGCCTCCTTCTGCCTCGAGGCAGAAGGAGGCT GAGAAAGTTTTTT |
| 65 | FDPS shRNA sequence #4R | GCAGAAGGAGGCTGAGAAAGTGAGCTCACTTTCTCAGCC TCCTTCTG |
| 66 | FDPS shRNA sequence #4TT | GCAGAAGGAGGCTGAGAAAGTTTACTTTCTCAGCCTCCTT CTGCTTTTT |
| 67 | FDPS sequence #4L | GCAGAAGGAGGCTGAGAAAGTACTTTCTCAGCCTCCTTCT GCTTTTT |
| 68 | FDPS miR30 sequence #1 | AAGGTATATTGCTGTTGACAGTGAGCGACACTTTCTCAGC CTCCTTCTGCGTGAAGCCACAGATGGCAGAAGGAGGCTG AGAAAGTGCTGCCTACTGCCTCGGACTTCAAGGGGCT |
| 69 | FDPS miR30 sequence #3 | AAGGTATATTGCTGTTGACAGTGAGCGACACTTTCTCAGC CTCCTTCTGCGTGAAGCCACAGATGGCAGAAGGGCTGAG AAAGTGCTGCCTACTGCCTCGGACTTCAAGGGGCT |
| 70 | GGPS1 shRNA sequence #1 | GCTTGAAGCTAAAGCCTATAACTCGAGTTATAGGCTTTAG CTTCAAGCTTTTT |
| 71 | GGPS1 shRNA sequence #2 | GTACATTATCTTGAGGATGTACTCGAGTACATCCTCAAGA TAATGTACTTTTT |
| 72 | GGPS1 shRNA sequence 3 | CCTGAGCTAGTAGCCTTAGTACTCGAGTACTAAGGCTACT AGCTCAGGTTTTT |
| 73 | GGPS1 target sequence #1 | GCTTGAAGCTAAAGCCTATAA |
| 74 | GGPS1 target sequence #2 | GTACATTATCTTGAGGATGTA |
| 75 | GGPS1 target sequence #3 | CCTGAGCTAGTAGCCTTAGTA |
| 76 | IDI1 shRNA sequence | GCCAGTGGTGAAATTAAGATACTCGAGTATCTTAATTTCA CCACTGGCTTTTT |
| 77 | IDI1 target sequence | GCCAGTGGTGAAATTAAGATA |
| 78 | Fam-labeled TaqMan probe | TAGCATCTCCTATCTCTGGGTGCCC |
| 79 | FDPS forward primer | GTGCTGACTGAGGATGAGATG |
| 80 | FDPS reverse primer | CCGGTTATACTTGCCTCCAAT |
| 81 | Fam-labeled TaqMan probe | AGCGGGAAATCGTGCGTGAC |
| 82 | Actin forward primer | GGACCTGACTGACTACCTCAT |
| 83 | Actin reverse primer | CGTAGCACAGCTTCTCCTTAAT |

What is claimed is:

1. A viral vector, comprising at least one encoded RNA that, when expressed, inhibits production of at least one enzyme of the mevalonate pathway, further comprising at least one of an encoded butyrophilin family member, an encoded cytokine, or an encoded chemokine, wherein the at least one encoded RNA comprises a sequence having at least 95% identity with at least one of SEQ ID NO: 64; SEQ ID NO: 65; SEQ ID NO: 66; or SEQ ID NO: 67.

2. The viral vector of claim 1, wherein the at least one encoded RNA comprises a short hairpin (shRNA) or a microRNA.

3. The viral vector of claim 1, wherein the at least one enzyme is farnesyl diphosphate synthase (FDPS), gera-nylgeranyl-diphosphate synthase I (GGPSI), isopentenyl-diphosphate delta isomerase I (IDII), or farnesyl transferase (F-Tase).

4. The viral vector of claim 1, wherein the encoded butyrophilin family member comprises Butyrophilin 3A3 (BTN3A3), Butyrophilin 3A2 (BTN3A2), or Butyrophilin 3AI (BTN3AI1).

5. The viral vector of claim 1, wherein the viral vector is a lentiviral vector.

6. A lentiviral vector system for expressing a lentiviral particle comprising:

the lentiviral vector according to claim 5 at least one envelope plasmid for expressing an envelope protein for infecting a target cell; and at least one helper plasmid for expressing gag, pol, and rev genes, wherein the lentiviral vector, the at least one envelope plasmid, and the at least one helper plasmid are capable of transfecting a packaging cell, wherein, upon transfection, the packaging cell is capable of producing the lentiviral particle, and wherein the lentiviral particle is capable of infecting the target cell and capable of inhibiting the at least one enzyme involved in the mevalonate pathway within the target cell.

7. A lentiviral particle comprising:

an envelope protein for infecting a target cell; and the lentiviral vector according to claim 5.

8. The lentiviral particle of claim 7, wherein the target cell is a cancer cell.

* * * * *